(12) United States Patent
McCormack et al.

(10) Patent No.: US 8,623,054 B2
(45) Date of Patent: Jan. 7, 2014

(54) VERTEBRAL JOINT IMPLANTS AND DELIVERY TOOLS

(71) Applicant: Providence Medical Technology, Inc., San Francisco, CA (US)

(72) Inventors: Bruce M. McCormack, San Francisco, CA (US); Jeffrey D. Smith, Clayton, CA (US); Shigeru Tanaka, Half Moon Bay, CA (US); Edward Liou, Mountain View, CA (US); Edward Fletcher Eyster, St. Helena, CA (US); Jonathan Carver, Millbrae, CA (US); Joshua Druker, Redwood City, CA (US); Martin Leugers, San Francisco, CA (US); Kurin Tu, San Mateo, CA (US); Peter Lombrozo, Scotts Valley, CA (US)

(73) Assignee: Providence Medical Technology, Inc., Lafayette, CA (US)

( * ) Notice: Subject to any disclaimer, the term of this patent is extended or adjusted under 35 U.S.C. 154(b) by 0 days.

(21) Appl. No.: 13/627,812

(22) Filed: Sep. 26, 2012

(65) Prior Publication Data

US 2013/0023995 A1 Jan. 24, 2013

Related U.S. Application Data

(63) Continuation of application No. 12/653,283, filed on Dec. 10, 2009, now Pat. No. 8,425,558, which is a continuation-in-part of application No. 12/455,814, filed on Jun. 5, 2009, now Pat. No. 8,361,152, which is a continuation-in-part of application No. 12/317,682, filed on Dec. 23, 2008, now Pat. No. 8,267,966.

(60) Provisional application No. 61/169,601, filed on Apr. 15, 2009, provisional application No. 61/109,776, filed on Oct. 30, 2008, provisional application No. 61/059,723, filed on Jun. 6, 2008.

(51) Int. Cl.
*A61B 17/70* (2006.01)

(52) U.S. Cl.
USPC .......................................................... 606/247

(58) Field of Classification Search
USPC ............................................ 606/99, 247–248
See application file for complete search history.

(56) References Cited

U.S. PATENT DOCUMENTS

| 4,479,491 A | 10/1984 | Martin |
| 4,530,355 A | 7/1985 | Griggs |

(Continued)

FOREIGN PATENT DOCUMENTS

| DE | G 93 04 368.6 | 5/2003 |
| FR | 2 722 980 A1 | 2/1996 |

(Continued)

OTHER PUBLICATIONS

U.S. Appl. No. 29/435,381, filed Oct. 23, 2012, McCormack et al.

(Continued)

*Primary Examiner* — Sameh Boles
(74) *Attorney, Agent, or Firm* — Polsinelli PC

(57) ABSTRACT

A spinal joint distraction system for treating a facet joint including articular surfaces having a contour is disclosed and may include a delivery device including a generally tubular structure adapted to engage a facet joint, an implant adapted to be delivered through the delivery device and into the facet joint, the implant comprising two members arranged in opposed position, and an implant distractor comprising a generally elongate member adapted to advance between the two members of the implant causing separation of the members and distraction of the facet joint, wherein the implant is adapted to conform to the shape of the implant distractor and/or the articular surfaces of the facet upon being delivered to the facet joint. Several embodiments of a system, several embodiments of an implant, and several methods are disclosed including a method for interbody fusion.

26 Claims, 150 Drawing Sheets

(56) References Cited

U.S. PATENT DOCUMENTS

| | | |
|---|---|---|
| 4,772,287 A | 9/1988 | Ray et al. |
| 5,015,247 A | 5/1991 | Michelson |
| 5,026,373 A | 6/1991 | Ray et al. |
| 5,100,405 A | 3/1992 | McLaren |
| 5,135,528 A | 8/1992 | Winston |
| 5,236,460 A | 8/1993 | Barber |
| 5,484,437 A | 1/1996 | Michelson |
| 5,489,307 A | 2/1996 | Kuslich et al. |
| 5,505,732 A | 4/1996 | Michelson |
| 5,527,312 A | 6/1996 | Ray |
| 5,549,679 A | 8/1996 | Kuslich |
| 5,554,191 A | 9/1996 | Lahille et al. |
| 5,571,191 A | 11/1996 | Fitz |
| 5,593,409 A | 1/1997 | Michelson |
| 5,632,747 A | 5/1997 | Scarborough et al. |
| 5,653,763 A | 8/1997 | Errico et al. |
| 5,665,122 A | 9/1997 | Kambin |
| 5,674,295 A | 10/1997 | Ray et al. |
| 5,720,748 A | 2/1998 | Kuslich et al. |
| 5,741,253 A | 4/1998 | Michelson |
| 5,772,661 A | 6/1998 | Michelson |
| 5,797,909 A | 8/1998 | Michelson |
| 5,836,948 A | 11/1998 | Zucherman et al. |
| 5,879,353 A | 3/1999 | Terry |
| 5,885,299 A | 3/1999 | Winslow et al. |
| 5,891,147 A | 4/1999 | Moskovitz et al. |
| 5,895,426 A | 4/1999 | Scarborough et al. |
| 5,899,908 A | 5/1999 | Kuslich et al. |
| 5,928,238 A | 7/1999 | Scarborough et al. |
| 5,961,522 A | 10/1999 | Mehdizadeh |
| 5,976,146 A | 11/1999 | Ogawa et al. |
| 6,033,405 A | 3/2000 | Winslow et al. |
| 6,045,580 A | 4/2000 | Scarborough et al. |
| 6,063,088 A | 5/2000 | Winslow |
| RE36,758 E | 6/2000 | Fitz |
| 6,080,155 A | 6/2000 | Michelson |
| 6,090,143 A | 7/2000 | Meriwether et al. |
| 6,096,038 A | 8/2000 | Michelson |
| 6,099,531 A | 8/2000 | Bonutti |
| 6,102,950 A | 8/2000 | Vaccaro |
| 6,149,650 A | 11/2000 | Michelson |
| RE37,005 E | 12/2000 | Michelson et al. |
| 6,159,245 A | 12/2000 | Meriwether et al. |
| 6,190,388 B1 | 2/2001 | Michelson et al. |
| 6,190,414 B1 | 2/2001 | Young et al. |
| 6,210,412 B1 | 4/2001 | Michelson |
| RE37,161 E | 5/2001 | Michelson et al. |
| 6,224,595 B1 | 5/2001 | Michelson |
| 6,224,607 B1 | 5/2001 | Michelson |
| 6,224,630 B1 | 5/2001 | Bao et al. |
| 6,248,110 B1 | 6/2001 | Reiley et al. |
| 6,264,656 B1 | 7/2001 | Michelson |
| 6,267,763 B1 | 7/2001 | Castro |
| 6,270,498 B1 | 8/2001 | Michelson |
| 6,283,966 B1 | 9/2001 | Houfburg |
| 6,315,795 B1 | 11/2001 | Scarborough et al. |
| 6,402,784 B1 | 6/2002 | Wardlaw |
| 6,423,063 B1 | 7/2002 | Bonutti |
| 6,423,083 B2 | 7/2002 | Reiley et al. |
| 6,425,919 B1 | 7/2002 | Lambrecht |
| 6,436,098 B1 | 8/2002 | Michelson |
| 6,436,142 B1 | 8/2002 | Paes et al. |
| 6,443,988 B2 | 9/2002 | Felt et al. |
| 6,451,023 B1 | 9/2002 | Salazar et al. |
| 6,454,807 B1 | 9/2002 | Jackson |
| 6,478,796 B2 | 11/2002 | Zucherman et al. |
| 6,500,206 B1 | 12/2002 | Bryan |
| 6,514,256 B2 | 2/2003 | Zucherman et al. |
| 6,565,574 B2 | 5/2003 | Michelson |
| 6,569,186 B1 | 5/2003 | Winters et al. |
| 6,575,919 B1 | 6/2003 | Reiley et al. |
| 6,579,319 B2 | 6/2003 | Goble et al. |
| 6,582,432 B1 | 6/2003 | Michelson |
| 6,607,530 B1 | 8/2003 | Carl et al. |
| 6,610,091 B1 | 8/2003 | Reiley |
| 6,626,905 B1 | 9/2003 | Schmiel et al. |
| 6,632,235 B2 | 10/2003 | Weikel et al. |
| 6,635,060 B2 | 10/2003 | Hanson et al. |
| 6,641,582 B1 | 11/2003 | Hanson et al. |
| 6,648,893 B2 | 11/2003 | Dudasik |
| 6,652,584 B2 | 11/2003 | Michelson |
| 6,663,647 B2 | 12/2003 | Reiley et al. |
| 6,666,866 B2 | 12/2003 | Martz et al. |
| 6,679,886 B2 | 1/2004 | Weikel et al. |
| 6,682,535 B2 | 1/2004 | Hoogland |
| 6,685,742 B1 | 2/2004 | Jackson |
| 6,709,458 B2 | 3/2004 | Michelson |
| 6,712,853 B2 | 3/2004 | Kuslich |
| 6,719,773 B1 | 4/2004 | Boucher et al. |
| 6,723,095 B2 | 4/2004 | Hammerslag |
| 6,733,534 B2 | 5/2004 | Sherman |
| 6,740,093 B2 | 5/2004 | Hochschuler et al. |
| 6,770,074 B2 | 8/2004 | Michelson |
| 6,793,679 B2 | 9/2004 | Michelson |
| 6,805,715 B2 | 10/2004 | Reuter et al. |
| 6,808,537 B2 | 10/2004 | Michelson |
| 6,840,941 B2 | 1/2005 | Rogers et al. |
| 6,875,213 B2 | 4/2005 | Michelson |
| 6,899,719 B2 | 5/2005 | Reiley et al. |
| 6,921,403 B2 | 7/2005 | Cragg et al. |
| 6,923,813 B2 | 8/2005 | Phillips et al. |
| 6,958,077 B2 | 10/2005 | Suddaby |
| 6,962,606 B2 | 11/2005 | Michelson |
| 6,966,930 B2 | 11/2005 | Arnin et al. |
| 6,972,035 B2 | 12/2005 | Michelson |
| 6,979,333 B2 | 12/2005 | Hammerslag |
| 7,001,385 B2 | 2/2006 | Bonutti |
| 7,008,453 B1 | 3/2006 | Michelson |
| 7,033,362 B2 | 4/2006 | McGahan et al. |
| 7,033,392 B2 | 4/2006 | Schmiel et al. |
| 7,033,394 B2 | 4/2006 | Michelson |
| 7,066,961 B2 | 6/2006 | Michelson |
| 7,083,623 B2 | 8/2006 | Michelson |
| 7,101,398 B2 | 9/2006 | Dooris et al. |
| 7,115,128 B2 | 10/2006 | Michelson |
| 7,118,598 B2 | 10/2006 | Michelson |
| 7,128,760 B2 | 10/2006 | Michelson |
| 7,156,877 B2 | 1/2007 | Lotz et al. |
| 7,166,110 B2 | 1/2007 | Yundt |
| 7,179,263 B2 | 2/2007 | Zdeblick et al. |
| 7,207,991 B2 | 4/2007 | Michelson |
| 7,264,622 B2 | 9/2007 | Michelson |
| 7,273,498 B2 | 9/2007 | Bianchi et al. |
| 7,288,093 B2 | 10/2007 | Michelson |
| 7,291,149 B1 | 11/2007 | Michelson |
| 7,300,440 B2 | 11/2007 | Zdeblick et al. |
| 7,326,211 B2 | 2/2008 | Padget et al. |
| 7,326,214 B2 | 2/2008 | Michelson |
| 7,371,238 B2 | 5/2008 | Soboleski et al. |
| 7,399,303 B2 | 7/2008 | Michelson |
| 7,410,501 B2 | 8/2008 | Michelson |
| 7,431,722 B1 | 10/2008 | Michelson |
| 7,445,636 B2 | 11/2008 | Michelson |
| 7,452,359 B1 | 11/2008 | Michelson |
| 7,452,369 B2 | 11/2008 | Barry |
| 7,465,304 B1 | 12/2008 | Haufe et al. |
| 7,476,226 B2 | 1/2009 | Weikel et al. |
| 7,476,251 B2 | 1/2009 | Zucherman et al. |
| 7,479,160 B2 | 1/2009 | Branch et al. |
| 7,491,205 B1 | 2/2009 | Michelson |
| 7,500,992 B2 | 3/2009 | Li |
| 7,517,358 B2 | 4/2009 | Peterson |
| 7,524,333 B2 | 4/2009 | Lambrecht et al. |
| 7,569,054 B2 | 8/2009 | Michelson |
| 7,569,057 B2 | 8/2009 | Liu et al. |
| 7,580,743 B2 | 8/2009 | Bourlion et al. |
| 7,591,851 B2 | 9/2009 | Winslow et al. |
| 7,601,170 B2 | 10/2009 | Winslow et al. |
| 7,608,077 B2 | 10/2009 | Cragg et al. |
| 7,608,107 B2 | 10/2009 | Michelson |
| 7,641,664 B2 | 1/2010 | Pagano |
| 7,648,523 B2 | 1/2010 | Mirkovic et al. |
| 7,655,027 B2 | 2/2010 | Michelson |
| 7,662,173 B2 | 2/2010 | Cragg et al. |

(56) References Cited

U.S. PATENT DOCUMENTS

| | | |
|---|---|---|
| 7,682,378 B2 | 3/2010 | Truckai et al. |
| 7,686,805 B2 | 3/2010 | Michelson |
| 7,686,807 B2 | 3/2010 | Padget et al. |
| 7,699,878 B2 | 4/2010 | Pavlov et al. |
| 7,708,761 B2 | 5/2010 | Petersen |
| 7,722,619 B2 | 5/2010 | Michelson |
| 7,763,024 B2 | 7/2010 | Bertagnoli et al. |
| 7,763,050 B2 | 7/2010 | Winslow et al. |
| 7,776,090 B2 | 8/2010 | Winslow et al. |
| 7,789,898 B2 | 9/2010 | Peterman |
| 7,824,431 B2 | 11/2010 | McCormack |
| 7,837,713 B2 | 11/2010 | Petersen |
| 7,846,183 B2 | 12/2010 | Blain |
| 7,846,184 B2 | 12/2010 | Sasso et al. |
| 7,850,733 B2 | 12/2010 | Baynham et al. |
| 7,862,589 B2 | 1/2011 | Thramann |
| 7,879,098 B1 | 2/2011 | Simmons |
| 7,887,565 B2 | 2/2011 | Michelson |
| 7,892,286 B2 | 2/2011 | Michelson |
| 7,896,903 B2 | 3/2011 | Link |
| 7,901,439 B2 | 3/2011 | Horton |
| 7,914,530 B2 | 3/2011 | Michelson |
| 7,922,729 B2 | 4/2011 | Michelson |
| 7,922,766 B2 | 4/2011 | Grob et al. |
| 7,935,136 B2 | 5/2011 | Alamin et al. |
| 7,988,712 B2 | 8/2011 | Hale et al. |
| 7,998,174 B2 | 8/2011 | Malandain et al. |
| 8,007,534 B2 | 8/2011 | Michelson |
| 8,029,540 B2 | 10/2011 | Winslow et al. |
| 8,043,334 B2 | 10/2011 | Fisher et al. |
| 8,062,303 B2 | 11/2011 | Berry et al. |
| 8,066,705 B2 | 11/2011 | Michelson |
| 8,097,034 B2 | 1/2012 | Michelson |
| 8,100,944 B2 | 1/2012 | Lauryssen et al. |
| 8,118,838 B2 | 2/2012 | Winslow et al. |
| 8,128,660 B2 | 3/2012 | Mitchell et al. |
| 8,133,261 B2 | 3/2012 | Fisher et al. |
| 8,142,503 B2 | 3/2012 | Malone |
| 8,147,553 B2 | 4/2012 | Vresilovic et al. |
| 8,162,981 B2 | 4/2012 | Vestgaarden |
| 8,172,877 B2 | 5/2012 | Winslow et al. |
| 8,197,513 B2 | 6/2012 | Fisher et al. |
| 8,267,966 B2 | 9/2012 | McCormack et al. |
| 8,361,152 B2 | 1/2013 | McCormack et al. |
| 8,425,558 B2 | 4/2013 | McCormack et al. |
| 2002/0026195 A1 | 2/2002 | Layne et al. |
| 2002/0107519 A1 | 8/2002 | Dixon |
| 2002/0143343 A1 | 10/2002 | Castro |
| 2002/0147496 A1 | 10/2002 | Belef et al. |
| 2002/0147497 A1 | 10/2002 | Belef et al. |
| 2002/0165612 A1 | 11/2002 | Gerber et al. |
| 2002/0169471 A1 | 11/2002 | Ferdinand |
| 2003/0028251 A1 | 2/2003 | Mathews |
| 2003/0139816 A1 | 7/2003 | Michelson |
| 2004/0059337 A1 | 3/2004 | Hanson et al. |
| 2004/0073217 A1 | 4/2004 | Michelson |
| 2004/0087948 A1 | 5/2004 | Suddaby |
| 2004/0087956 A1 | 5/2004 | Weikel et al. |
| 2004/0106999 A1 | 6/2004 | Mathews |
| 2004/0133277 A1 | 7/2004 | Michelson |
| 2004/0133280 A1 | 7/2004 | Trieu |
| 2004/0162562 A1 | 8/2004 | Martz |
| 2004/0215344 A1 | 10/2004 | Hochschuler et al. |
| 2005/0015149 A1 | 1/2005 | Michelson |
| 2005/0049705 A1 | 3/2005 | Hale et al. |
| 2005/0055096 A1 | 3/2005 | Serhan et al. |
| 2005/0065518 A1 | 3/2005 | Michelson |
| 2005/0065519 A1 | 3/2005 | Michelson |
| 2005/0065609 A1 | 3/2005 | Wardlaw |
| 2005/0080422 A1 | 4/2005 | Otte et al. |
| 2005/0090829 A1 | 4/2005 | Martz et al. |
| 2005/0090901 A1 | 4/2005 | Studer |
| 2005/0119680 A1 | 6/2005 | Dykes |
| 2005/0124993 A1 | 6/2005 | Chappuis |
| 2005/0159650 A1 | 7/2005 | Raymond et al. |
| 2005/0159746 A1 | 7/2005 | Grob et al. |
| 2005/0216018 A1 | 9/2005 | Sennett |
| 2005/0240188 A1 | 10/2005 | Chow et al. |
| 2005/0251146 A1 | 11/2005 | Martz et al. |
| 2005/0251257 A1 | 11/2005 | Mitchell et al. |
| 2005/0267480 A1 | 12/2005 | Suddaby |
| 2006/0036247 A1 | 2/2006 | Michelson |
| 2006/0036323 A1 | 2/2006 | Carl et al. |
| 2006/0041311 A1 | 2/2006 | McLeer |
| 2006/0058793 A1 | 3/2006 | Michelson |
| 2006/0058878 A1 | 3/2006 | Michelson |
| 2006/0079905 A1 | 4/2006 | Beyar et al. |
| 2006/0085074 A1 | 4/2006 | Raiszadeh |
| 2006/0095028 A1 | 5/2006 | Bleich |
| 2006/0095036 A1 | 5/2006 | Hammerslag |
| 2006/0111779 A1 | 5/2006 | Peterson |
| 2006/0111780 A1 | 5/2006 | Petersen |
| 2006/0149289 A1 | 7/2006 | Winslow et al. |
| 2006/0184172 A1 | 8/2006 | Michelson |
| 2006/0190081 A1 | 8/2006 | Kraus et al. |
| 2006/0195109 A1 | 8/2006 | McGahan et al. |
| 2006/0200137 A1 | 9/2006 | Soboleski et al. |
| 2006/0200138 A1 | 9/2006 | Michelson |
| 2006/0206118 A1 | 9/2006 | Kim et al. |
| 2006/0235391 A1 | 10/2006 | Sutterlin, III |
| 2006/0241626 A1 | 10/2006 | McGahan et al. |
| 2006/0241758 A1 | 10/2006 | Peterman et al. |
| 2006/0247633 A1 | 11/2006 | Winslow et al. |
| 2006/0247650 A1 | 11/2006 | Yerby et al. |
| 2006/0259142 A1 | 11/2006 | Dooris et al. |
| 2006/0276790 A1 | 12/2006 | Dawson et al. |
| 2006/0276801 A1 | 12/2006 | Yerby et al. |
| 2006/0276897 A1 | 12/2006 | Winslow et al. |
| 2007/0016196 A1 | 1/2007 | Winslow et al. |
| 2007/0016218 A1 | 1/2007 | Winslow et al. |
| 2007/0032871 A1 | 2/2007 | Michelson |
| 2007/0055245 A1 | 3/2007 | Sasso et al. |
| 2007/0055263 A1 | 3/2007 | Way et al. |
| 2007/0073402 A1 | 3/2007 | Vresilovic et al. |
| 2007/0123888 A1 | 5/2007 | Bleich et al. |
| 2007/0135814 A1 | 6/2007 | Farris |
| 2007/0135921 A1 | 6/2007 | Park |
| 2007/0150061 A1 | 6/2007 | Trieu |
| 2007/0161991 A1 | 7/2007 | Altarac et al. |
| 2007/0179617 A1 | 8/2007 | Brown et al. |
| 2007/0225721 A1 | 9/2007 | Thelen et al. |
| 2007/0276491 A1 | 11/2007 | Ahrens |
| 2007/0288014 A1 | 12/2007 | Shadduck et al. |
| 2007/0299451 A1 | 12/2007 | Tulkis |
| 2008/0021457 A1 | 1/2008 | Anderson et al. |
| 2008/0108996 A1 | 5/2008 | Padget et al. |
| 2008/0140207 A1 | 6/2008 | Olmos et al. |
| 2008/0161810 A1 | 7/2008 | Melkent |
| 2008/0161929 A1 | 7/2008 | McCormack et al. |
| 2008/0167657 A1 | 7/2008 | Greenhalgh |
| 2008/0177311 A1 | 7/2008 | Winslow et al. |
| 2008/0255564 A1 | 10/2008 | Michelson |
| 2008/0255622 A1 | 10/2008 | Mickiewicz et al. |
| 2008/0287955 A1 | 11/2008 | Michelson |
| 2009/0131986 A1 | 5/2009 | Lee et al. |
| 2009/0138053 A1 | 5/2009 | Assell et al. |
| 2009/0177205 A1 | 7/2009 | McCormack et al. |
| 2009/0306671 A1 | 12/2009 | McCormack et al. |
| 2009/0312763 A1 | 12/2009 | McCormack et al. |
| 2010/0069912 A1 | 3/2010 | McCormack et al. |
| 2010/0086185 A1 | 4/2010 | Weiss |
| 2010/0093829 A1 | 4/2010 | Gorman |
| 2011/0022089 A1 | 1/2011 | Assell et al. |
| 2011/0082548 A1 | 4/2011 | Assell et al. |
| 2013/0006364 A1 | 1/2013 | McCormack et al. |
| 2013/0012994 A1 | 1/2013 | McCormack et al. |
| 2013/0013070 A1 | 1/2013 | McCormack et al. |
| 2013/0018474 A1 | 1/2013 | McCormack et al. |
| 2013/0023996 A1 | 1/2013 | McCormack et al. |
| 2013/0030440 A1 | 1/2013 | McCormack et al. |

(56) References Cited

U.S. PATENT DOCUMENTS

| | | |
|---|---|---|
| 2013/0030532 A1 | 1/2013 | McCormack et al. |
| 2013/0110168 A1 | 5/2013 | McCormack et al. |
| 2013/0123922 A1 | 5/2013 | McCormack et al. |

FOREIGN PATENT DOCUMENTS

| | | |
|---|---|---|
| WO | WO 99/49818 A1 | 10/1999 |
| WO | WO 00/35388 A1 | 6/2000 |
| WO | WO 00/53126 A1 | 9/2000 |
| WO | WO 01/01895 A1 | 1/2001 |
| WO | WO 02/34120 A2 | 5/2002 |
| WO | WO 02/38062 A2 | 5/2002 |
| WO | WO 02/076335 A2 | 10/2002 |
| WO | WO 2006/058221 A2 | 6/2006 |
| WO | WO 2006/130791 A2 | 12/2006 |

OTHER PUBLICATIONS

U.S. Appl. No. 29/435,385, filed Oct. 23, 2012, McCormack et al.
U.S. Appl. No. 29/448,474, filed Mar. 12, 2013, McCormack et al.
U.S. Appl. No. 29/448,467, filed Mar. 12, 2013, McCormack et al.
Final Office Action, U.S. Appl. No. 12/559,193, mailed Feb. 13, 2013, 10 pages.
Non-Final Office Action, U.S. Appl. No. 13/614,372, mailed Jun. 26, 2013, 22 pages.
Non-Final Office Action, U.S. Appl. No. 13/627,850, mailed Jul. 25, 2013, 23 pages.
Notice of Allowance, U.S. Appl. No. 12/559,193, mailed Apr. 22, 2013, 8 pages.
Response to Final Office Action, U.S. Appl. No. 12/559,193, filed Apr. 12, 2013, 8 pages.
Response to Non-Final Office Action, U.S. Appl. No. 12/559,193, filed Dec. 13, 2012, 7 pages.
Response to Restriction, U.S. Appl. No. 13/614,372, filed May 16, 2013, 6 pages.
Response to Restriction, U.S. Appl. No. 13/614,508, filed Jun. 1, 2013, 6 pages.
Response to Restriction, U.S. Appl. No. 13/614,577, filed Jun. 1, 2013, 6 pages.
Response to Restriction, U.S. Appl. No. 13/627,825, filed Jun. 1, 2013, 6 pages.
Response to Restriction, U.S. Appl. No. 13/627,850, filed Jun. 1, 2013, 5 pages.
Response to Restriction, U.S. Appl. No. 13/627,865, filed Jun. 1, 2013, 6 pages.
Restriction Requirement, U.S. Appl. No. 13/614,372, mailed Apr. 17, 2013, 6 pages.
Restriction Requirement, U.S. Appl. No. 13/614,508, mailed May 3, 2013, 6 pages.
Restriction Requirement, U.S. Appl. No. 13/614,577, mailed May 2, 2013, 6 pages.
Restriction Requirement, U.S. Appl. No. 13/627,825, mailed May 2, 2013, 7 pages.
Restriction Requirement, U.S. Appl. No. 13/627,850, mailed May 2, 2013, 7 pages.
Restriction Requirement, U.S. Appl. No. 13/627,865, mailed May 6, 2013, 5 pages.
Advisory Action, U.S. Appl. No. 12/317,682, dated Apr. 6, 2012, 3 pages.
Advisory Action, U.S. Appl. No. 12/455,814, dated Aug. 16, 2012, 3 pages.
Amendment and Response to Office Action, U.S. Appl. No. 12/110,548, filed May 5, 2009, 11 pages.
Amendment, U.S. Appl. No. 11/618,619, filed May 5, 2008, 10 pages.
Corrected Response to Restriction Requirement, U.S. Appl. No. 12/317,682, filed Sep. 2, 2011, 15 pages.
Final Office Action, U.S. Appl. No. 11/618,619, mailed Aug. 8, 2008, 10 pages.
Final Office Action, U.S. Appl. No. 12/110,548, mailed Feb. 26, 2010, 4 pages.
Final Office Action, U.S. Appl. No. 12/317,682, mailed Feb. 10, 2012, 8 pages.
Final Office Action, U.S. Appl. No. 12/350,609, mailed Apr. 25, 2012, 10 pages.
Final Office Action, U.S. Appl. No. 12/455,814, mailed Jun. 6, 2012, 12 pages.
Final Office Action, U.S. Appl. No. 12/653,283, mailed Mar. 21, 2012, 8 pages.
Final Office Action, U.S. Appl. No. 12/653,283, mailed Nov. 19, 2012, 8 pages.
Goel, Atul et al., Facetal Distraction as Treatment for Single- and Multilevel Cervical spondylotic Radiculopathy and Myelopathy: A Preliminary Report. J Neurosurg Spine 14:689-696, Jun. 2011; published online Mar. 18, 2011; DOI: 10.3171/2011.2.SPINE10601.
International Search Report and WO, International patent application No. PCT/US2009/056841, dated Apr. 9, 2010.
International Search Report and WO, PCT/US2009/006478, dated Jun. 29, 2010.
International Search Report and Written Opinion, International patent application No. PCT/US07/89146, dated Nov. 3, 2008.
International Search Report and Written Opinion, International patent application No. PCT/US2009/030461, dated Aug. 17, 2009.
International Search Report and Written Opinion, International patent application No. PCT/US2009/003423, dated Dec. 14, 2009.
Interview summary, U.S. Appl. No. 11/618,619, mailed Mar. 18, 2008, 3 pages.
Non-Final Office Action, U.S. Appl. No. 11/618,619, mailed Jan. 3, 2008, 12 pages.
Non-Final Office Action, U.S. Appl. No. 12/110,548, mailed Feb. 17, 2009, 11 pages.
Nonfinal Office Action, U.S. Appl. No. 12/317,682, dated Sep. 15, 2011, 25 pages.
Non-final Office Action, U.S. Appl. No. 12/350,609, dated Oct. 18, 2011, 27 pages.
Non-Final Office Action, U.S. Appl. No. 12/455,814, dated Jan. 24, 2012, 30 pages.
Non-Final Office Action, U.S. Appl. No. 12/559,193, mailed Sep. 18, 2012, 26 pages.
Non-Final Office Action, U.S. Appl. No. 12/653,283, mailed Feb. 10, 2012, 7 pages.
Non-Final Office Action, U.S. Appl. No. 12/653,283, mailed Jul. 18, 2012, 5 pages.
Nonfinal Office Action, U.S. Appl. No. 12/653,283, dated Aug. 9, 2011, 20 pages.
Non-Final Office Action, U.S. Appl. No. 12/889,122, dated Mar. 29, 2012, 20 pages.
Notice of Allowance, U.S. Appl. No. 12/110,548, mailed Mar. 29, 2010, 5 pages.
Notice of Allowance, U.S. Appl. No. 12/110,548, mailed Jul. 14, 2010, 10 pages.
Notice of Allowance, U.S. Appl. No. 12/317,682, mailed May 11, 2012, 10 pages.
Notice of Allowance, U.S. Appl. No. 12/455,814, mailed Oct. 2, 2012, 6 pages.
Notice of Allowance, U.S. Appl. No. 12/653,283, mailed Feb. 28, 2013, 10 pages.
Notice of Allowance, U.S. Appl. No. 12/889,122, mailed Sep. 25, 2012, 7 pages.
Notice of Non-Responsive Amendment, U.S. Appl. No. 12/317,682, dated Aug. 8, 2011, 2 pages.
Office Action (Quayle), U.S. Appl. No. 12/653,283, dated Dec. 22, 2011, 8 pages.
Office Action (Restriction), U.S. Appl. No. 12/317,682, dated Apr. 22, 2011, 14 pages.
Office Action (Restriction), U.S. Appl. No. 12/350,609, dated Jun. 14, 2011, 6 pages.
Office Action (Restriction), U.S. Appl. No. 12/455,814, dated Apr. 20, 2011, 14 pages.
Office Action (Restriction), U.S. Appl. No. 12/653,283, dated Jun. 24, 2011, 9 pages.

(56) References Cited

OTHER PUBLICATIONS

Partial International Search Report, International patent application No. PCT/US2009/030461, dated May 13, 2009.
Partial International Search Report, International patent application No. PCT/US2009/003423, dated Sep. 14, 2009.
Partial International Search Report, International patent application No. PCT/US2009/056841, dated Dec. 10, 2009.
Partial International Search Report, International patent application No. PCT/US2009/006478, dated Apr. 7, 2010.
Press Release, Interventional Spine, Inc., FDA Grants Conditional Approval to Interventional Spine's PercuDyn System IDE Application (Jul. 1, 2008).
Press Release, Interventional Spine, Inc., Interventional Spine, Inc. Introduces the PERPOS Fusion Facet Prep Kit (Oct. 14, 2008).
Press Release, minSURG Corp., Orthopedic Development Corporation's TruFUSE Procedure Tops 1,750 Patients in First Year (Sep. 24, 2007).
RCE/Amendment, U.S. Appl. No. 12/350,609, filed Jul. 24, 2012, 19 pages.
Response to Advisory Action, U.S. Appl. No. 12/317,682, filed Apr. 24, 2012, 4 pages.
Response to Advisory Action, U.S. Appl. No. 12/455,814, filed Sep. 5, 2012, 6 pages.
Response to Final Office Action, U.S. Appl. No. 12/317,682, filed Mar. 22, 2012, 17 pages.
Response to Final Office Action, U.S. Appl. No. 12/455,814, filed Aug. 6, 2012, 13 pages.
Response to Final Office Action, U.S. Appl. No. 12/653,283, filed Jun. 15, 2012, 7 pages.
Response to Final Office Action, U.S. Appl. No. 12/653,283, filed Feb. 19, 2013, 5 pages.
Response to Non-Final Office Action and Terminal Disclaimer, U.S. Appl. No. 12/889,122, filed Jun. 27, 2012, 8 pages.
Response to Non-Final Office Action, U.S. Appl. No. 12/317,682, filed Dec. 13, 2011, 19 pages.
Response to Non-Final Office Action, U.S. Appl. No. 12/350,609, filed Feb. 17, 2012, 16 pages.
Response to Non-Final Office Action, U.S. Appl. No. 12/455,814, filed Apr. 24, 2012, 15 pages.
Response to Non-Final Office Action, U.S. Appl. No. 12/653,283, filed Dec. 6, 2011, 14 pages.
Response to Non-Final Office Action, U.S. Appl. No. 12/653,283, filed Mar. 8, 2012, 9 pages.
Response to Non-Final Office Action, U.S. Appl. No. 12/653,283, filed Oct. 18, 2012, 6 pages.
Response to Quayle Action, U.S. Appl. No. 12/653,283, filed Feb. 1, 2012, 3 pages.
Response to Restriction Requirement, U.S. Appl. No. 12/350,609, filed Aug. 15, 2011, 14 pages.
Response to Restriction, U.S. Appl. No. 12/317,682, filed May 16, 2011, 15 pages.
Response to Restriction, U.S. Appl. No. 12/455,814, filed May 16, 2011, 10 pages.
Response to Restriction, U.S. Appl. No. 12/559,193, filed Jul. 17, 2012, 6 pages.
Response to Restriction, U.S. Appl. No. 12/653,283, filed Jul. 22, 2011, 8 pages.
Restriction Requirement, U.S. Appl. No. 12/559,193, dated Apr. 18, 2012, 10 pages.
US 7,063,700, 06/2006, Michelson (withdrawn)

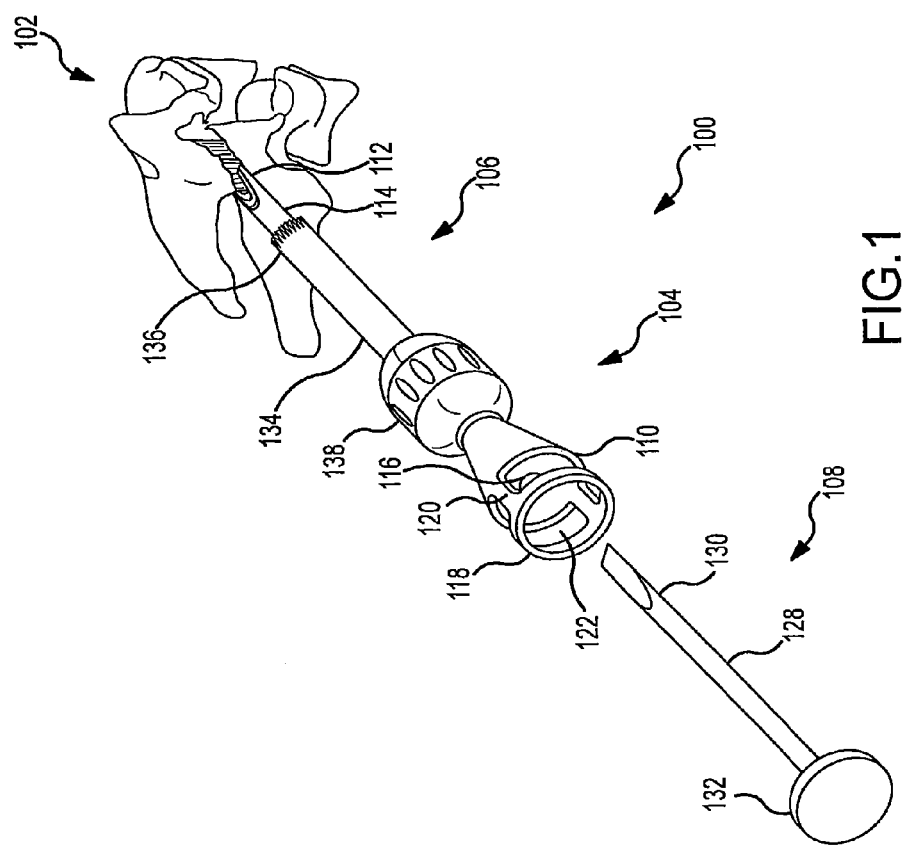

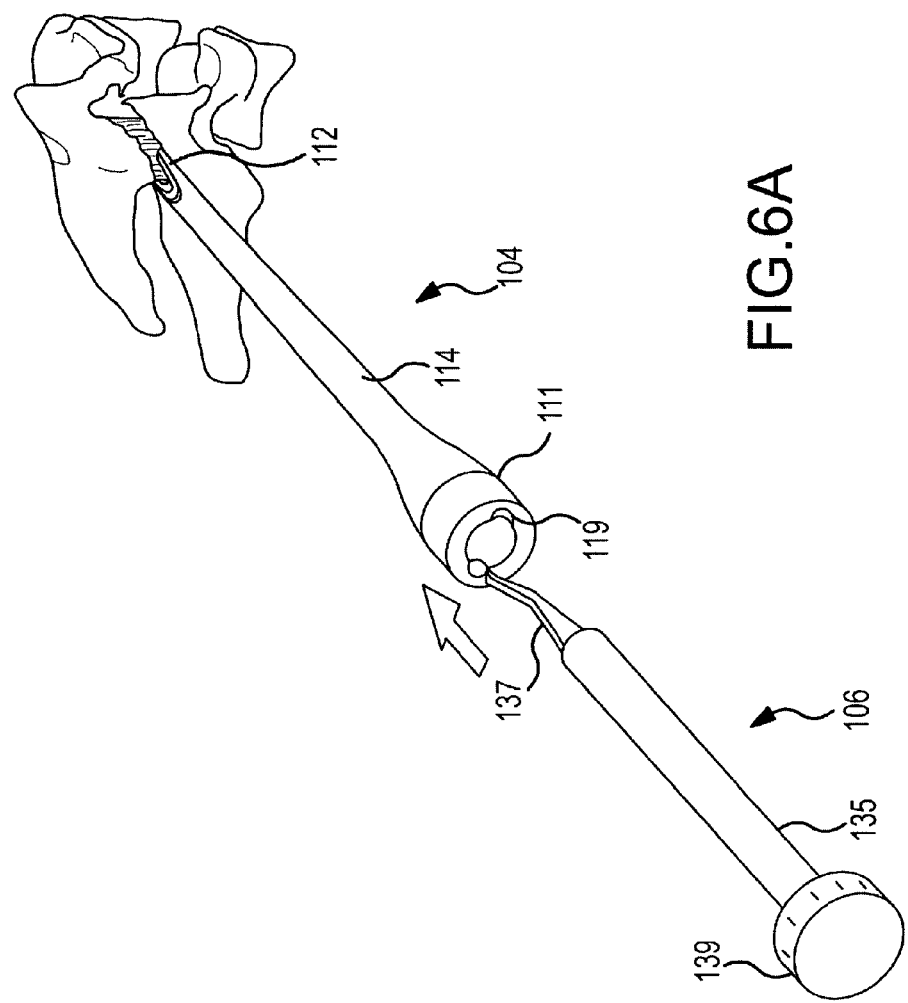

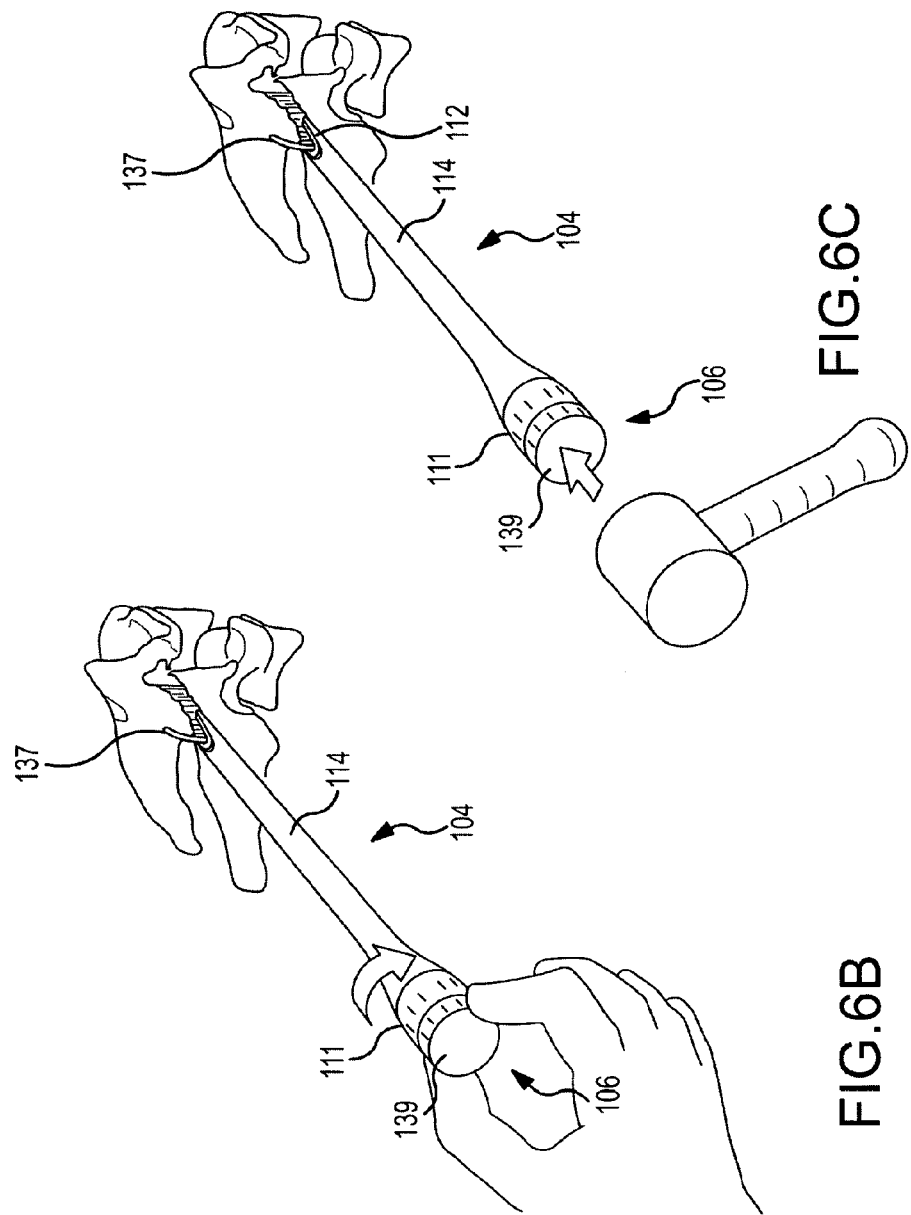

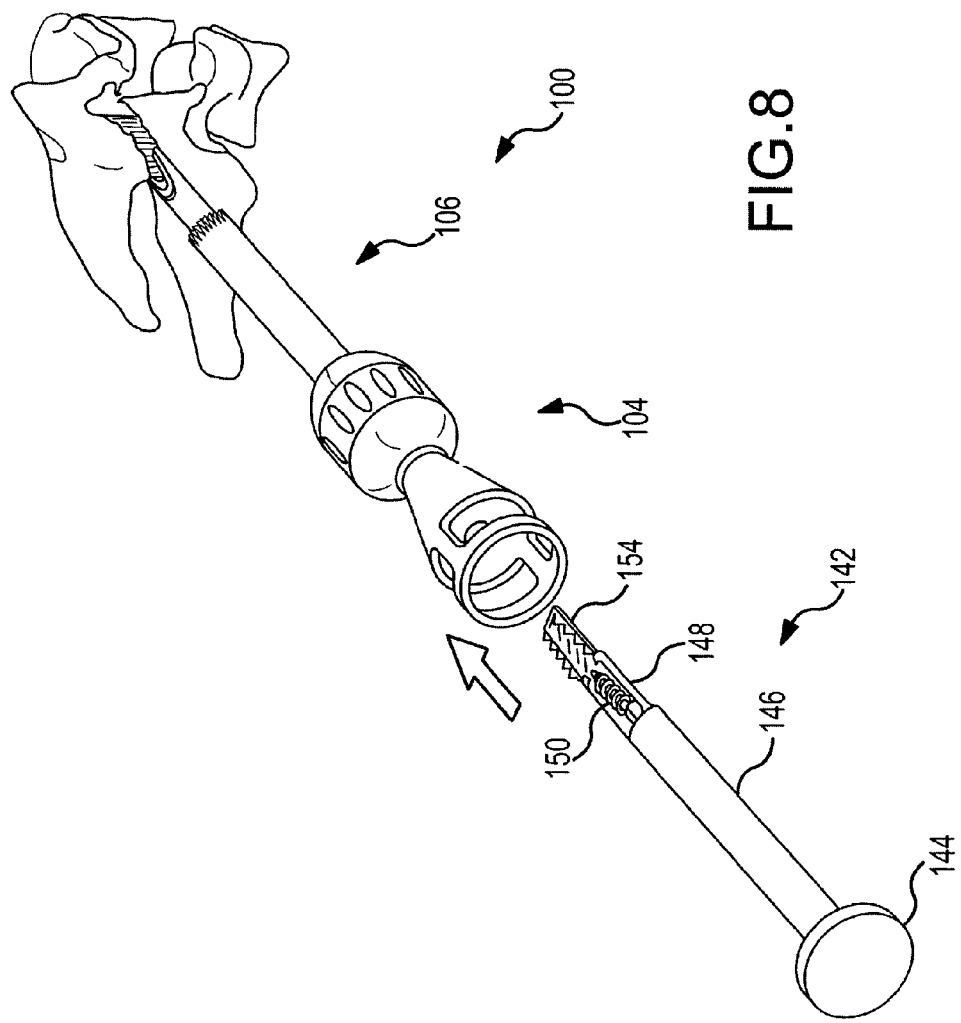

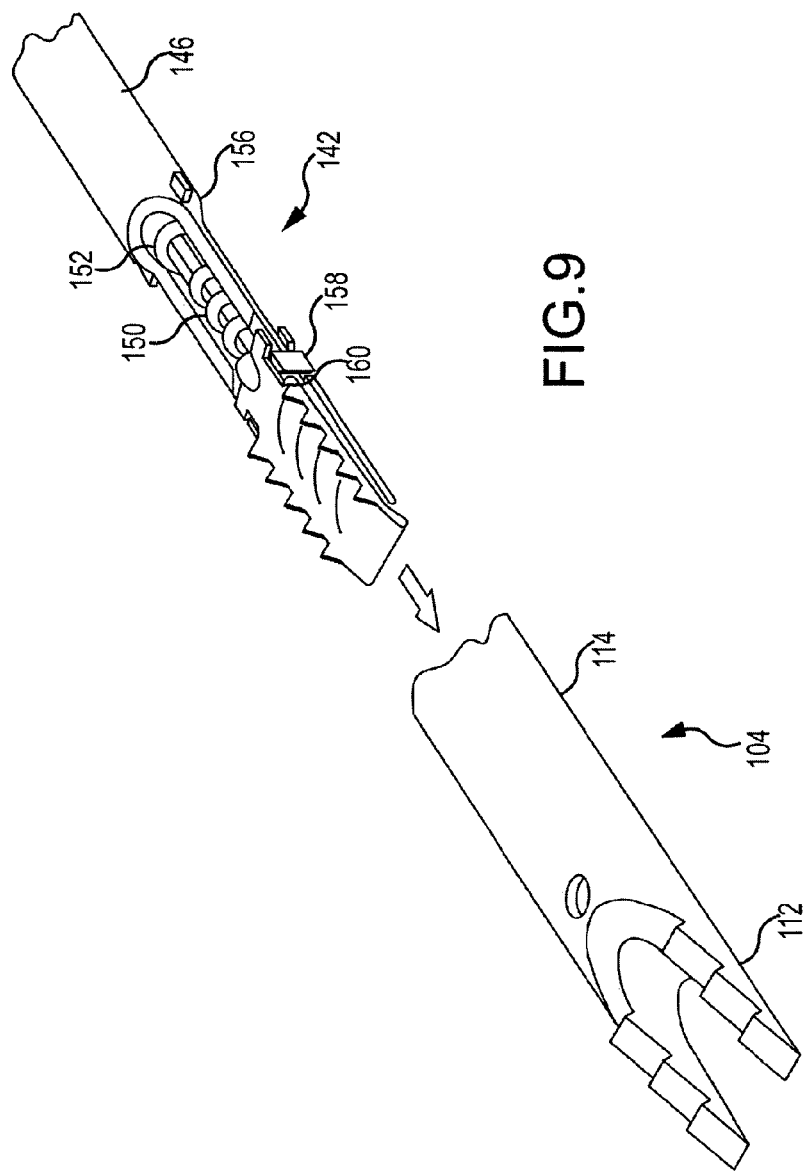

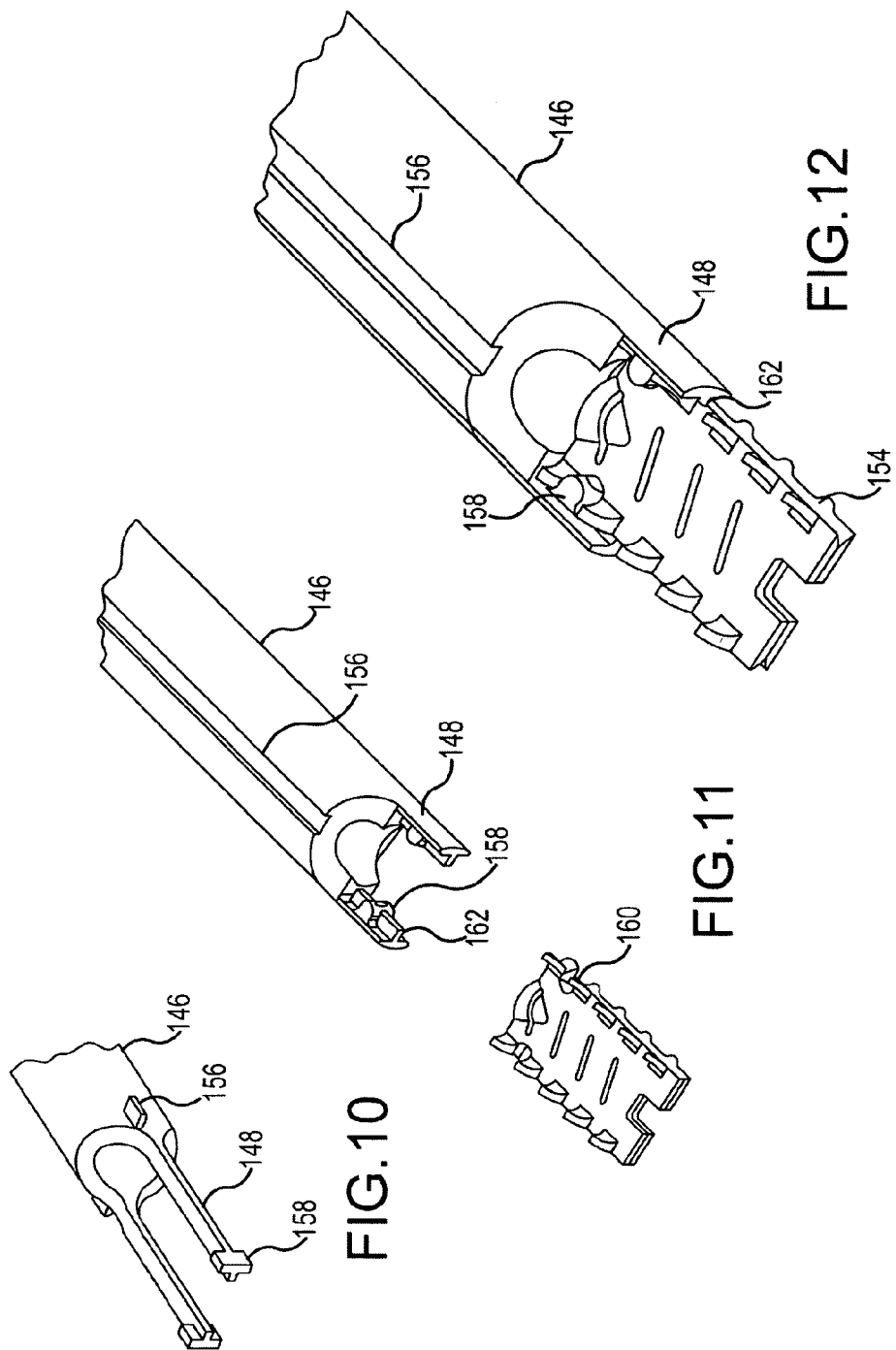

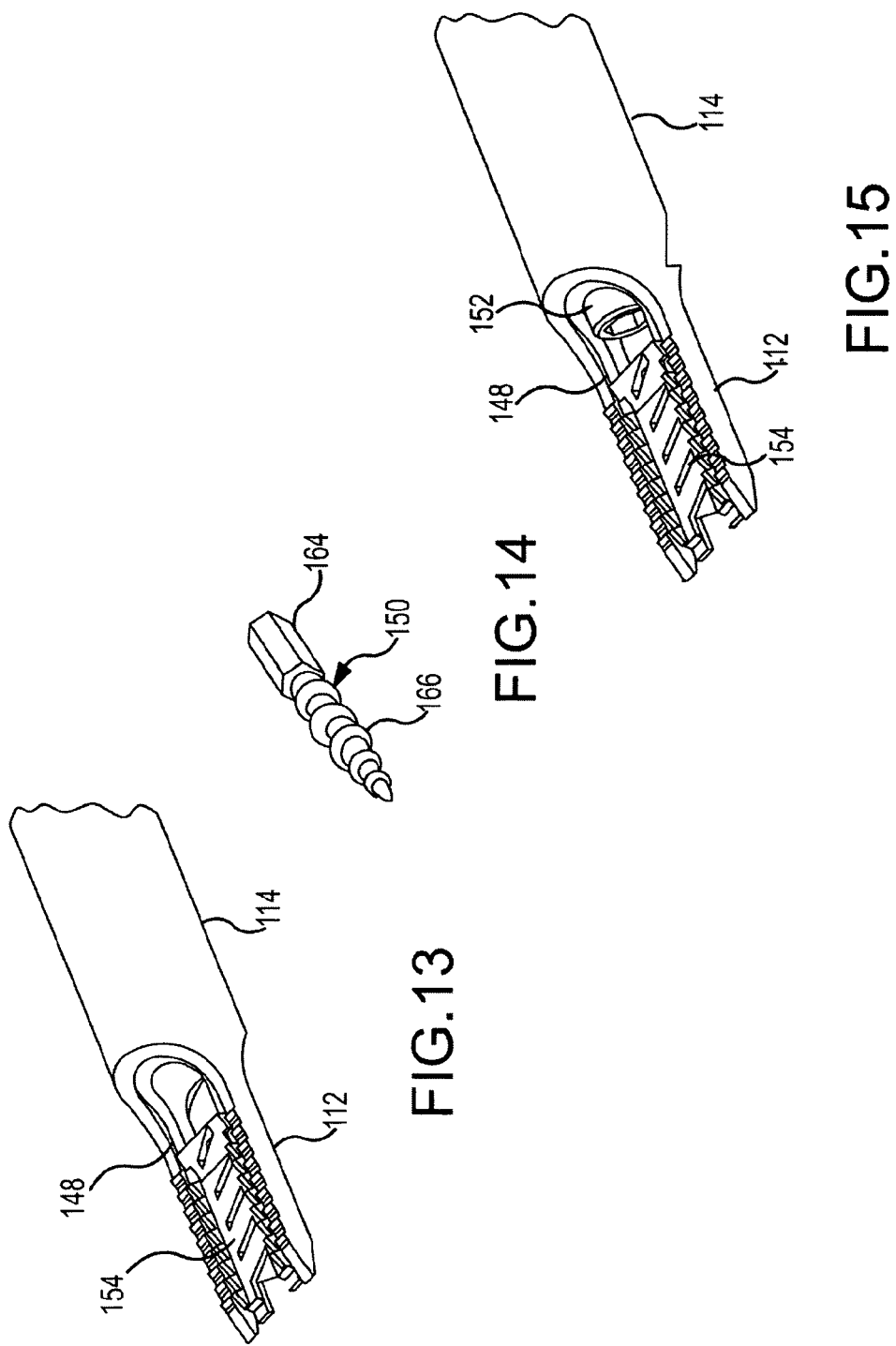

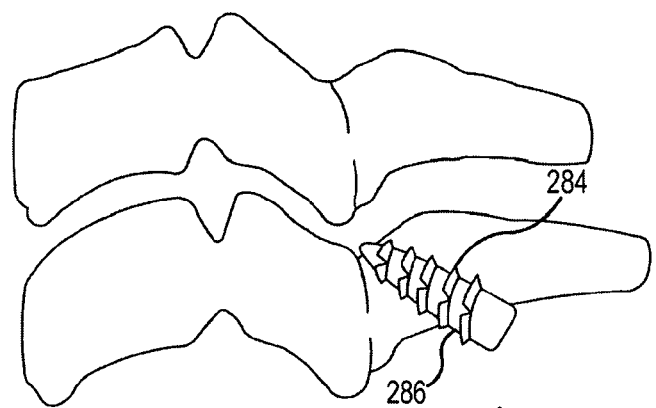
FIG.39A
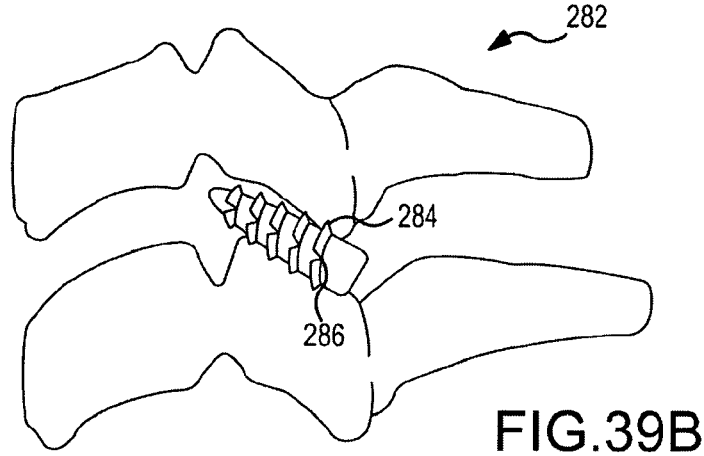
FIG.39B
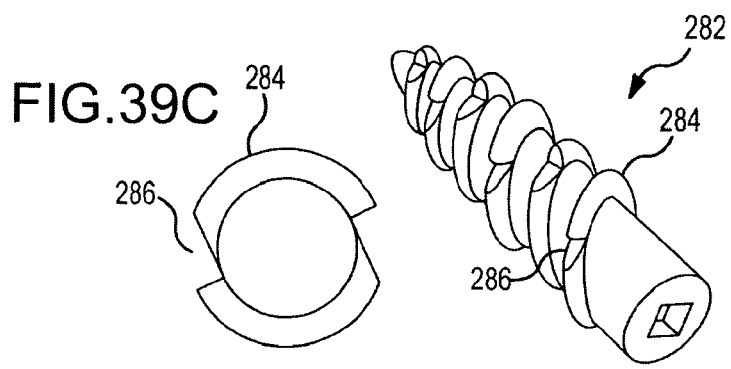
FIG.39C
FIG.39D

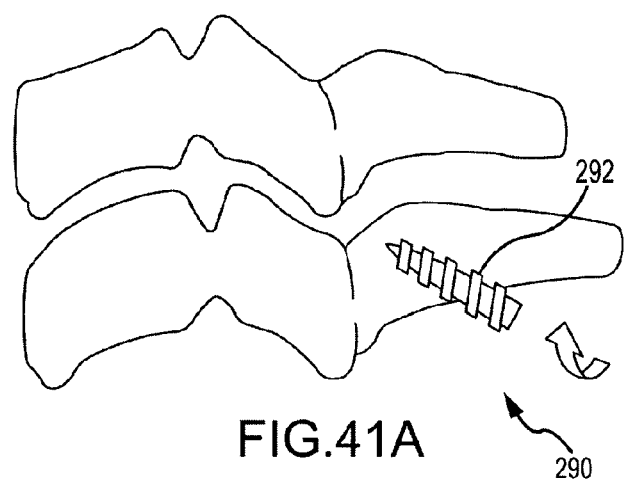
FIG.41A
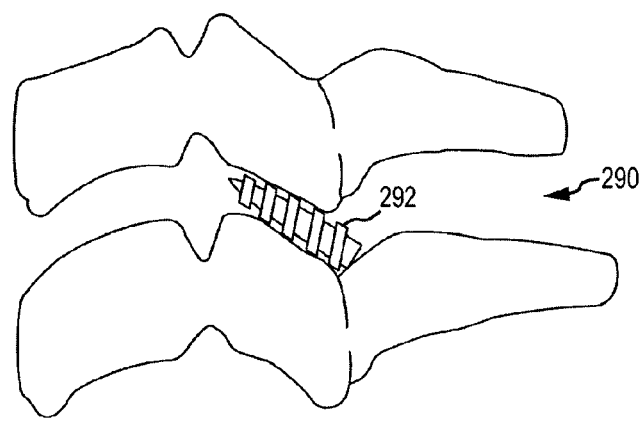
FIG.41B
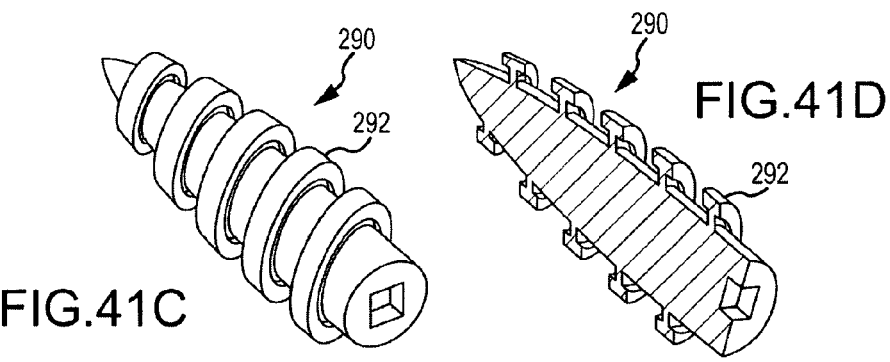
FIG.41C
FIG.41D

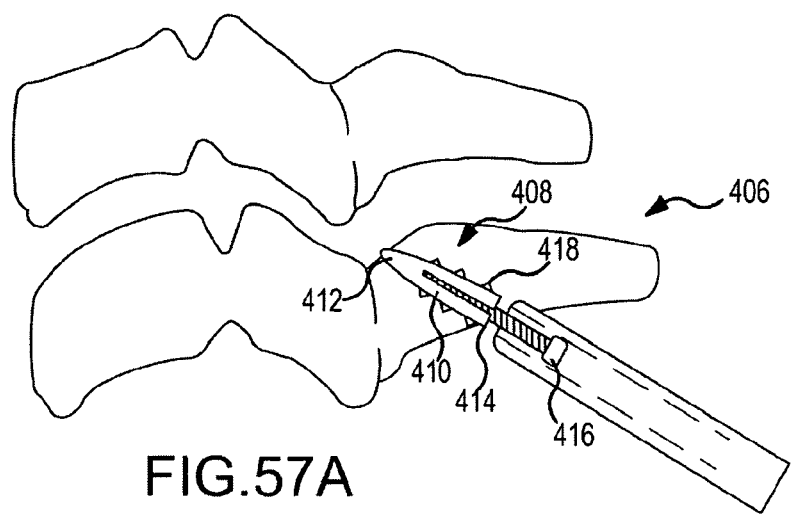
FIG.57A
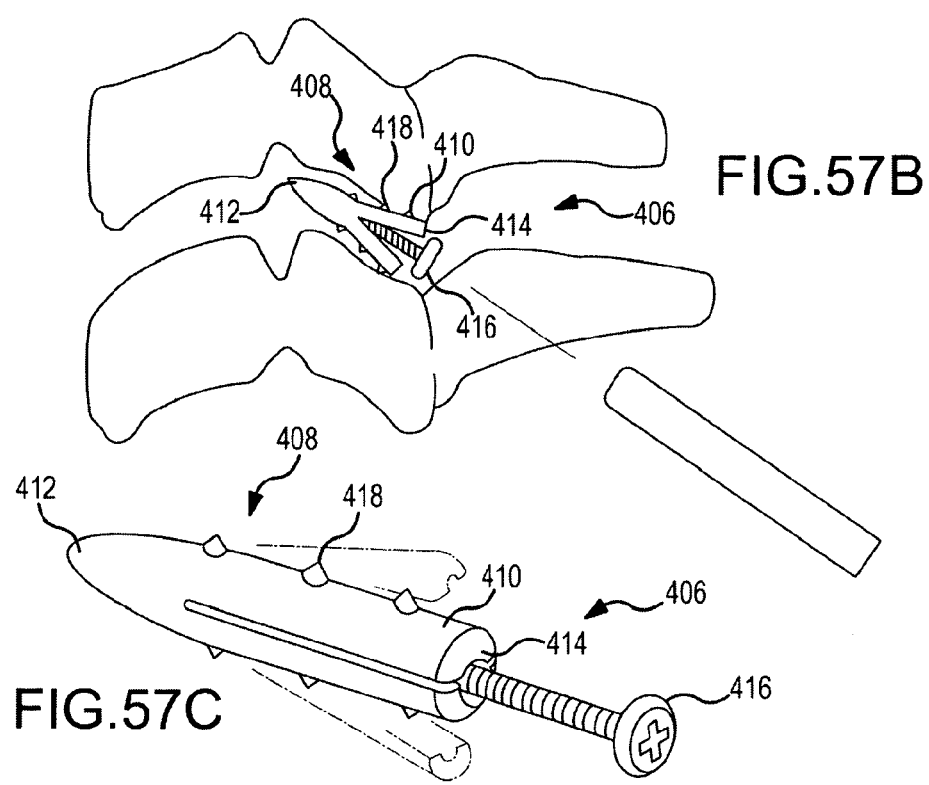
FIG.57B
FIG.57C

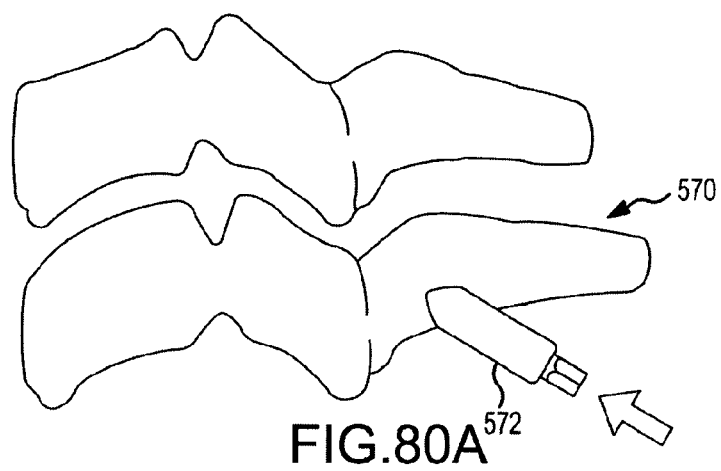
FIG.80A
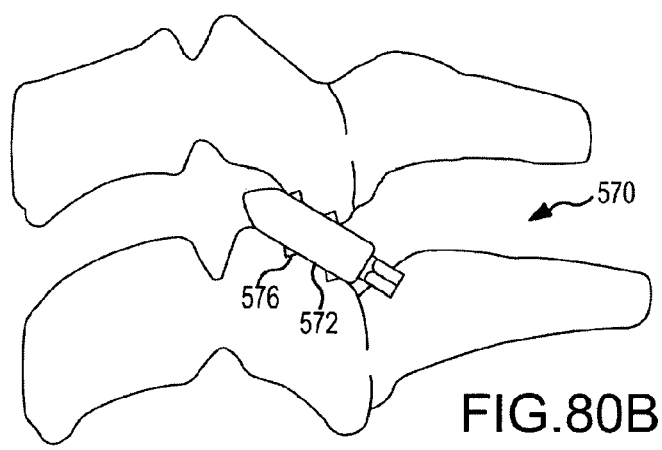
FIG.80B
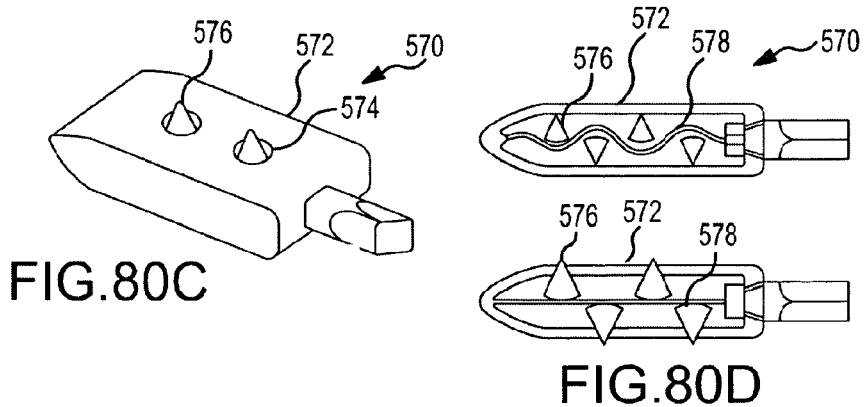
FIG.80C
FIG.80D

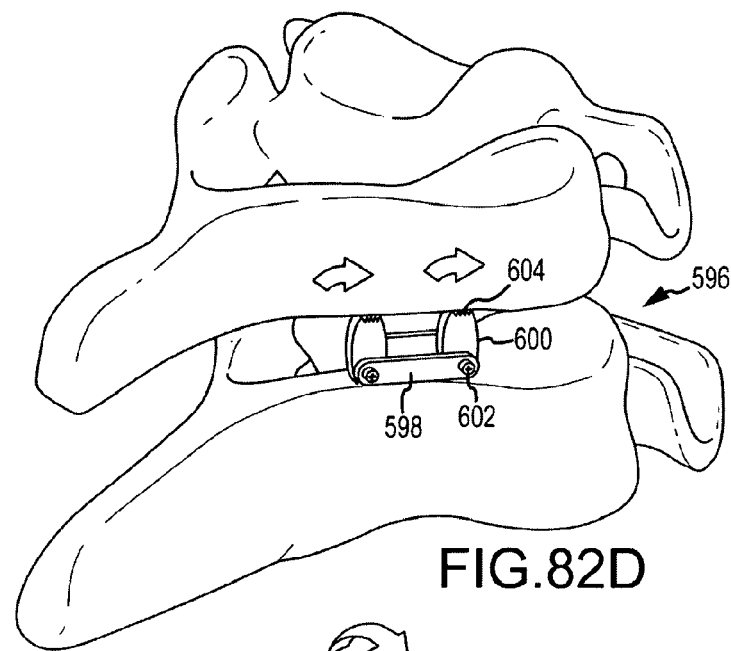
FIG.82D
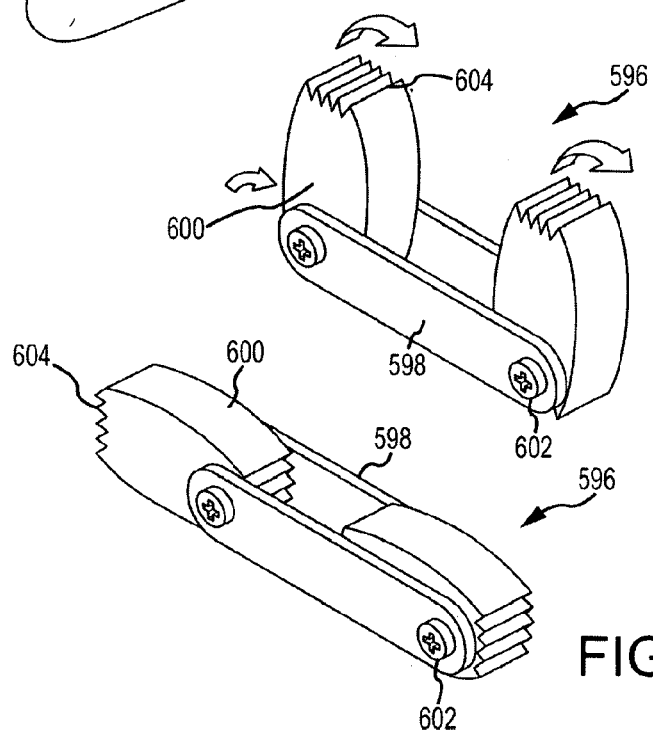
FIG.82E
FIG.82F

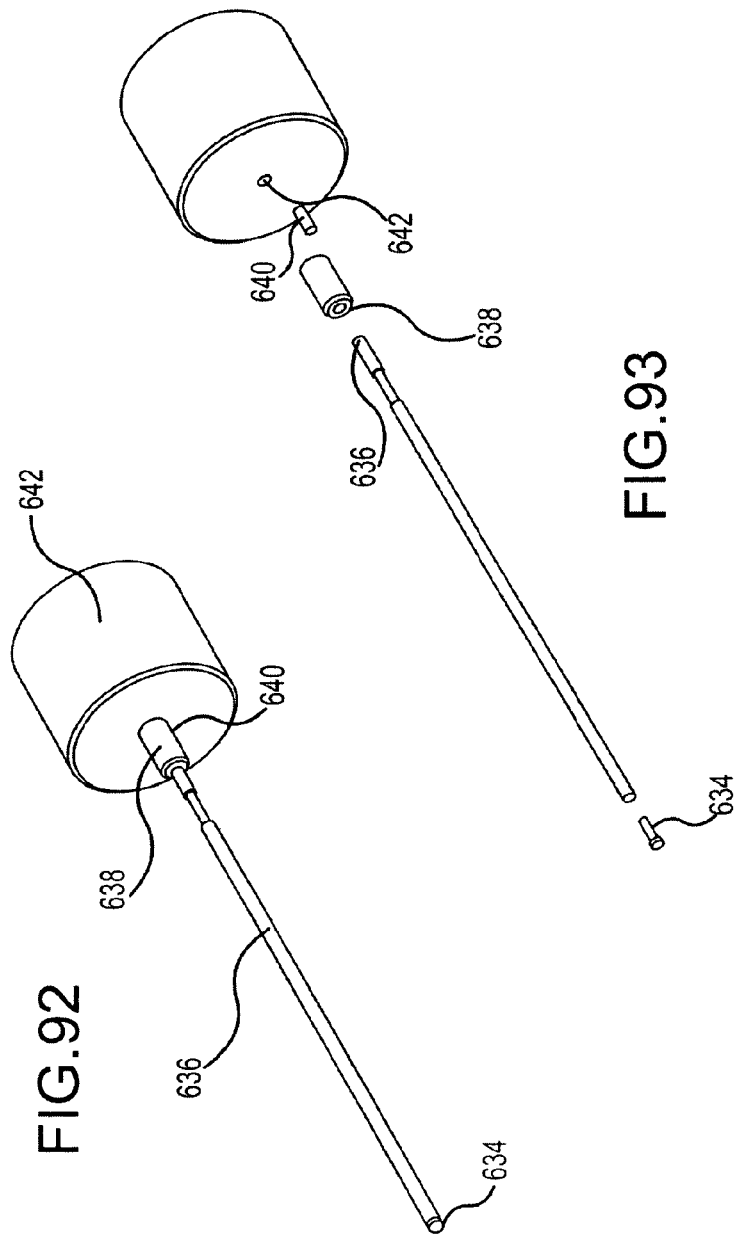

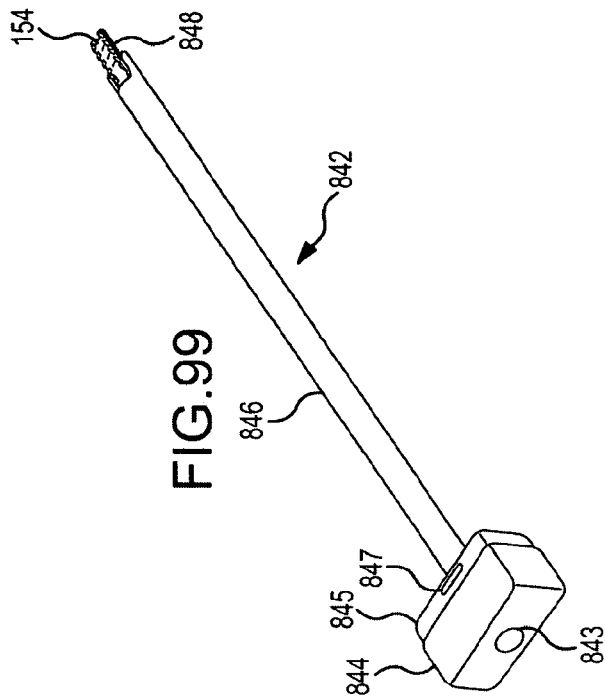
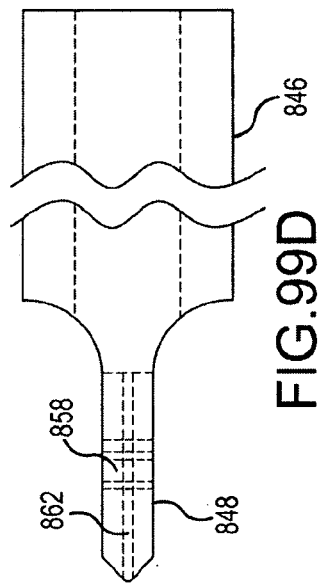
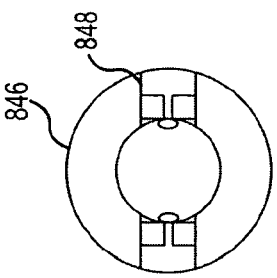
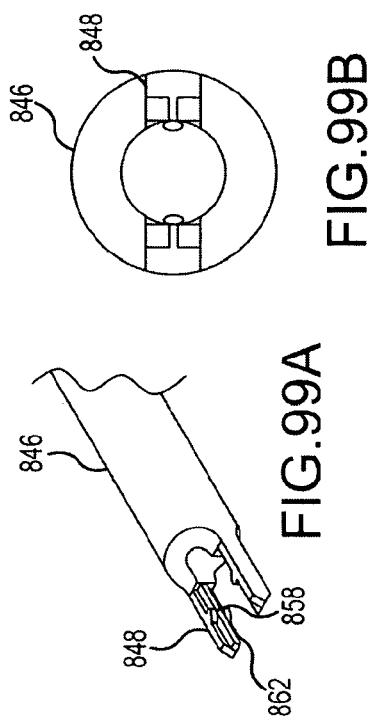
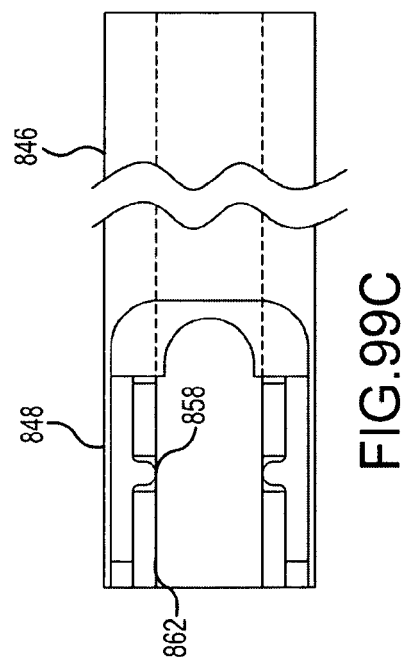

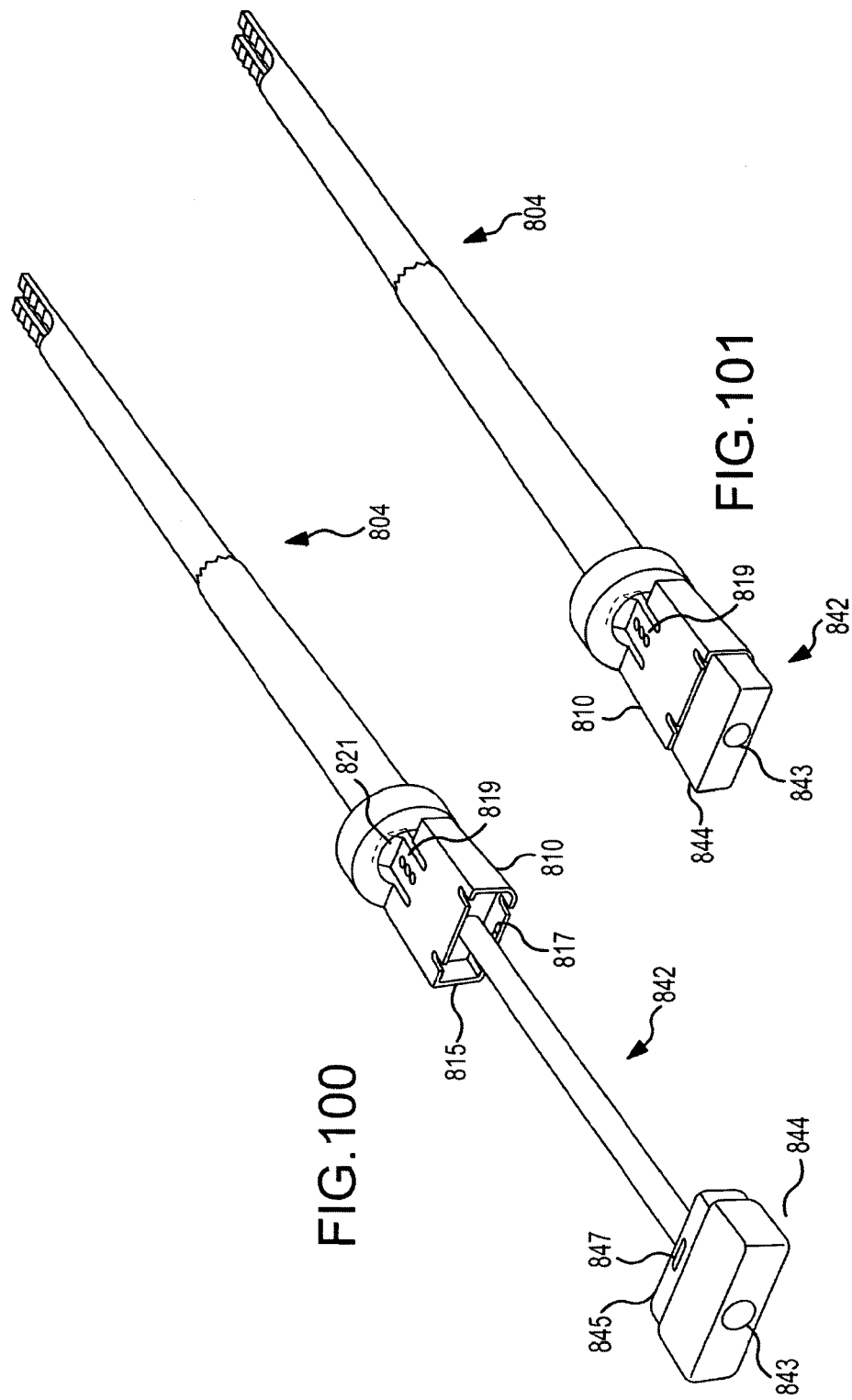

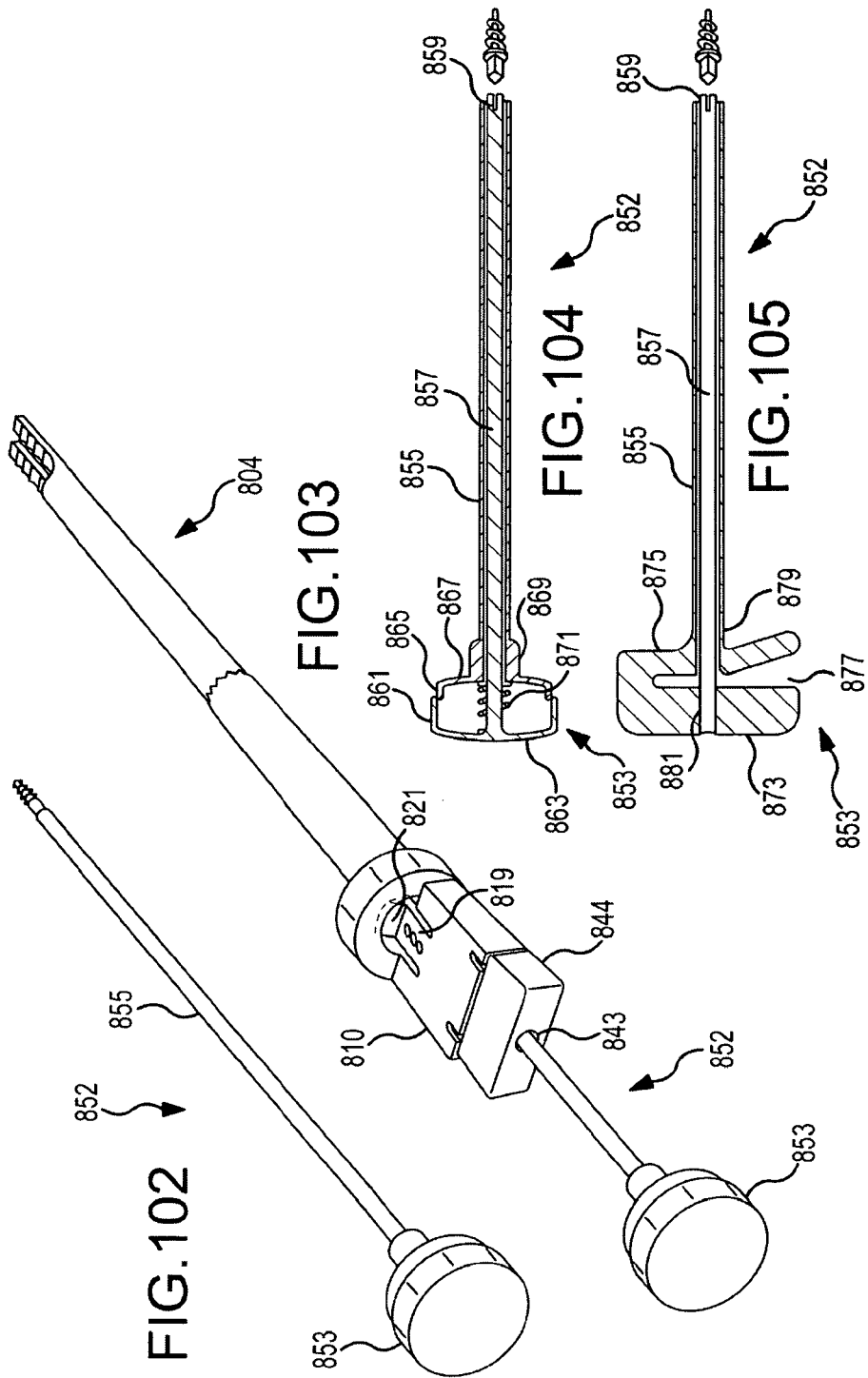

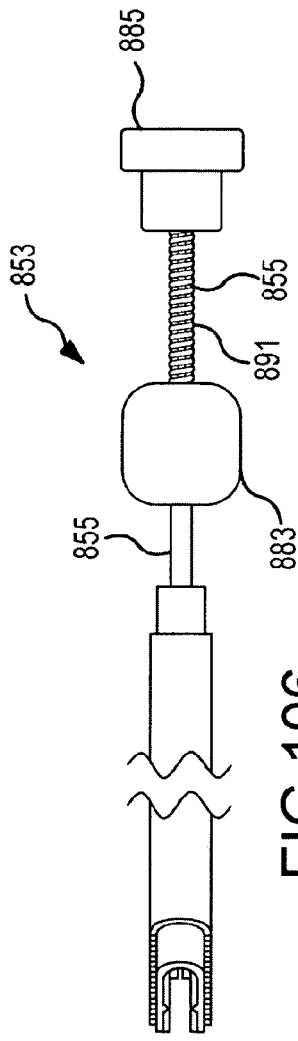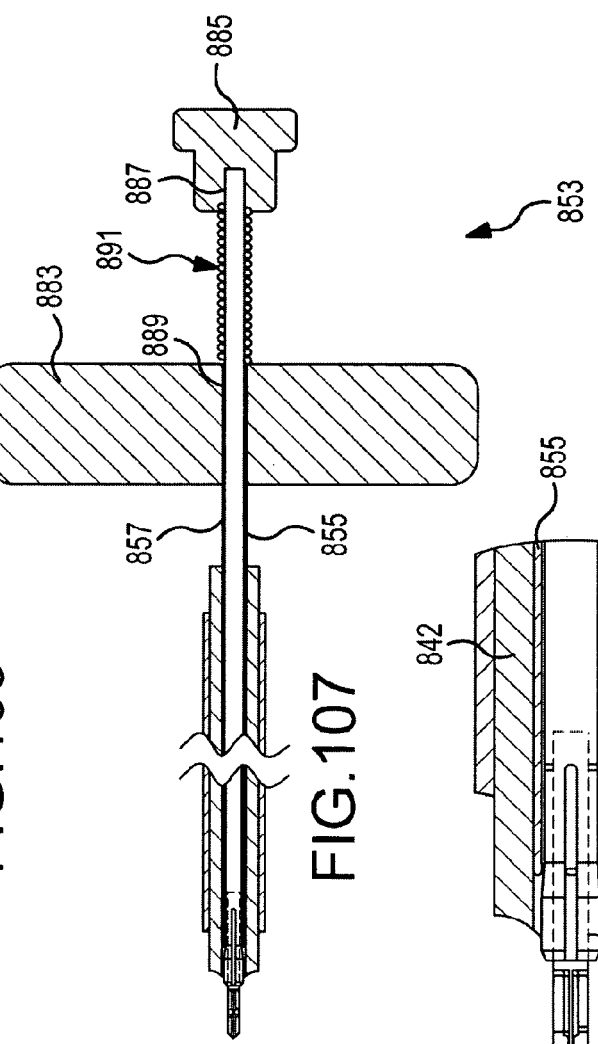

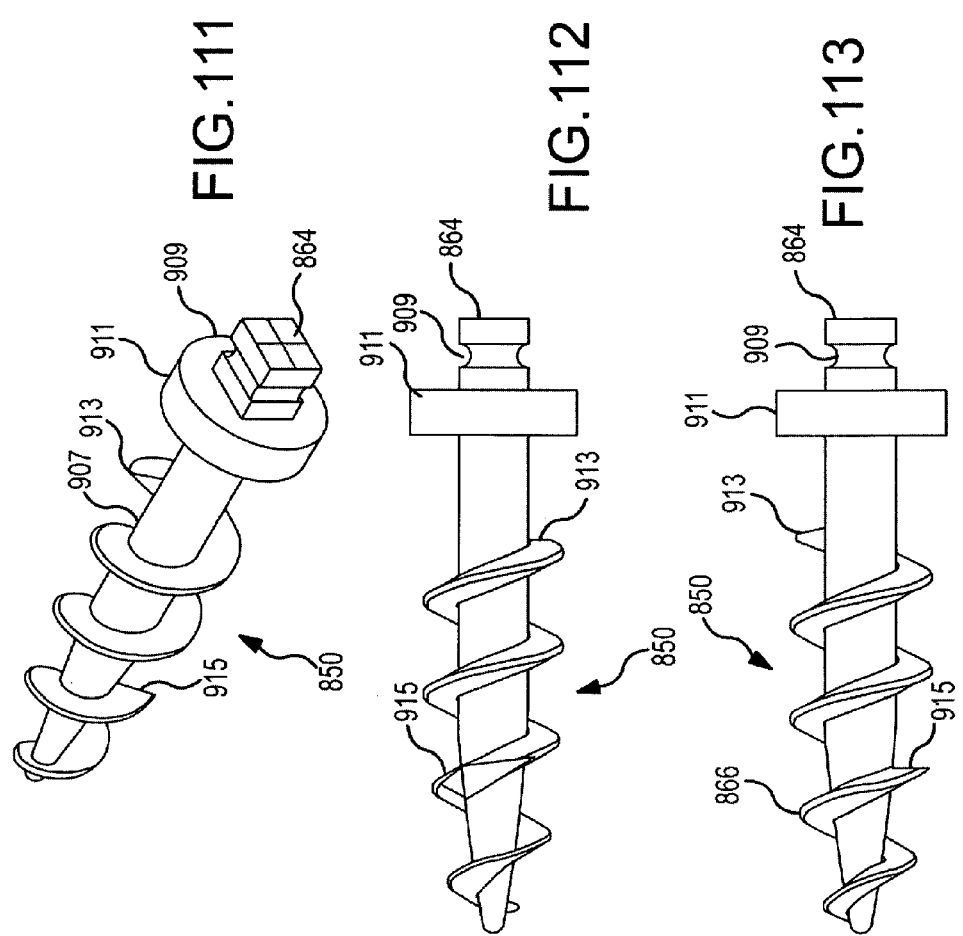

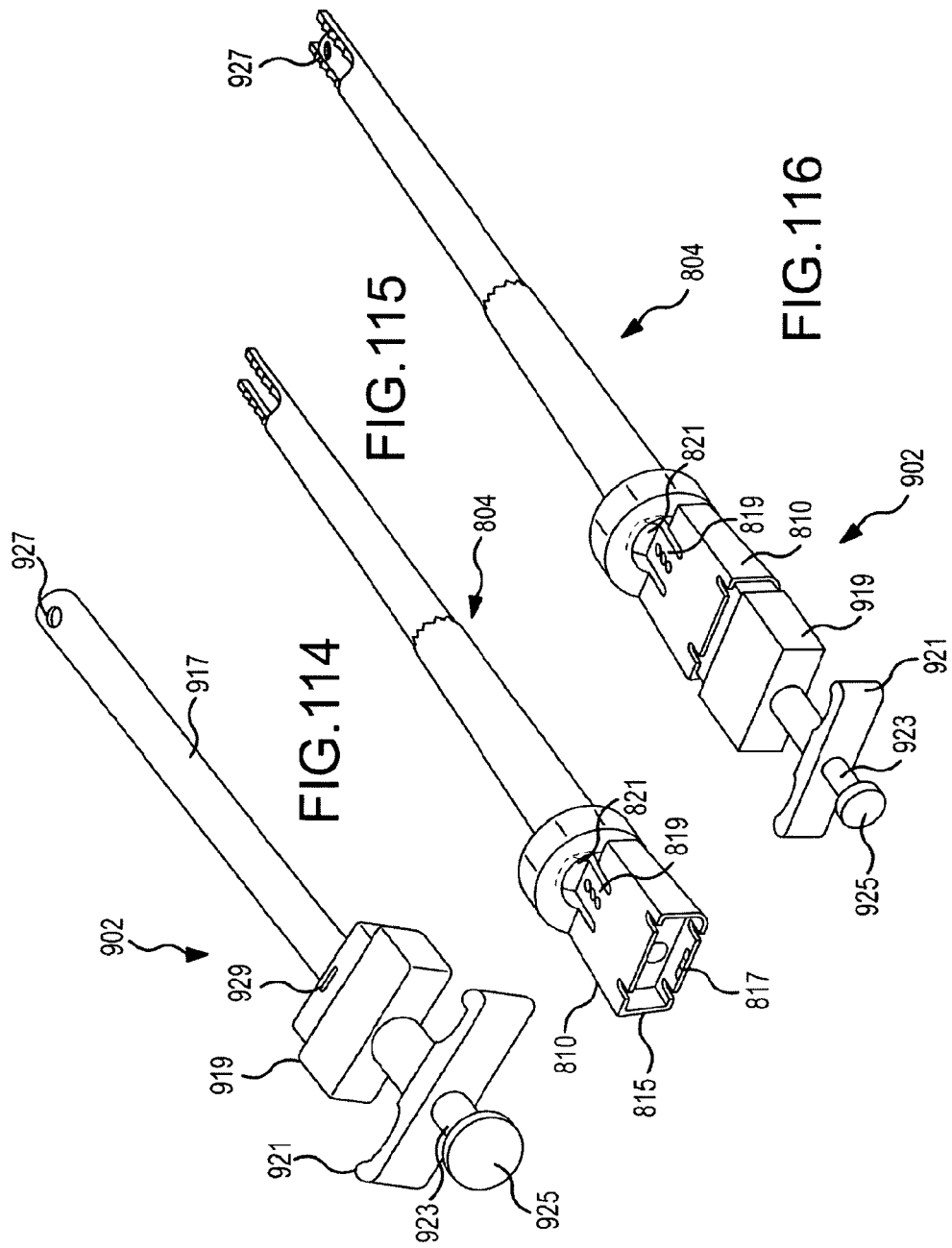

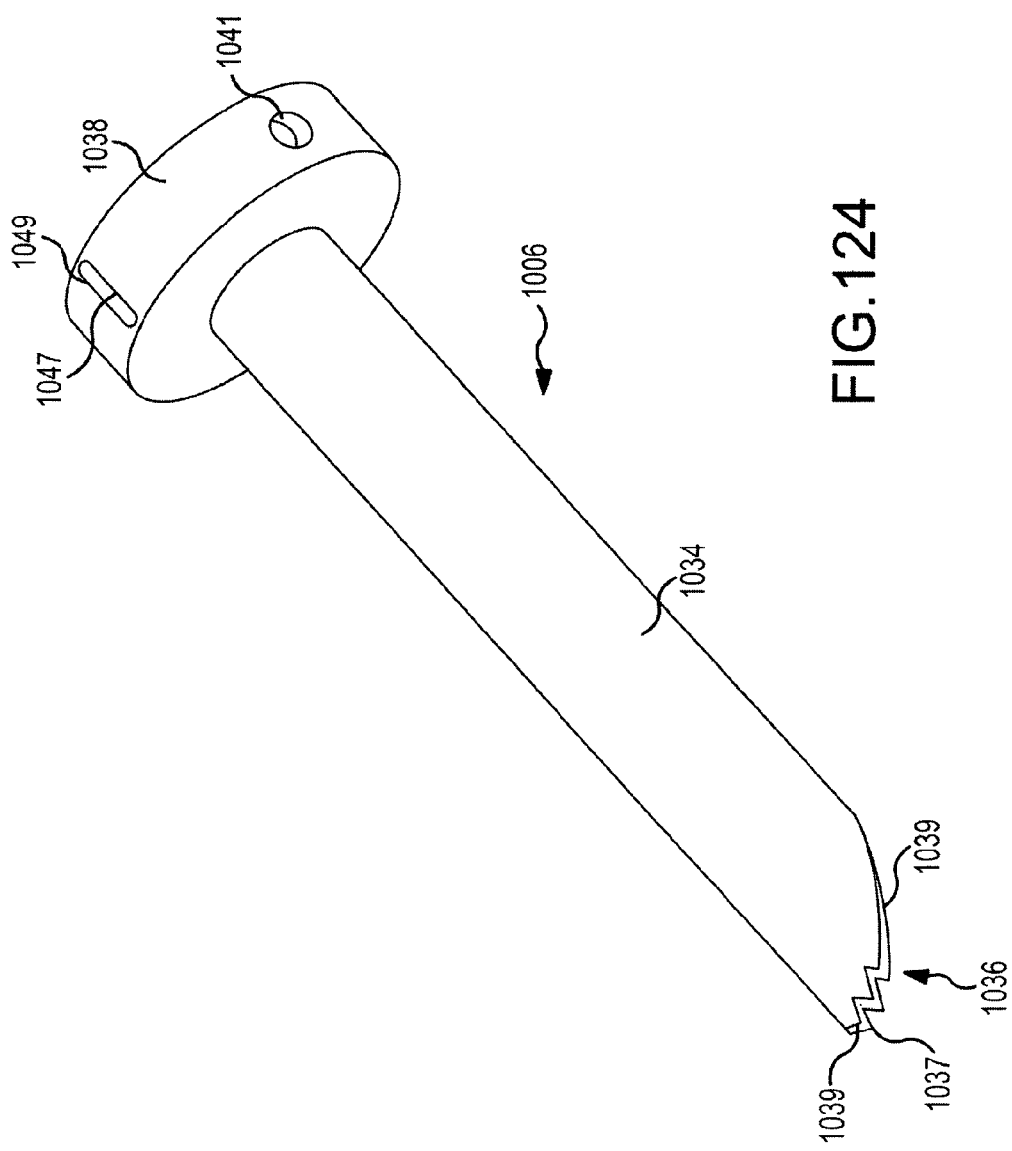

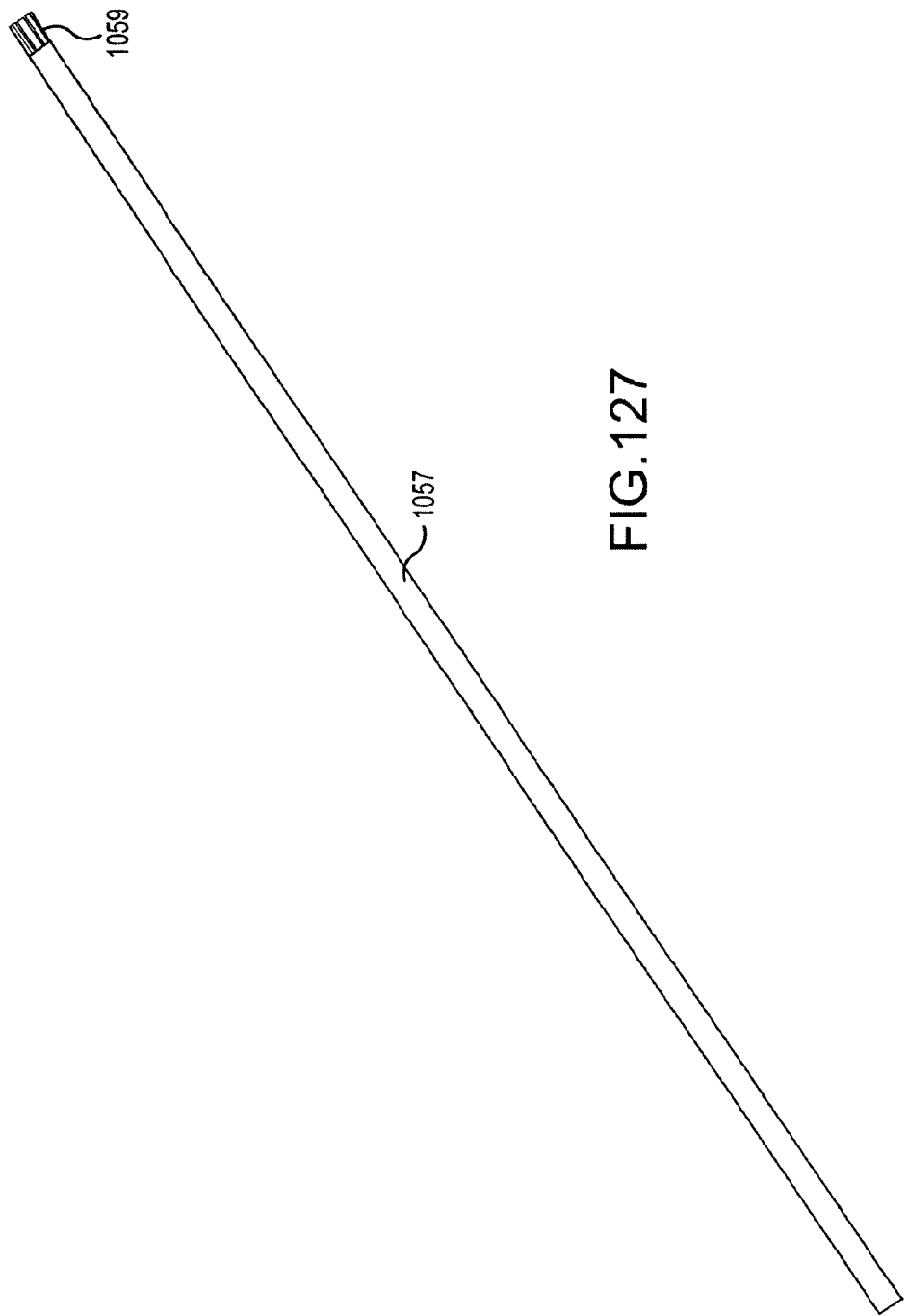

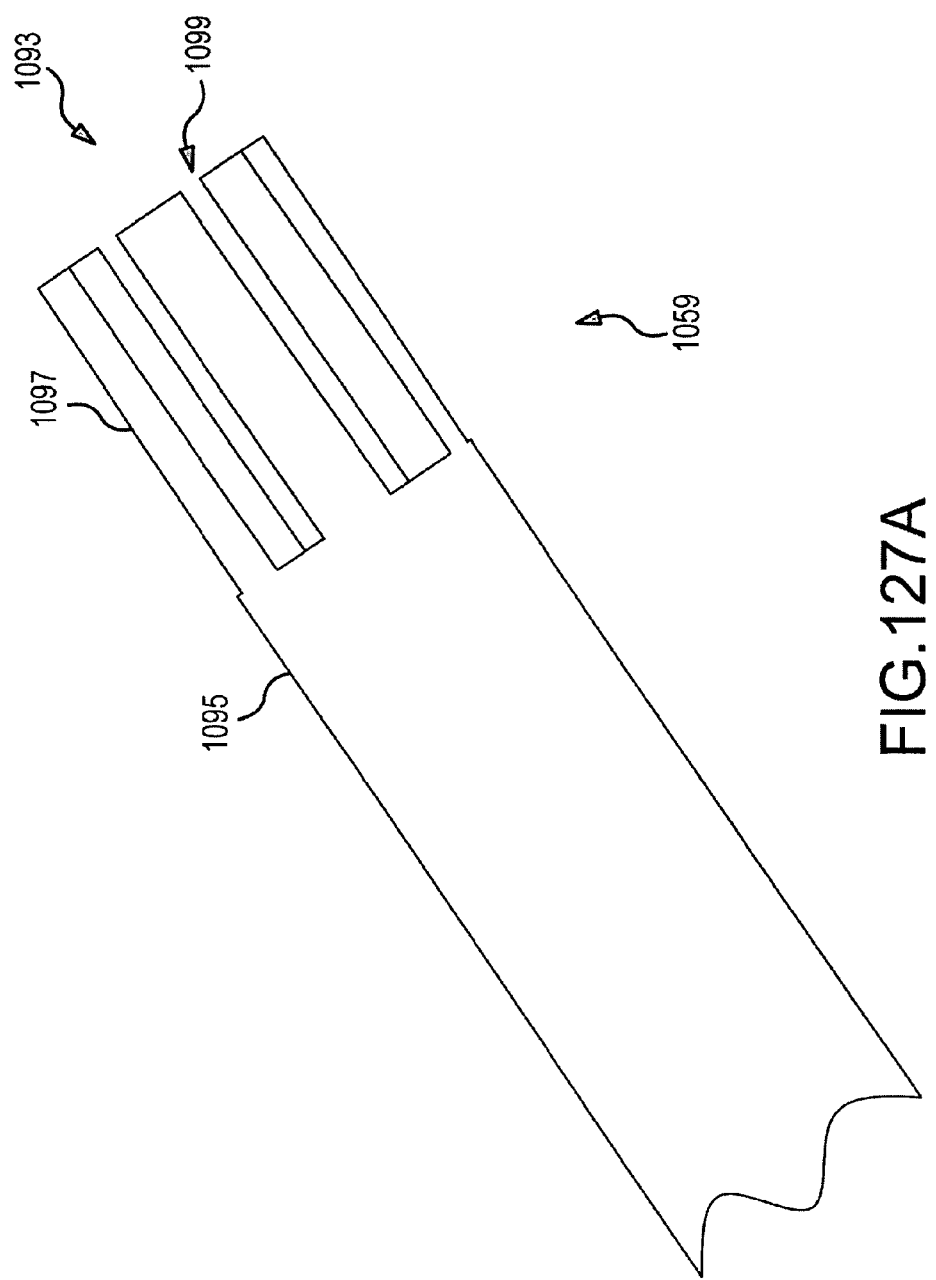

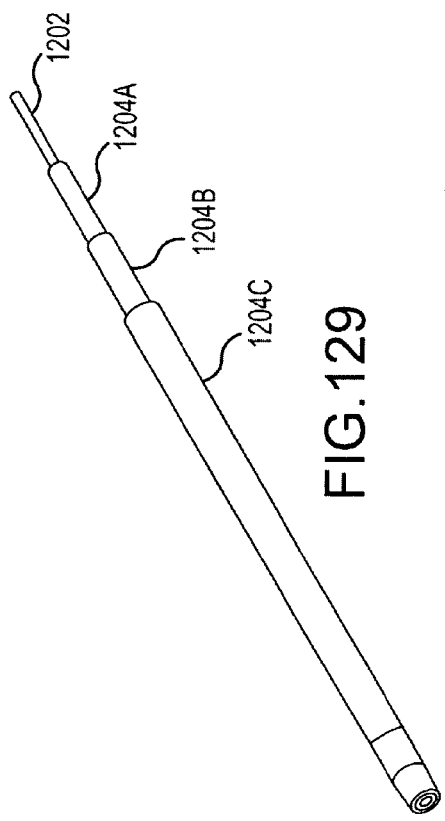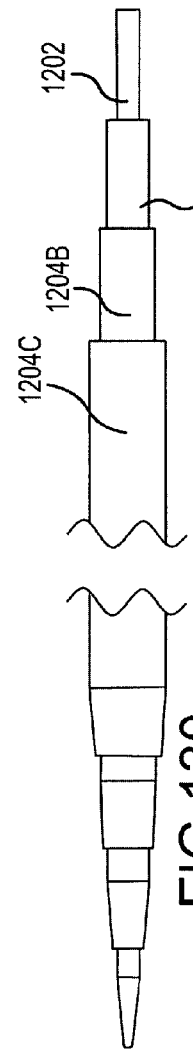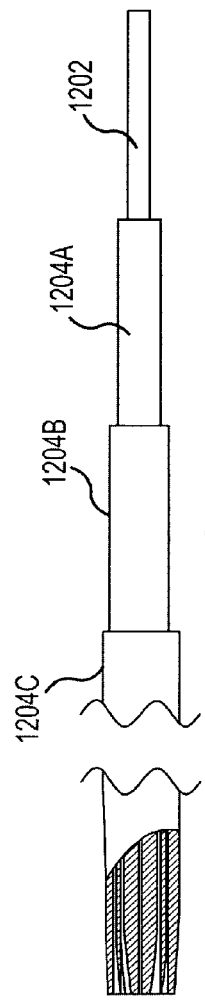
FIG. 129
FIG. 130
FIG. 131

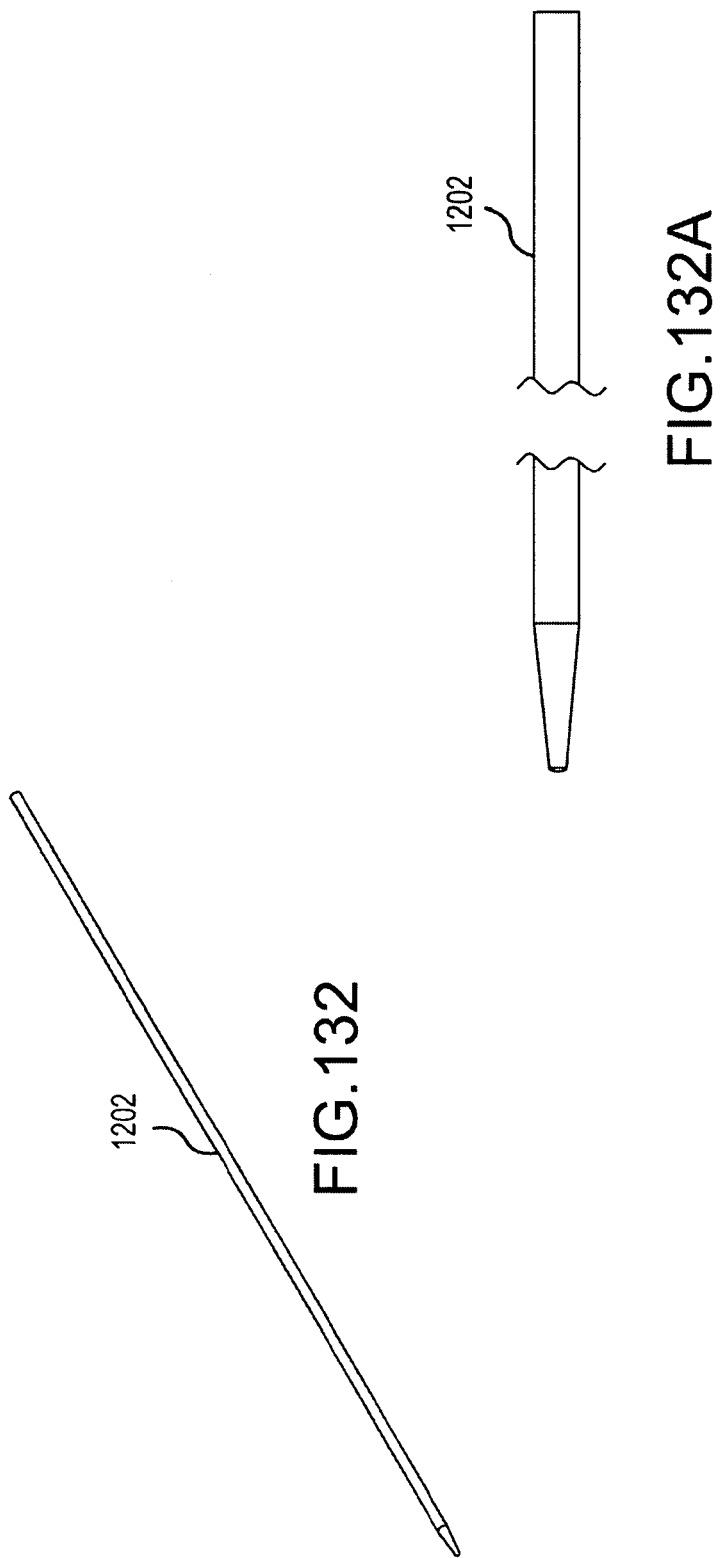

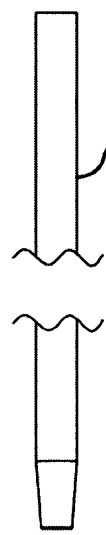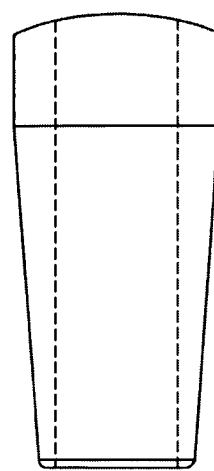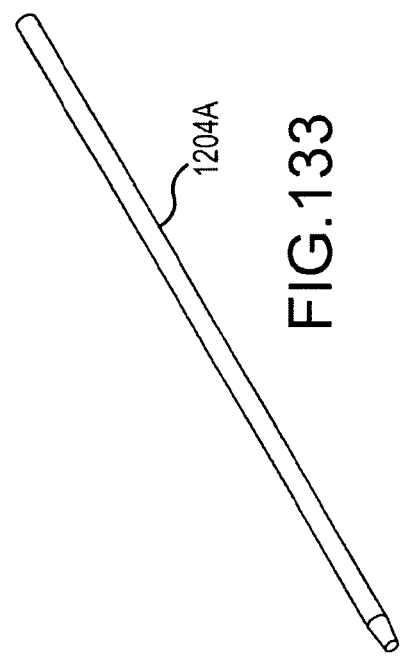

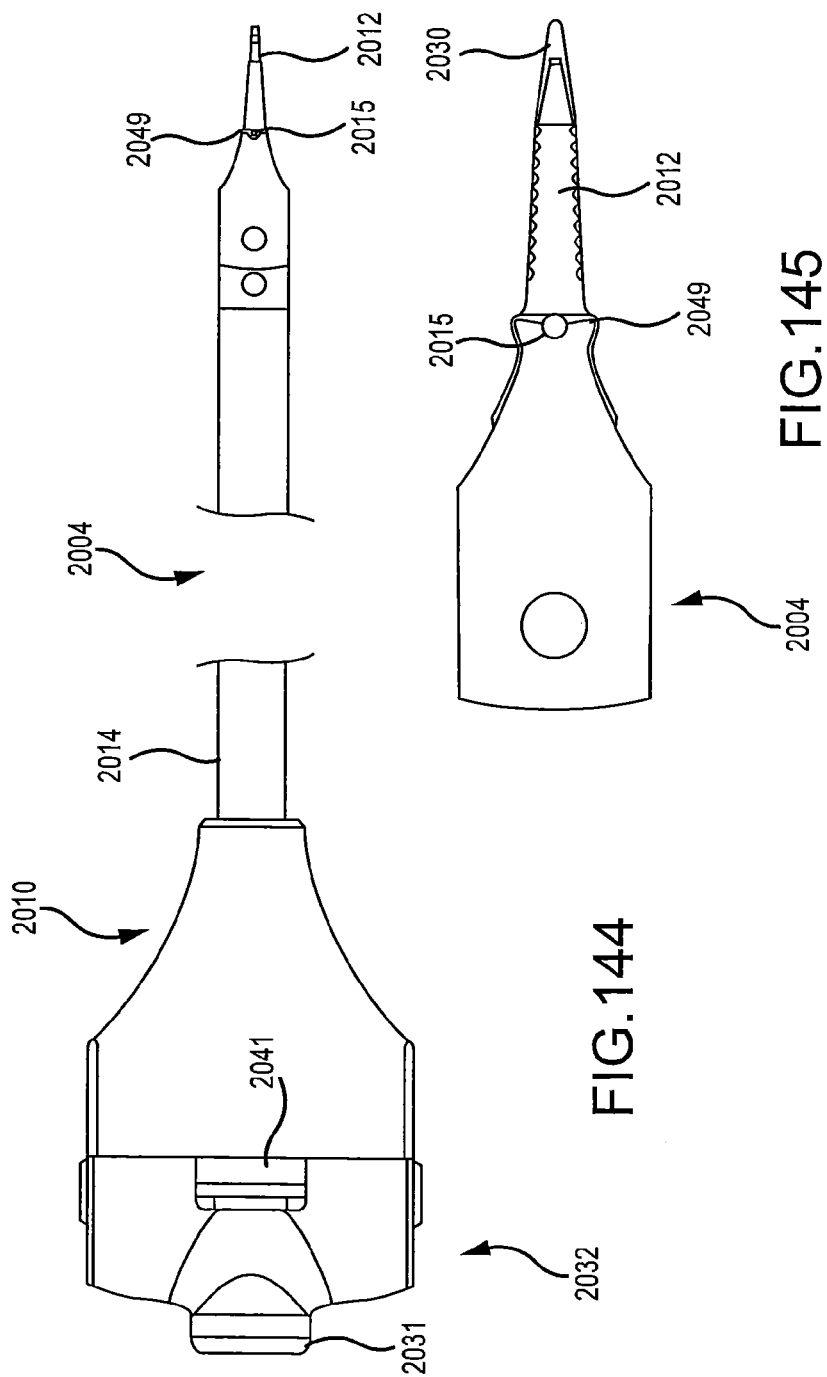

(all measurements in mm unless noted)

Implant

| Plate thickness | 0.38 |
|---|---|
| A-P length | 12.3 |
| Width 1 (outside teeth) | 5.5 |
| Width 2 (inside teeth, at vertical) | 4.8 |
| Width 3 (inside teeth, at base) | 4 |
| Closed height 1 (incl. teeth) | 2.3 |
| Closed height 2 (at volcano) | 2.3 |
| Closed height 3 (plates only) | 0.76 |
| Fully Deployed max height 1 (incl. teeth) | 5 |
| Fully Deployed max height 2 (at volcano) | 4.4 |
| Fully Deployed max height 3 (plates only) | 3.1 |
| Fully Deployed plate angle (estimate) | 10 deg |
| Screw slot width | 0.85 |
| Screw slot length | 2.95 |
| Tooth height (from plate surface) | 0.75 |
| Tooth thickness | 0.38 |
| Scissor joint height | 1.34 |

FIG. 163

Delivery Device

| Main shaft outside diameter | 9 |
|---|---|
| Overall length | 267 |
| exposed shaft length | 222 |
| Fork outside width | 8 |
| Fork width at tip | 7 |
| Fork inside gap | 6 |
| Fork arm width | 1 |
| Fork tip height | 1.5 |
| Distance, from Fork arm tip to 4mm height spot | 12.5 |
| Fork arm taper angle, from arm tip to 4mm height spot | 10 |
| Distance, from 4mm height spot on Fork arm to full 9mm dia. | 2.5 |
| Fork shoulder curvature angle (approx.) | 37 deg. |
| Fork serration depth | 0.25 |
| Square opening height | 5 |
| Square opening width | 6 |

FIG. 164

Implant Distractor

| Shaft diameter (max) | 2.2 |
|---|---|
| Max diameter (incl. thread) | 3.8 |
| A-P length | 13 |
| Head diameter | 12.25 |
| Head height | 2.5 |
| Driver slot width | 1 |
| Driver slot depth | 1.5 |
| Thread pitch | 2 |
| Thread height (approx) | 0.8 |
| Tip taper angle (approx. at tip) | 8 deg |

FIG. 165

Chisel

| Width | 5.5 |
|---|---|
| Height | 4.25 |
| Length | 300 |
| Tip thickness (at end) | 0.4 |
| Tip thickness (at start of main taper) | 1.85 |
| Tip chamfer angle | 60 deg |
| Tip taper angle | 10 deg |
| Tip Length (from distal end to main shaft) | 12 |
| Serration depth | 0.4 |
| Serration width | 0.6 |
| Lateral orientation marker dia. | 2 |
| Proximal hole dia. | 3 |
| Proximal shaft protrusion | 12 |
| Pry bar slot width | 10 |
| Pry bar slot height (combined with Guide Tube Handle slot) | 2 |

FIG. 166

Place Holding Chisel

| Width | 5.5 |
|---|---|
| Height | 4.25 |
| Length | 300 |
| Tip marker dia. | 0.5 |

(Other features same as Chisel)

FIG. 167

(all measurements in mm unless noted)

Driver Assembly

| Main shaft outside diameter | 5.5 |
|---|---|
| Main shaft inside diameter | 4 |
| Overall length | 320 |
| Holder arm outside width | 5.5 |
| Holder arm width (avg) | 0.77 |
| Holder arm tip height | 1 |
| Holder arm height at Implant stop | 1.9 |
| Distance, from Holder arm tip to Implant stop | 5.4 |
| Holder arm taper angle, from arm tip to implant stop (incl) | 10 |
| Distance, from implant stop to full 5.5mm dia. | 3.2 |
| Holder tip shoulder curvature angle (approx.) | 22 deg |
| Implant retention pin dia. (max) | 1 |
| Implant retention pin height | 0.4 |
| Screwdriver shaft diameter | 3.8 |
| Screwdriver blade thickness (avg) | 1 |
| Screwdriver knob diameter | 28 |
| Screwdriver knob height | 18 |
| Handle width | 44 |
| Handle thickness | 14 |
| Handle height (with "cage") | 57 |

FIG. 168

Decorticator

| Blade outside diameter | 10.5 |
|---|---|
| Blade wall thickness | 0.7 |
| Blade inside diameter | 9.2 |
| Blade length | 140 |
| Blade tip angle | 60 deg |
| Tooth height | 2.4 |
| Tooth angle (incl) | 18 deg |
| Handle diameter (round side) | 25 |
| Handle length (straight side) | 10 |
| Handle height | 8 |
| Handle distal taper | 45 deg |
| Handle thickness (straight side) | 7.25 |

FIG. 169

Malleting Tool

| Length | 160 |
|---|---|
| Handle length | 117 |
| Handle cross section | 10x10 |
| Head length | 43 |
| Head outside width | 30 |
| Head U-slot width | 9.5 |

FIG. 170

VERTEBRAL JOINT IMPLANTS AND DELIVERY TOOLS

CROSS-REFERENCE TO RELATED APPLICATIONS

The present application claims priority to, and is a continuation of, U.S. patent application Ser. No. 12/653,283, which was filed Dec. 10, 2009, and is entitled Vertebral Joint Implants and Delivery Tools.

Application Ser. No. 12/653,283 is a continuation-in-part ("CIP") application of U.S. patent application Ser. No. 12/455,814, which was filed on Jun. 5, 2009, is entitled Facet Joint Implants and Delivery Tools and claims priority to: U.S. Provisional Application No. 61/059,723, which was filed on Jun. 6, 2008 and is entitled Spine Distraction Device; U.S. Provisional Application No. 61/109,776, which was filed on Oct. 30, 2008 and is entitled Facet Joint Implants; and U.S. Provisional Application No. 61/169,601, which was filed on Apr. 15, 2009 and is entitled Facet Joint Implants and Delivery Tools.

The Ser. No. 12/455,814 application also claims priority to, and is a CIP application of, U.S. patent application Ser. No. 12/317,682, which was filed on Dec. 23, 2008, is entitled Facet Joint Implants and Delivery Tools, and claims priority to Provisional Applications 61/059,723 and 61/109,776. The contents of all of the above-mentioned patent applications are all hereby incorporated by reference herein in their entireties.

FIELD OF THE INVENTION

The following detailed description relates to a device for distracting the spine. More particularly the description relates to a tool for distracting a facet joint of the spine and an implant for maintaining the distracted position of the joint. More particularly the description relates to an implant that may be used together with a tool to distract a facet joint, the implant remaining in place separated from the tool. In some instances, the implant itself may extract the joint.

BACKGROUND

Chronic back problems cause pain and disability for a large segment of the population. Adverse spinal conditions may be characteristic of age. In particular, spinal stenosis (including, but not limited to, central, canal, and lateral stenosis) and facet arthropathy may increase with age. Spinal stenosis results in a reduction of foraminal area (i.e. the available space for the passage of nerves and blood vessels), which may compress cervical nerve roots and cause radicular pain. Both neck extension and ipsilateral rotation, in contrast to neck flexion, may further reduce the foraminal area and contribute to pain, nerve root compression, and neural injury.

Cervical disc herniations may be a factor in spinal stenosis and may predominantly present upper extremity radicular symptoms. In this case, treatment may take the form of closed traction. A number of closed traction devices are available that alleviate pain by pulling on the head to increase foraminal height. Cervical disc herniations may also be treated with anterior and posterior surgery. Many of these surgeries are performed through an anterior approach, which requires a spinal fusion. These surgeries may be expensive and beget additional surgeries due to changing the biomechanics of the neck. There is a three percent incidence of re-operation after cervical spine surgery. Moreover, these surgeries may be highly invasive leading to long recovery times.

There is a need in the art for a device and procedure to increase foraminal height to reduce radicular symptoms of patients suffering the effects of spinal stenosis. There is also a need for the device to be adapted to allow for the procedure to be minimally invasive and to avoid modifying the biomechanics of the spine.

SUMMARY OF THE INVENTION

In one embodiment, a spinal joint distraction system may include a driver assembly including a tubular shaft having a longitudinal axis and a pair of implant holder arms positioned on a distal end of the tubular shaft, where the arms are configured to hold a spinal implant. In another embodiment, the driver assembly may also include an implant distractor positioned along the longitudinal axis near the distal end of the tubular shaft, an internal actuator positioned within the tubular shaft and adapted to advance the implant distractor, and a distractor knob adapted to control the internal actuator. In another embodiment, the system may also include a delivery device with a tubular shaft, a receiving assembly positioned on a proximal end of the tubular shaft, and a pair of forks extending from a distal end of the tubular shaft, where the may be adapted to penetrate a facet joint and the delivery device may be adapted to slidably receive the driver assembly. In some embodiments, the system may include an implant adapted for holding by the implant holding arms of the driver assembly. In some other embodiments, the system may include a chisel with a shaft portion, a tip at a distal end of the shaft, and a head at a proximal end of the shaft, where the delivery device is adapted to receive the chisel, and the head of the chisel is adapted to be tapped by a driving member to insert the tip of the chisel into a facet joint. In still other embodiments, the system may include an injector with a cannula with a closed distal end and two exit doors positioned on opposite sides of the distal end, a plunger with a seal positioned within the cannula, a stop disc at a proximal end of the cannula, and a handle positioned on a proximal end of the plunger, where the delivery device is further adapted to receive an injector.

In another embodiment, the internal actuator may be a stand alone device insertable into the driver assembly. In another embodiment, the internal actuator may include a handle and an internal rod, the internal rod being adapted to hold an implant distractor, and the handle being configured to release the implant distractor. In another embodiment, the system may include a collet positioned on a distal end of the internal rod, the collet adapted to securely hold the implant distractor.

In another embodiment, a spinal distraction implant may include an upper member and a lower member, the upper and lower member being generally rectangular and each having a distal edge, a proximal edge, and two parallel lateral edges, the upper and lower member positioned adjacent and substantially parallel to each other and having an inner surface and an outer surface, the distal edges of the upper and lower member connected to each other and the proximal edges adapted to receive an implant distractor, and teeth positioned along the lateral edges of at least one of the upper or lower member and extending outwardly. In another embodiment, the implant may include flanges extending substantially orthogonally from a proximal end of the upper and lower members. In some embodiments, the flanges may include openings for receiving anchors to anchor the implant to a lateral mass of a facet joint. In another embodiment, the implant may include a truncated threaded slot adapted to engage a cross-cut thread feature of an implant distractor. In another embodiment, the upper and lower members may each include an interlocking scissor feature.

In another embodiment, a method of distracting a facet joint of the spine may include inserting a delivery device to access the facet joint of a patient, inserting a driver assembly holding an implant into the delivery device, and actuating the driver assembly thereby distracting the implant.

In another embodiment, a spinal distraction implant may include an upper member, a lower member, and a proximal member, the upper and lower members being generally rectangular and each having a distal edge and two parallel lateral edges, the upper and lower members extending generally continuously into each other to form the proximal member, the upper and lower member positioned adjacent and substantially parallel to each other and having an inner surface and an outer surface, the proximal member being generally perpendicular relative to the upper and lower members, at least one of the upper and lower members further including threaded slots adapted to receive threads of an implant distractor and outwardly extending teeth positioned along the lateral edges of at least one of the upper or lower members. In another embodiment, the proximal member may include a penetration for receiving an implant distractor.

In another embodiment, a spinal distraction implant may include a threaded bolt with a proximal end terminating in a head, a proximal non-threaded block positioned along the bolt and abutting the head of the bolt, a distal threaded block positioned a distance away from the proximal threaded block, and a plurality of expansion members positioned between the proximal and the distal threaded blocks. In one embodiment, the plurality of expansion members may be V-shaped members. In another embodiment, the plurality of V-shaped members may be adapted to deformably flatten out and expand laterally when compressed between the distal and proximal blocks. In another embodiment, the plurality of expansion members may be planar plates with slotted holes such that when freely positioned on the bolt, the plates are positioned in a skewed position relative to a longitudinal axis of the bolt. In another embodiment, the planar plates may be adapted to engage one another and thus position themselves perpendicular to the bolt when compressed between the distal and proximal blocks.

In another embodiment, a spinal distraction implant may include a pair of stacked structures separated by a sloping plane, the structures having an engagement surface along the plane including ratchet teeth. In one embodiment, a first structure of the pair of stacked structures increases in thickness in a proximal direction and a second structure of the pair of stacked structures increases in thickness in a distal direction.

In another embodiment, a spinal distraction implant may include a generally tapered shaft in the form of a screw, the shaft defining a longitudinal axis and having a length, the shaft having threads along an outer surface for engaging articular surfaces of a facet joint. In one embodiment, the threads may be notched along the length of the implant creating serrations for cutting into the articular surfaces of a facet joint. In another embodiment, the threads may include leaf springs for preventing backing out of the implant. In another embodiment, the threads may have a T-shaped cross-section. In another embodiment, the implant may include a relatively broad head with a decorticating feature on a distal surface thereof. In another embodiment, the decorticating feature may include tabs projecting distally from the head. In another embodiment, the decorticating feature may include spurs. In another embodiment, the head may be in the form of a floating collar and be free to pivot about the longitudinal axis of the implant in a ball and socket type fashion. In another embodiment, the implant may include a torque limiting mechanism. In another embodiment, the shaft may include a hollow cavity and take the form of a cone, the cone being made from a relatively malleable material, the implant further including an inner core support member for use when inserting the implant and for removal once the implant is in place. In still another embodiment, the generally tapered shaft may be a first tapered shaft and the implant may also include a second generally tapered shaft in the form of a screw where the second generally tapered shaft may be positioned adjacent to the first generally tapered shaft and have communicative threaded serrations such that when one shaft is rotated, the other shaft rotates in the opposite direction. In another embodiment, the implant may include an arm type locking mechanism, the arm being biased in a distal direction such that when implanted the arm provides a biasing force to maintain friction on the threads. In another embodiment, the arm may have engaging teeth. In another embodiment, the implant may include flaps extending from the head of the shaft and including teeth for engaging a lateral mass of a facet joint.

In another embodiment, a spinal distraction implant may include a plate and a orthogonally positioned bumper, the superior aspect of the bumper having a rounded surface for opposing the lateral mass of a superior vertebra, the implant including an anchoring screw for securing the implant to a lateral mass of a facet joint.

In another embodiment, a spinal distraction implant may include a wedge insertable between facet surfaces, the wedge having teeth on at least one of an anterior and inferior surface thereof. In another embodiment, the implant may also include a diagonally placed anchor screw positioned through the implant for advancing into the surface of a facet joint.

In another embodiment, a spinal distraction implant may include an anterior hook, a posterior hook, and a bolt joining the anterior and posterior hook. In another embodiment, the anterior hook may be C-shaped with a lip and the posterior hook may be S-shaped with a lip, the anterior hook adapted to engage the anterior aspect of the inferior facet and the posterior hook adapted to engage the posterior aspect of the posterior facet.

In another embodiment, a spinal distraction implant may include an insert and tabs positioned to extend orthogonally from a proximal end of the insert. In one embodiment, the insert may be rectangular and the tabs may have holes for receiving an anchor.

In another embodiment, a spinal distraction implant may include a collapsible diamond shaped structure including two opposing threaded corners, and two opposing non-threaded corners including pads. The implant may also include a bolt threaded through the threaded corners of the diamond shaped structure, where actuating the bolt draws the threaded corners together and extends the non-threaded corners.

In another embodiment, a spinal distraction implant may include an upper member, a lower member, a hinge connecting the upper member to the lower member, and a brace member for maintaining the implant in an open position.

In another embodiment, a spinal distraction implant may include a generally cylindrically shaped member including at least two sections separated by a slot, the sections connected together at distal ends to form a tip, the member adapted to receive a screw to cause it to expand, and the outer surface of the sections including teeth for engaging articular surfaces of a facet joint.

In another embodiment, a method of securing a superior verterbra may include applying a force to the superior vertebra to increase the foraminal area between the superior vertebra and an inferior vertebra and placing an angled screw through a superior facet, through a facet capsule, and into an inferior facet.

In another embodiment, a spinal distraction implant may include a collapsible triangular shaped implant including a central shaft and at least two springing leaves connected to the distal end of the shaft, extending proximally along the shaft, and biased in a direction to form an arrow shape, where the implant may be collapsed within a tube and delivered to a site where the tube is removed and the implant is allowed to expand.

In another embodiment, a spinal distraction implant may include a facet spacer plate and screw, wherein the screw may be inserted diagonally through a facet surface to engage the facet spacer plate thereby forcing separation of a facet joint.

In another embodiment, the spacer may have a C-shape and the screw may pass through the spacer plate prior to entering the spinal structure.

In another embodiment, a spinal distraction implant may include a first bracket, second bracket, and a bolt extending between the brackets, where the brackets are adapted to separate when the bolt is turned. In another embodiment, the first and second brackets may be adapted to be attached to a lateral mass of a facet joint. In yet another embodiment, the first and second brackets may include a leg adapted to be inserted into a facet joint.

In another embodiment, a spinal distraction implant may include a triangular shaped wedge, an anchor screw positioned diagonally through the wedge, and a malleable flap extending from the wedge including teeth for engaging a lateral mass of a facet joint.

In another embodiment, a spinal distraction implant may include an anchoring plug, an expandable plate, and two external plates, where securing the external plates to a lateral mass of a facet joint and inserting the anchoring plug causes the facet joint to separate.

In another embodiment, a spinal distraction implant may include a delivery system and at least two nitinol hooks, where the hooks may be flattened and inserted with the delivery system and once in place may be allowed to assume their pre-flattened shape.

In another embodiment, a spinal distraction implant may include a hollow screw sleeve having barbs adapted to be ejected from a retracted position and a wedge adapted to be inserted in the hollow screw sleeve to eject the barbs.

In another embodiment, a spinal distraction implant may include a collapsible nut positioned over a bolt, the bolt defining a longitudinal axis, where advancing the bolt may cause the nut to collapse along the longitudinal axis in an accordion shape, thereby expanding laterally.

In another embodiment, a spinal distraction implant may include a collapsible plate positioned over a bolt, the bolt defining a longitudinal axis, where advancing the bolt causes the plate to collapse along the longitudinal axis in an accordion shape, thereby expanding laterally.

In another embodiment, a spinal distraction implant may include a wire surrounding a block in a helical fashion, the wire adapted to contract and expand laterally when pulled taught or released respectively.

In another embodiment, a spinal distraction implant may include an outer housing and an internal spring, where the housing may be biased to be in a laterally broad position when the spring is in a neutral position.

In another embodiment, a spinal distraction implant may include a pair of stacked structures separated by a sloping plane and a fastener positioned at an angle through the pair of structures thereby preventing relative movement along the plane.

In another embodiment, a spinal distraction implant may include a collapsible cylinder with side cutouts, the cylinder made from a resilient elastic material.

In another embodiment, a spinal distraction implant may include a distal tip of a delivery tool, where the tip is adapted to distract a facet joint and detach from the delivery tool.

In another embodiment, a spinal distraction implant may include a housing, a central gear rotatably positioned within the housing, and two plates slidably positioned in the housing and positioned opposite one another adjacent to the central gear and including teeth for engaging the gear, where rotating the gear slidably extends the plates beyond an outer surface of the housing in opposite directions.

In another embodiment, a spinal distraction implant may include a triangularly bent plate with a first and second bracket on each side, the first bracket adapted to receive an anchor screw and the second bracket including teeth for biting into a lateral mass of a facet joint.

In another embodiment, a spinal distraction implant may include a rotatable cone with a longitudinal axis including a shoulder with a ledge defining a cam surface and an anchor screw, where the shoulder is adapted to be inserted into a facet joint and the implant rotated to cause a superior facet to ride upward along the cam surface and distract the joint, wherein the screw may be advanced to secure the implant.

In another embodiment, a spinal distraction implant may include a housing with penetrations for ejection of spikes, internal spikes positioned with the housing and in alignment with the penetrations, and an internal wire routed through the spike positions, where pulling the wire taught forces the spikes from the housing to engage articular surfaces of a facet joint.

In another embodiment, a spinal distraction implant may include a housing, a cavity within the housing, penetrations on lateral surfaces of the housing extending from the cavity through the wall of the housing, spikes positioned to be ejected through the penetrations, the spikes having a beveled inner surface, and a piston having a torpedo shaped distal end positioned within the cavity, where advancing the piston engages the torpedo shaped distal end with the beveled inner surface of the spikes causing them to eject through the penetrations and engage articular surfaces of a facet joint.

In another embodiment, a spinal distraction implant may include two parallel equal length side bars and at least two struts pivotably positioned between the side bars at each end, the struts having textured surfaces on each end thereof, where the struts may be pivoted to lie in plane with and parallel to the side bars and once in position in a facet joint, may be pivoted substantially perpendicular to the side bars to distract the facet joint.

In another embodiment, a spinal joint distraction system may include a delivery device with a tubular shaft, a receiving assembly positioned on a proximal end of the tubular shaft and including a seating cavity, and a pair of forks extending from a distal end of the tubular shaft, the forks adapted to penetrate a facet joint. The system may also include a chisel including a shaft with a chamfered tip, the chisel being adapted for slidable insertion through the delivery device. The system may further include a decorticator sleevably positioned on the tubular shaft of the delivery device, the decorticator including a tubular shaft portion with a chamfered distal end, a plurality of serrated teeth at the distal tip of the chamfered end, a beveled edge extending along the periphery of the chamfered distal end, and a handle positioned on the proximal end of the tubular shaft portion, the handle having a bore adapted to receive a gripping tool and a threaded bore for receiving a set screw. The system may also include a driver assembly adapted for slidable insertion through the delivery device, the driver assembly including an implant shaft, a handle positioned on the proximal end of the implant shaft, and implant holding arms extending from the distal end of the implant shaft. The system may also include an internal actuator adapted for slidable insertion through the driver assembly and further adapted to advance an implant distractor, the internal actuator including a longitudinal shaft, a handle positioned on the proximal end of the longitudinal shaft and adapted to rotatably advance the implant distractor, and an internal rod including an engagement feature adapted to secure the implant distractor. The system may further include an injector adapted for slidable insertion through the delivery device, the injector including a longitudinal delivery shaft, a seating feature positioned around the shaft, and a plunger adapted to pass through the longitudinal delivery shaft causing ejection of material from the distal end of the longitudinal delivery shaft.

In another embodiment, a spinal joint distraction system may include a delivery device with a decorticator sleevably positioned thereon, a chisel adapted for insertion through the delivery device, a driver assembly adapted for insertion through the delivery device and further adapted to hold an implant, an internal actuator adapted for insertion through the driver assembly and adapted to deliver and advance an implant distractor thereby distracting the implant, and an injector adapted for insertion through the delivery device and further adapted to deliver flowable material to or around the joint.

In another embodiment, a spinal distraction implant may include an upper member and a lower member each with a distal end, the distal end of the lower member coupled to the distal end of the upper member, and an implant distractor adapted to be advanced between the upper and lower member and separate the upper and lower members causing the upper and lower member to pivot relative to one another about their respective distal ends.

In another embodiment, a spinal distraction implant may include an upper member and a lower member each including a distal edge, a proximal edge, and two parallel lateral edges, the edges defining a generally rectangular shape, an inner surface, an outer surface, a threaded slot passing through the member from the inner surface to the outer surface, a truncated threaded slot passing through the member from the inner surface to the outer surface, a plurality of teeth spaced along the two parallel lateral edges, a guide feature positioned on the proximal edge, and an interlocking scissor feature positioned on the distal edge. The implant may also include an implant distractor including a cylindrical body tapering to a point at a distal end, a coil shaped thread feature having an abrupt proximal end and being interrupted by at least one cross-cut, and an annular stop ring; wherein the upper and lower members may be pivotally coupled to one another via their respective interlocking scissor features, the respective guide features on the upper member and the lower member may oppose one another and may be adapted to receive and guide the distal end of the implant distractor between the upper and lower members, the respective threaded slots on the upper and lower member may be adapted to receive the coil shaped thread feature, and the respective truncated threaded slots may be adapted to engage the abrupt proximal end or the at least one cross-cut of the coil-shaped thread feature.

In another embodiment, a method of distracting a facet joint of the spine may include dilating a path to a facet joint using a dilator set, inserting a chisel into the facet joint, advancing a delivery device over the chisel and inserting forks of the delivery device into the facet joint, removing the chisel from the joint, inserting a driver assembly with an implant into the delivery device, seating the driver assembly in the delivery device thereby positioning the implant between the forks of the delivery device and in the facet joint, inserting an internal actuator into the driver assembly and advancing an implant distractor into the implant thereby distracting the implant, actuating a button on the internal actuator thereby releasing a grip on the implant distractor and removing the internal actuator and the driver assembly, and inserting an injector and injecting a flowable material into or around the facet joint.

In another embodiment, a method of distracting a facet joint of the spine may include inserting a chisel into a facet joint to provide initial distraction and decorticate the surface of the joint, inserting a delivery device over the chisel to maintain the initial distraction, inserting an implant through the delivery device and into the joint, the implant having teeth adapted to engage the surfaces of the joint, distracting the implant by advancing an implant distractor, the implant distractor having a coil-shaped thread feature for engaging threaded slots of the implant, the implant distractor further having cross-cut threads for engaging truncated threaded slots on the implant, wherein, advancing the implant distractor includes causing the cross-cut threads to engage the truncated threaded slots and prevent backing out of the implant, and releasing the implant distractor and removing the delivery device thereby leaving the implant and the implant distractor in place in the joint.

In another embodiment, a spinal joint distraction system may include a delivery device, a driver assembly adapted for insertion through the delivery device and further adapted to hold an implant, and an internal actuator adapted for insertion through the driver assembly and adapted to deliver and advance an implant distractor thereby distracting the implant.

In another embodiment, a spinal joint distraction system may include a driver assembly adapted to hold an implant and an internal actuator adapted for insertion through the driver assembly and adapted to deliver and advance an implant distractor thereby distracting the implant.

In another embodiment, a spinal joint distraction system may include an implant, an implant distractor adapted to engage the implant, and an internal actuator adapted to advance the implant distractor thereby distracting the implant.

In another embodiment, a method of distracting a facet joint of the spine may include inserting a delivery device into a facet joint, inserting an implant through the delivery device and into the joint, and distracting the implant by advancing an implant distractor.

In another embodiment, a method of distracting a facet joint of the spine may include partially engaging an implant distractor with an implant and engaging the implant distractor with an internal actuator to form an assembly, inserting the implant portion of the assembly into the facet joint, and distracting the facet joint.

In another embodiment, a spinal distraction implant may include an upper member and a lower member each with a distal end, the distal end of the lower member coupled to the distal end of the upper member, wherein the upper member and lower member each comprise a plurality of threaded slots adapted to engage an implant distractor.

In another embodiment, a spinal distraction implant may include an upper member and a lower member each with a distal end, the distal end of the lower member including an interlocking scissor feature coupled to a corresponding interlocking scissor feature included on the distal end of the upper member.

In another embodiment, a spinal distraction implant comprising an upper member and a lower member, each with a distal end, the distal end of the lower member coupled to the distal end of the upper member, wherein the implant is adapted to receive an implant distractor between the upper and lower member.

In another embodiment, a spinal distraction implant may include an upper member and a lower member, the upper member and lower member coupled at respective distal ends, the upper and lower members being biased toward a position parallel to one another.

In another embodiment, a spinal joint distraction system for treating a facet joint including articular surfaces having a contour can include a delivery device including a generally tubular structure adapted to engage a facet joint, an implant adapted to be delivered through the delivery device and into the facet joint, the implant comprising two members arranged in opposed position, and an implant distractor comprising a generally elongate member adapted to advance between the two members of the implant causing separation of the members and distraction of the facet joint, wherein the implant is adapted to conform to the shape of the implant distractor upon being delivered to the facet joint. The system can also include a driver assembly adapted to hold the implant and advance the implant distractor and the driver assembly can further be adapted for insertion through the delivery device. The system can also include a chisel adapted for insertion through the delivery device to facilitate initial engagement with the facet joint and a decorticator can be provided for lateral engagement with the delivery device. A malleting tool can be included with a first end adapted to engage the decorticator for a malleting process and a second end adapted to facilitate separation of parts of the system and an injector can be provided and adapted for insertion through the delivery device and further can be adapted to deliver a bone paste.

In another embodiment, a spinal joint distraction system can include a delivery device and chisel assembly adapted to engage a facet joint and a driver assembly adapted to hold and distract an implant, where the driver assembly can be adapted for insertion through the delivery device to deliver and distract the implant. The system can also include a place holding chisel adapted to replace the chisel and maintain the established position of the delivery device and chisel assembly. The delivery device can include a tubular shaft and a receiving assembly positioned on a proximal end of the tubular shaft and the chisel of the assembly can include a handle having a connection feature adapted to engage the receiving assembly. The connection feature can include a protrusion or recess adapted to form a detent relationship with an opposing protrusion or recess respectively. In another embodiment, the connection feature can include a latch type feature positioned on a deflectable portion of the handle, wherein advancing the chisel handle toward the receiving assembly causes the latch type feature to snap into place and depressing the deflectable portion of the handle releases the latch type feature. The receiving assembly can include a malleting anvil positioned on a proximal face of the receiving assembly and the chisel can include a slot cavity adapted to receive the malleting anvil and a malleting head adapted to engage the malleting anvil to resist relative motion between the delivery device and the chisel during malleting. The delivery device of the assembly can include forks adapted to penetrate the facet joint and it can also include a bull nose positioned on the surface of the forks near the intersection of the forks with the tubular structure, where the bull nose can be adapted to mark the position of the delivery device. The system can also include an indication hole positioned along the lateral side of the delivery device near the intersection of the forks and the tubular structure. The driver assembly can include an implant shaft having a diameter substantially equal to or less than a width of the implant and can also include a handle with a malleting bar adapted to transfer malleting blows to the driver assembly. The driver assembly can also include a slot cavity having a bearing surface where the slot cavity can be adapted to receive the malleting anvil of the receiving assembly and the bearing surface can be adapted to engage the malleting anvil to resist relative motion between the delivery device and the driver assembly during malleting. A decorticator can also be provided and can be adapted for positioning upon the delivery device from a lateral side of the delivery device. The decorticator can include a U-shaped longitudinally extending member with teeth on a distal end and it can include a malleting element at a proximal end adapted to distribute malleting blows to the longitudinally extending member. The driver assembly can include arms adapted to hold an implant and the arms can be positioned within a boundary defined by a width of the implant.

In another embodiment, a spinal distraction implant for the distraction of a facet joint having articular surfaces can include a first and a second member arranged in opposing position. Each of the first and second member can include a threaded slot passing through the member adapted to receive a thread feature and a plurality of teeth spaced along two parallel lateral edges, the teeth adapted to engage the articular surfaces of the facet joint, where the implant is constructed from a malleable material and is further adapted to conform to the shape of the articular sufaces upon being distracted within a facet joint. The plurality of teeth can have a linearly sloped distal face and a proximal face positioned orthogonally to the respective first or second member and the teeth can be equally spaced. The first and second members can each have an interlocking enagement feature on respective distal edges, wherein the first and second members engage one another via their respective interlocking engagement features. The first and second members can also be coupled together via a weld.

In another embodiment, a method of distracting a facet joint and a contralateral facet joint of a spine can include inserting a delivery device and chisel assembly into the facet joint, removing the chisel from the assembly and replacing the chisel with a place holding chisel, removing the delivery device from the facet joint, inserting the delivery device and chisel assembly into the contralateral facet joint, removing the chisel from the assembly, placing and distracting a first implant in the contralateral facet joint, removing the delivery device from the contralateral facet joint, placing the delivery device back in the facet joint via the place holding chisel, placing and distracting a second implant in the facet joint. The place holding chisel can be a radiolucent chisel and the method can also include performing lateral fluoroscopy to determine proper placement of the first implant.

In another embodiment, a method of distracting a facet joint of the spine can include inserting a delivery device and chisel assembly into the facet joint to provide initial distraction and decorticate the surface of the joint, removing the chisel assembly from the delivery device, inserting a driver assembly through the delivery device, the driver assembly holding an implant and further comprising an implant distractor adapted to distract the implant, distracting the implant, and removing the driver assembly and the delivery device. The method can also include positioning the delivery device and chisel assembly by selectively malleting a proximal end thereof and/or selectively malleting a proximal end of the driver assembly. A decorticator can be positioned on the delivery device from the lateral side of the device and the method can include advancing the decorticator along the length of the driver assembly, positioning a malleting tool against the proximal end of the decorticator, and malleting the malleting tool to forcibly advance the decorticator and decorticate the lateral mass of the facet joint. The decorticator can be retracted, rotated, and re-advanced to a new position for malleted with the malleting tool to decorticate a different location. Intra-operative patient symptom feedback can also be obtained.

In another embodiment, a spinal distraction implant delivery tool can include an implant and an assembly, where the assembly includes a means for holding the implant, a means for positioning the implant within a facet joint, and a means for distracting the implant. The implant can include a first substantially planar member and a second substantially planar member arranged in parallel and opposing position to the first substantially planar member and a biasing connection connecting the first and second planar members to one another, the biasing connection adapted to create a biasing force directed toward biasing the members toward the parallel and opposing position. The means for holding can include a pair of implant holding arms, the arms adapted to pass between the planar members and force them apart against the biasing force. The holding arms can each include a means for engaging the implant. The means for distracting the implant can include an implant distractor and a means for rotatably advancing the implant distractor. The implant distractor can include a generally elongate member adapted to pass between the substantially planar members and force the members apart against the biasing force.

In another embodiment, a method of performing an interbody fusion can include inserting a delivery device and chisel assembly into a joint between vertebral bodies of the spine, removing the chisel assembly from the delivery device, and inserting a driver assembly through the delivery device. The driver assembly can hold an implant and an implant distractor adapted to distract the implant. The method can also include distracting the implant and removing the driver assembly and the delivery device. In some embodiments, the method can further include repeating the steps to place a second implant in the joint.

Further aspects of the invention will be brought out in the following portions of the specification, wherein the detailed description is for the purpose of fully disclosing preferred embodiments of the invention without placing limitations thereon.

BRIEF DESCRIPTION OF THE DRAWINGS

FIG. 1 is a perspective view of a delivery device and chisel positioned relative to a facet joint of a spine, according to certain embodiments.

FIG. 6A-6C are perspective views of a delivery device and an internal decorticator, according to certain embodiments.

FIG. 8 is a perspective view of a delivery device with a driver assembly and implant poised for insertion into the delivery device, according to certain embodiments.

FIG. 9 is a close-up view of a distal end of a driver assembly and a delivery device, according to certain embodiments.

FIG. 10 is close-up view of a distal end of a driver assembly, according to certain embodiments.

FIG. 11 is a perspective view of an implant and a distal end of a driver assembly, according to certain embodiments.

FIG. 12 is a perspective view of distal end of a driver assembly holding an implant, according to certain embodiments.

FIG. 13 is a perspective view of a distal end of a driver assembly positioned within a delivery device, according to certain embodiments.

FIG. 14 is a perspective view of an implant distractor, according to certain embodiments.

FIG. 15 is a perspective view of a distal end of a driver assembly positioned within a delivery device, according to certain embodiments.

FIGS. 39A-D include side and perspective views of an implant, according to certain embodiments.

FIGS. 41A-D include side and perspective views of an implant, according to certain embodiments.

FIGS. 57A-C include side and perspective views of an implant, according to certain embodiments.

FIGS. 80A-D include side and perspective views of an implant, according to certain embodiments.

FIGS. 82A-F include side and perspective views of an implant, according to certain embodiments.

FIGS. 92 and 93 are perspective views of a part of a driver assembly portion of the kit shown in FIGS. 85 and 86.

FIGS. 99-99D are several views of a driver assembly according to certain embodiments.

FIGS. 100-101 depict relative positions of a driver assembly and a delivery device according to certain embodiments.

FIGS. 102-103 depict relative positions of an internal actuator, a driver assembly, and a delivery device according to certain embodiments.

FIG. 104 is a side view of an internal actuator according to certain embodiments.

FIG. 105 is a side view of an internal actuator according to certain embodiments.

FIGS. 106-108 are several side and cross-section view of an internal actuator according to certain embodiments.

FIGS. 111-113 include several views of an implant distractor according to certain embodiments.

FIG. 114 is a perspective view of an injector according to certain embodiments.

FIGS. 115-116 depict relative positions of an injector and a delivery device according to certain embodiments.

FIG. 124 is a perspective view of a decorticator according to certain embodiments.

FIG. 125 is a perspective view of a driver assembly according to certain embodiments.

FIG. 126 is a perspective view of an internal actuator according to certain embodiments.

FIGS. 126A and 126B are cross-sectional views of an internal actuator according to certain embodiments.

FIGS. 127 and 127A are perspective views of an internal rod with a collet according to certain embodiments.

FIG. 128 is a perspective view of an injector according to certain embodiments.

FIGS. 129-131 are several view of a dilator set according to certain embodiments.

FIGS. 132 and 132A are two views of a dilator rod according to certain embodiments.

FIGS. 133, 133A, and 133B are several views of a dilator sleeve according to certain embodiments.

Figure 134:
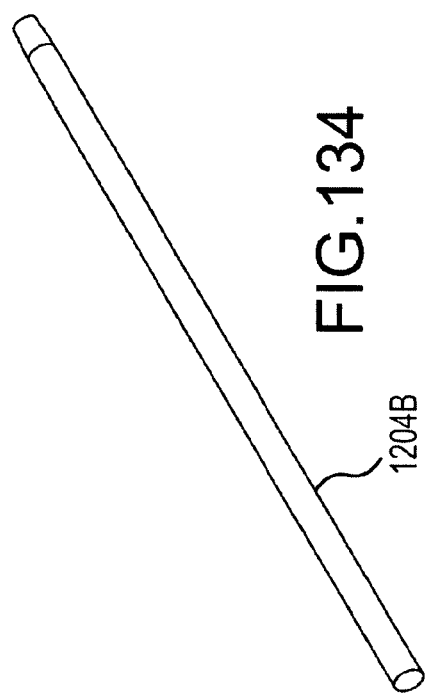
Figure 134A:
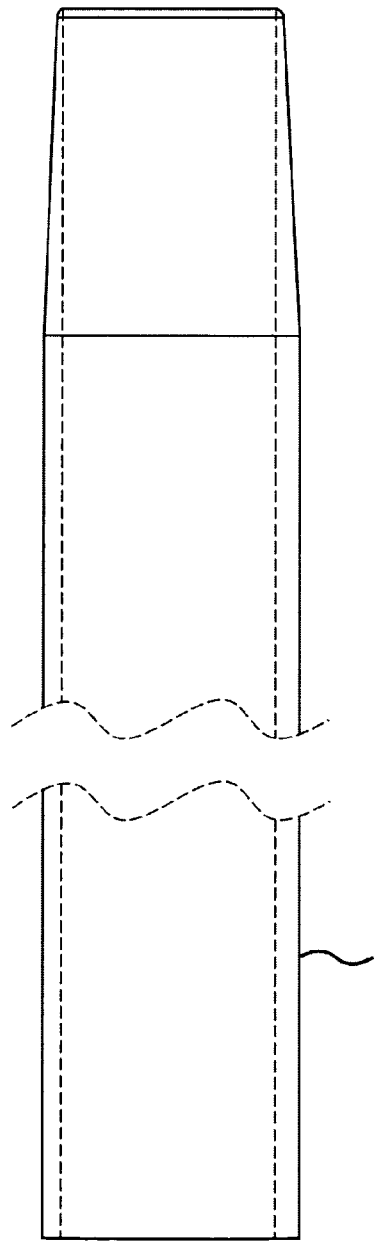

FIGS. 134 and 134A are two views of a dilator sleeve according to certain embodiments.

Figure 135A:
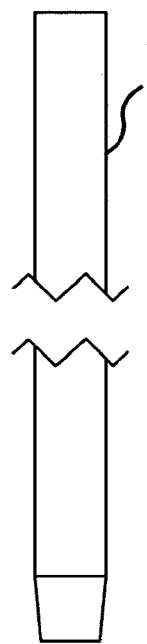
Figure 135B:
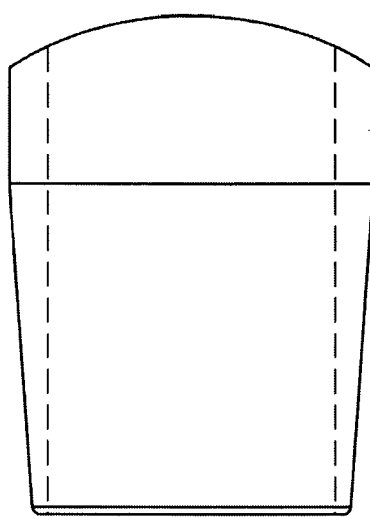
Figure 135:
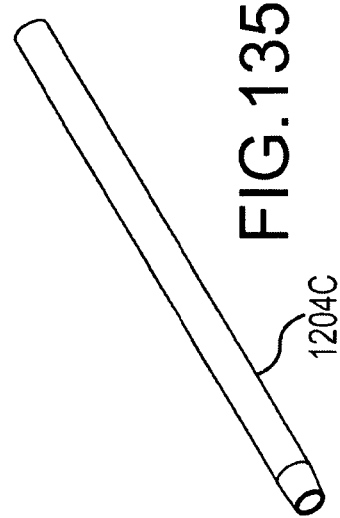

FIGS. 135, 135A, and 135B are several views of a dilator sleeve according to certain embodiments.

Figure 136:
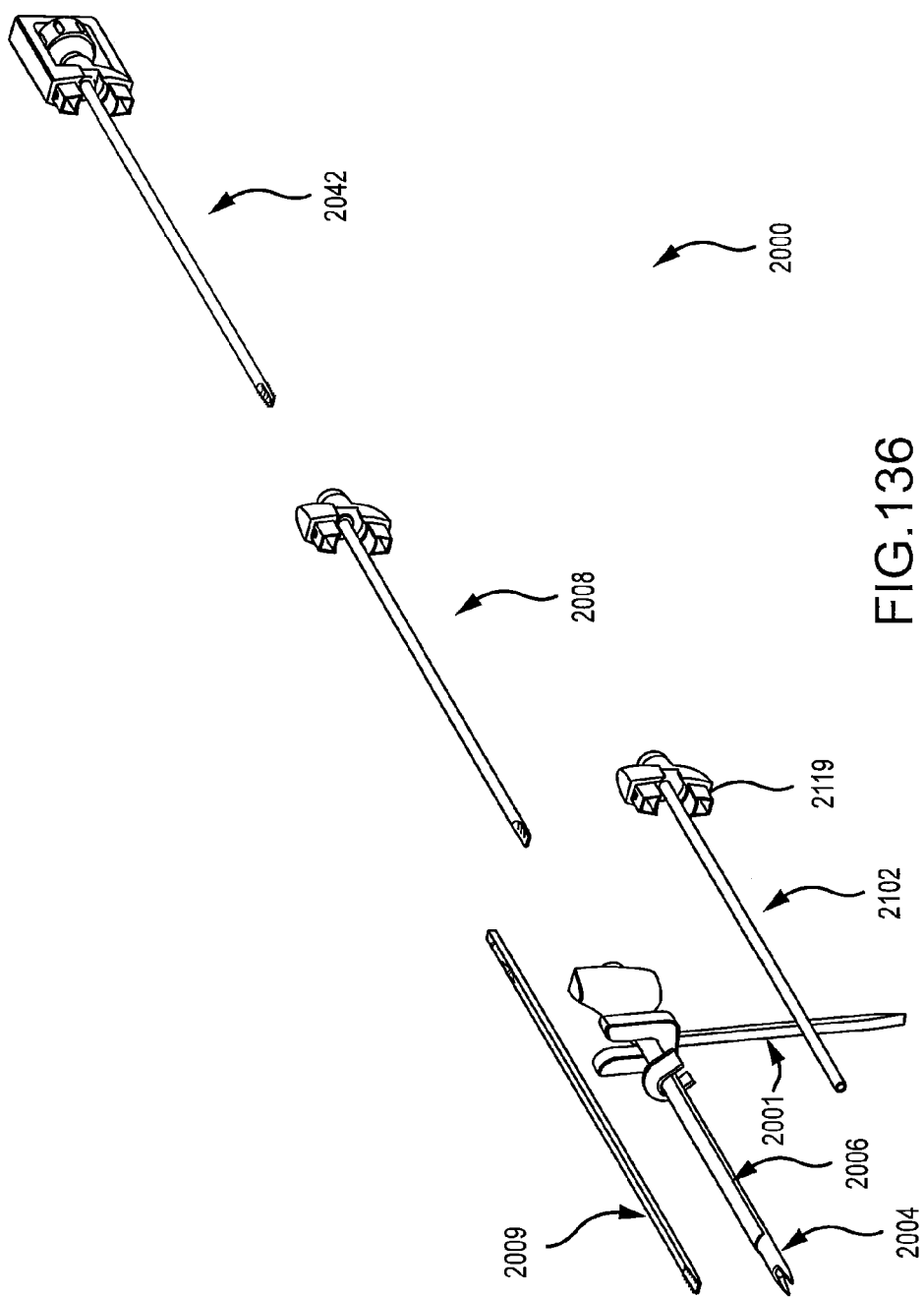

FIG. 136 includes a perspective view of several parts of a tool according to certain embodiments.

Figure 137:
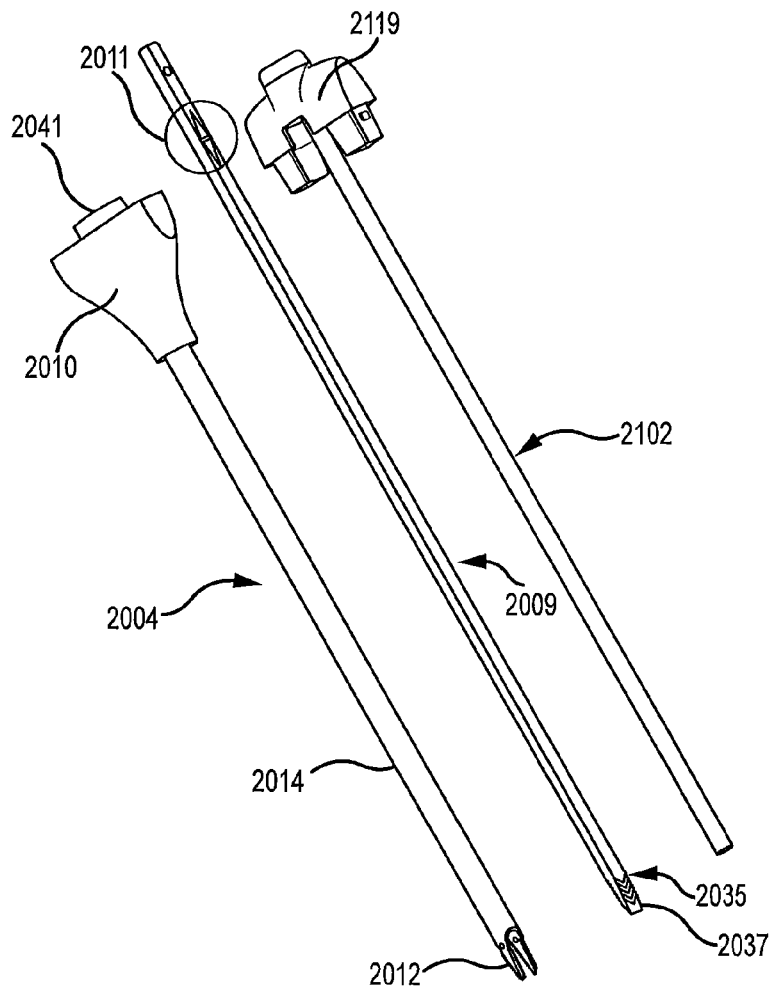

FIG. 137 includes a perspective view of several parts of the tool of FIG. 136.

Figure 138:
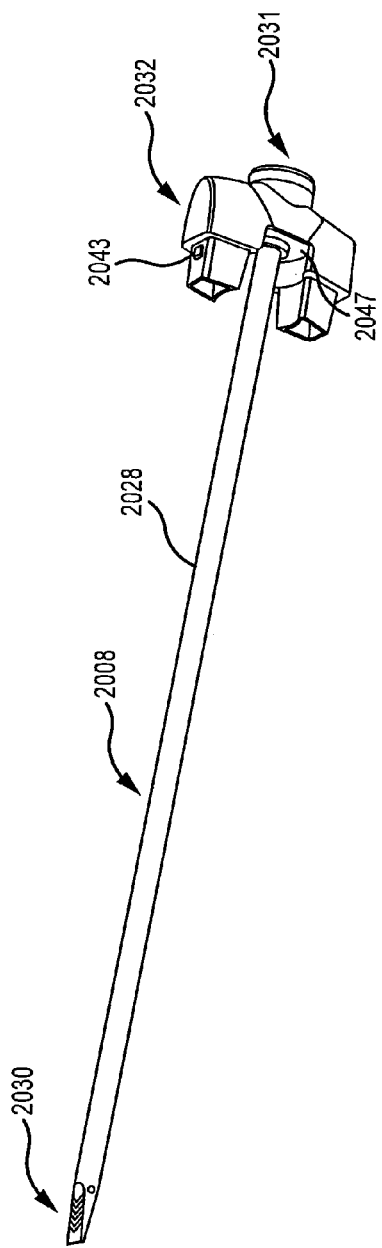

FIG. 138 is a perspective view of a chisel of the tool of FIG. 136.

Figures 139A, 139B, 139C:
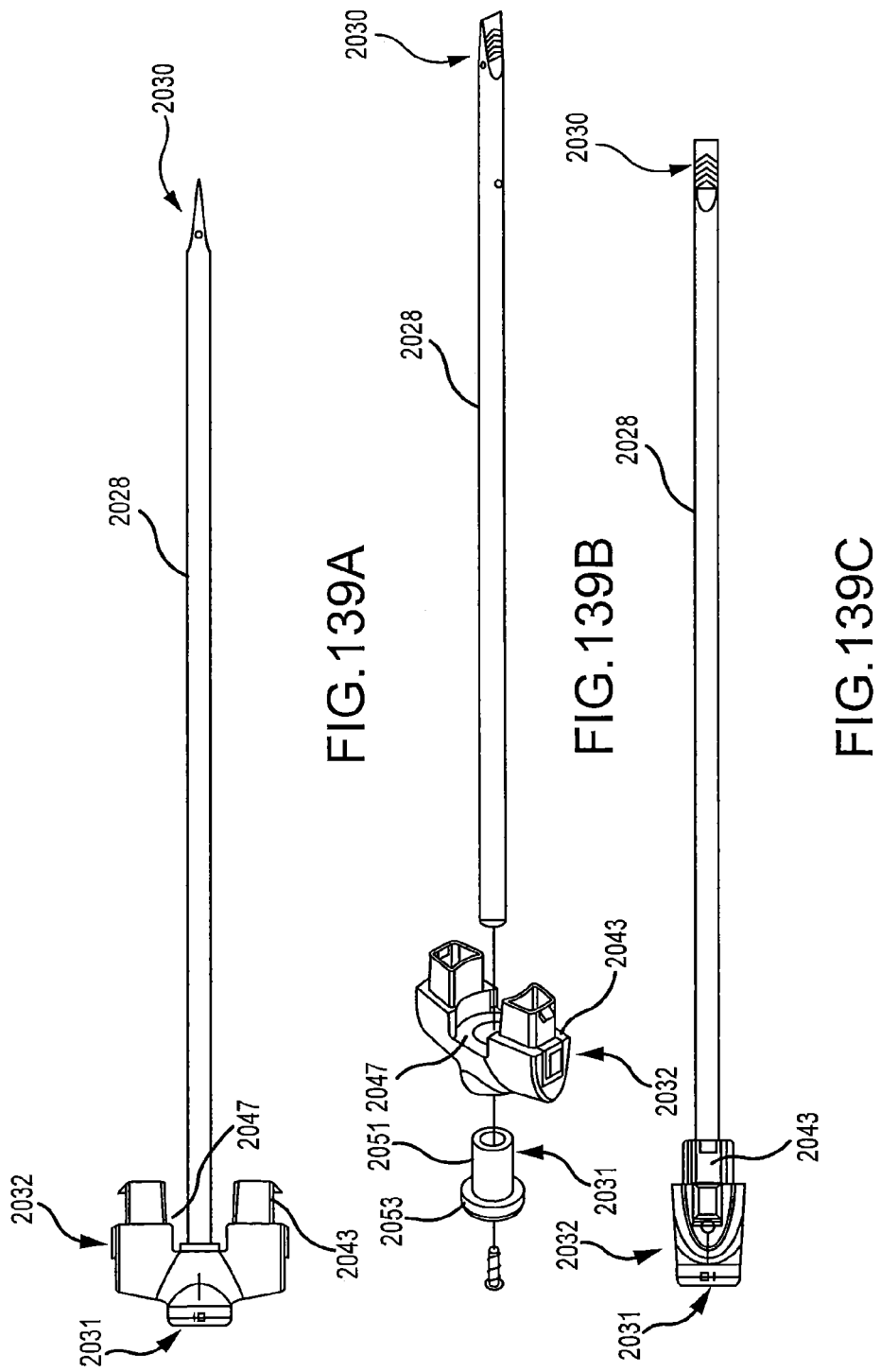

FIGS. 139A-C include several views of a chisel of the tool of FIG. 136.

Figure 140:
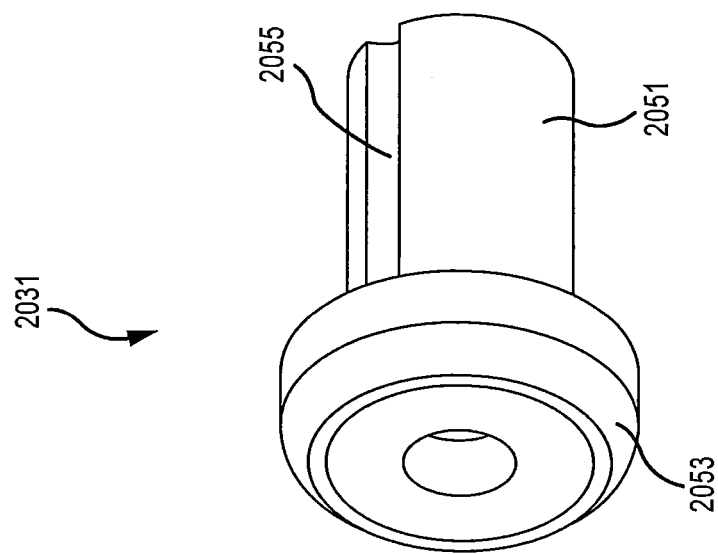

FIG. 140 is a perspective view of a malleting head of the chisel of FIG. 138.

Figure 141:
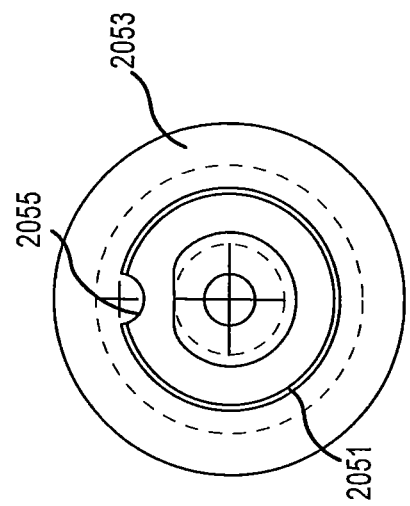

FIG. 141 is a top view thereof.

Figure 142:
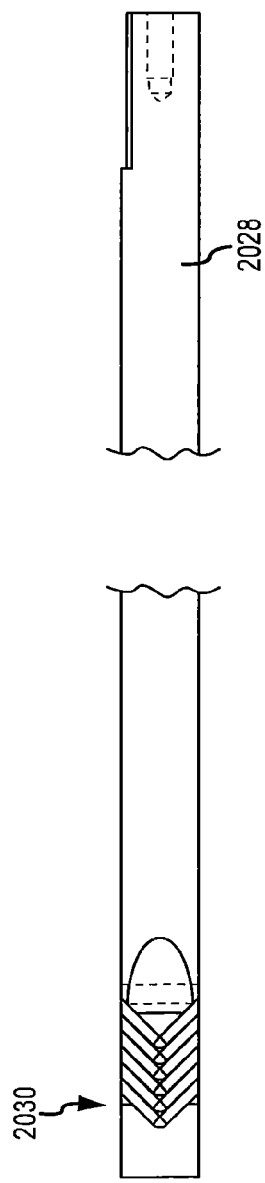

FIG. 142 is a top view of a shaft portion of the chisel of FIG. 138.

Figure 143:
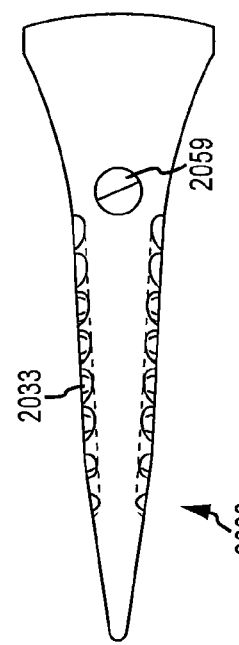

FIG. 143 is a close up side view of a tip of the chisel of FIG. 138.

FIG. 144 is a top view of a chisel and delivery device of the tool of FIG. 136.

FIG. 145 is a close up side view of a tip of a chisel and delivery device of the tool of FIG. 136.

Figure 146:
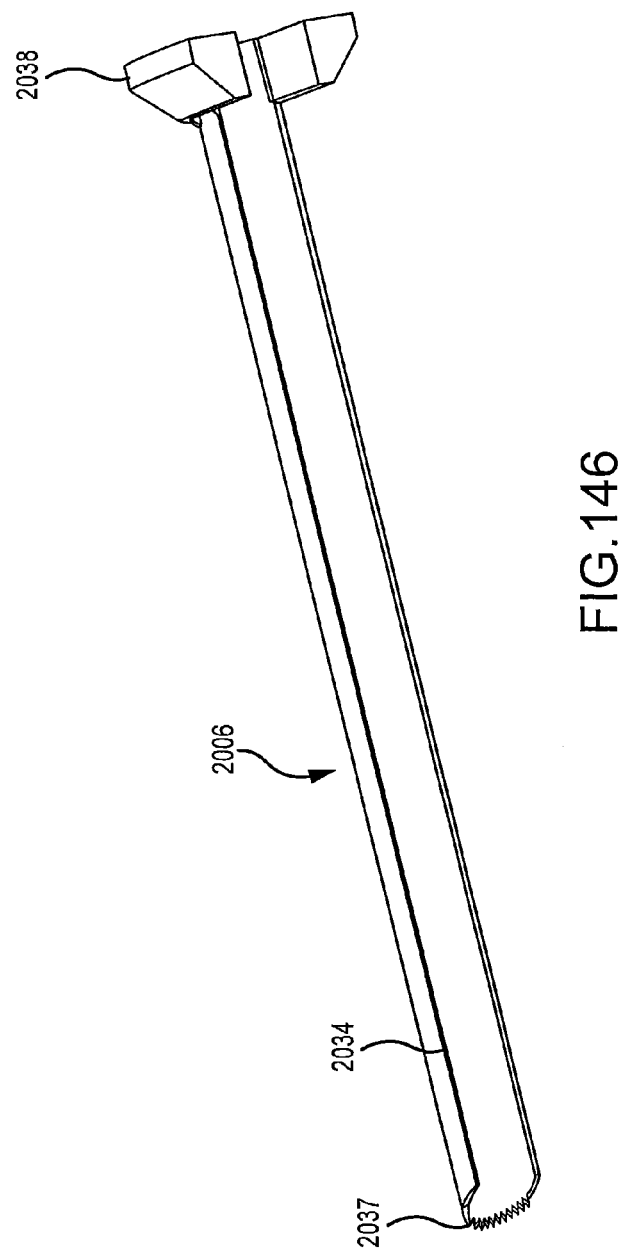

FIG. 146 is a perspective view of a decorticator of the tool of FIG. 136.

Figure 147:
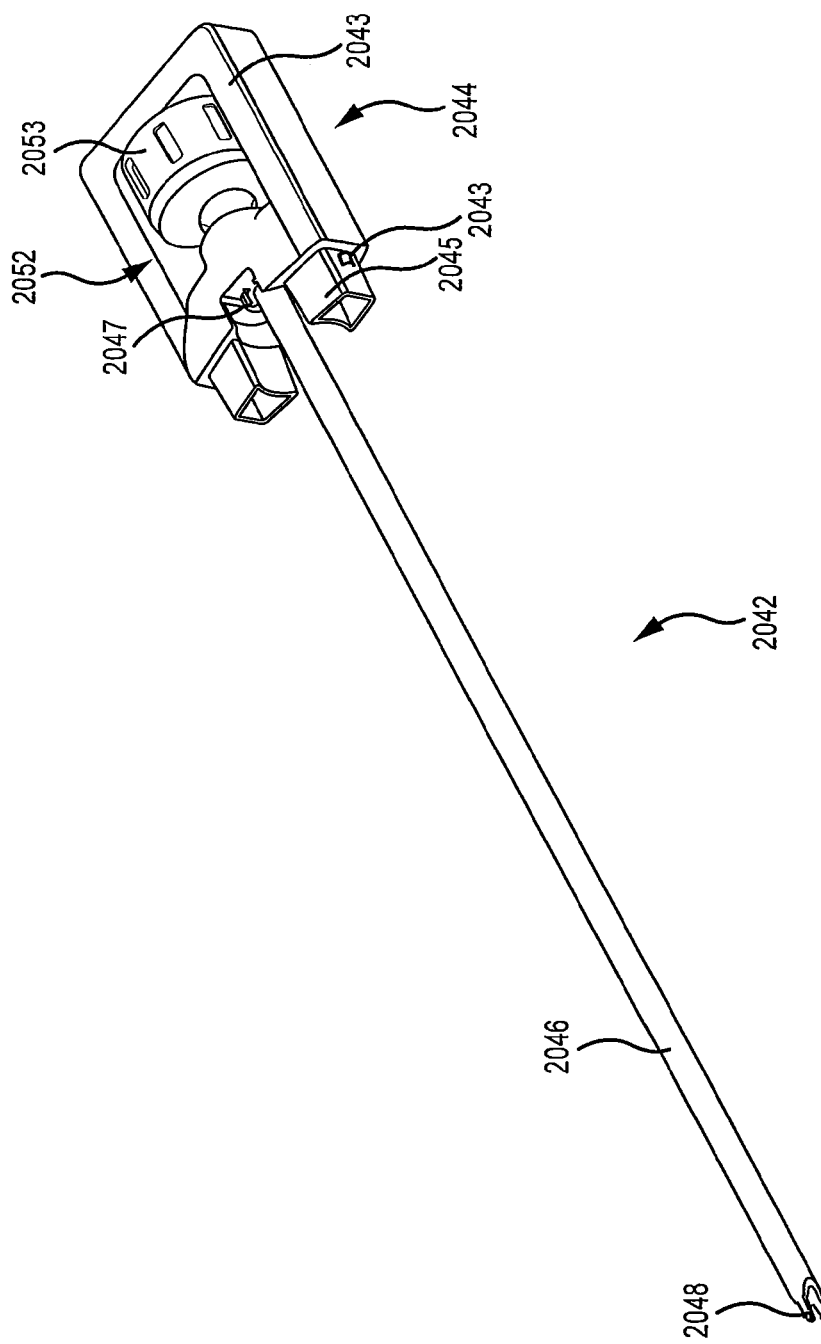

FIG. 147 is a perspective view of a driver assembly of the tool of FIG. 136.

Figure 148:
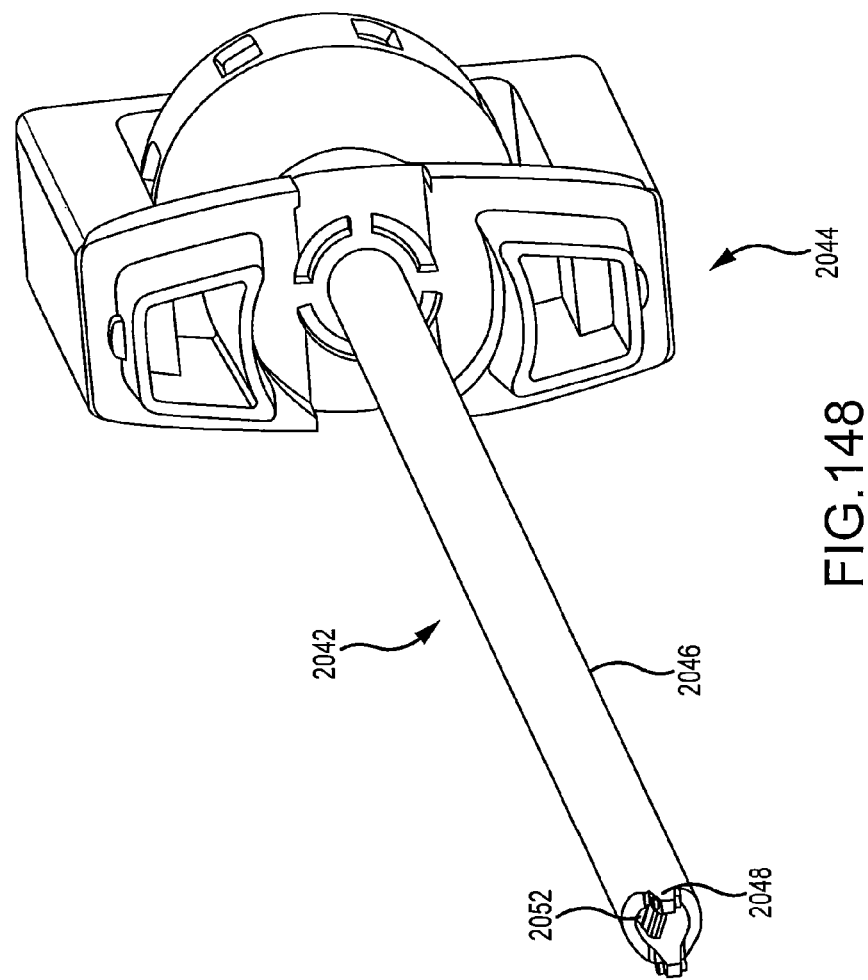

FIG. 148 is a perspective view thereof.

Figure 149:
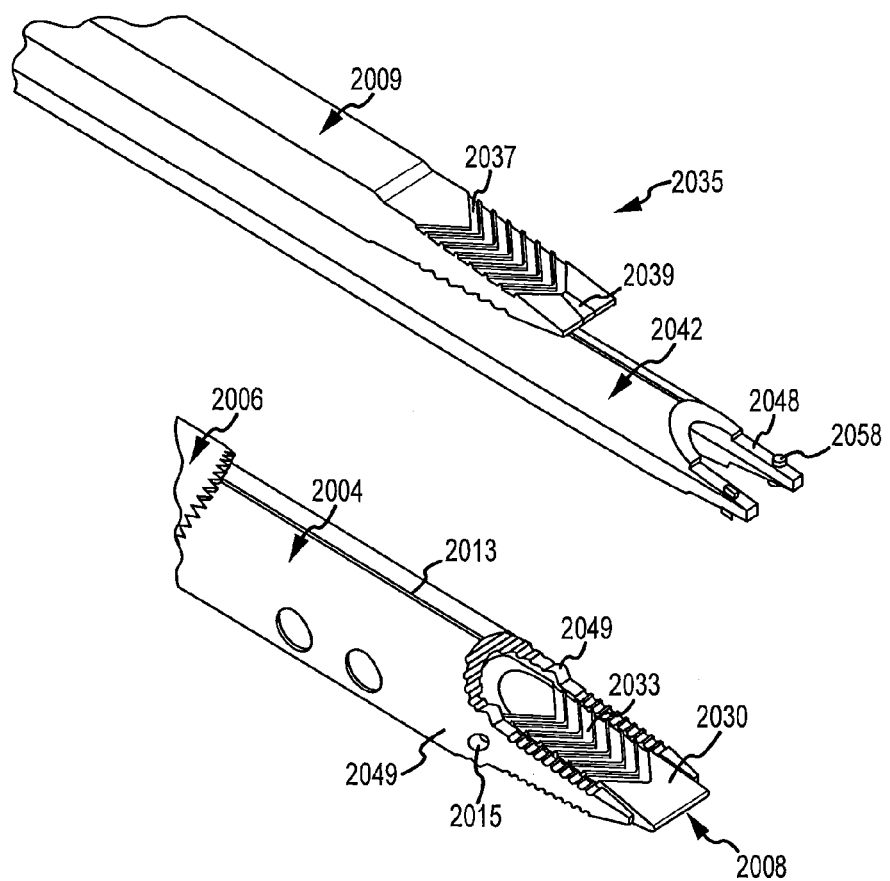

FIG. 149 is a perspective view of several tips of several of the elements of the tool of FIG. 136.

Figure 150:
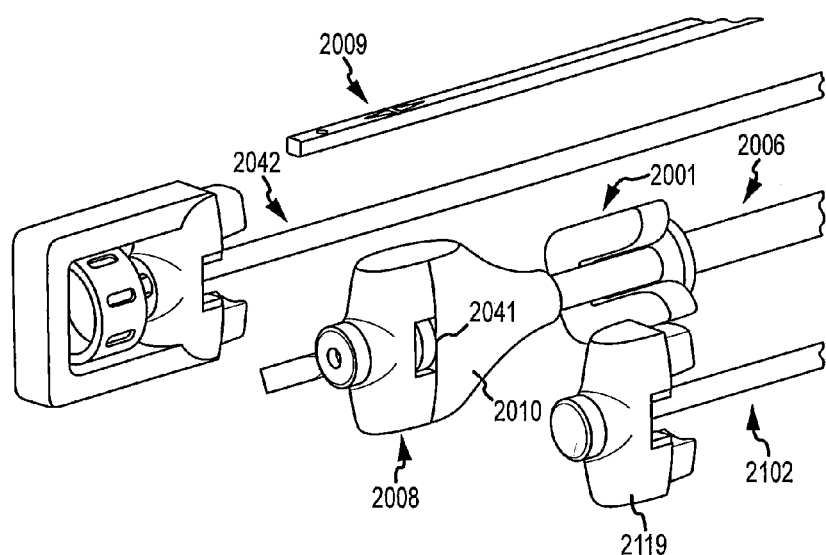

FIG. 150 is a perspective view of the proximal ends of several of the elements of the tool of FIG. 136.

Figure 151:
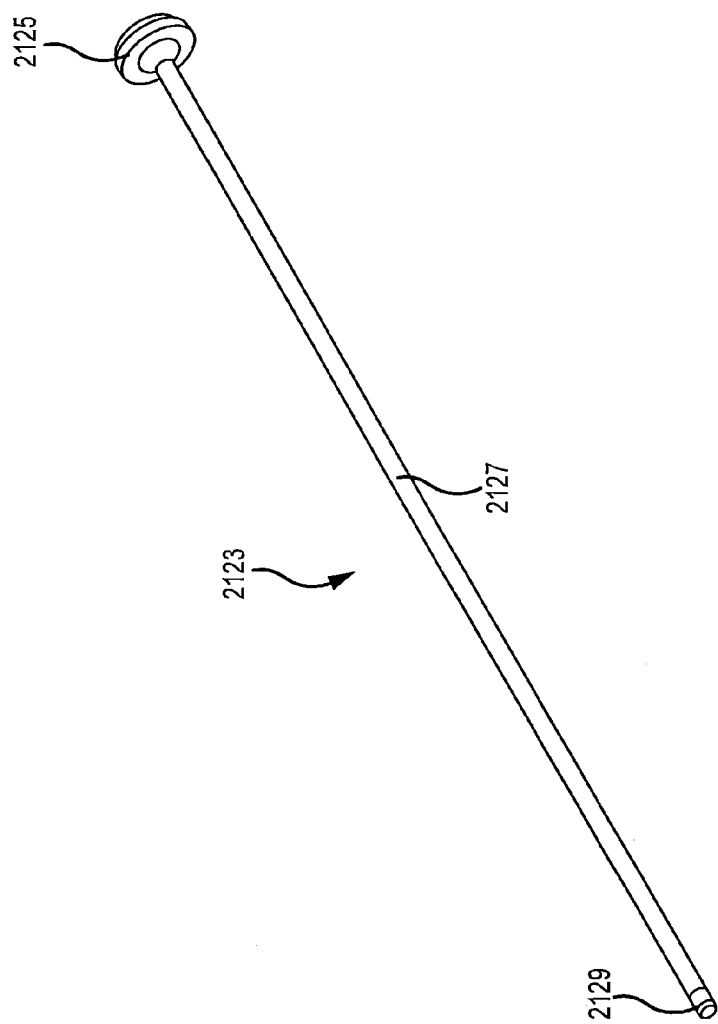

FIG. 151 is a perspective view of a plunger of the injector of the tool of FIG. 136.

Figure 152:
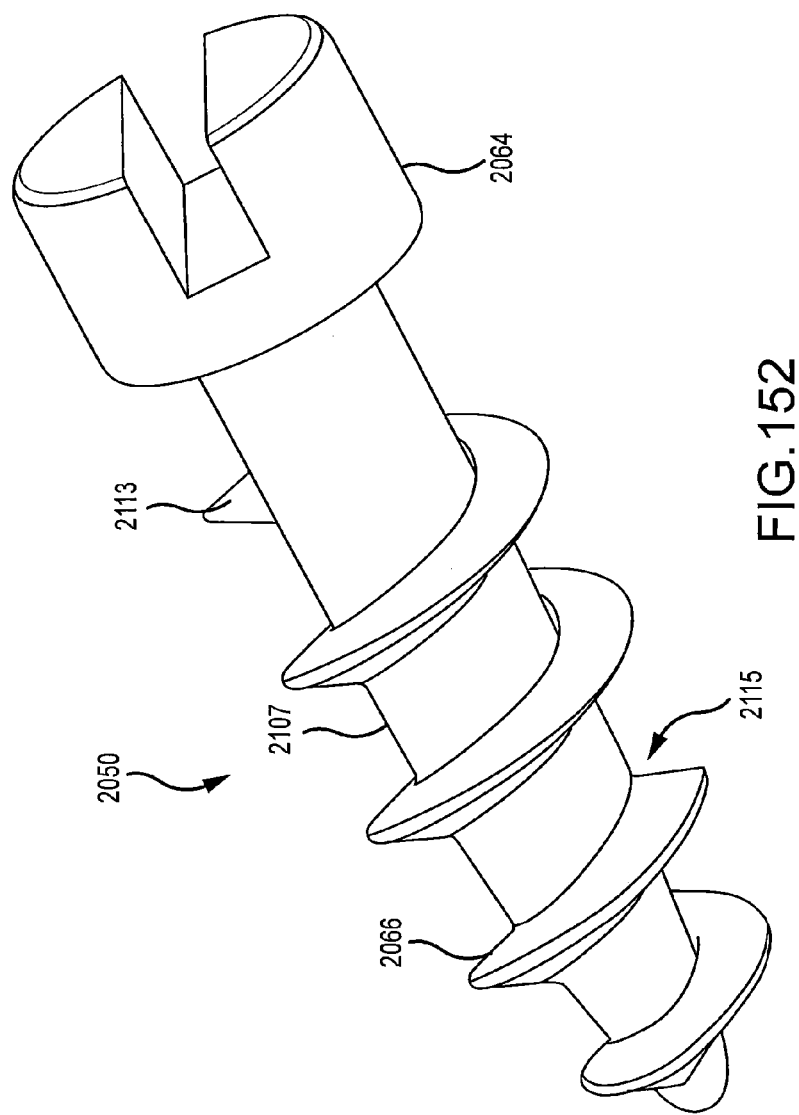

FIG. 152 is a perspective view of an implant distractor, according to certain embodiments.

Figure 153:
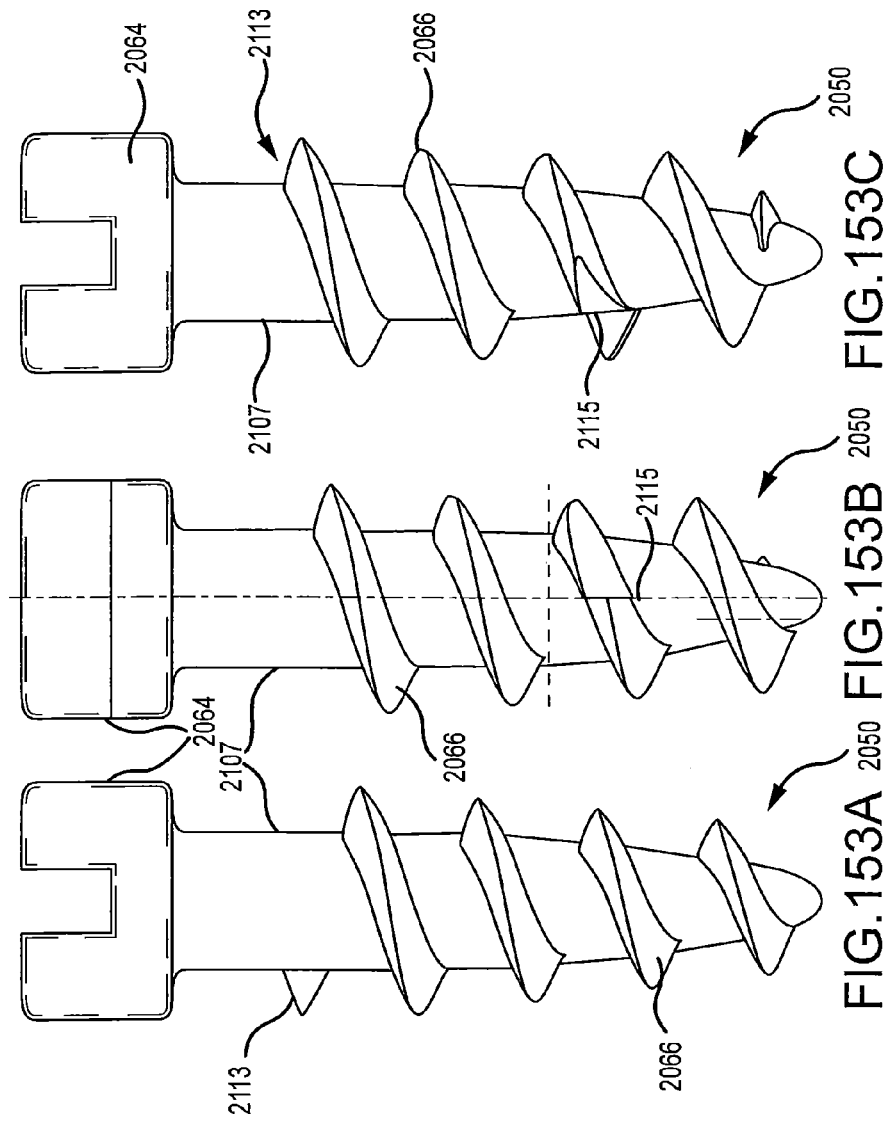

FIG. 153A-C are several side views thereof.

Figure 154:
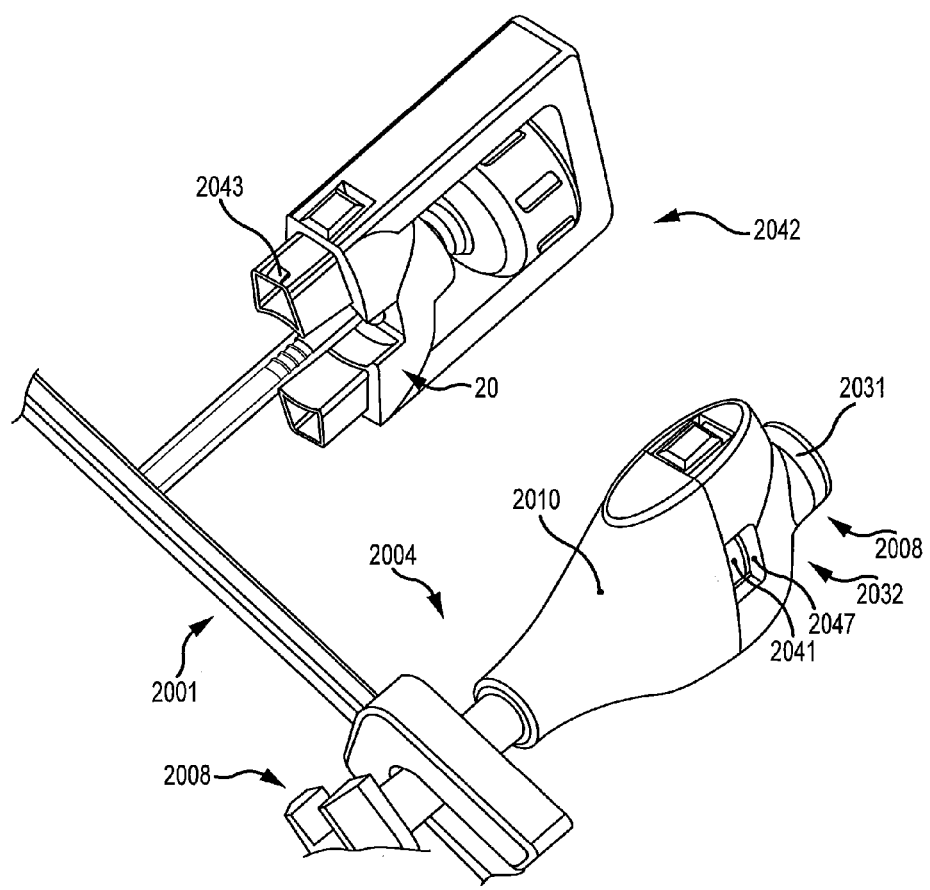

FIG. 154 is a perspective view of several handles and their engaging features for engaging with the receiving assembly of the delivery device of the tool of FIG. 136.

Figure 155:
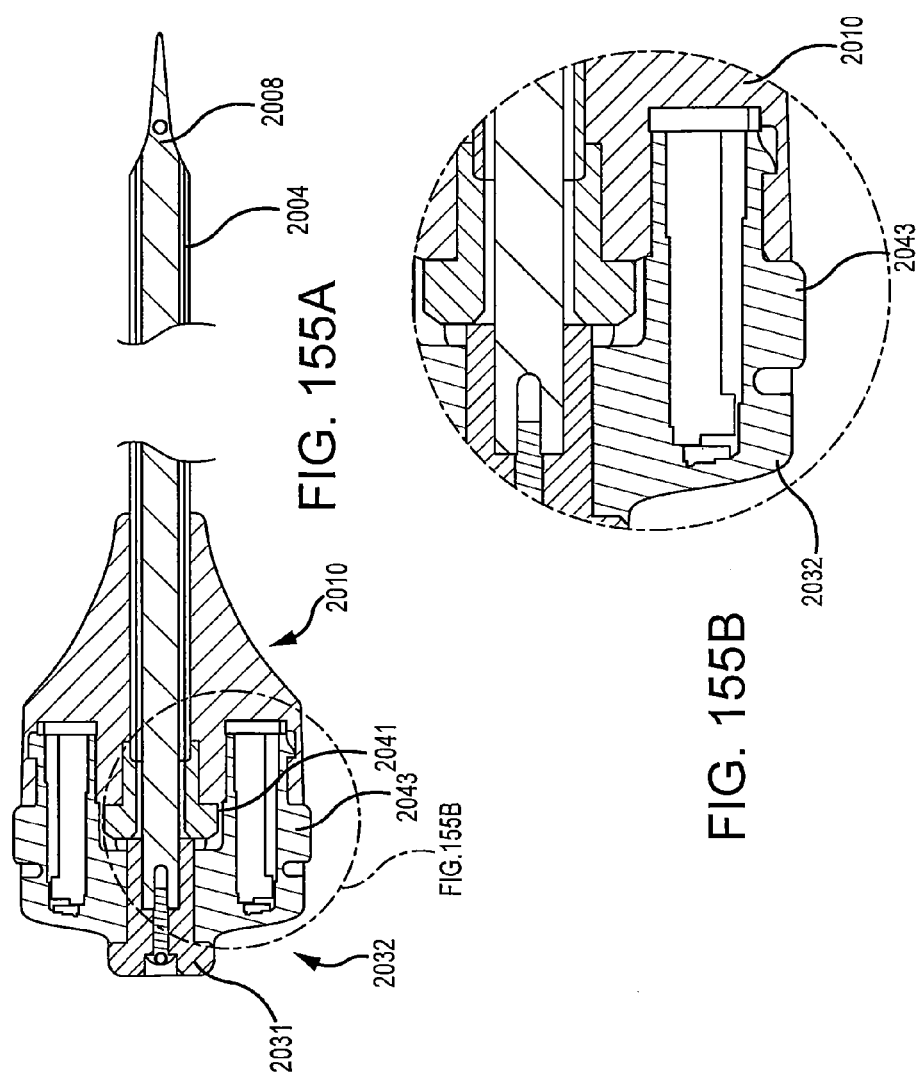

FIG. 155A-B include a cross-sectional view and close-up view thereof.

Figure 156:
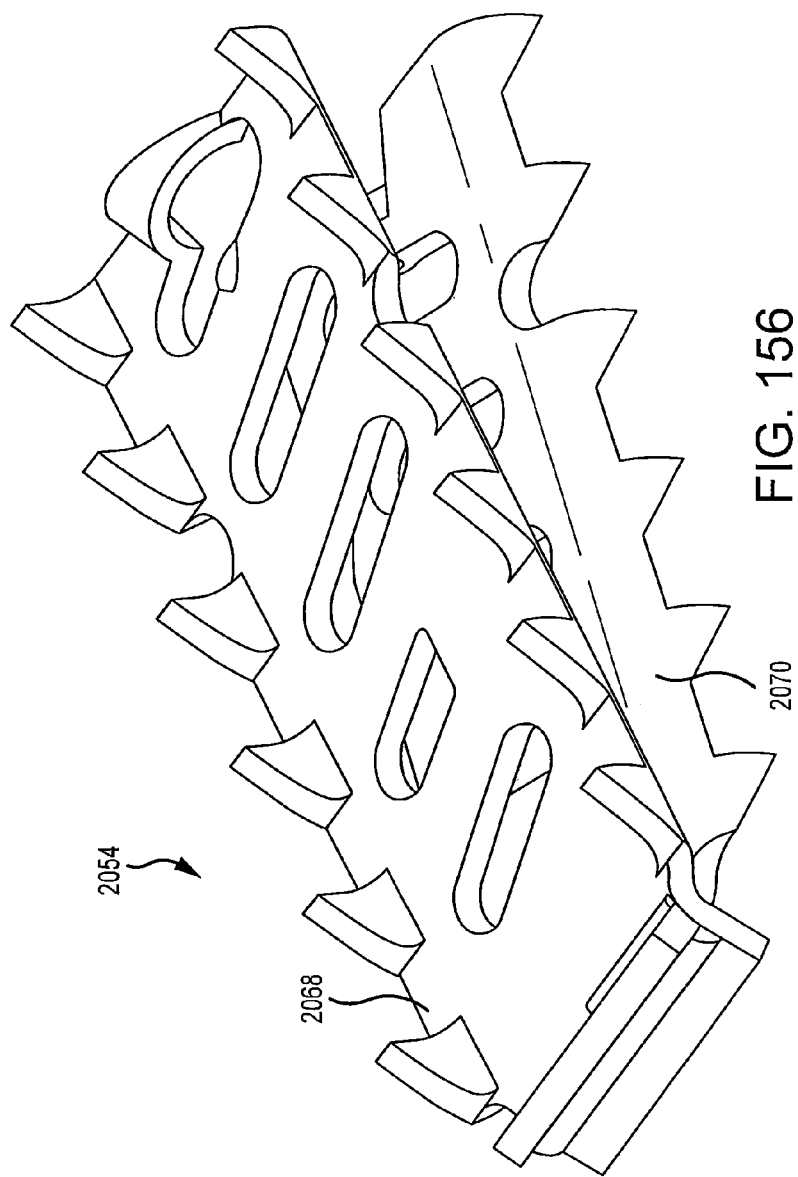

FIG. 156 is a perspective view of an implant according to certain embodiments.

FIG. 157-161B include several perspective views thereof including the relationship of the implant to a facet joint.

Figure 162:
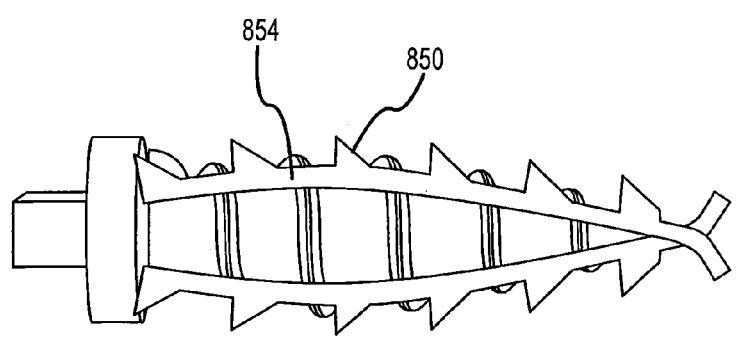

FIG. 162 is a side view of a mechanically tested implant, according to certain embodiments.

FIG. 163 is a table of exemplary dimensions of an implant.

FIG. 164 is a table of exemplary dimensions of a delivery device.

FIG. 165 is a table of exemplary dimensions of an implant distractor.

FIG. 166 is a table of exemplary dimensions of a chisel.

FIG. 167 is a table of exemplary dimensions of a place holding chisel.

FIG. 168 is a table of exemplary dimensions of a driver assembly.

FIG. 169 is a table of exemplary dimensions of a decorticator.

FIG. 170 is a table of exemplary dimensions of a malleting tool.

Figure 171:
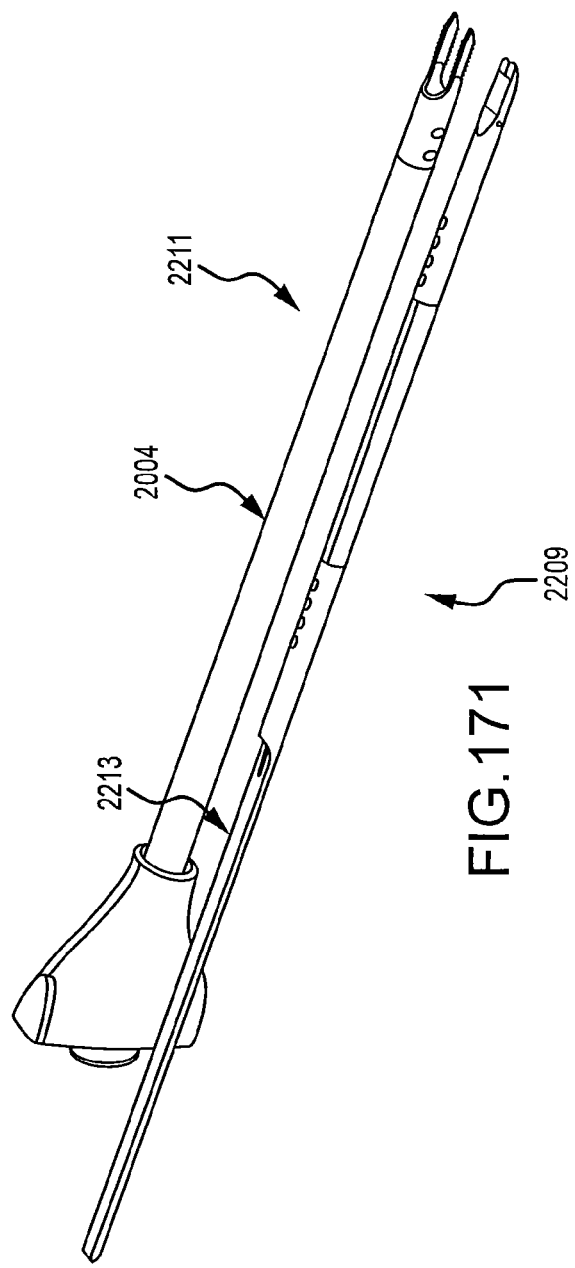

FIG. 171 is a perspective view of a chisel according to certain embodiments.

Figure 172:
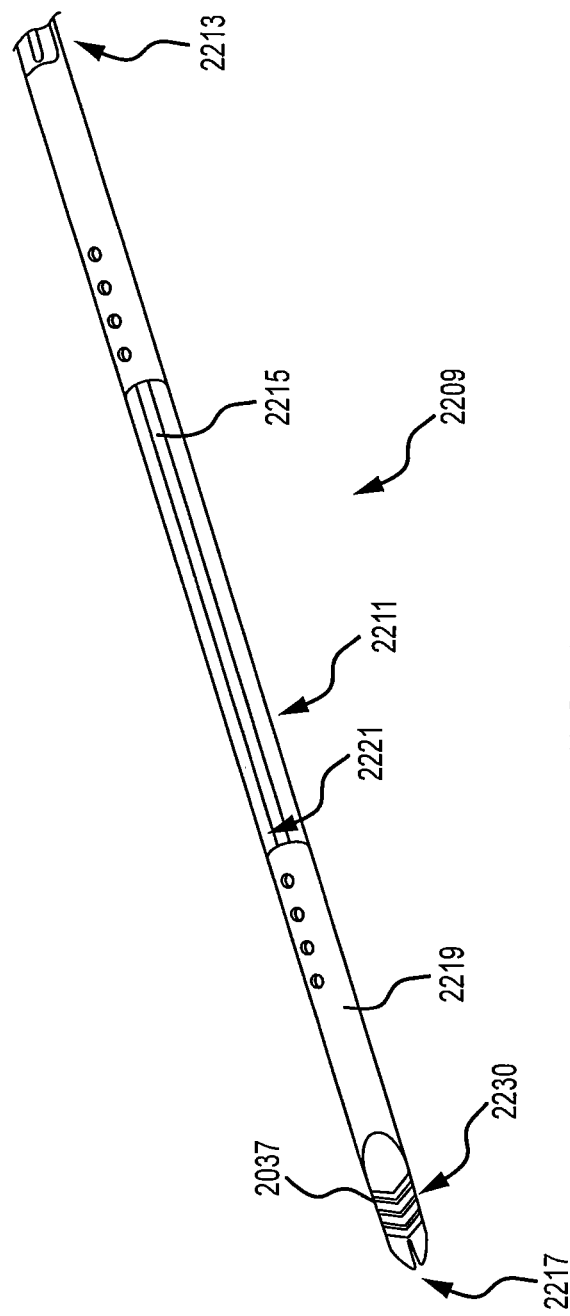

FIG. 172 is a top perspective view of a distal portion thereof.

Figure 173:
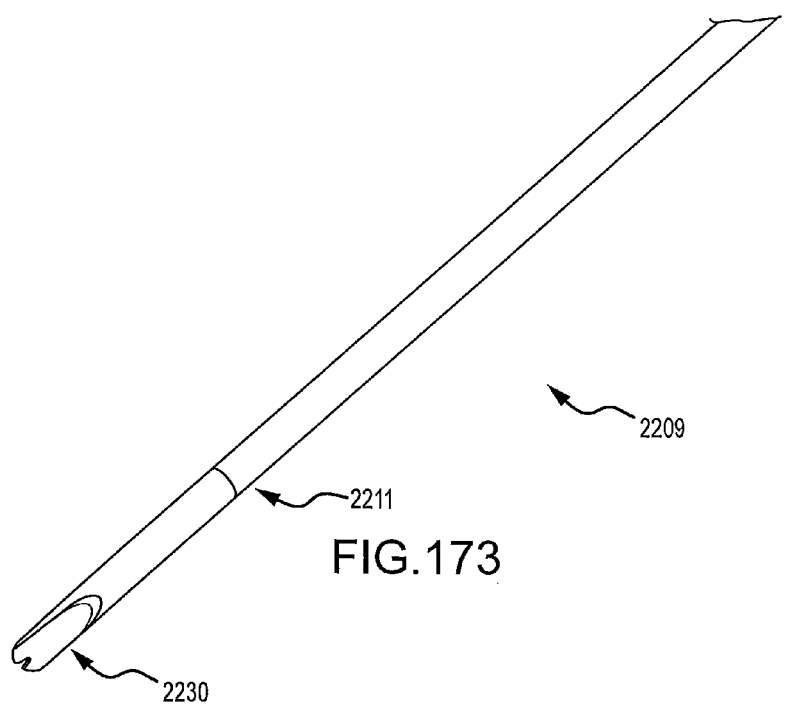

FIG. 173 is a bottom perspective view of a distal portion thereof.

Figure 174:
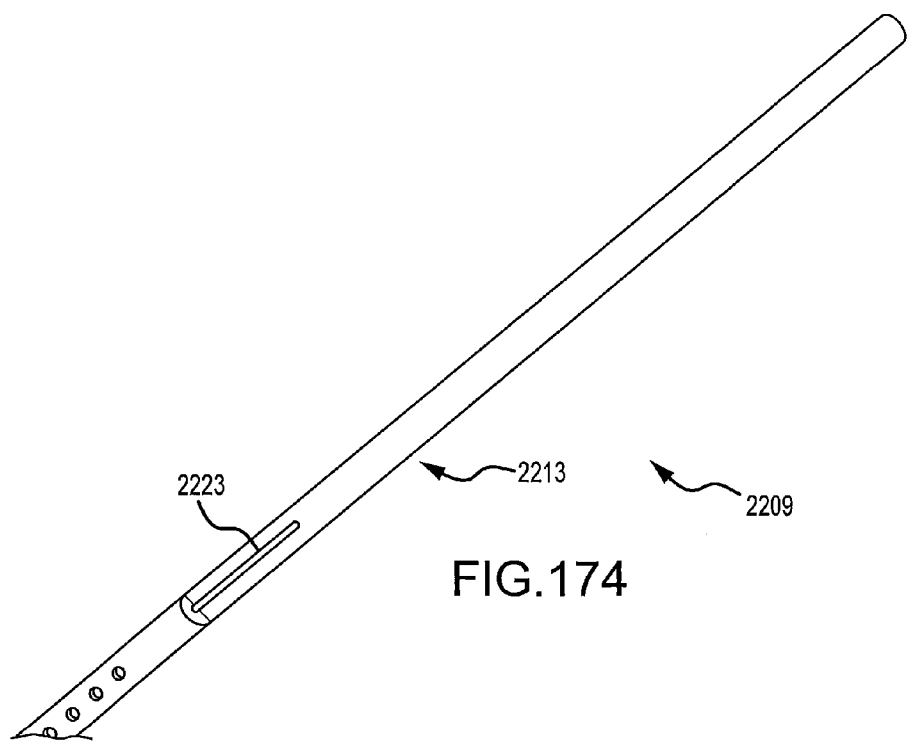

FIG. 174 is a perspective view of a proximal portion thereof.

Figure 175:
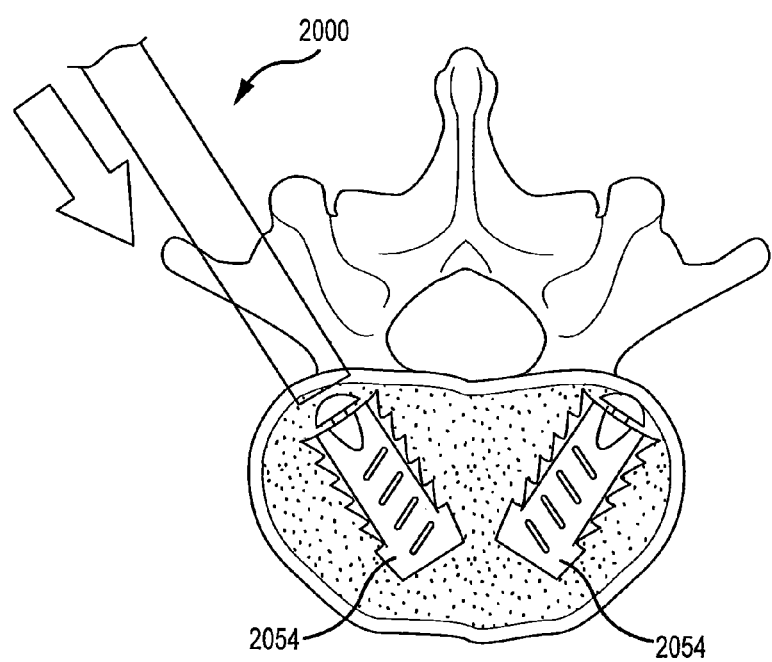

FIG. 175 is a top view of implants positioned in a joint between two vertebral bodies.

Figure 176:
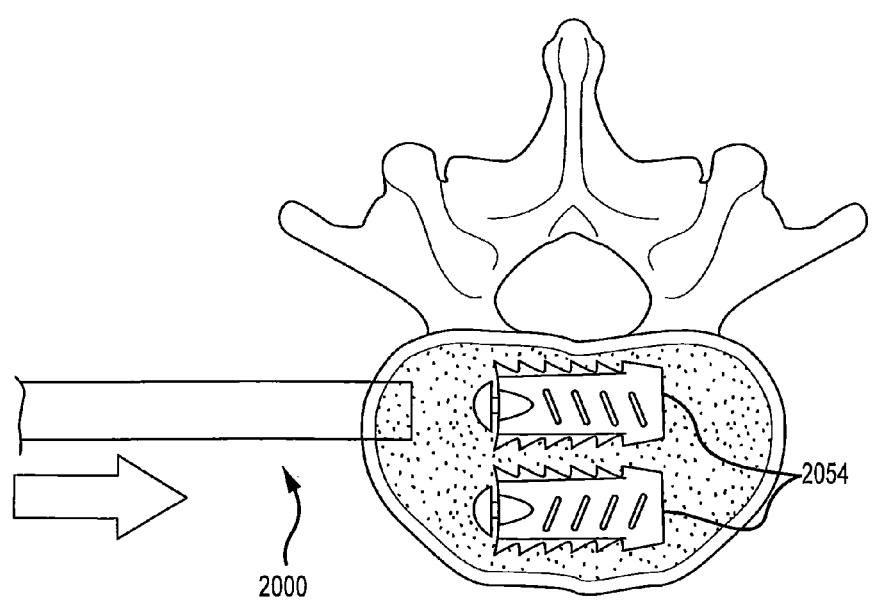

FIG. 176 is another top view of implants positioned in a joint between two vertebral bodies.

Figure 177:
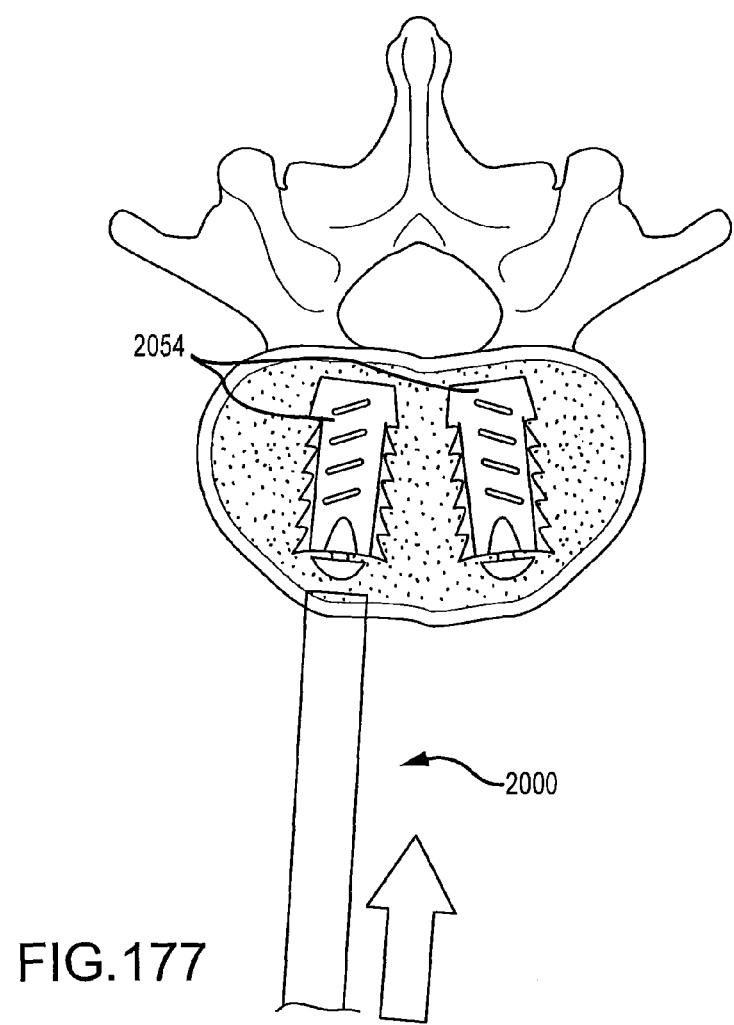

FIG. 177 is yet another top view of implants positioned in a joint between two vertebral bodies.

FIGS. 178-185 depict several methods according to certain embodiments.

DETAILED DESCRIPTION OF THE INVENTION

The following description generally relates to devices and methods for treating spinal stenosis. Spinal stenosis reflects a narrowing of one or more areas of the spine often in the upper or lower back. This narrowing can put pressure on the spinal cord or on the nerves that branch out from the compressed areas. Individual vertebrae of the spine are positioned relative to each other and their separation is maintained by discs separating main vertebral bodies and by capsules positioned within facet joints. The discs and capsules are separated from the bone of their respective joints by cartilage. Spinal stenosis is often indicative of degeneration of a disc, a capsule, or the cartilage in a joint, which leads to a compression of the joints and the narrowing mentioned.

As such, the following detailed description includes discussion of a device for distracting a facet joint of the spine to remedy this condition. The device may include a tool and an implant for distracting and maintaining the distracted position of the joint. Several embodiments of an implant are described in addition to several embodiments of a tool. In addition, several embodiments are described where the implant and the tool work together to distract the facet joint and thereafter leave the implant behind to maintain the distraction of the joint. In short, the device may be adapted to access a facet joint by inserting a delivery tool and an implant, forcibly separate the associated articular surfaces with the tool, the implant, or both, and leave the implant in place to maintain the separation of the articular surfaces. This approach may allow for maintaining the distraction of the joint, thereby relieving symptoms associated with spinal stenosis.

The present application hereby incorporates the following U.S. patent applications by reference herein in their entireties: U.S. patent application Ser. No. 11/618,619, which was filed on Dec. 29, 2006 and is entitled Cervical Distraction Device; U.S. Provisional Patent Application No. 61/020,082, which was filed on Jan. 9, 2008 and is entitled Methods and Apparatus for Accessing and Treating the Facet Joint; U.S. Provisional Application No. 61/059,723, which was filed on Jun. 6, 2008 and is entitled Spine Distraction Device; U.S. Provisional Application No. 61/097,103, which was filed on Sep. 15, 2008 and is entitled Cervical Distraction/Implant Delivery Device; U.S. Provisional Application No. 61/109,776, which was filed on Oct. 30, 2008 and is entitled Facet Joint Implants; U.S. Non-provisional application Ser. No. 12/317,682, which was filed on Dec. 23, 2008 and is entitled Facet Joint Implants and Delivery Tools; U.S. Non-provisional application Ser. No. 12/350,609, which was filed on Jan. 8, 2009 and is entitled Method and Apparatus for Accessing and Treating the Facet Joint; U.S. Provisional Application 61/169,601, which was filed on Apr. 15, 2009 and is entitled Facet Joint Implants and Delivery Tools; U.S. Non-provisional application Ser. No. 12/455,814, which was filed on Jun. 5, 2009 and is entitled Facet Joint Implants and Delivery Tools; and U.S. Non-provisional application Ser. No. 12/559,193, which was filed on Sep. 14, 2009 and is entitled Cervical Distraction/Implant Delivery Device.

Referring now to FIGS. 1-28, a first embodiment of a tool and an implant is shown. FIG. 1 shows the tool 100 in position posterior to the spine 102. The tool 100 includes a delivery device 104, a decorticator 106, and a chisel 108.

The delivery device 104 may include a receiving assembly 110 at a proximal end, anchoring forks 112 at a distal end, and a generally tubular shaft 114 defining a longitudinal axis and extending between the receiving assembly 110 and the anchoring forks 112. The tubular shaft 114 may have an annular shaped cross-section with an inner radius and an outer radius, where the difference between the two radii defines a thickness of the tubular shaft 114.

The receiving assembly 110 of the delivery device 104 may have a generally conical outer surface defining a generally hollow volume or solid mass. The conical outer surface may have a longitudinal axis that coincides with that of the tubular shaft 114. The conical outer surface may be defined by a first radius at a proximal end and a second radius at a distal end. Where the tubular shaft 114 and the receiving assembly 110 are manufactured as one piece, the second radius may match the outer radius of the tubular shaft. Alternatively, the distal end of the receiving assembly 110 may be adapted for a press fit over the proximal end of the tubular shaft 114. The receiving assembly 110 may also include a longitudinally extending bore 116 having an inner radius matching that of the tubular shaft 114 or may have a conically shaped inner surface leading to the tubular shaft 114. The receiving assembly 110 may also include a relatively thin annular ring 118 offset from its distal end by two relatively thin extension elements 120. The space between the proximal end of the conical portion of the receiving assembly 110 and the distal end of the annular ring 118 may define an access opening 122.

In another embodiment as shown in FIGS. 6A-6C, a receiving assembly 111 may not include the annular ring 118 and the extension elements 120, but may remain generally conical and may include the longitudinally extending bore 116. In addition, near the proximal end of the receiving assembly 111, seating recesses 119 may be included. These recesses 119 may be positioned on opposing sides of the bore 116 and may recess into the proximal end of the receiving assembly 111 and the inner surface of the bore 116. These recesses may function to receive positionally matched protrusions from any one or all of the devices being inserted into the deliver device. As such, the recesses 119, may allow for orienting the devices properly relative to the forks 112 positioned in the facet joint. It is noted that any number of recesses may be provided and that any orientation may be used, either symmetrical or non-symmetrical, such that one or several orientations may be controlled. That is, an asymmetrical arrangement may allow for only one proper insertion position as opposed to the symmetrical orientation shown, which may allow for two proper insertion positions.

Figures 2, 3:
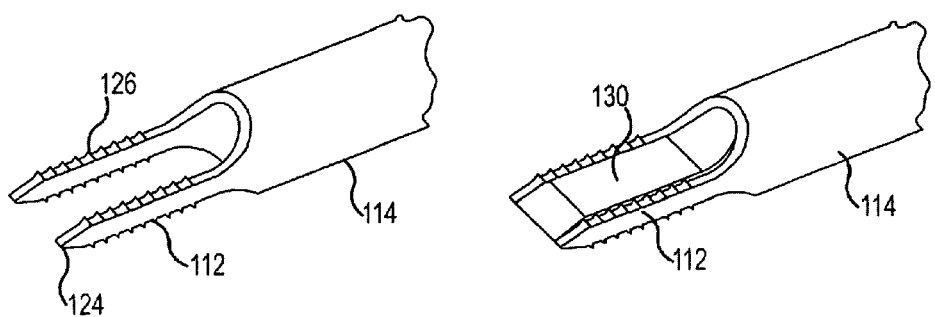
FIG. 2 is a perspective view of a distal end of a delivery device, according to certain embodiments.
FIG. 3 is a perspective view of a distal end of a delivery device with an advanced chisel, according to certain embodiments.

As shown in more detail in FIG. 2, the delivery device 104 may include two anchoring forks 112 formed by coping two opposing portions of the distal end of the tubular shaft 114. The forks 112 may have a generally V-shaped tip 124 at their distal end and may have a generally rectangular cross-section extending from the V-shaped tip 124 to the proximal end of the forks 112. The rectangular cross-section may have an inside face and an outside face where the inside face faces the longitudinal axis of the delivery device 104. The rectangular cross-section may also have opposing surfaces connecting the inside face to the outside face and completing the rectangular cross-section. At the proximal end of the forks 112, as suggested by the coping mentioned above, the cross-section may gradually change from rectangular to a shape matching that of half of the annular shape of the tubular shaft portion. The forks 112 may also include serrations or teeth along the opposing surfaces to assist with anchoring the delivery device 104.

Referring again to FIG. 1, the chisel 108 may have a generally cylindrical cross-section forming a shaft 128. The shaft 128 may have a radius substantially equal to the inner radius of the tubular shaft 114 portion of the delivery device 104 allowing for slidable insertion of the chisel 108 within the delivery device 104. The chisel 108 may include a basic single or doubly chamfered tip 130 at a distal end or may have a coped distal end. The chisel 108 may also include a head 132 at a proximal end. The head 132 may be a generally solid material and may have a generally flat distal face and a spherically shaped proximal face. The shaft 128 and tip 130 portion of the chisel 108, measured from the distal face of the head 132 to the distal end of the chamfered tip 130, may have a length substantially equal to the distance from a proximal face of the annular ring 118 of the delivery device 104 to the distal tip of the delivery device 104.

Figure 1A:
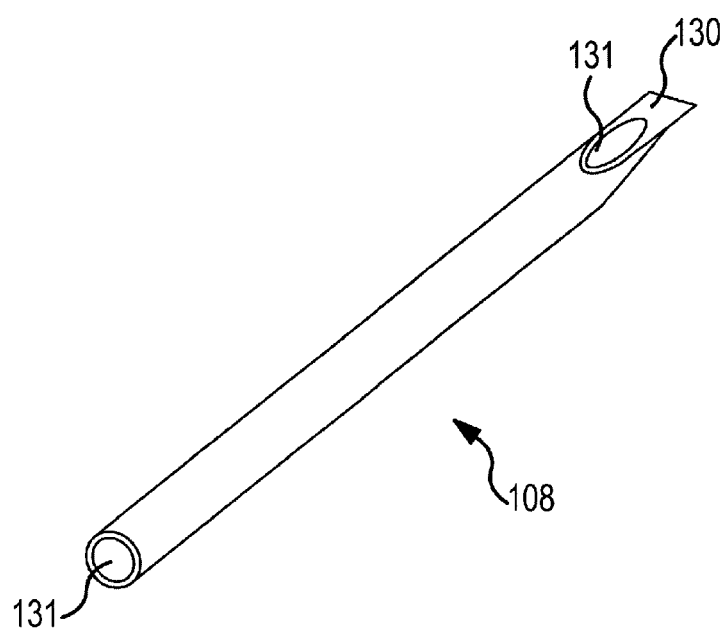
FIG. 1A is a perspective view of a chisel according to certain embodiments.

In another embodiment, the chisel 108 may include a longitudinal lumen 131 as shown in FIG. 1A. While not shown, this embodiment may also include the head 132 shown in FIG. 1 and the lumen 131 may extend there through. The lumen 131 in the chisel 108 may be used for advancing a scope along with the chisel 108 to properly place the chisel 108 and the delivery device 104. The lumen 131 may also be used to provide suction or fluid flushing to the surgical site to remove or flush debris created by inserting the serrated forks 112 of the delivery device 104 and the tip 130 of the chisel 108.

As shown in FIG. 3, the tip 130 of the chisel 108 may have a coped shaped similar to that of the forks 112 of delivery device 104. In this condition, the tip 130 may include a generally V-shaped distal end matching that of the forks 112. The tip 130 may have a width substantially equal to twice the inner radius of the tubular shaft 114 of the delivery device 104 such that the tip 130 extends between the two inside faces of the forks 112.

Figure 4:
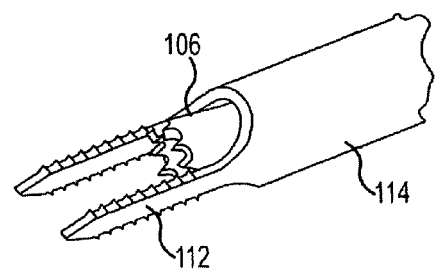
FIG. 4 is a perspective view of a distal end of a delivery device with an advanced internal decorticator, according to certain embodiments.

Referring again to FIG. 1, the decorticator 106 may have a tubular shaft 134 portion, an abrasive distal end 136, and a handle 138 at a proximal end. The tubular shaft 134 may have an inner radius substantially equal to the outer radius of the tubular shaft 114 of the delivery device 104 and may allow for sliding movement of the decorticator 106 along the length of the delivery device 104 and rotationally around the delivery device 104. The abrasive distal end 136 may include serrated teeth as shown, or may include a more flat annular surface with a gritty surface. The handle 138 may have a generally cylindrical portion with randomly or patterned raised portions or recesses adapted to assist gripping the handle. The proximal and distal ends of the handle 138 may be generally spherical. It is noted that the decorticator 106 may alternatively be separate from the delivery device 104 and may be slidably inserted within the delivery device 104 as shown in FIG. 4. In this embodiment, the decorticator 106 may be inserted, advanced to the implantation site, and rotated similar to the decorticator 106 described above to roughen the bone surface.

In still another embodiment, a decorticator 106 may take the form of a relatively sharp pick, as shown in FIG. 6A-6C. As shown in FIG. 6A, the decorticator 106 may include a control handle 139 for advancing and pivoting the device. The control handle 139 may be connected to a tubular shaft 135, which may be connected to a sharp flexible tip 137. As shown, the tip 137 may be relatively thin and may have a neutral position relative to the longitudinal axis of the delivery device 104 so as to position the tip 137 within the boundary defined by the inner surface of the delivery device 104. As such, when inserted in the delivery device 104, the tip 137 may slide readily through the delivery device 104. When the decorticator 106 is advanced to the distal end of the delivery device 104, the tip 137 may be rotated and maneuvered to decorticate the surface of the lateral mass. It is noted that the shaft 135 may be relatively narrow when compared to the inner bore of the delivery device 104 to facilitate better maneuverability of the tip of the decorticator as it extends out the end of the deliver device. The decorticator may be used as shown in FIGS. 6B and 6C to rotationally scrape or longitudinally penetrate the lateral mass of a facet joint. A driving member may be used to assist the decorticating process.

Figure 5:
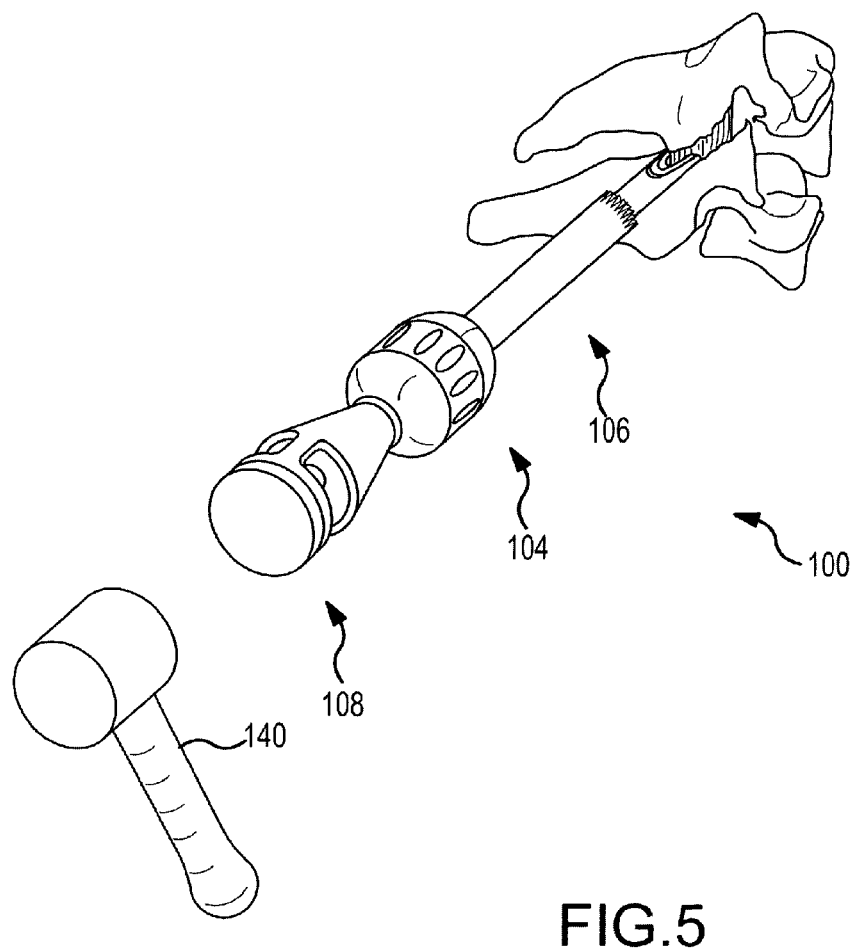
FIG. 5 is a perspective view of a delivery device and chisel positioned relative to a facet joint of a spine with a driving member positioned proximally to the chisel head, according to certain embodiments.

Referring now to FIG. 5, the tool 100 is shown with the chisel 108 fully inserted into the delivery device 104 such that the distal face of the head 132 of the chisel 108 is in abutting relationship with the annular ring 118 of the receiving assembly 110 on the delivery device 104. The distal tip 130 of the chisel 108 thus extends to the distal end of the delivery device 104. A hammer 140 is shown for use in tapping the proximal end of the chisel 108 and thus advancing the forks 112 of the delivery device 104 and the tip 130 of the chisel 108 into the facet joint. As the chisel 108 and the delivery device 104 are advanced into the joint, the forks 112 of the delivery device may channel into the fact surface and displace or remove tissue. In some embodiments, this may be removed by a suction lumen in the chisel. Once the chisel 108 and delivery device 104 are tapped into place, the chisel 108 may be removed and the serrations on the opposing surfaces of the forks 112 may aid in anchoring the delivery device 104 in the joint and preventing dislodgement.

Figure 6:
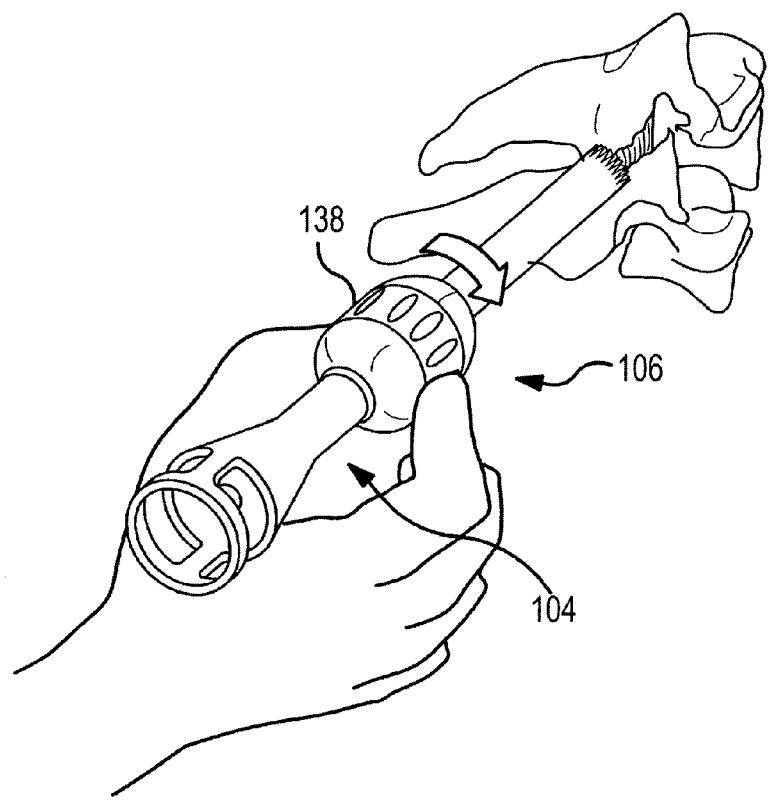
FIG. 6 is a perspective view of a delivery device with an exterior decorticator in an advanced position, according to certain embodiments.

FIG. 6 shows the decorticator 106 in an advanced position along the length of the delivery device 104 such that the distal end is in contact with the bone surfaces surrounding the facet joint. The handle 138 is being used to rotate the decorticator 106 around the perimeter of the delivery device 104 to roughen the associated bone surfaces. Alternatively, either of the internal decorticators shown in FIG. 4 or 6A-6C may be used.

Figure 7:
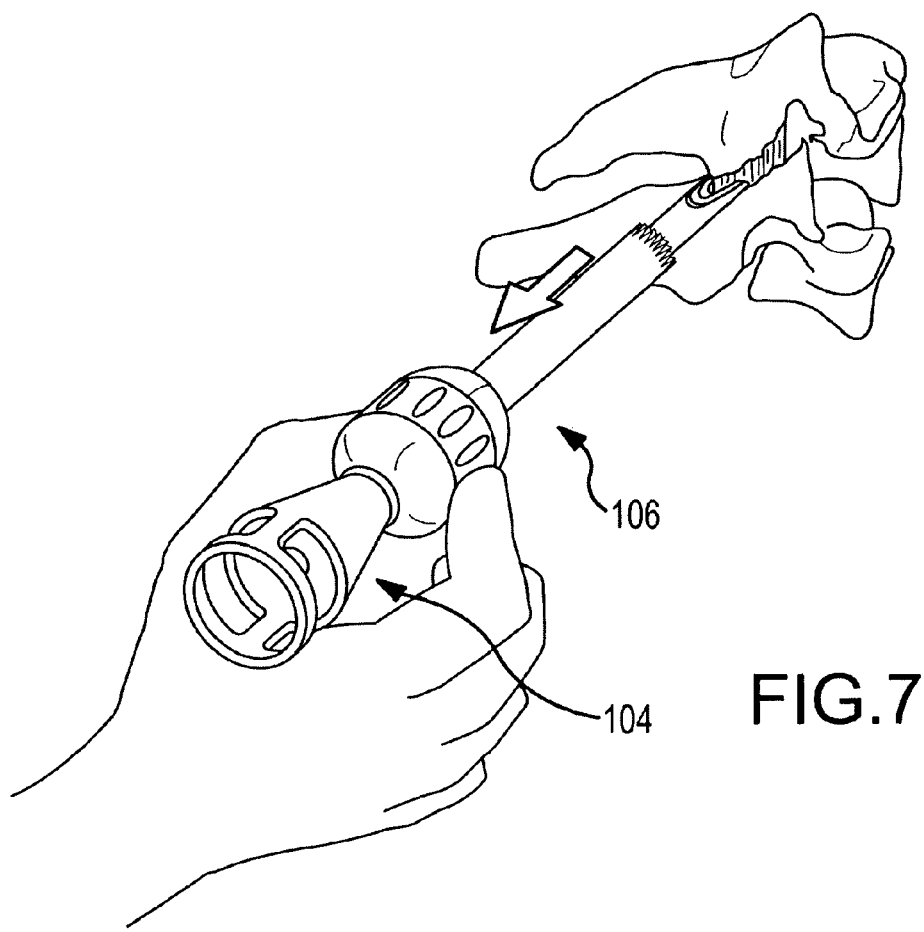
FIG. 7 is a perspective view of a delivery device with an exterior decorticator being retracted, according to certain embodiments.

FIG. 7 shows the decorticator 106 retracted and also shows the resulting roughened bone surfaces.

Referring now to FIG. 8, the tool 100, including the delivery device 104 and retracted decorticator 106, is shown lodged in a facet joint. Also shown is a driver assembly 142 portion of the tool 100. The driver assembly 142 includes a distractor knob 144, an implant shaft 146, implant holding arms 148, an implant distractor 150, and an internal actuator 152(not shown). The driver assembly 142 shown is holding an implant 154 and is poised for insertion into the delivery device 104.

Referring now to FIGS. 9-15 several views of the driver assembly 142 are shown. In FIG. 9, a portion of the delivery device 104 is shown for receiving the driver assembly 142. The distal end of the driver assembly 142 is also shown. FIG. 10 shows a close-up view of the distal end of the driver assembly 142 where the implant 154, the implant distractor 150 and the internal actuator 152 are not shown. As shown, the implant shaft 146 of the driver assembly 142 defines a longitudinal axis thereof and has a generally annular cross-section with an inner radius and an outer radius where the difference between the two radii defines the wall thickness of the shaft 146. The outer radius of the implant shaft 146 is substantially equal to the inner radius of the tubular shaft 114 of the delivery device 104. The implant shaft 146 also includes a keyway feature 156 for preventing relative rotation between the tubular shaft 114 of the delivery device 104 and the implant shaft 146 of the driver assembly 142 when inserted. As shown, the keyway feature 156 may include a pair of tabs on opposing sides of the implant shaft 146 for engaging with a corresponding longitudinal slot in the inner surface of the tubular shaft 114 of the delivery device 104. In another embodiment, this keyway feature 156 may be in the form of a longitudinal slot in the outer surface of the implant shaft 146 of the driver assembly 142, as shown in FIG. 11, which may receive an internal ridge, tab, or other protrusion from the inner surface of the tubular shaft 114 of the delivery device 104.

With continued reference to FIG. 10, two arms 148 are shown extending from the distal end of the implant shaft 146. The arms 148 may be formed by coping opposing surfaces of the implant shaft 146. As shown, the arms 148 have a generally rectangular cross-section with an inside face facing the longitudinal axis of the implant shaft 146 and an opposite outside face. The inside and outside faces of the cross-section are connected by two opposing faces. The arms 148 may include an engagement feature 158 at a distal end for engaging an implant 154. As shown, the engagement feature 158 may include a generally rectangular element positioned orthogonal to the arms 148 and flush with the outside face of the arms. As shown in FIG. 9, the implant 154 may slide over the distal end of the arms 148 and may include a receiving feature 160 for receiving the engagement feature 158 of each of the arms 148.

Referring now to FIG. 11, another embodiment of the arms 148 is shown in relation to an implant 154. In this embodiment, the arms 148 may still be formed by coping opposing surfaces of the implant shaft 146. In this embodiment, the outside face of the arm 148 may be a continuation of the outside surface of the implant shaft 146. However, the inside face of the arm 148 is more detailed than that of the embodiment shown in FIG. 10. That is, as shown in FIG. 11, the inside surface may include a longitudinal ridge 162 extending the length of the arm 148. The arm 148 may also include a bull nose engagement feature 158 extending transverse to the longitudinal axis of the implant shaft 146 along the inside face of the arm 148. As shown in FIG. 12, where the arms 148 are engaged with and holding the implant 154, the longitudinal ridges 162 of each arm 148 are positioned between upper and lower planar members of the implant 154 and the bull nose engagement features 158 are positioned in the U-shaped receiving feature slots 160 on the lateral edges of the implant 154.

The implant distractor 150 is shown in FIG. 9 and a close-up view is shown in FIG. 14. The implant distractor 150 may be a generally narrow conical element tapered to a point at a distal end. At a proximal end, the implant distractor 150 is shown to include an extruded hexagon shape 164. In the present embodiment, the outer surface of the implant distractor 150 includes a continuous coil-shaped thread feature 166. The implant distractor 150 is shown positioned proximal to the implant 154 and engaged by the internal actuator 152. Those of skill in the art will understand and appreciate that the implant distractor 150 may take on a variety of shapes and sizes other than that shown in the present embodiment. For example, the implant distractor 150 may be a triangular shaped wedge, a generally conical shape without threads, or other shape adapted to cause separation and distraction of a facet joint.

Referring again to FIG. 9, the internal actuator 152 is visible extending from the distal end of the implant shaft 146. The internal actuator 152 generally includes a longitudinal shaft positioned within the driver assembly 142. The internal actuator 152 may have a radius substantially equal to the inner radius of the driver assembly 142 and may be adapted for slidable longitudinal and rotational movement relative to the driver assembly 142. The internal actuator 152 may be moved relative to the implant shaft 146 longitudinally, rotationally, or both via the distractor knob 144 and may cause a corresponding motion of the implant distractor 150. As such, the internal actuator 152 may advance the implant distractor 150 into the implant 154 thus expanding the implant 154 in the joint causing distraction of the joint. The distal end of the internal actuator 152 may include a hex driver type tip as most clearly shown in FIG. 15 for engaging the extruded hexagonal shaped proximal end of the implant distractor 150. Those skilled in the art will understand and appreciate that several driving engagements are known in the art including flat screwdriver types, phillips head types, square drive, etc. and that these are within the scope of the invention.

In one embodiment, when the driver assembly 142 is inserted, it may carry the internal actuator 152, the implant distractor 150, as well as the implant 154 with it. However, to properly position the driver assembly 142 and the implant 154, some force may be required via a mallet or other member driving member. In this embodiment, the internal actuator 152 may be slightly isolated from the driver assembly 142, so as to avoid advancing the internal actuator 152, and thus the implant distractor 150, when forcing the driver assembly 142 into the joint. This isolation may help to avoid inadvertently advancing the internal actuator 152 and the implant distractor 150, thus avoiding inadvertent distration prior to proper placement. The isolation of the internal actuator 152 from the driver assembly may take the form of a loosely fitting threaded engagement between the driver assembly 142 and the internal actuator 152. Alternatively, this isolation may be in the form of a clip between the two features.

For a detailed discussion of an implant 154 according to certain embodiments, reference is now made to FIGS. 16-24.

Figure 16:
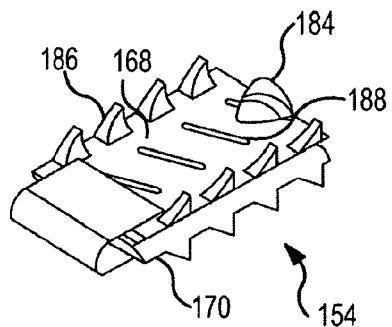
FIG. 16 is a perspective view of an implant according to certain embodiments.
Figure 16A:
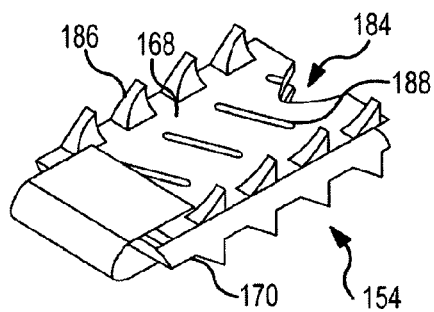
FIG. 16A is a perspective view of an implant showing a guide feature, according to certain embodiments.
Figure 16B:
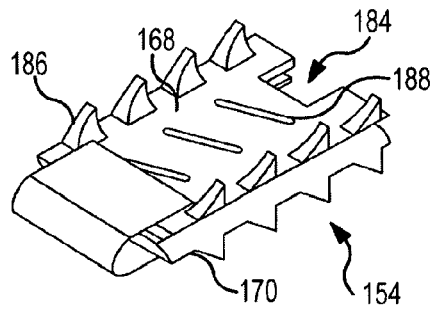
FIG. 16B is a perspective view of an implant showing a guide feature, according to certain embodiments.
Figure 17:
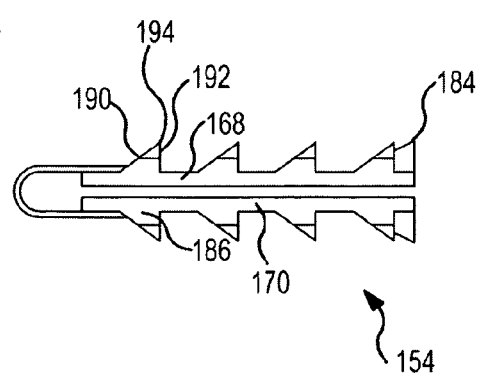
FIG. 17 is a side view of an implant according to certain embodiments.
Figure 18:
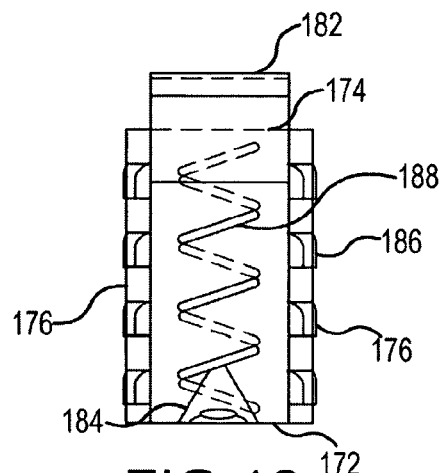
FIG. 18 is a top view of an implant according to certain embodiments.
Figure 18A:
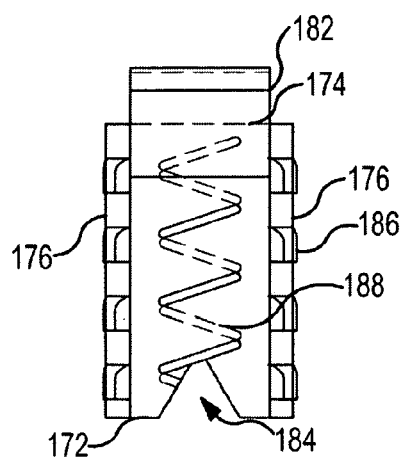
FIG. 18A is a top view of an implant showing the guide feature of FIG. 16A, according to certain embodiments.
Figure 18B:
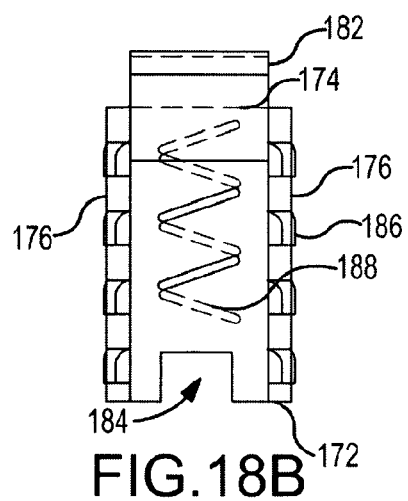
FIG. 18B is a top view of an implant showing the guide feature of FIG. 16B, according to certain embodiments.
Figure 23:
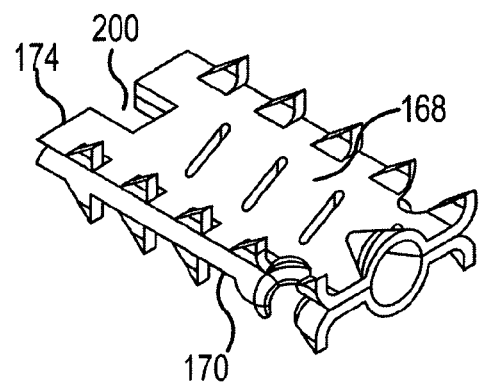
FIG. 23 is a perspective view of an implant according to certain embodiments.
Figure 23A:
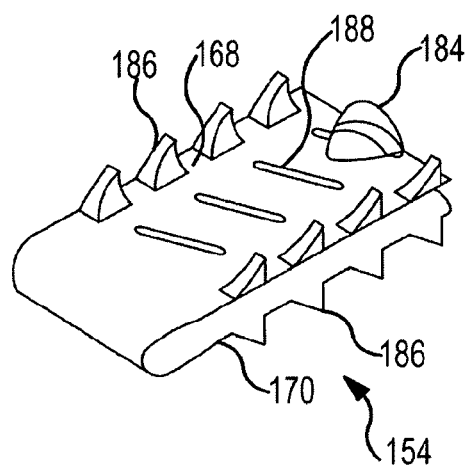
FIG. 23A is a perspective view of an implant according to certain embodiments.
Figure 24:
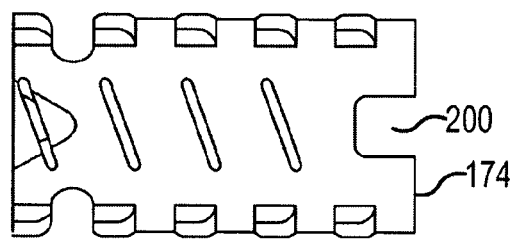
FIG. 24 is a top view of an implant according to certain embodiments.
Figure 24A:
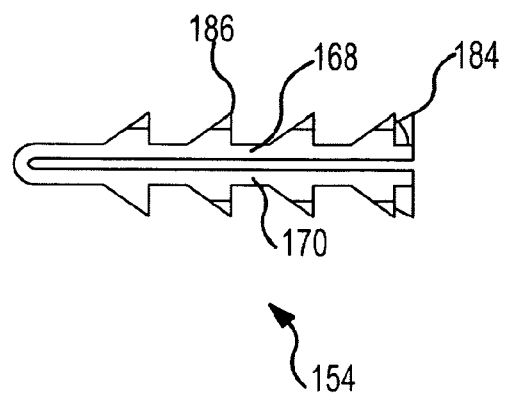
FIG. 24A is a side view of the implant shown in FIG. 23A, according to certain embodiments.

As can be understood from FIGS. 16 and 17, the implant 154 may include upper 168 and lower 170 members. The members 168, 170 may be generally planar and may also be generally rectangular. As most clearly shown in FIG. 18, each of the upper 168 and lower 170 members may include a proximal edge 172, a distal edge 174, and a pair of parallel lateral edges 176 extending longitudinally between the distal edges 174 and the proximal edges 172. The distal 174 and proximal edges 172 may be generally square edges, while the lateral edges 176 may be defined by a radiused curve. As shown in cross-section in FIG. 19, the inner surface 178 of the upper 168 and lower 170 member may be generally flat as it approaches the lateral edge 176. Gradually, the inner surface 178 departs from generally flat and follows a radiused curve until it intersects with the outer surface 180. The members 168, 170 may be joined at their respective distal edges 174 by a U-member 182 to form a leading end. Alternatively, as shown in FIGS. 23 and 24, the leading end may be formed via a weld (not shown) that couples the distal edges 174 of the planar members 168, 170 together. In yet another embodiment, the upper 168 and lower 170 members may be formed from a single plate bent to create the implant as shown in FIGS. 23A and 24A. In any or all of these embodiments, the planar members 168, 170 may be biased by the leading end to be generally parallel to each other, the inner faces 178 of the planar members 168, 170 facing each other in an opposed fashion and abutting or nearly abutting each other. A guide feature 184 may be included on each of the upper 168 and lower 170 members as well as teeth 186 projecting outwardly from the outer faces 180 of the members 168, 170. The receiving features 160 mentioned above with respect to FIGS. 11 and 12 may also be included. Threaded slots 188 may also be included in each planar member 168, 170 for receiving the coil-shaped thread feature 166 on the implant distractor 150.

With continued reference to FIGS. 16 and 17, the guide feature 184 may take the form of a half-conical feature and may be positioned at or near the proximal edge 172 of each of the upper 168 and lower 170 members. The half-conical feature may begin at the proximal edge 172 with the widest radius of the half-conical feature and may taper to a zero or approximately zero radius as the half-conical feature extends in the direction of the distal edge 174. Where the upper 168 and lower 170 members are in parallel position, the half conical features may oppose one another and function to receive and guide an advancing implant distractor 150. As such, like the upper 168 and lower 170 members described above, the half-conical features may also include threaded slots 188 for receiving the coil-shaped thread feature 166 on the implant distractor 150. In other embodiments, the half-conical feature may not actually be a full half cone. Instead, the proximal end of the feature may be a segment of a circle and the feature may be relatively subtle in the form of a cone segment. In another embodiment the guide feature 184 may include a V-shaped notch or a rectangular notch in the proximal end of the upper 168 and lower 170 members as shown in FIGS. 16A and 18A and FIGS. 16B and 18B respectively. Those skilled in the art will understand and appreciate that other shaped notches or elements may be positioned on proximal end of the upper 168 and lower 170 members to guide the implant distractor 150, and these elements are within the scope of the present disclosure.

Figure 19:
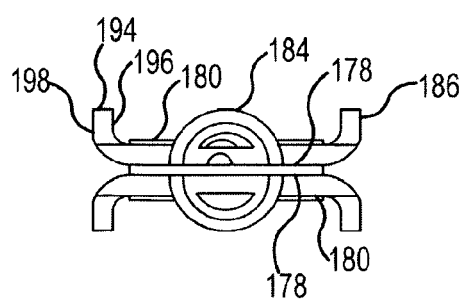
FIG. 19 is a proximal end view of an implant according to certain embodiments.

As shown, the upper 168 and lower 170 members may also each include teeth 186 projecting outwardly (e.g. a direction opposite the position of the other upper or lower member) from the outer surfaces 180 of the upper 168 and lower 170 members. As shown in FIG. 17, the teeth 186 may be equally spaced along each lateral edge 176 and may have a linearly sloped distal face 190 and a proximal face 192 oriented orthogonally to its respective upper 168 or lower 170 member. The distal face 190 and proximal face 192 may intersect to form a point 194. The teeth 186 may also be bounded by opposing inside 196 and outside 198 lateral faces separated by a thickness approximately equal to the thickness of the upper 168 and lower 170 members. As shown in FIG. 19, the outside face 198 of the teeth 186 follows an extension of the radiused curve formed by the inner surface 178 of the upper 168 or lower 170 member at the lateral edge 176, this curve being referred to as a first radiused curve. Additionally, the inside face 196 of the teeth 186 follows a second radiused curve offset from the first radiused curve, such that the teeth 186 have a generally constant thickness from the location where they depart from the outer surface 180 of the upper 168 or lower 170 member to the point 194. The radiused shape of the teeth 186 allows the implant 154 to slidably engage the inside of the delivery device 104 when it is advanced toward the implantation site. Those skilled in the art will understand and appreciate that one, as opposed to both, of the upper 168 and lower 170 members may include teeth 186 to facilitate freedom of motion of the facet joint once the implant 154 is in place.

Figure 20:
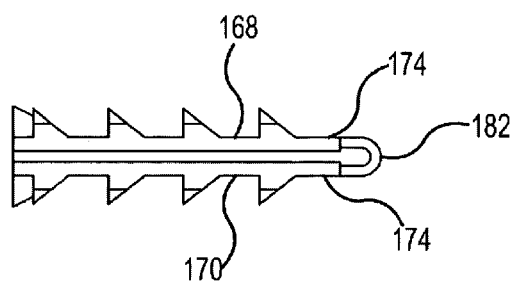
FIG. 20 is a side view of an implant according to certain embodiments.
Figure 21:
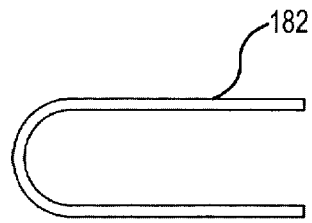
FIG. 21 is side view of a U-member according to certain embodiments.
Figure 22:
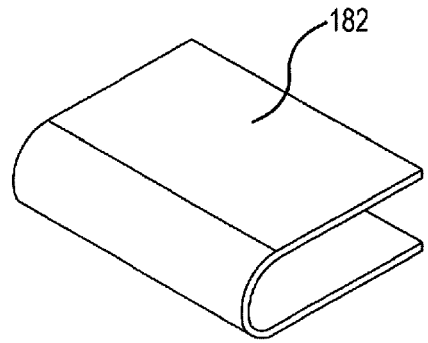
FIG. 22 is a perspective view of a U-member according to certain embodiments.

As shown in FIGS. 16 and 17, where a U-member 182 is used to connect the upper 168 and lower 170 members, the U-member 182 may overlap the upper 168 and lower 170 members. Alternatively, as shown in FIG. 20, the U-member 182 may attach to the distal ends 174 of the upper 168 and lower 170 members via a butt joint. In either case, the U-member 182 may be fastened via welding, fusing, or other techniques known in the art. As shown in FIGS. 21 and 22, the U-member 182 may be a relatively thin, generally rectangular piece of material formed into the shape of the letter 'U'. The rectangular piece of material may have a length defined by the amount of overlap of the upper member 168 and the lower member 170 in addition to the length associated with hairpin or U portion of the member 182. The width of the rectangular plate may be substantially equal to the distance between the teeth 186 of the upper 168 and lower 170 members. The U-member 182 may be adapted to provide the parallel biased position mentioned and yet allow distraction of the upper 168 and lower 170 member when a separation force is applied, the proximal edge 172 of the upper 168 and lower 170 member distracting more than the distal edge 174.

As shown in FIGS. 23 and 24, where the distal edges 174 of the upper 168 and lower 170 member are joined via welding, the distal edges 174 may include a notch to facilitate more weld length and to cause flexure to occur in the upper 168 and lower 170 members rather than in the weld itself. Also shown in FIGS. 23 and 24 are the U-shaped receiving feature slots 160 for receiving the bull nosed engagement features 158 of the arms 148 of the driver assembly 142. As shown most clearly in FIG. 24, the U-shaped receiving feature slots 160 are positioned between the equally spaced teeth 186 and extend into the lateral edges 176 of the upper 168 and lower 170 member just beyond the inside edge of where the teeth 186 begin extending from the outer surfaces 180.

The receiving feature 160 may take several forms including a rectangular notch in the lateral edge 176 of the upper 168 and lower 170 member or a U-shaped notch. The receiving feature 160 may be adapted to receive an engagement feature 158 positioned on the arm 148 of the driver assembly 142. The receiving feature 160 may be any shaped recess and may be adapted to be engaged by the engagement feature 158 so as to prevent or limit relative longitudinal motion between the arms 148 and the implant 154, when the implant 154 is in the neutral position. However, when in an expanded or distracted position, the receiving features 160 may be such that they are lifted free of the engagement feature 158 of the arms 148, thus allowing relative longitudinal motion between the driver assembly 142 and the implant 154.

Figure 25:
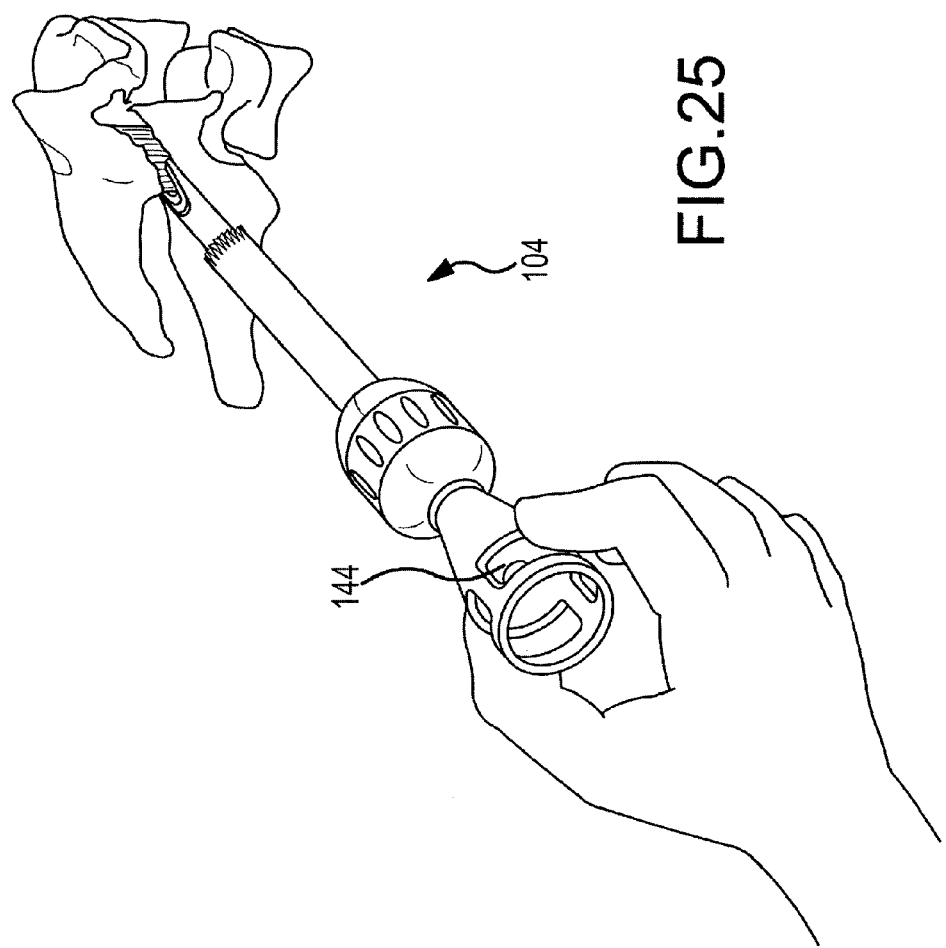
FIG. 25 is perspective view of a deliver device with a driver assembly inserted and advance, according to certain embodiments.
Figure 26:
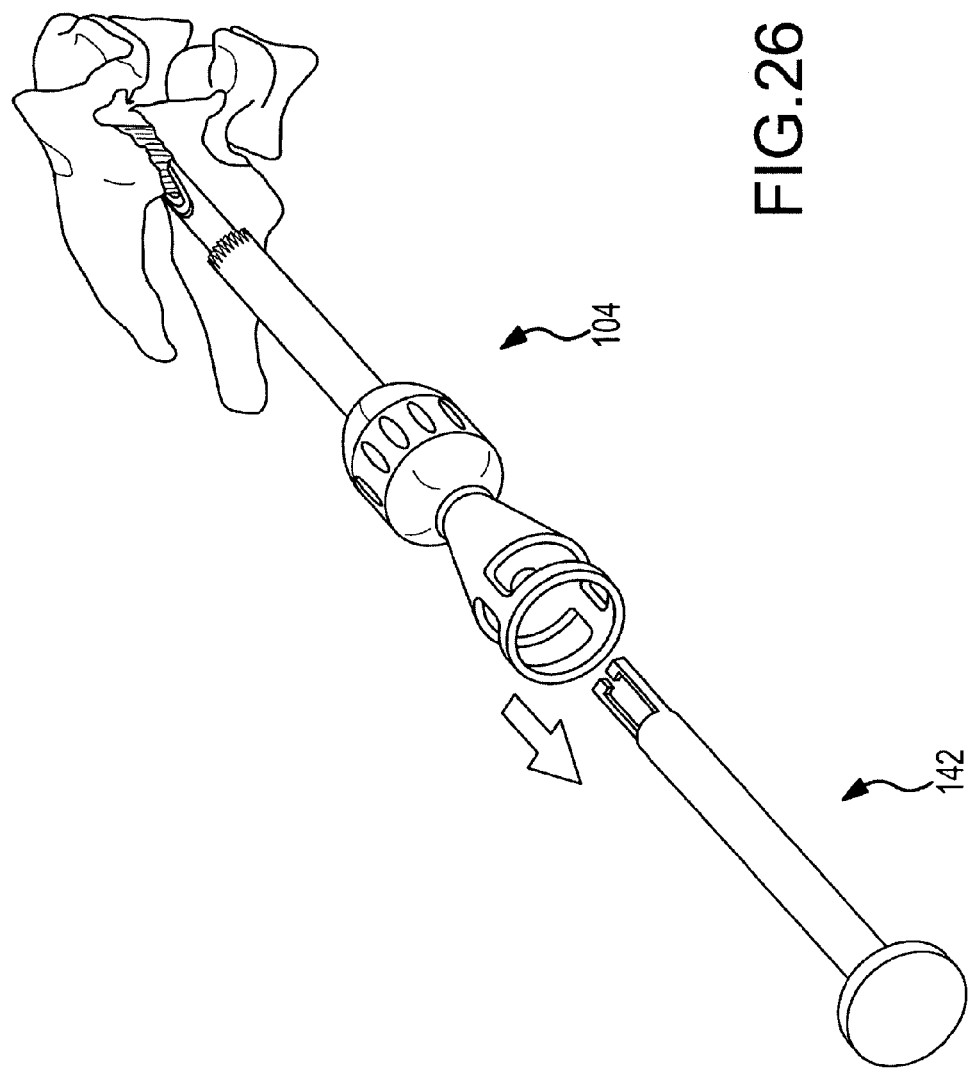
FIG. 26 is perspective view showing the removal of the driver assembly from the delivery device having left the implant behind, according to certain embodiments.

The driver assembly 142 and implant 154 described with respect to FIGS. 8-24, may be used to distract a facet joint. With the delivery device 104 positioned as shown and described with respect to FIG. 7, the implant 154 may be positioned to be held by the arms 148 of the driver assembly 142. The driver assembly 142 and implant 154 may then be inserted into the delivery device 104 and slidably advanced such that the implant 154 is positioned between the forks 112 of the delivery device 104 and within the facet joint. The advanced position of the driver assembly 142 and implant 154 within the delivery device 104 may be most clearly seen in FIG. 13. The proximal end of the driver assembly 142 may be tapped on to fully advance the driver assembly 142 and properly position the implant 154. The implant shaft 146 of the driver assembly 142 may be prevented from rotating by the keyway feature 156 securing it against relative rotation with respect to the delivery device 104. As such, once positioned, the distractor knob 144 of the driver assembly 142 may be turned, as shown in FIG. 25, thereby advancing the internal actuator 152 and further advancing the implant distractor 150. In the embodiment described, the coil-shaped thread feature 166 on the implant distractor 150 may engage the threaded slots 188 of the half-conical features 184 of the upper 168 and lower 170 members of the implant 154. As such, the implant distractor 150 may be guided and remain in position to further engage the threaded slots 188 on the upper 168 and lower 170 members. As the implant distractor 150 continues to advance, those of skill in the art will understand and appreciate that its tapered shape advancing between the upper 168 and lower 170 members will force the upper 168 and lower 170 members of the implant 154 apart causing them to pivot about a point defined by the attachment to each other at their distal ends 174. As the implant 154 continues to be distracted, the upper 168 and lower 170 members of the implant 154 are laterally separated such that they clear the engagement features 158 on the arms 148 of the driver assembly 142. As shown in FIG. 26, when the implant distractor 150 has been fully advanced and the implant 154 is in place, the driver assembly 142 may be slidably removed from the delivery device 104 leaving behind the implant distractor 150 and the implant 154.

Figure 27:
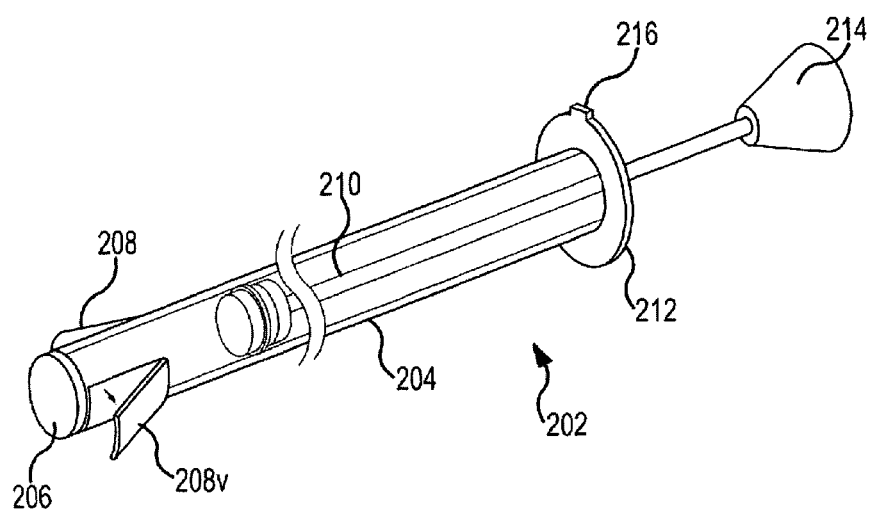
FIG. 27 is a perspective view of an injector, according to certain embodiments.

FIG. 27 shows yet another device, the device being adapted for placing bone paste over the implant 154 in the joint. An injector 202 is shown and includes a syringe type cannula 204 with a closed distal end 206 and two exit doors 208 positioned on opposite sides of the distal end 206 of the cannula 204. The cannula 204 includes a plunger 210 with a seal and further includes a stopping disc 212 at its proximal end, the plunger 210 penetrating the stopping disc 212 and having a handle 214. The cannula 204 may have an outer radius substantially equal to that of the inner radius of the delivery device 104 to allow for slidable engagement of the two devices. The disc 212 at the proximal end is generally flat and is adapted to engage the receiving assembly 110 of the delivery device 104 and provide a stop point for the injector 202 when inserted into the delivery device 104. As shown, the cannula 204 may contain a bone paste material in a liquid form.

Figure 28:
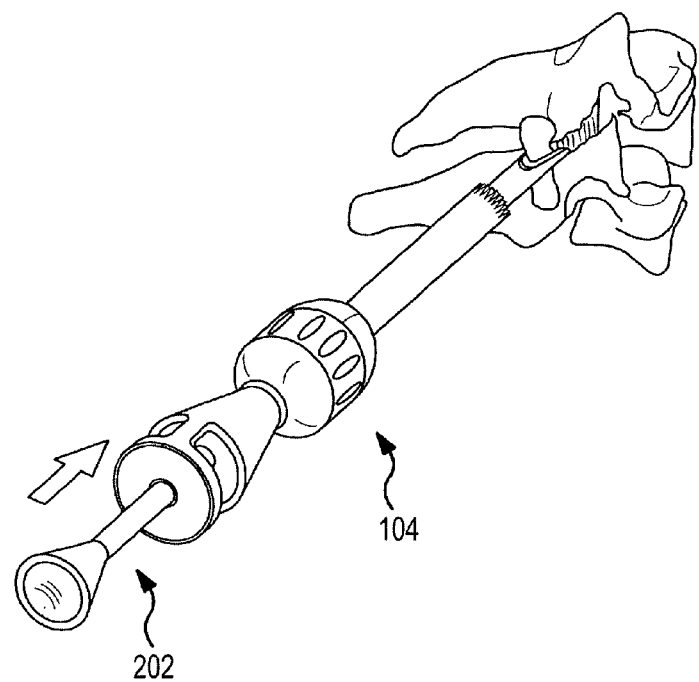
FIG. 28 is a perspective view of a delivery device with an advanced injector inserted and ejecting a material, according to certain embodiments.

As shown in FIG. 28, the injector 202 may be inserted into the delivery device 104 and slidably advanced such that the distal end 206 is near the implantation site and the disc 212 abuts the annular ring 118 of the receiving assembly 110 of the delivery device 104. The injector 202 may be rotatably positioned such that the doors 208 are positioned to open perpendicular to a line connecting the distal ends of the forks 112. The disc 212 may include tabs 216 for such positioning relative to the annular ring 118 on the receiving assembly 110. Once in position, the plunger 210 may be actuated to compress the bone paste material creating an internal pressure which forces the exit doors 208 open allowing the bone paste to escape and flow over the implantation site.

The above description has included some references to use to allow for a better understanding of the structure. Below is a more detailed discussion of that use including the devices and techniques for distracting and retaining a facet joint in a distracted and forwardly translated condition. The implantation procedure may be performed under conscious sedation in order to obtain intra-operative patient symptom feedback.

Initially an incision may be made in the patients back. Tools known in the art may be used to create this incision and to open an access path through the tissues of the back to access the spine. Once an access path is created, the chisel 108 described above may be inserted into the delivery device 104 and the two of them may be inserted through the incision and the distal tip 130 may be positioned adjacent the target facet joint. It is noted that visualization may be provided by first inserting a scope down the delivery device 104 rather than the chisel 108. Additionally, an incision in the facet joint capsule may be made prior to beginning the procedure, and thus prior to insertion of the chisel 108. Once the distal tip of the delivery device 130 is properly positioned adjacent the facet joint and any other preparation steps are completed, the chisel 108 may be inserted. Once the chisel 108 and delivery device 104 are properly positioned, the head 132 of the chisel 108 may be tapped with a driving device 140 such as a hammer or other instrument to advance the distal tip 130 of the chisel 108 and the forks 112 of the delivery device 104 into the facet joint. Once the delivery device 104 is properly positioned, the chisel 108 may be removed. At this point, the implant 154 may be placed in the driver assembly 142 and the implant 154 and driver assembly 142 may be slidably advanced through the delivery device 104. The forks 112 of the delivery device 104 may be holding the facet joint slightly distracted. As such, the implant 154, in its flat and parallel position, may slide relatively easily into the facet joint. To the extent that it does not, the proximal end of the driver assembly 142 may be tapped to properly advance and position the implant 154. Once properly positioned, the distractor knob 144 on the driver assembly may be rotated or otherwise actuated to activate the internal actuator 152. The internal actuator 152 advances the implant distractor 150 into the implant 154 and thus distracts the implant 154. It is noted here that the distraction of the implant 154 may cause the upper 168 and lower 170 member of the implant 154 to clear the engagement features 158 of the holder arms 148 thus allowing the driver assembly 142 to be freely removed from the delivery device 104 leaving the implant 154 and the implant distractor 150 behind. The injector 202 may then be advanced through the delivery device 104 and positioned to allow the doors 208 to open in a direction approximately perpendicular to the forks 112 of the delivery device 104. The handle 214 may be depressed thus advancing the plunger 210 and ejecting the bone paste or other anchoring material. The injector 202 may then be removed. The delivery device 104 may also be removed and the incision closed.

Figure 29:
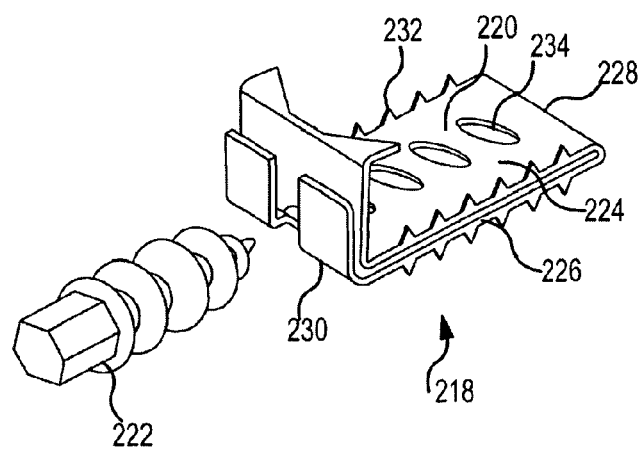
FIG. 29 is a perspective view of an implant in a collapsed position according to certain embodiments.
Figure 30:
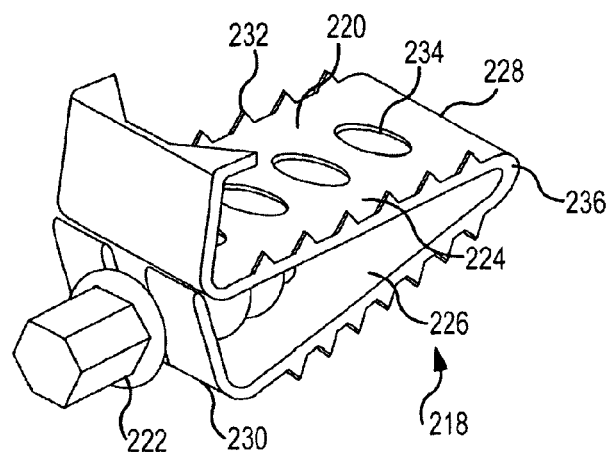
FIG. 30 is a perspective view of an expanded implant according to certain embodiments.

Those skilled in the art will understand and appreciate that several modifications or variations from the above the identified embodiments may be made while still falling within the scope and spirit of the present disclosure. For example, several alternative actuation mechanisms at the proximal end of the tool for actuating the distracting elements of the tool may be available. Additionally, several alternative implants may be available. For example, as shown in FIGS. 29 and 30, an implant 218 similar to that previously described is shown and includes a body 220 and a screw 222. The body 220 includes an upper 224 and lower 226 face joined together at a leading end 228 and separated from each other at a trailing end 230.

As shown in FIG. 29, when the screw 222 is not received in the body 220, the upper 224 and lower 226 faces may reside against each other such that the body 220 is generally flat. As shown in FIG. 30, when the screw 222 is received in the body 220, the upper 224 and lower 226 faces may be separated from each other, the degree of separation increasing as the screw 222 is increasingly received in the body 220. As the upper 224 and lower 226 faces are separated from each other, the body 220 takes on more of a wedge shape, with the leading end 228 being the narrow end of the wedge and the trailing end 230 being the wide end. The faces may include teeth 232 and the trailing end 230 of the upper face 224 may be formed to project towards the leading end, both of these features assisting in the implant 218 anchoring to the bone facet surfaces. Holes 234 may exist in the faces 224, 226 such that when the screw 222 is received in the body 220, the thread edges of the screw 222 may project through the holes 234 to bite into the facet surfaces. The wedge shape of the implant 218 may facilitate anchoring the implant 218 within the facet joint and may also facilitate distraction, translation, or subluxation of the facet surfaces relative to each other.

As can be understood from FIG. 29, the collapsed and flattened body 220 may be placed between the opposing surfaces of the facet joint. The posterior or trailing end 230 of the body 220 is configured to be capable of receiving a screw, bolt, or some other inserted component 222. As indicated in FIG. 30, upon insertion of the screw, bolt, etc. 222, the body 220 begins to expand. This expansion and separation is enabled by a hinge 236 at the anterior or leading end 228 of the body 220. As the body 220 expands, sharp directional teeth, cleats, or keels 232 on the opposing (superior & inferior) surfaces or faces 224, 226 of the body 220 may become anchored in the cortical bone of the opposing facet surfaces. These teeth, cleats, or keels 232 may engage the facet surfaces and provide acute fixation of the body 220 within the facet joint. The teeth, cleats, or keels 232 may be included on only one surface 224, 226 as opposed to both surfaces 224, 226 so as to allow for a movement of the joint after placement of the implant 218.

The distraction and separation of the facet joint via the expanded implant (see FIG. 30) may increase foraminal area and reduce the symptoms associated with nerve root compression.

Figure 31:
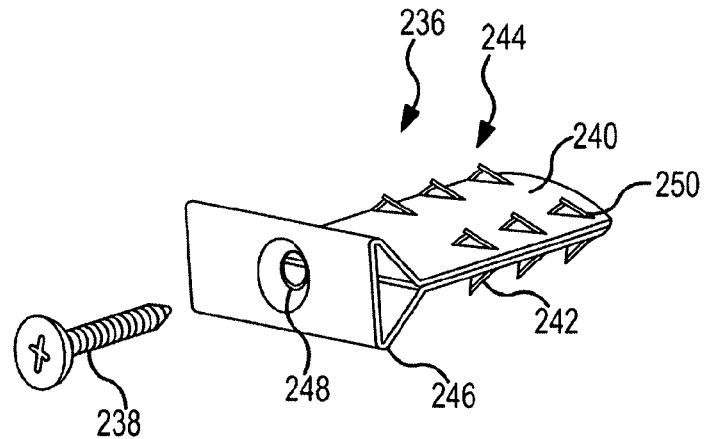
FIG. 31 is a perspective view of an implant in a collapsed position according to certain embodiments.
Figure 32:
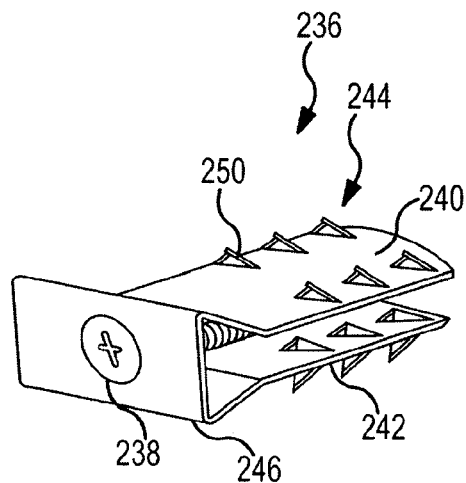
FIG. 32 is a perspective view of an expanded implant according to certain embodiments.

Another implant embodiment is depicted in FIGS. 31 and 32, wherein a screw 238 also acts to spread apart the faces 240, 242 of the body 244 of the implant 236. In this embodiment, the implant 236 may have an upper 240 and a lower 242 member positioned adjacent to each other. The upper 240 and lower 242 member may be substantially rectangular with a distal edge a proximal edge and parallel lateral edges. The distal edge may be slightly radiused. The upper 240 and lower 242 members may be connected along their distal edge by a connection member 246 in the form of a triangularly bent plate or other connection. The connection member may include a penetration 248 adapted to receive an implant distractor 238. As with the previous embodiments, the implant 236 may include teeth 250 on the outer surface of the upper member 240 or the lower member 242 or both as shown. In one embodiment, the implant 236 may be formed from a single plate and folded to create the shape shown. In use, the implant 236 may be positioned in a facet joint and the implant distractor 238 may be advanced thereby separating the upper 240 and lower 242 member and distracting the joint. Similar to that discussed above with respect to FIGS. 29 and 30, such an embodiment as depicted in FIGS. 31 and 32 may have holes (not shown in FIGS. 31 and 32) in the body surfaces 240, 242 so as to allow the threads of the implant distractor 238 to extend through the surfaces of the body 244 to bite into the facet surfaces.

Figure 33:
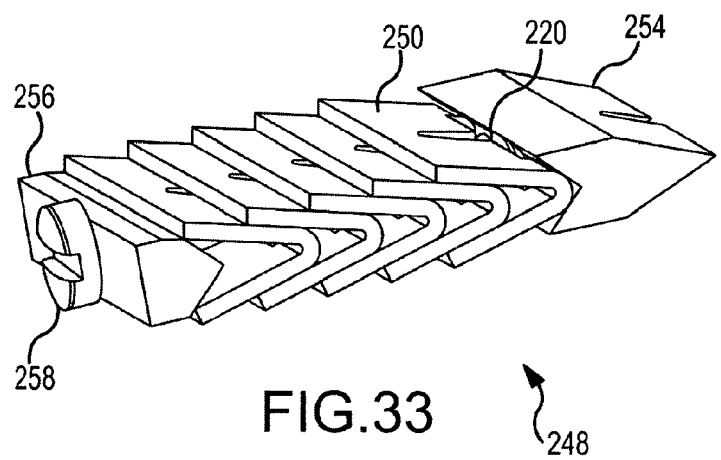
FIG. 33 is a perspective view of an implant in a collapsed position according to certain embodiments.
Figure 34:
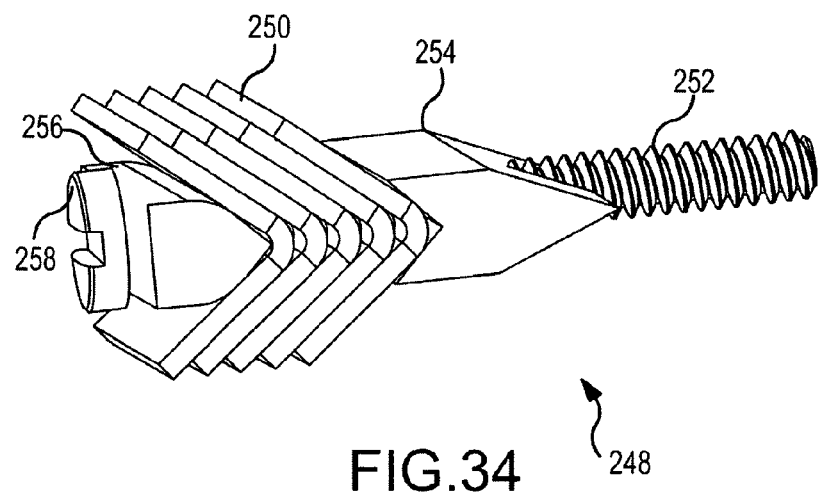
FIG. 34 is a perspective view of an expanded implant according to certain embodiments.

FIGS. 33 and 34 depict isometric views of another implant 248 with V-shaped members 250 residing on a threaded bolt 252 between an anterior threaded block 254 and a posterior non-threaded block 256. The V-shaped members 250 may slidably engage the bolt 252. As shown in FIG. 33, the V-shaped members 250 are in a non-expanded state and are spaced apart from each other along the length of the bolt 252. The implant 248 may be inserted into the facet joint in the non-expanded state depicted in FIG. 33. As can be understood from FIG. 34, the bolt 252 may be rotated to cause the anterior threaded block 254 to travel along the bolt 252 towards the posterior non-threaded block 256. It is noted that in use, the rotation of the blocks 254, 256 may be prevented by their position within a facet joint, thus causing the anterior threaded block 245 to travel rather than rotate when the bolt 252 is rotated. The posterior non-threaded block 256 may be in abutting position against the head 258 of the bolt 252 thereby preventing it from moving away from the anterior thread block 254. Thus, as the anterior threaded block 254 advances toward the posterior non-threaded block 256, the V-shaped members 250 are squeezed together. As the V-shaped members 250 are increasingly squeezed together between the blocks 254, 256, the V-shaped members 250 are increasingly expanded outward, thereby biting into the facet joint surfaces to anchor the implant 248 in the facet joint and distract, translate and/or subluxate the facet surfaces relative to each other.

Figure 35:
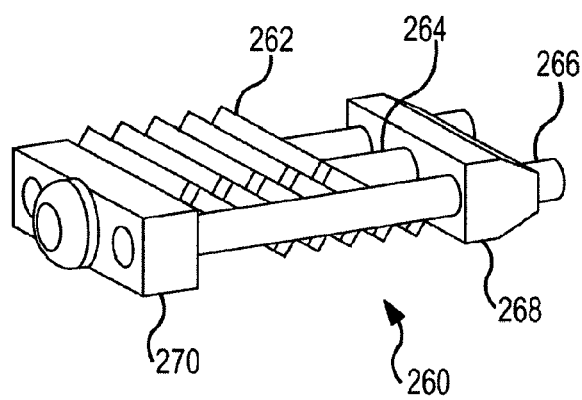
FIG. 35 is a perspective view of an implant in a collapsed position according to certain embodiments.

FIGS. 35-36 and 37A-D, depict isometric views of another implant 260 with planar plates or leaves 262 residing on a threaded bolt 264 and parallel shafts 266 between an anterior threaded block 268 and a posterior non-threaded block 270. As shown in FIG. 35, the planar plates 262 are in a skewed non-expanded state and are spaced apart from each other along the length of the bolt 264 such that may lie generally flat or, more specifically, at approximately 45 degrees on the bolt 264 and shafts 266. The plates 262 may include a slotted hole for receiving the bolt 264, which allows for the position described. The implant 260 may be inserted into the facet joint in the non-expanded state depicted in FIG. 35. As can be understood, the bolt 264 may then be rotated to cause the anterior threaded block 268 to travel along the bolt 264 towards the posterior non-threaded block 270, thereby causing the planar plates 262 to squeeze together. As the planar plates 262 are increasingly squeezed together between the blocks 268, 270, the planar plates 262 are increasingly expanded outward or, more specifically, are caused to be generally perpendicular to the bolt 264 and shafts 266. As a result, the planar plates 262 bite into the facet joint surfaces to anchor the implant 260 in the facet joint and distract, translate and/or subluxate the facet surfaces relative to each other.

Figure 36:
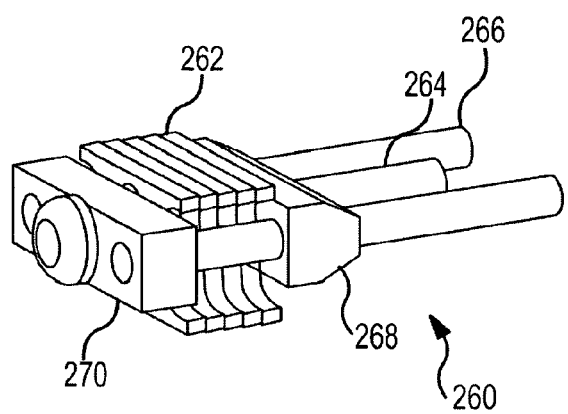
FIG. 36 is a perspective view of an expanded implant according to certain embodiments.
Figure 37A:
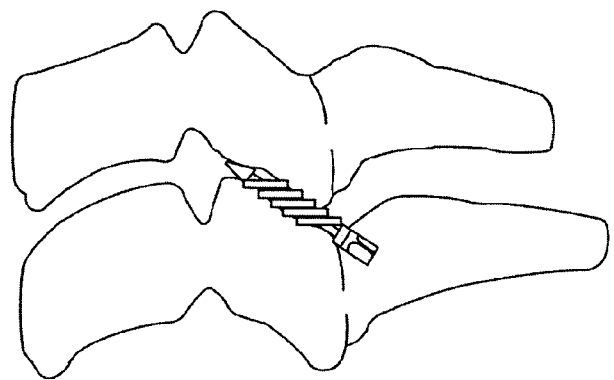
FIGS. 37A-D include side and perspective views of an implant, according to certain embodiments.
Figure 37B:
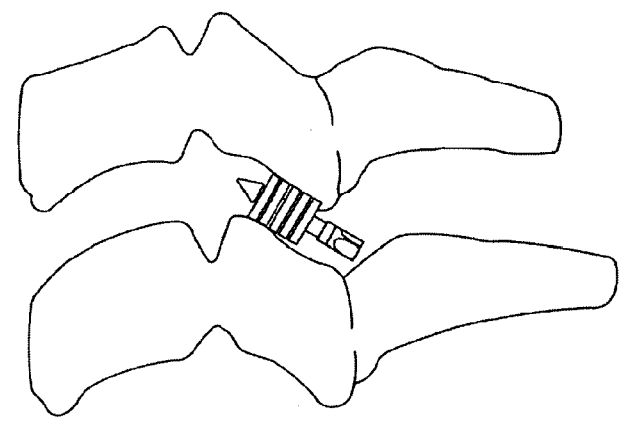
Figure 37C:
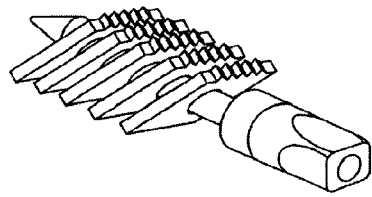
Figure 37D:
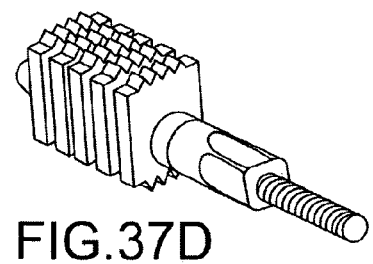

FIGS. 37A-D show an embodiment, which combines features of the embodiment shown in FIGS. 33 and 34 with features of the embodiment shown in FIGS. 35 and 36.

Figure 38A:
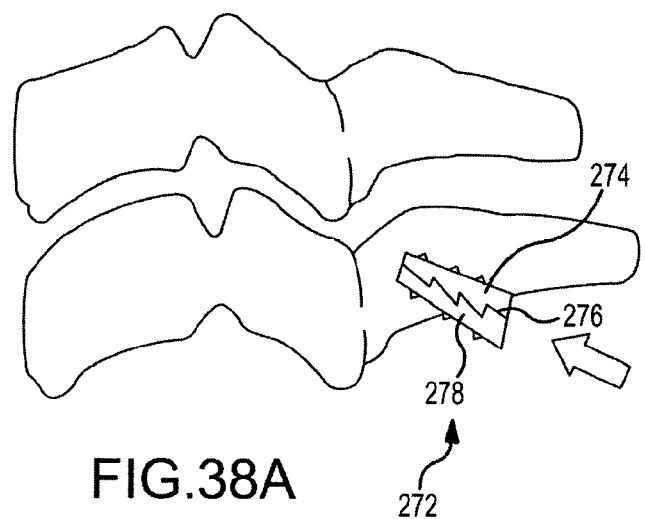
FIGS. 38A-C include side and perspective views of an implant, according to certain embodiments.
Figure 38B:
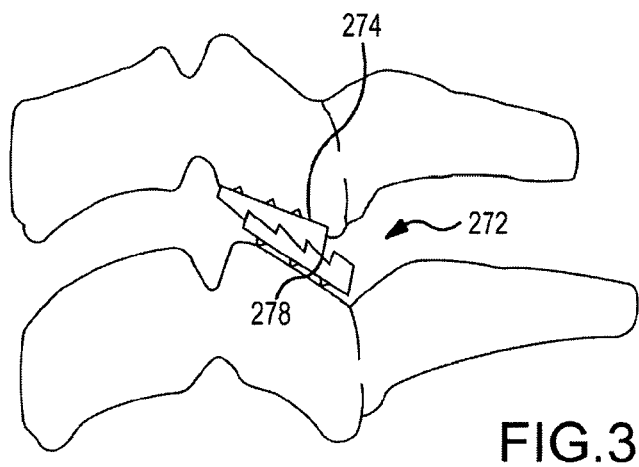
Figure 38C:
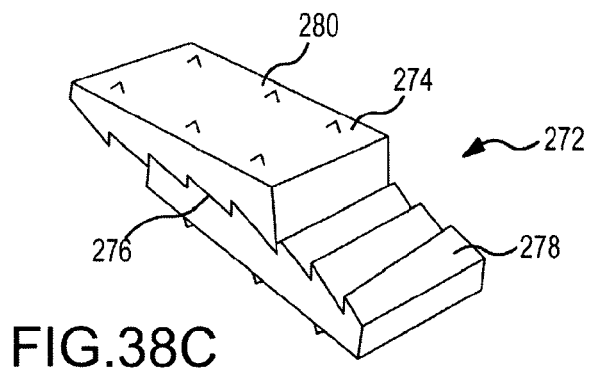

FIGS. 38A-C shows another embodiment of an implant 272. The implant 272 may include two stacked structures 274 that interface along a plane 276. Each structure 274 may include opposing ratchet teeth 278 along the plane. The position and orientation of the ratchet teeth 278 may be such that relative translation between the two structures 274 is allowed when a force is applied to each structure 274 in opposing directions. That is, once the implant 272 is properly positioned within the facet, a device may be use to apply a force to the superior structure 274 which causes forward translation of that structure 274 relative to the inferior structure 274. The ratchet teeth 278 on the superior structure 274 may slide up the slope of the teeth 278 on the inferior structure 274 until opposing apexes of teeth 278 pass by each other causing the two structures 274 to nest in a new relative position, the displacement being equal to the length of the teeth 278. Each structure 274, or only one of the structures 274, may increase in thickness along its length, such that continual relative ratcheted displacement creates a greater overall thickness. The increasing thickness of the implant structures 274 may cause distraction and forward translation in the facet joint. The opposing facet surfaces may be separated and the superior vertebra may be pushed anterior relative to the inferior vertebra. In addition, anchoring teeth 280 may be provided on the outer surface of both structures 274 of the implant 272 to provide acute fixation to the articular surfaces. The implant 272 may be configured in a number of different shapes including, but not limited to, a wedge, a double wedge, a rectangular box, and "v"shaped.

Figure 40A:
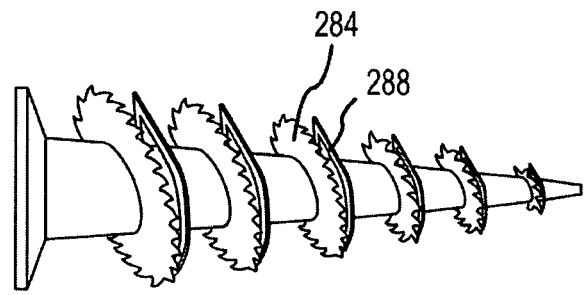
FIGS. 40A-C include side views of an implant, according to certain embodiments.
Figures 40B, 40C:
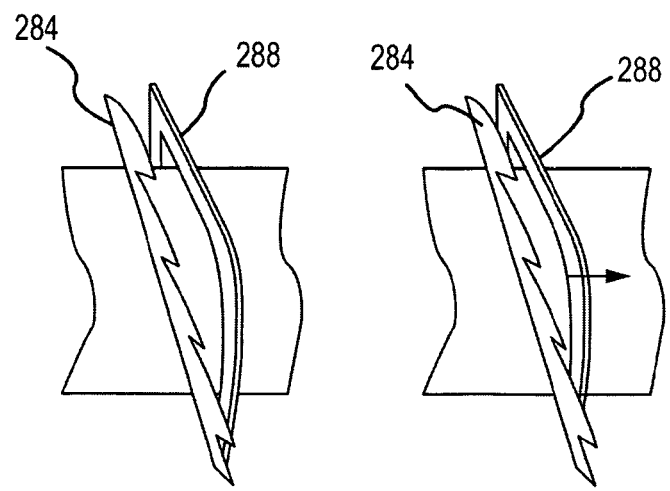

FIGS. 39A-D show another embodiment of an implant 282. In this embodiment, a screw like implant 282 may be inserted between the facet. The insertion of this screw may serve to distract the joint surfaces resulting in a decompression of the nerve root. Additionally, the threads 284 of the screw may include V-shaped notches 286 in the threads 284 spaced throughout the length of the screw creating serrated teeth. As the screw implant 282 is threaded progressively further anterior, the serrated teeth may cut/bore into the cortical bone of the opposing facet surfaces. The defect in the bone these serrations produce may prevent the implant 282 from backing out posteriorly or migrating medial/lateral because the threads 284 are configured with the serrated teeth to allow the implant 282 to catch or "bite" in the bone if any posterior withdraw or backing out occurs. Additionally or alternatively, as shown in FIGS. 40A-C, the screw threads 284 may include a leaf spring 288 to maintain friction of the threads 284 against the newly cut threads in the bone thereby preventing the screw from backing out.

FIGS. 41A-D show another embodiment similar to the one shown in FIGS. 39A-D. That is, in this embodiment, the implant 290 may take the form of a screw, but the threads 292 of the screw may have a T-shaped profile as shown in FIG. 41D. In addition, the flat surface of the T-shaped profile may define a diameter at any given point along the length of the screw. In one embodiment, the diameter may increase over the length of the screw and not be limited to just the tip like a traditional screw. As such, when the implant 290 is placed, the more it is advanced into the facet joint, the more separation it creates.

FIGS. 42A-F show another embodiment of an implant 294. In this embodiment, the implant 294 may again take the form of screw. The screw may have a washer or extra broad head 296 with sharp protrusions 298 on the distal surface of the head 296 that engage the superior and inferior lateral mass surfaces as the screw is inserted into the facet joint. The engagement of the sharp protrusions 298 may occur as a result of both the longitudinal translation of the screw together with the rotational motion causing the sharp protrusions 298 to cut into the lateral mass surface as the screw is advanced and rotated. As the washer 296 rotates, the sharp protrusions 298 roughen the lateral masses and create a fracture environment. This fracture environment causes osteoblastic activity that will lead to bone production and assist in fusion of the joint at the lateral mass. Moreover, the moat created by the rotating and cutting protrusions 298 may begin to lock the facet surfaces together.

Figure 42A:
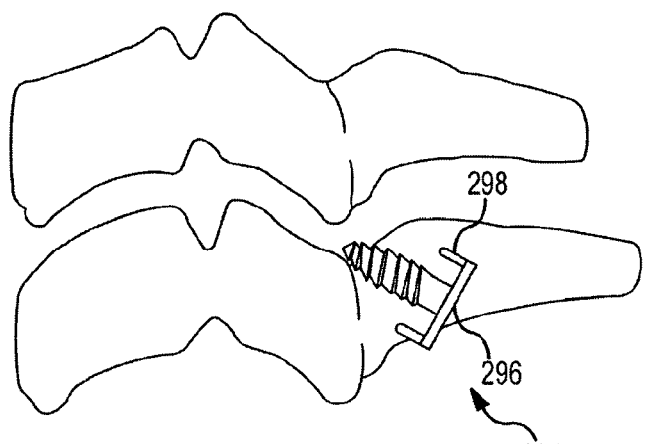
FIGS. 42A-F include side and perspective views of an implant, according to certain embodiments.
Figure 42B:
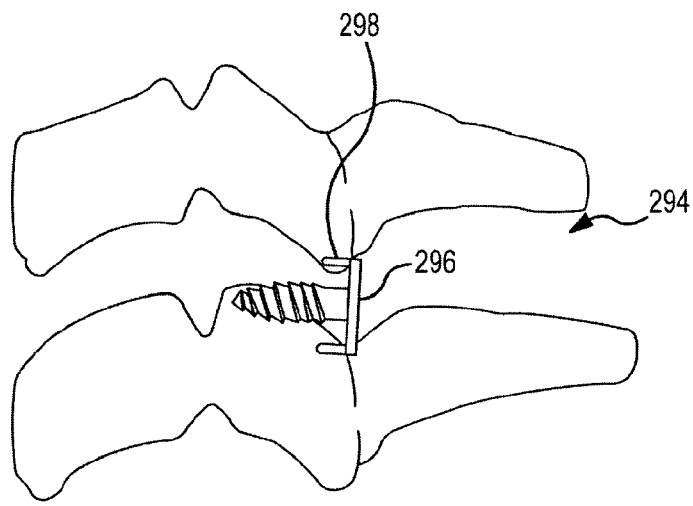
Figure 42C:
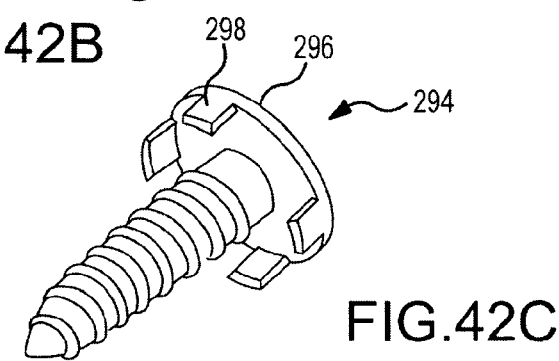
Figure 42D:
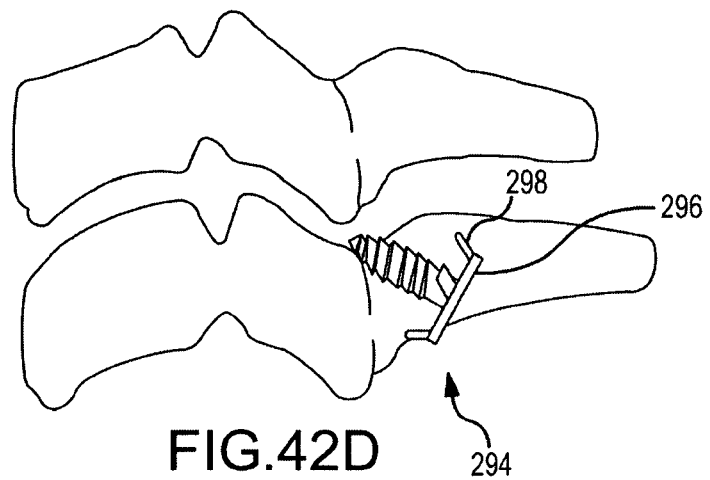
Figure 42E:
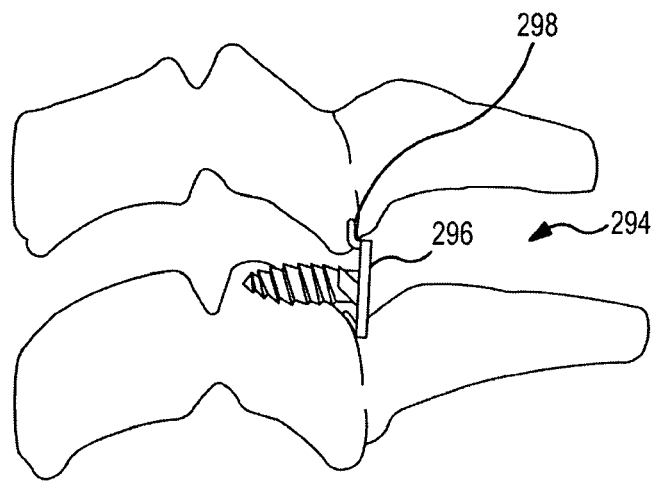
Figure 42F:
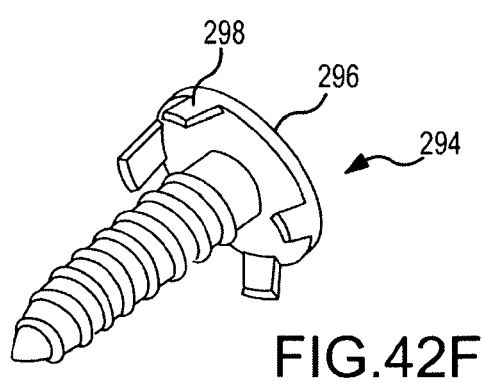
Figure 43A:
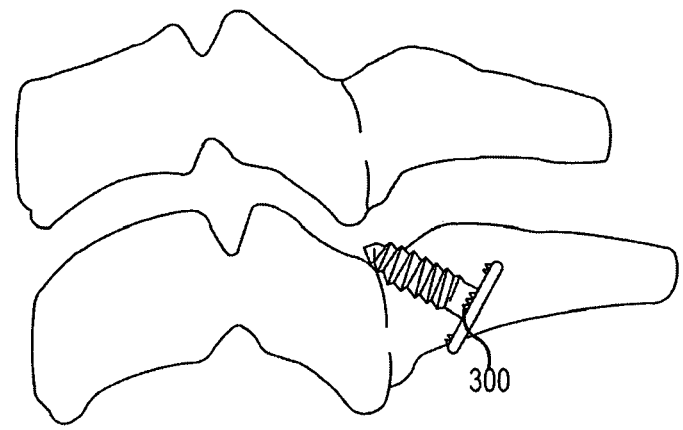
FIGS. 43A-C include side and perspective views of an implant, according to certain embodiments.
Figure 43B:
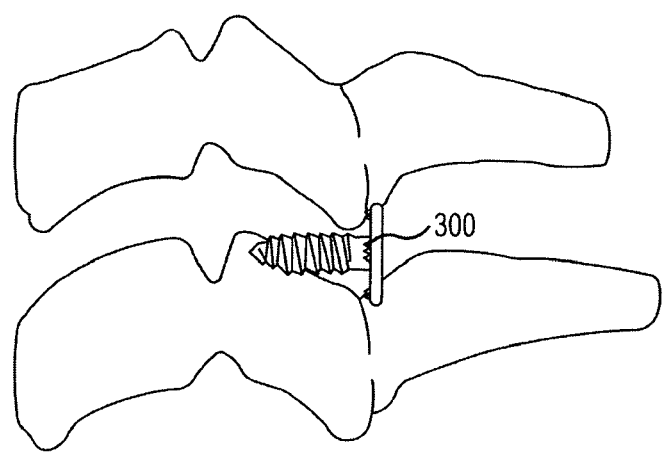
Figure 43C:
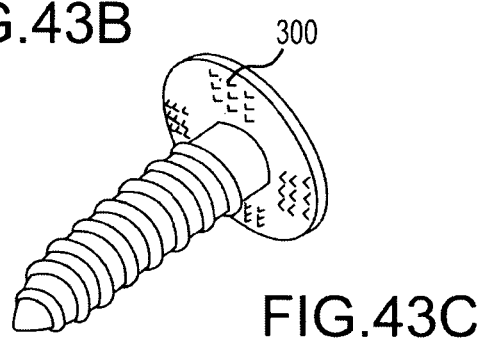
Figure 44A:
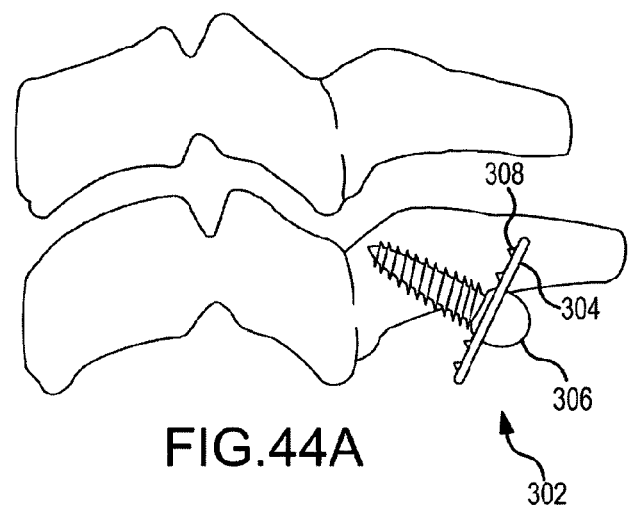
FIGS. 44A-D include side and perspective views of an implant, according to certain embodiments.
Figure 44B:
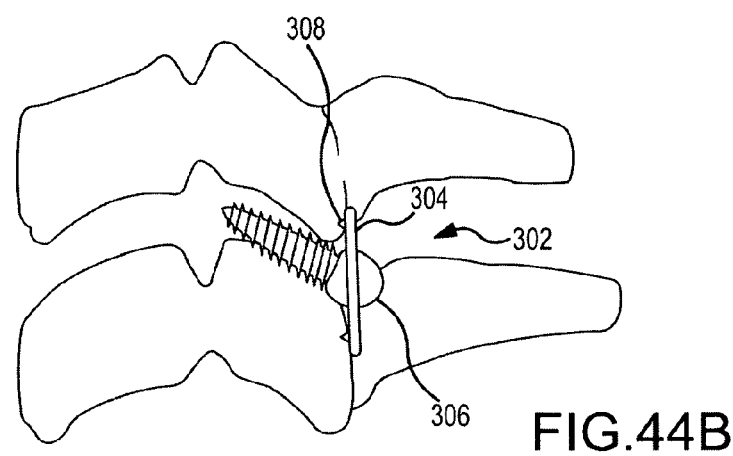
Figure 44C:
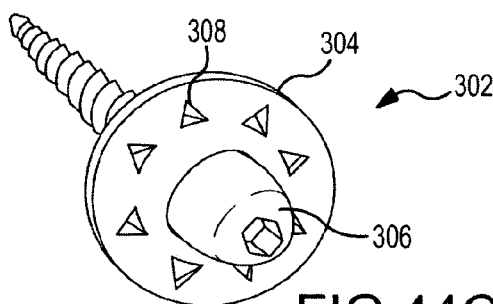
Figure 44D:
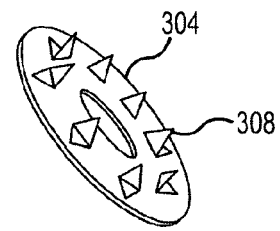
Figure 45A:
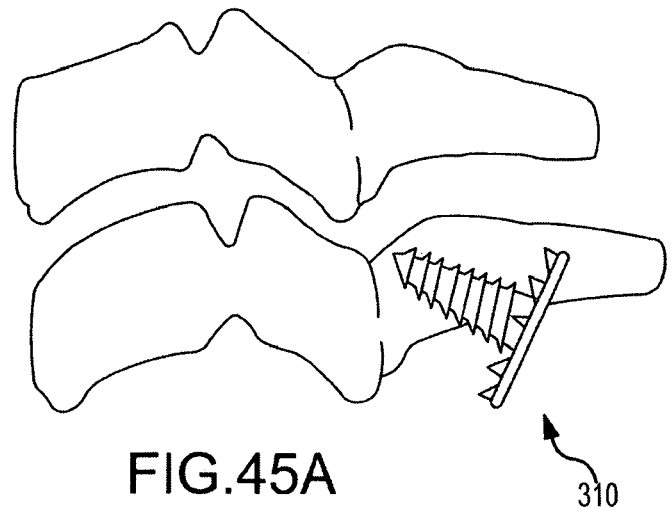
FIGS. 45A-D include side and perspective views of an implant, according to certain embodiments.
Figure 45B:
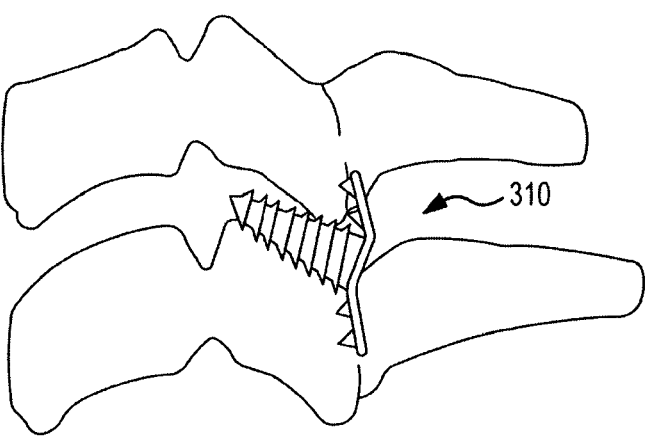
Figure 45C:
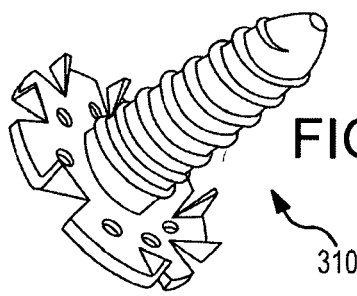
Figure 45D:
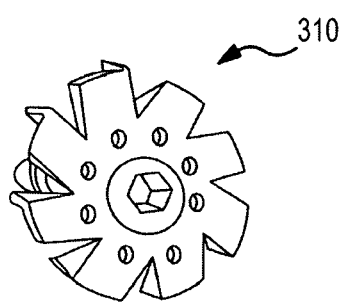
Figure 46A:
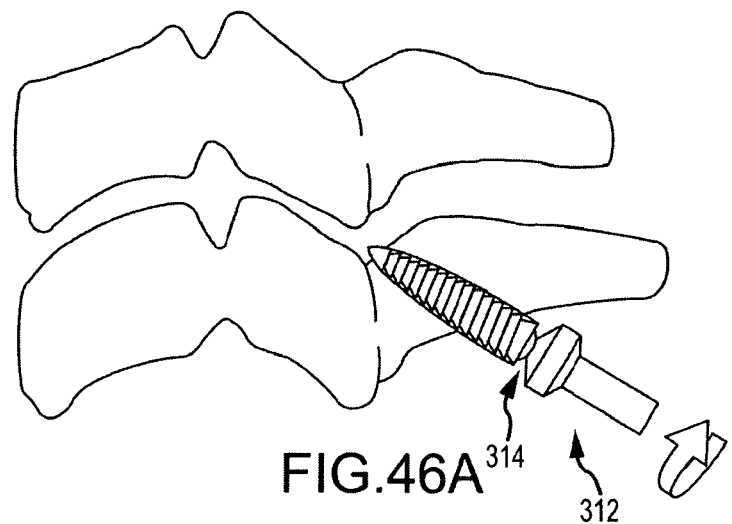
FIGS. 46A-D include side and perspective views of an implant, according to certain embodiments.
Figure 46B:
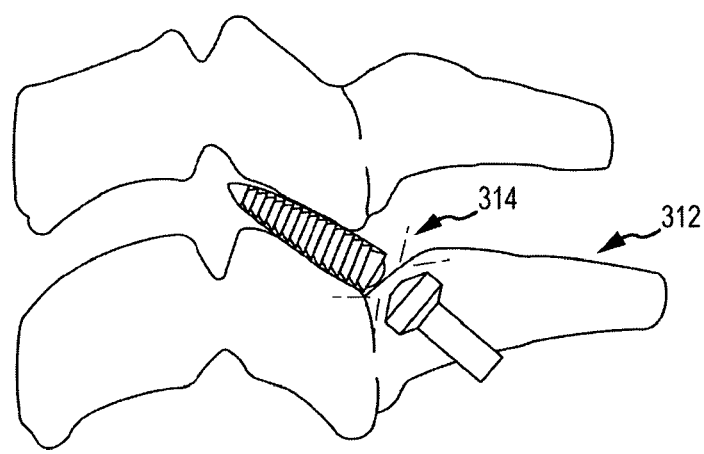
Figures 46C, 46D:
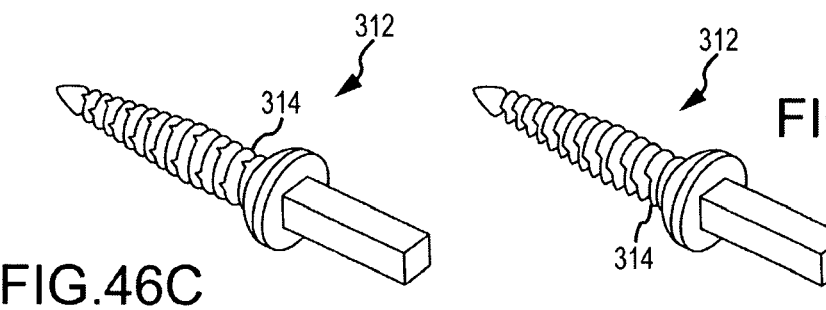

In the present embodiment, the protrusions 298 may be tab like and cut relatively deeply into the lateral mass. In addition as shown in FIGS. 42D-F, the tabs may position themselves as shown where the superior tab is flared to engage the lateral mass and the inferior tab is wedged into the joint. In this configuration, the tabs may act to further distract the joint beyond that provided by the diameter of the screw portion of the impant. In other embodiments, as shown in FIGS. 43A-C, the sharp protrusions 300 may be sharp prongs or spurs adapted to roughen the surface.

FIGS. 44A-D show another embodiment of an implant 302. In this emodiment, a facet distraction implant 302 has a floating collar 304 for use with a screw type implant. As shown, the collar 304 may be positioned to pivot about the head 306 of the screw due to the spherical shaped head 306 on the screw in a ball and socket fashion. The floating collar 304 allows the screw implant to accommodate irregular, non-planar surfaces of the lateral mass and may aid in the prevention of reverse threading of the implant 302 once the screw has been advanced to the proper position within the facet. As shown, the screw may be implanted to provide distraction and forward translation of the joint. The floating collar 304 may include teeth or spikes 308 that roughen/decorticate the cortical bone of the superior and inferior lateral masses resulting in the creation of a fracture environment. This may improve the chance of posterior lateral mass facet fusion.

FIGS. 45A-D show yet another embodiment of a decorticating screw type implant 310.

FIGS. 46A-D show another embodiment of an implant 312. In this embodiment, a structural implant 312 is inserted between the opposing surfaces of a facet joint. This implant 312 may be in the form of a screw as described above or may be a different implant requiring a torque or other force to be applied to anchor the implant 312 in the facet joint. As shown, when the implant 312 is inserted increasingly more anterior within the facet, a torque limiting mechanism 314 within the device may measure the force or torque applied to the system. Once a predermined value of torque or force is achieved, the distal end of the system may detach causing the imlant 312 to become a permanent distraction implant.

In the case of a screw implant, the torque limiting mechanism 314 may be a necked down portion of the device creating a calibrated weakened portion intended to fail when a specified torque is exceeded.

In this embodiment, the implant 312 may also include a number of anit migration features to prevent backout. These features may include directional teeth, roughened surfaces, keels, spikes, or other features known in the art. As with other implants, the geometry of the implant may cause distraction of the joint and lead to a more pronounced forward translation of the joint as the opposing facet surfaces separate.

Figure 47A:
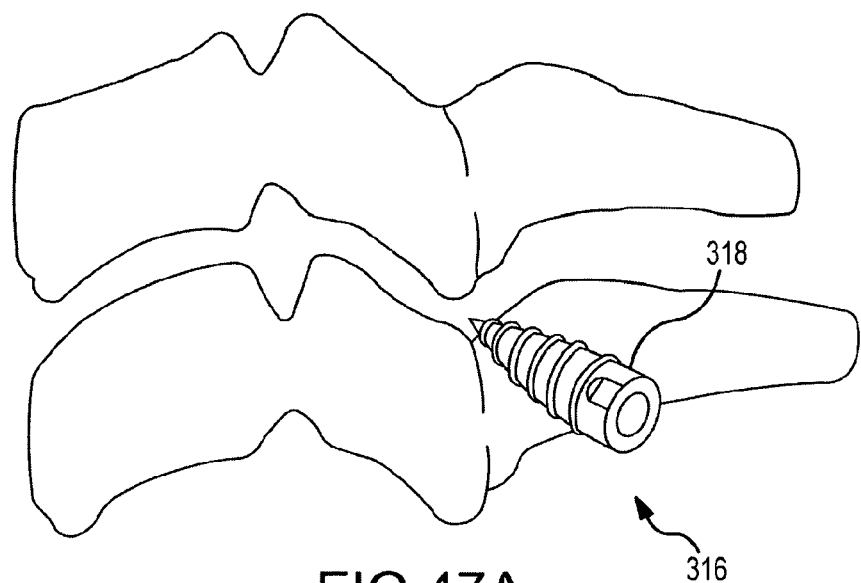
FIGS. 47A-B include side views of an implant, according to certain embodiments.
Figure 47B:
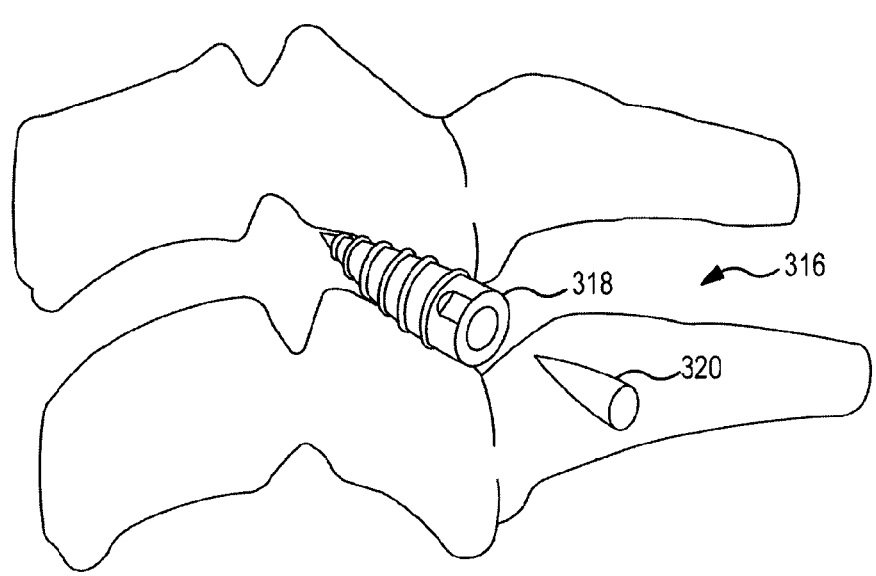

FIGS. 47A-B show another embodiment of an implant 316. In this embodiment, again a screw shaped implant 316 may be inserted into the facet to distract the facet surfaces and increase foraminal height resulting in a decompression of a symptomatic nerve root. In this embodiment, however, the implant may include two main components. First, the implant 316 may include a relatively stiff but maleable cone-shaped screw structure 318 with aggressive threads for biting into the opposing surfaces of the facet joint. These threads may have a number of variations for preventing movement of the implant after it is implanted. Second, the implant may include an inner core support member 320. The core support member 320 may be in place when the implant 316 is placed to assist in maintaining the shape of the screw structure 318. After placement, the core support member 320 may be removed. The maleability of the screw structure 318 may allow it to collapse slightly once the implant 316 is properly positioned and inserted. The collapsing of the screw structure 318 would change the alignment of the threads and prevent reverse threading that could lead to posterior migration.

Figure 48A:
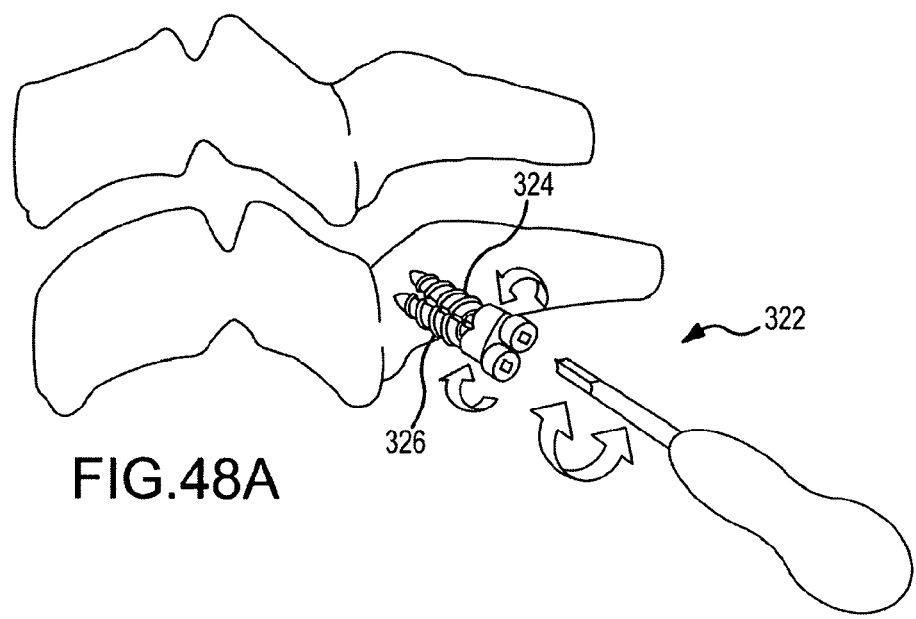
FIGS. 48A-C include side and end views of an implant, according to certain embodiments.
Figure 48B:
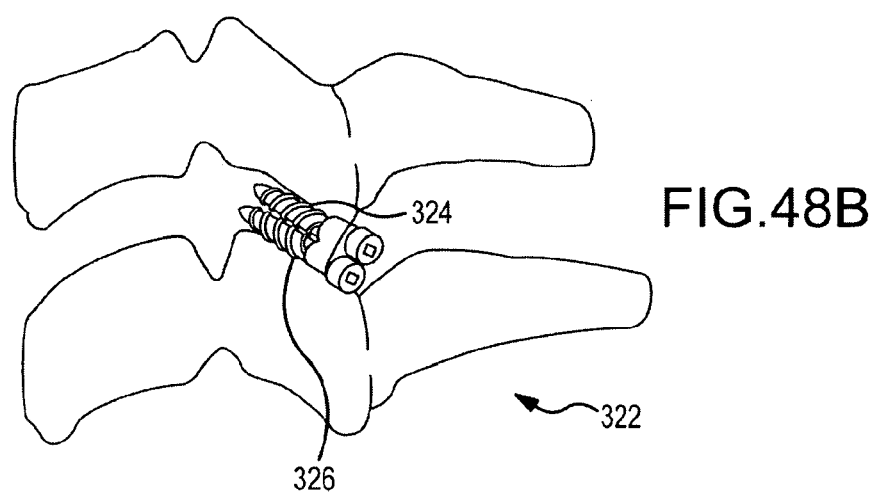
Figure 48C:
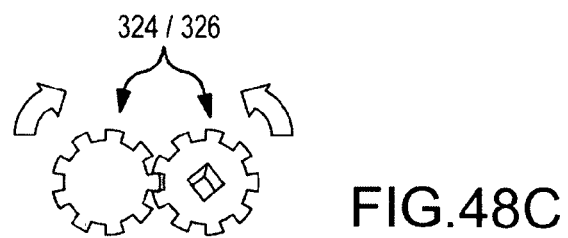

Yet another embodiment is show in FIGS. 48A-C. In this embodiment, a superior 324 and an inferior 326 screw may be used to create an implant 322. The two screws 324, 326 may have communicative threaded serrations that work in opposition to one another. As such, when the inferior screw 326 is rotated, the threads may interact with the superior screw 324 causing it to rotate in the opposite direction. Moreover, the threads on the inferior screw 326 and superior screw 324 are such that opposite direction rotation draws both screws 324, 326 in to the facet joint. As the screws 324, 326 enter the joint, the facet surfaces are distracted apart from one another and the threads of the screw bite into the facet surfaces. The opposing rotation of the two screws 324, 326 may also assist in preventing back out of the implant or reverse threading/unscrewing. It is noted that several configurations may be used to create the opposite rotation of the screws. In one embodiment, a housing may be placed over each screw allowing the screws to freely rotate relative to the housing, but securing the screws adjacent to one another. In this embodiment, the opposite rotation may occur due to the threads engaging with one another as described above or the screw heads may have gear teeth for engaging one another and causing opposite rotation. In another embodiment, the screws may have gears on them positioned within the housing to engage one another and cause opposite direction rotation.

Figure 49A:
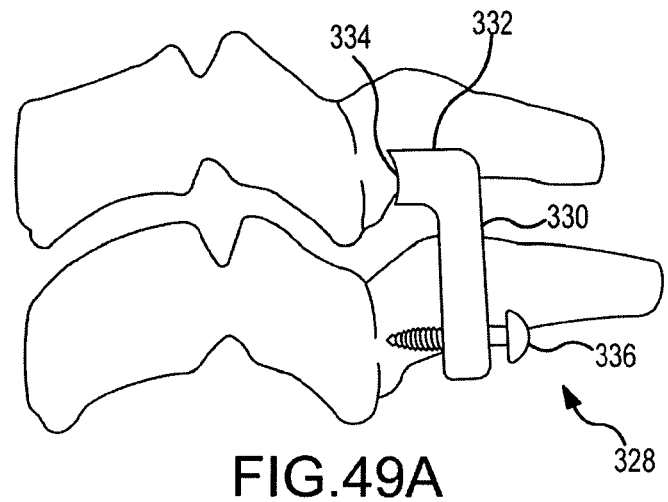
FIGS. 49A-C include side and perspective views of an implant, according to certain embodiments.
Figure 49B:
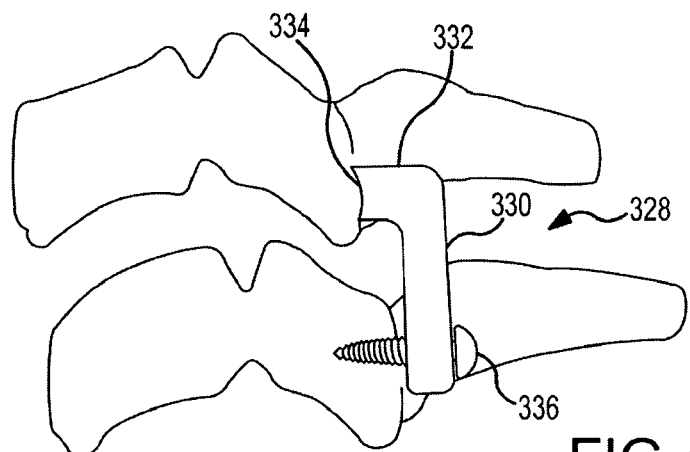
Figure 49C:
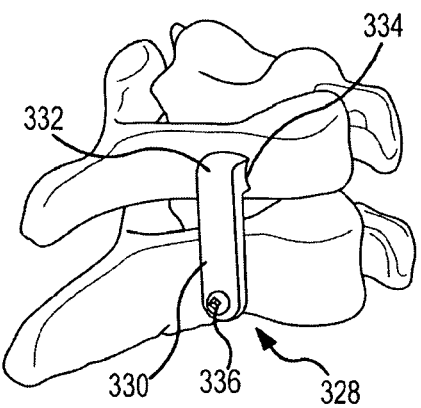

FIGS. 49A-C show yet another embodiment of an implant 328. In this embodiment, a translating system including a vertical plate 330 and a bumper 332 may be included. The superior aspect 334 of the bumper 332 may have a rounded concave surface for opposing the lateral mass of a superior vertebra. The translating system may be secured by anchoring a screw 336 to the lateral mass of an inferior vertebrae. The screw 336 may act as the foundation for a bumper system intended to push a superior vertebra forward (anterior) creating translation of the superior vertebra relative the inferior vertebra. This forward translation may create an increase in foraminal area and results in a decompression of the nerve root. The implant 328 may be configured to maintian permanent forward translation in order to prevent foraminal narrowing and nerve root compression. In addition, the implant 328 may provide rigid resistance when the superior vertebra exerts posterior translation vectors because it is anchored by the inferior lateral mass screw. The prevention of this posterior translation may keep the segment in a state of forward translation and preserve the associated increase in foraminal area.

Figure 50A:
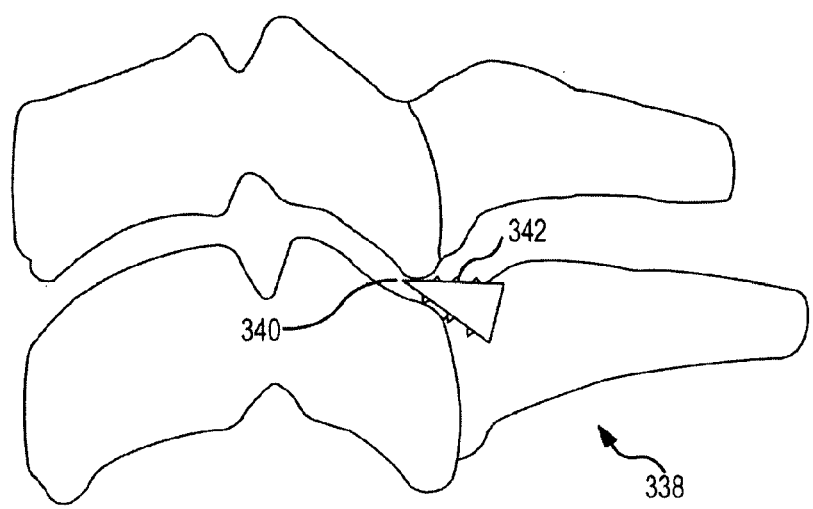
FIGS. 50A-B include side views of an implant, according to certain embodiments.
Figure 50B:
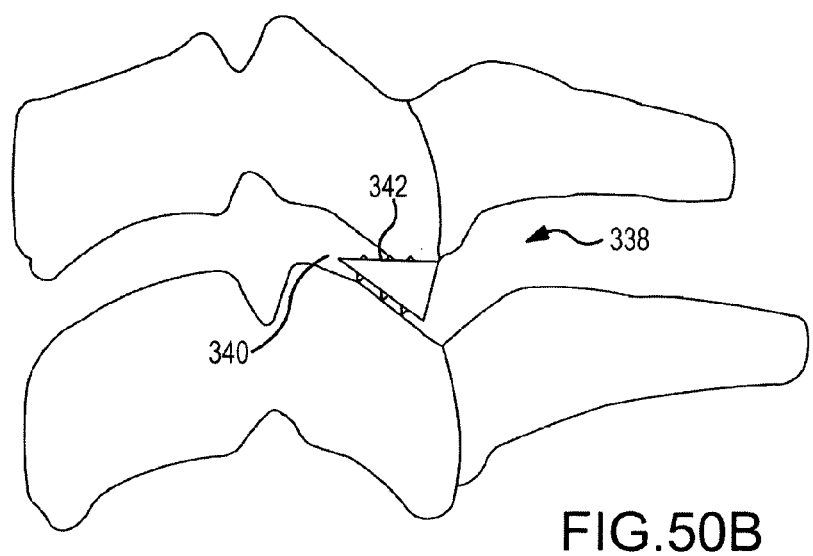

FIGS. 50A-B show another embodiment of an implant 338. In this embodiment, a wedge shaped or triangular implant 338 may be inserted between the face surfaces. The angled/pointed portion 340 with two acute line segments may allow the implant 338 to enter into the flat facet joint when sufficient force is applied. As the implant 338 is inserted progressivley more anterior, the distraction of the opposing facet surfaces may increase. This separation results in an increase of foraminal height and decompresses the symptomatic nerve root.

Figure 51A:
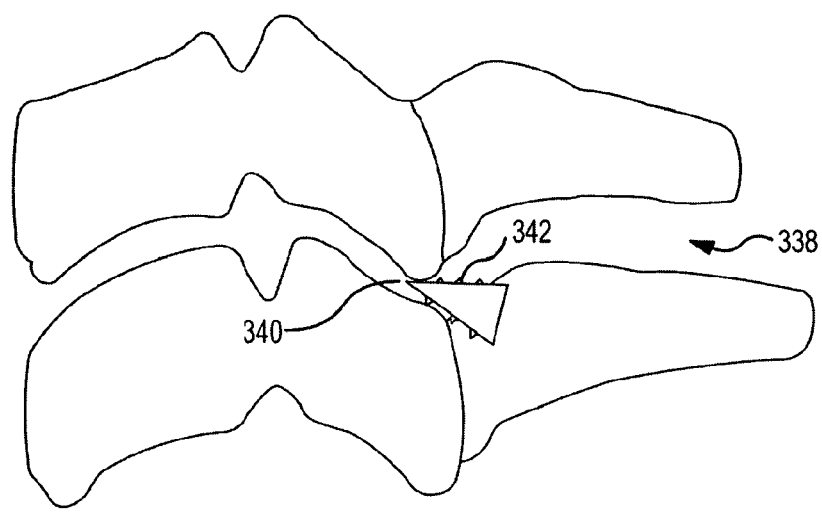
FIGS. 51A-B include side views of an implant, according to certain embodiments.
Figure 51B:
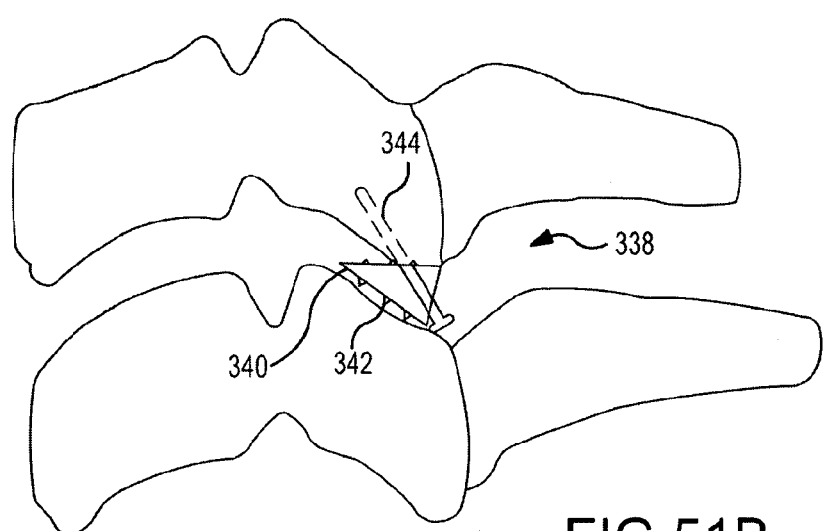

The surfaces of this implant 338 may include teeth, spikes, cleats, surfacace roughening, and/or keels 342 to help prevent migration or backout. In another configuration of this emobdiment, as shown in FIGS. 51A-B, the wedge shaped or triangular implant 338 may be anchored in position by one or two (one shown in FIG.) lateral mass screws/nails 344 that would connect the superior & inferior aspects of the implant 338 to the corresponding superior & inferior lateral masses of the affected segment.

Figure 52A:
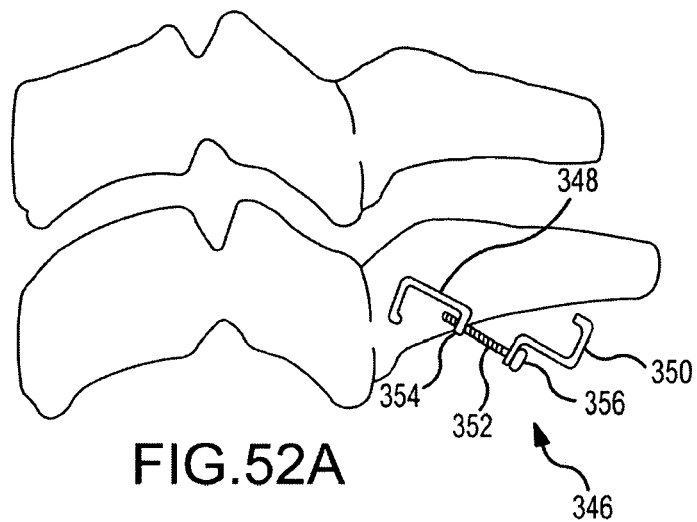
FIGS. 52A-C include side and perspective views of an implant, according to certain embodiments.
Figure 52B:
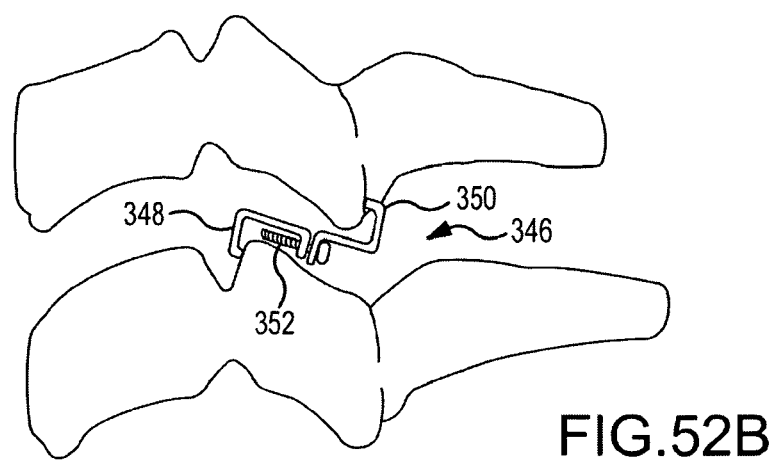
Figure 52C:
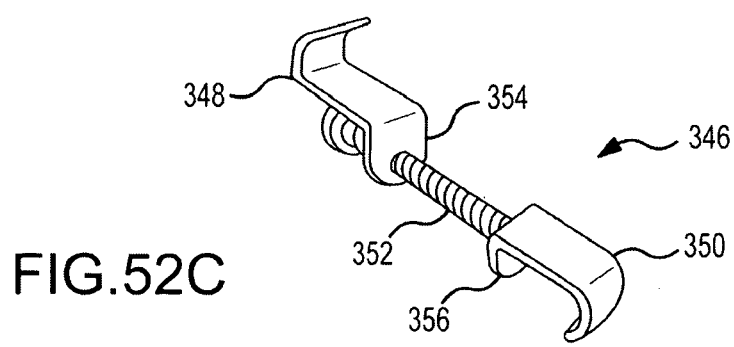

FIGS. 52A-C show another embodiment of an implant 346. In this embodiment, a distraction/translation system may include an anterior hook 348 and a posterior hook 350 joined by a threaded bolt 352. The anterior hook 348 may be placed over the anterior aspect of the inferior facet and the posterior hook 350 may be positioned posterior to the superior facet. The anterior hook 348 may have a C-shaped profile with a lip for engaging the anterior aspect of the inferior facet. The posterior hook 350 may have a S-shaped profile with a lip for engaging the posterior aspect of the superior facet. The threaded bolt 352 may be positioned through the facet joint and may threadably engage a posterior leg 354 of the anterior hook 348 and an anterior leg 356 of the posterior hook 350 as shown. As the bolt 352 is tightened and the hooks 348, 350 are drawn together, they create anterior translation of the superior vertebra relative to the inferior vertebra. This translation may result in increased foraminal area and nerve root decompression. The translation is maintained through the permanent placement of the hooks and bolt.

Figure 53A:
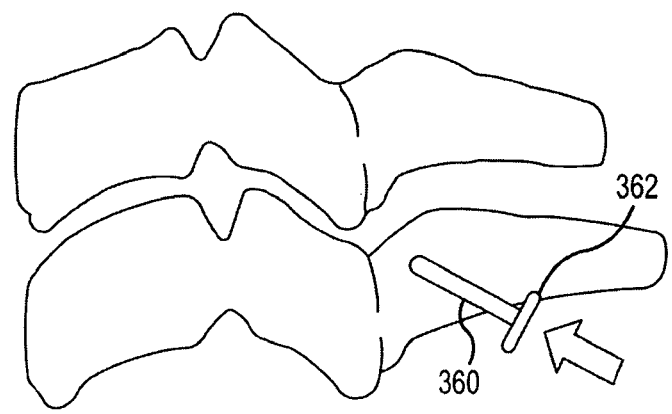
FIGS. 53A-C include side and perspective views of an implant, according to certain embodiments.
Figure 53B:
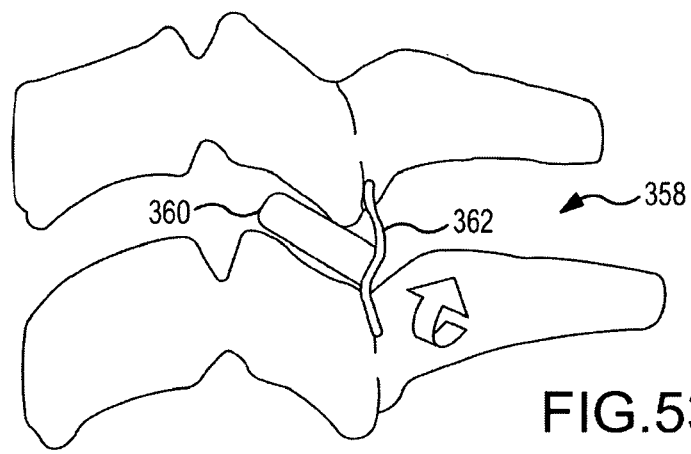
Figure 53C:
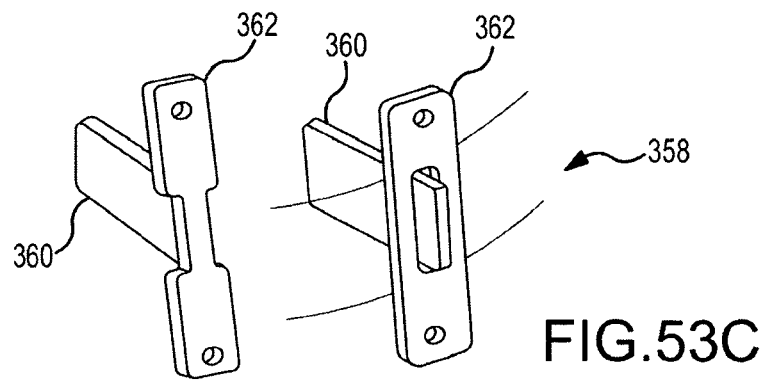

FIGS. 53A-C show another embodiment of an implant 358. In this embodiment, an insert 360 may be placed in the facet joint between two opposing facet surfaces. The geometry of the implant 358 could take a number of shapes including, but not limited to, rectangular, concical, triangular, or trapezoidal shape. Once the implant 358 is properly positioned, it may then be rotated some degree of rotation. This rotation may result in an increased height of the implant and cause facet surface separation and thus increased foraminal area and decompression of the symptomatic nerve root. In another configuration as shown in FIG. 53C, the rotated implant 358 may have outer tabs 362 that are capable of receiving a bone screw, nail, or pin that can be anchored in the superior and inferior lateral masses. These tabs 362 and anchors may assist in the prevention of implant migration leading to a reduction in the foraminal area.

Figure 54A:
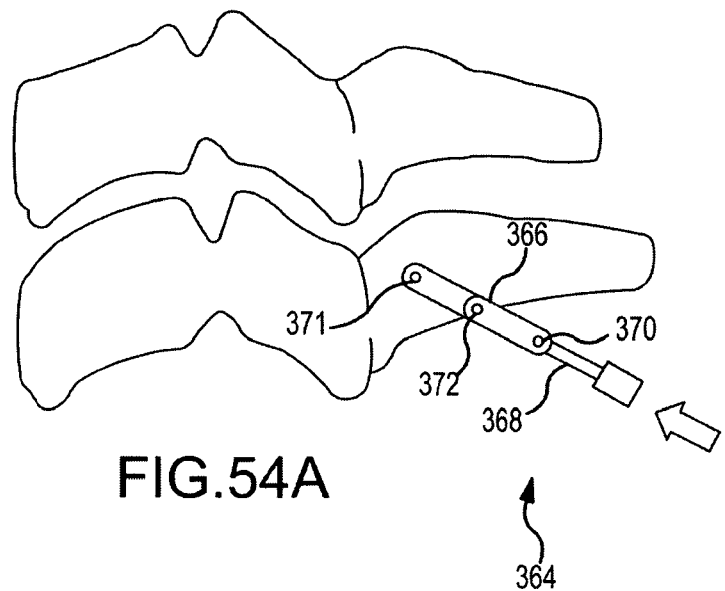
FIGS. 54A-C include side and perspective views of an implant, according to certain embodiments.
Figure 54B:
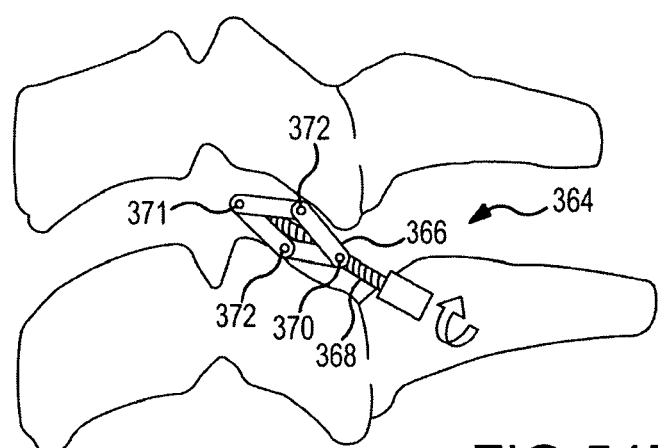
Figure 54C:
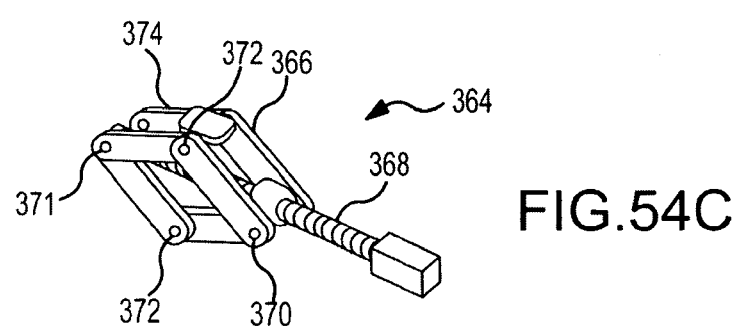

FIGS. 54A-C show another embodiment of an implant 364. In this embodiment, an implant 364 may take the form of a collapsible diamond shape 366 with an adjustment bolt 368 abutting a first corner 371 and threaded through an opposing corner 370 of the shape. The other corners 372 may include pads 374 for positioning against opposing articular faces of a facet joint. The implant 364 may be placed into the facet joint in a collapsed position and the adjustment bolt 368 may then be actuated to draw the opposing corners 371, 372 of the shape together thereby expanding the shape and pressing the pads 374 against the articular faces. As the shape expands, additional facet distraction is achieved resulting in an increased foraminal opening. This implant 364 may be provided in a number of geometries or materials to provide directional distraction where, for example, more distraction occurs near the posterior edge of the facet relative to the anterior edge of the facet. Additionally, the surface of the pad 374 may include teeth or keels to enable bone purchase in the facet.

Figure 55A:
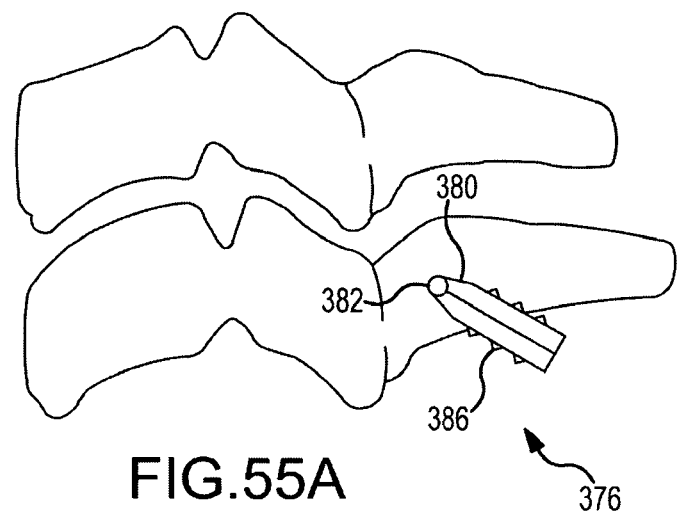
FIGS. 55A-C include side and perspective views of an implant, according to certain embodiments.
Figure 55B:
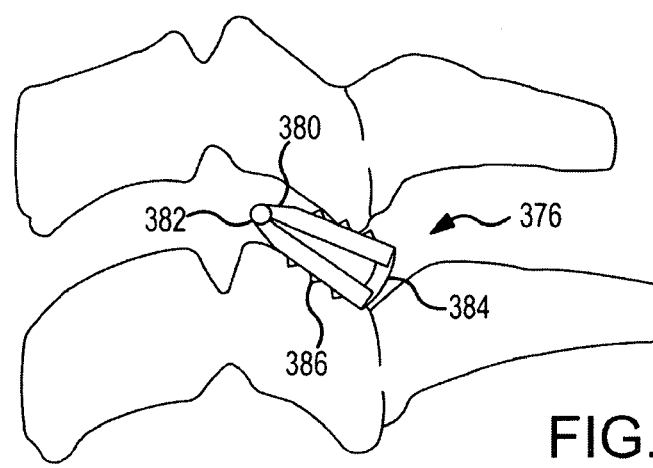
Figure 55C:
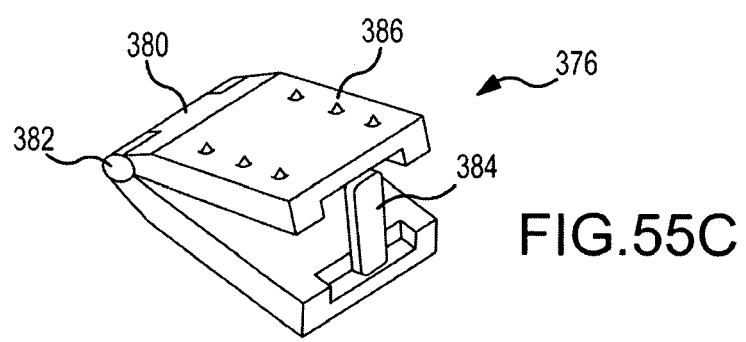

FIGS. 55A-C show another embodiment of an implant 376. In this embodiment, the implant 376 may take the form of an expandable hinged structure with an upper member 378 and a lower member 379 connected at their distal ends 380 by a hinge 382. The implant 376 may be placed between the facet surfaces in a collapsed state. The posterior aspect of the implant 376 may include a receiving slot that is able to receive a screw, bolt, or other activation system. Engaging this slot with an activator would cause the implant 376 to expand on its hinge 382 creating distraction and translation of the joint. For example, the activator may be a wedge, a turnable flat tool, a tapered screw, or any other device that may be inserted into the receiving slot to forcibly expand the upper 378 and lower 379 members. As shown, the hinge 382 may also include a brace member 384 for maintaining the poserior halves of the hinge in a separated position. The brace member 384 may be spring loaded or otherwise engaged with the hinge halves 378, 379 such that when expanded the brace 384 moves into position to support the open position of the hinge 382. In some embodiments, the upper 378 and lower 379 member of the implant 376 may have teeth, cleats, or keels 386 to engage the cortical bone of the opposing facet surfaces. These mechanisms would provide fixation of the implant 376 to the joint.

Figure 56A:
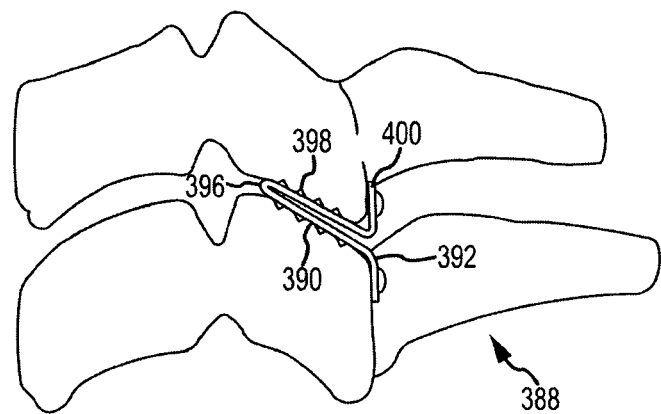
FIGS. 56A-C include side and perspective views of an implant, according to certain embodiments.
Figure 56B:
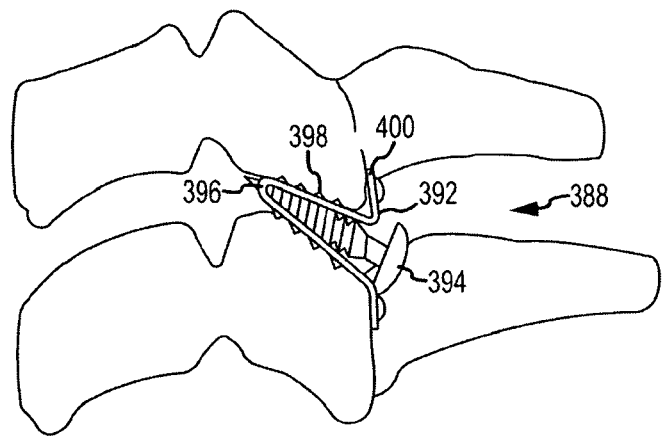
Figure 56C:
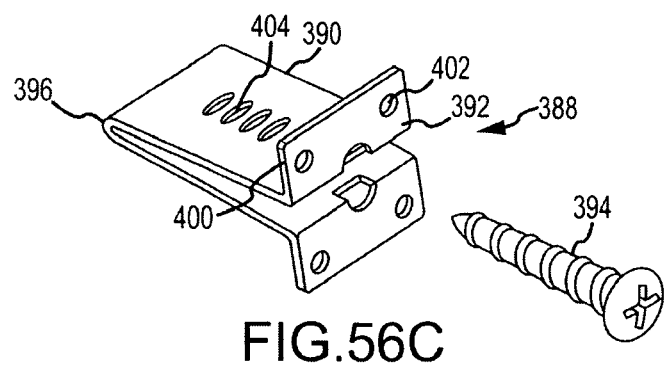

FIGS. 56A-C include another embodiment of an implant 388. In this embodiment, a collapsed and flattened structure 390 may be placed between the opposing surfaces of the facet joint. The posterior aspect 392 of the structure 390 may be configured to be capable of receiving a screw, bolt, or some other inserted component 394. Upon insertion of the screw, bolt, etc. 394, the structure may begin to expand. This expansion and separation may be enabled by a hinge 396 at the anterior aspects of the structure 390. As the structure 390 expands, sharp directional teeth, cleats, or keels 398 on the opposing (superior & inferior) surfaces of the structure may become anchored in the cortical bone of the opposing facet surfaces. These teeth, cleats, or keels 398 may engage the face surfaces and provide acute fixation of the structure within the facet joint. Together with the these teeth, cleats, or keels 398, or as an alternative to them, as shown, the proximal end of the implant 388 may also include flanges 400 that overlap the lateral mass of the facet joint. These flanges 400 may include holes 402 for anchoring the implant 388 to the superior and inferior facet masses, or to only one of the masses. In a related emodiment, the superior and inferior surfaces may have open ports 404 that enable the screw threads to exit the structure and gain purchase in the opposing facet surfaces. The distraction and separation of the joint may increase foraminal area and reduce the symptoms associated with nerve root compression.

FIGS. 57A-C show yet another embodiment of an implant 406. In this embodiment, the implant 406 may resemble a screw and wall anchor. The wall anchor portion 408 may be generally cylindrically shaped and include two half sections 410 separated by a slot or it may include a multitude of longitudinally extending sections 410. These sections 410 may be connected together at the tip 412 as shown or they may be connected together at the proximal end 414 of the implant 406 and at the tip 412 and may include several connections along the length of the implant 406. The implant 406 may have a sharp, triangular or conical tip 412 that allows for access into the flattened facet joint. Once the implant 406 is inserted into the facet surface, a screw, bolt, or other insertion component 416 may be inserted into the implant 406. As this component 416 is advanced the sections 410 may expand creating additional separation of the joint and alloiwong for measured distraction of the space. The sections 410 of the wall anchor portion 408 may include sharp directional teeth, cleats, or keels 418 that engage the cortical bone of the opposing facet surfaces.

Figure 58A:
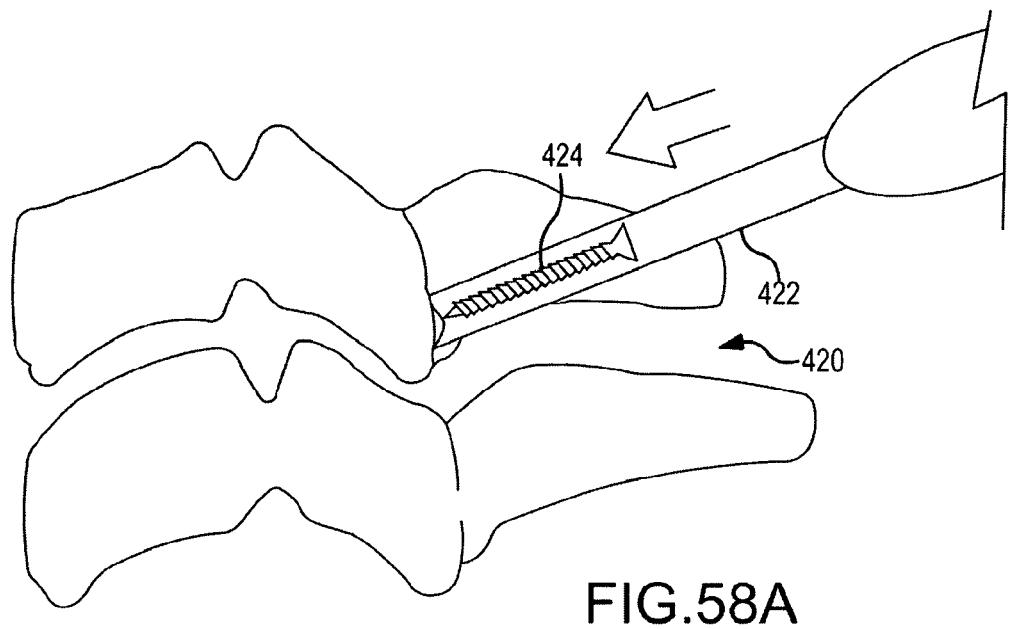
FIGS. 58A-B include side views of an implant, according to certain embodiments.
Figure 58B:
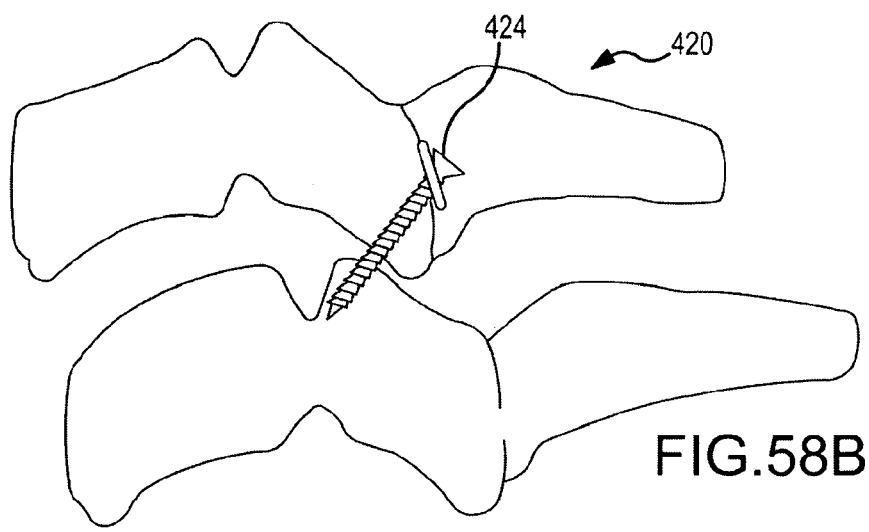

FIGS. 58A-B show yet another embodiment of an implant 420. In this embodiment, a tool 422 may be used to apply a force to the superior vertebra of a motion segment. This forward translation would result in an increase in foraminal area and reduced nerve root decompression. Following the forward translation of the motion segment, an angled screw 424 would be placed through the superior facet surface, facet capsule, and inferior facet surface. This screw 424 would provide temporary immobilization of the joint which leads to fusion.

Figure 59A:
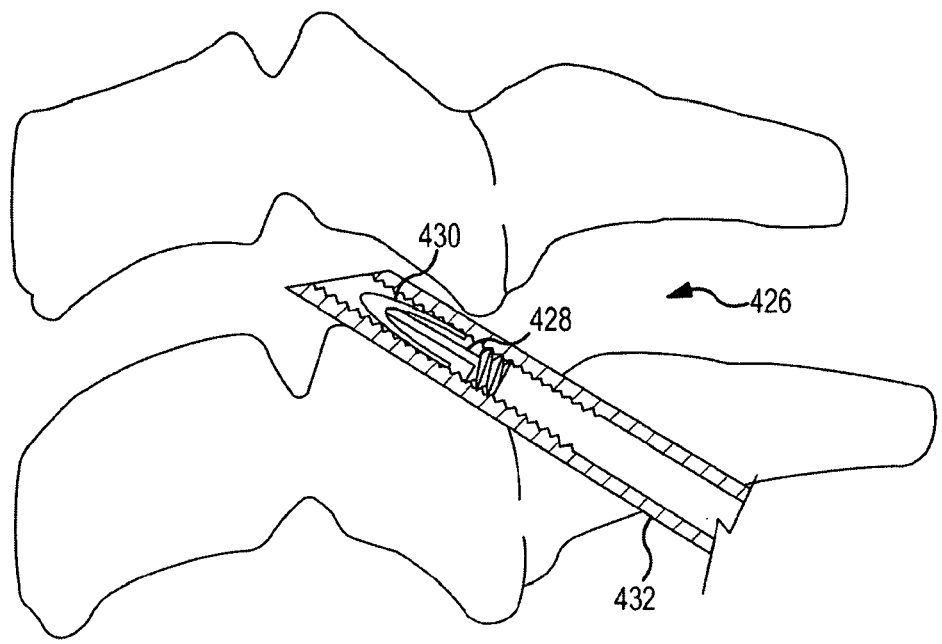
FIGS. 59A-B include side views of an implant, according to certain embodiments.
Figure 59B:
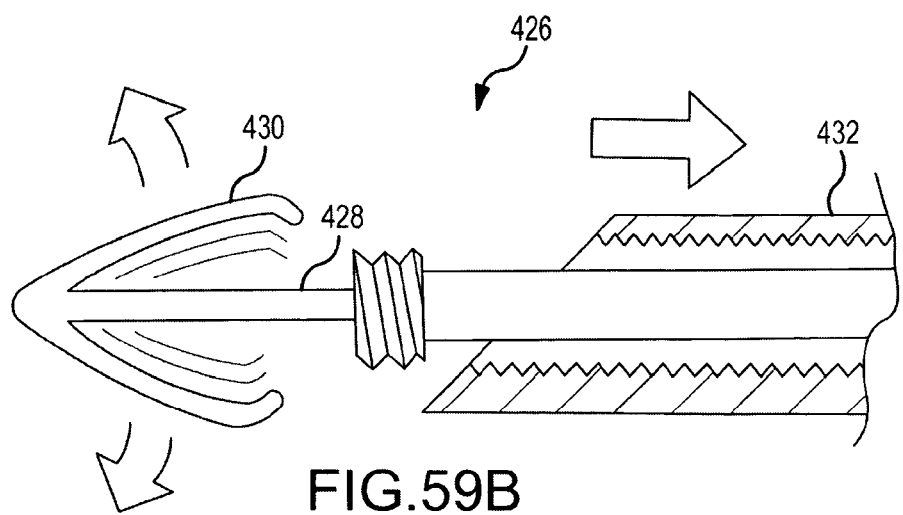

FIGS. 59A-B show yet another embodiment of an implant 426. In this embodiment, a collapsed, triangular shaped implant is inserted into the facet. The implant 426 may include a central shaft 428 and two or more springing leaves 430. The leaves 430 may be connected to the distal end of the shaft 428 and may extend proximally along the shaft 428. The leaves 430 may be connected at the distal end so as to be biased in a direction to form an arrow shape. The leaves 430 may be held in the compressed state by an insertion & delivery tool 432. The delivery tool's compression of the implant 426 prevents the superior and inferior surfaces of the implant 426 from springing open to a distracted position. Once the compressed implant 426 is positioned correctly, the delivery tool 432 may be removed. Removing the tools causes the leaves 430 to open/expand causing distraction and separation of the facet joint thus resulting in increased foraminal area and reduced nerve root compression.

Figure 60A:
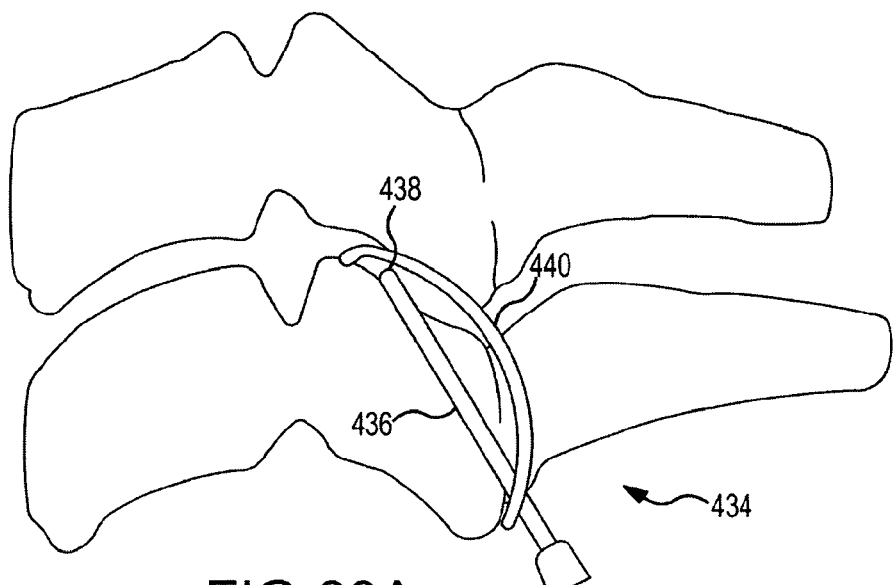
FIGS. 60A-B include side views of an implant, according to certain embodiments.
Figure 60B:
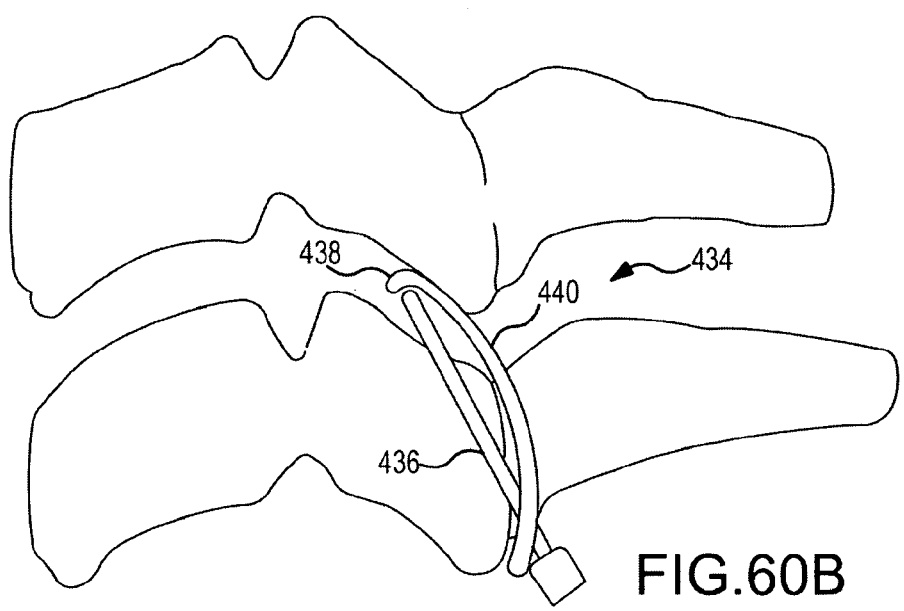

FIGS. 60A-B show yet another embodiment of an implant 434. This concept has at least three embodiments. The first embodiment consists of a direction facet joint screw 436 that is advanced through an inferior facet until it makes contact with the opposing superior facet. Once the screw 436 makes contact with superior facet surface, the energy applied to advance the screw 436 results in distraction and separation of the joint due to bearing of the screw tip 438 on the underside of the superior articular surface. In one variation of this embodiment, the hole for the screw in the inferior facet may be pre-drilled. When the screw is installed and encounters the superior facet, the screw may bite into the superior facet as it forces the fact upward and distracts the joint. Alternatively, in this embodiment, the screw may have a blunt tip 438 to distract the joint without biting into the superior facet.

In the second embodiment, as shown, a directional facet screw 436 may be advanced through the inferior facet surface until it engages with a facet spacer/plate 440 that is inserted in between the facet surfaces within the facet capsule. As the screw 436 makes contact with the facet spacer/plate 440, the flat surface of the spacer/plate 440 may push up against the opposing superior facet surface causes distraction and forward translation. This separation of the facet surfaces results in increased foraminal area and reduced nerve root compression.

In a third embodiment, the spacer/plate 440 may have a shape to allow the screw 436 to pass through a first end and the other end to be placed in the facet joint. In this embodiment, the C-shaped spacer 440 may be positioned in the joint, thereby slightly distracting the joint. The screw may then penetrate a first end of the spacer 440 thereby anchoring the spacer 440 in the joint. The screw may then be advanced through the inferior facet surface until it engages with the spacer/plate 440. As the screw 436 makes contact with the facet spacer/plate 440, the flat surface of the spacer/plate 440 may push up against the opposing superior facet surface causes distraction and forward translation. In some embodiments, the screw may penetrate the spacer and aid in fixing the joint.

Figure 61A:
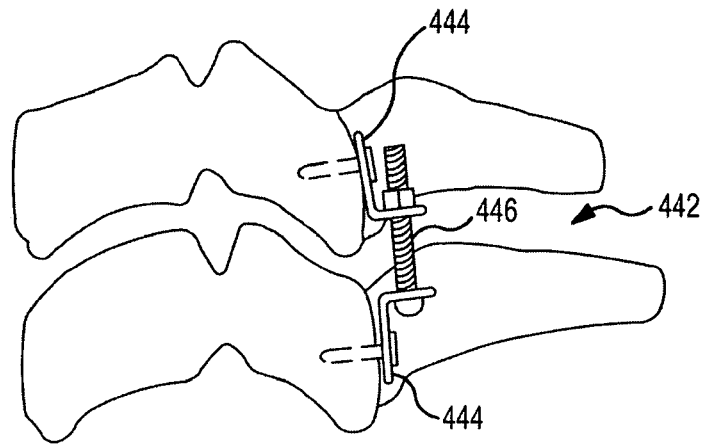
FIGS. 61A-C include side and perspective views of an implant, according to certain embodiments.
Figure 61B:
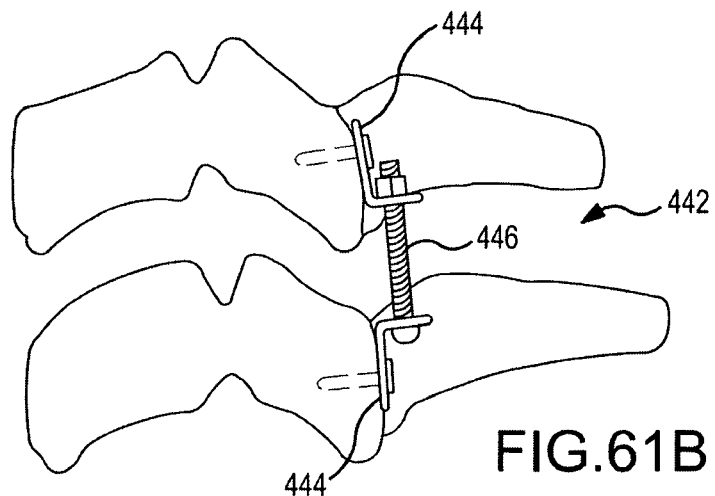
Figure 61C:
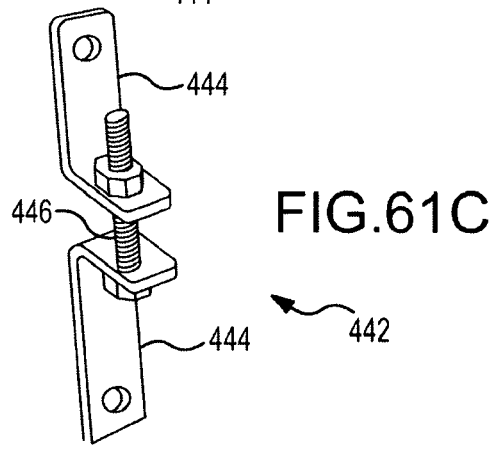

FIGS. 61A-C show yet another embodiment of an implant 442. In this embodiment, bracket type structures 444 may be attached to the superior and inferior lateral masses. The bracket type structures 444 may enable the attachment of a single bolt 446. The bolt 446 may be configured to create a distraction energy. That is, it may be connected to the inferior bracket 444 to allow rotation but not relative translation. In contrast, the bolt may threadably engage the superior bracket 444. As such, when the bolt 446 is "unscrewed" it may function to push the inferior and superior brackets 444 apart. This distraction may result in increased foraminal area and reduction in nerve root compression.

Figure 62A:
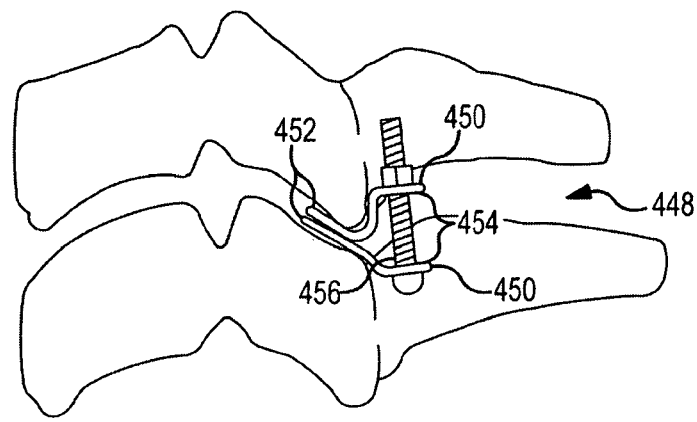
FIGS. 62A-C include side and perspective views of an implant, according to certain embodiments.
Figure 62B:
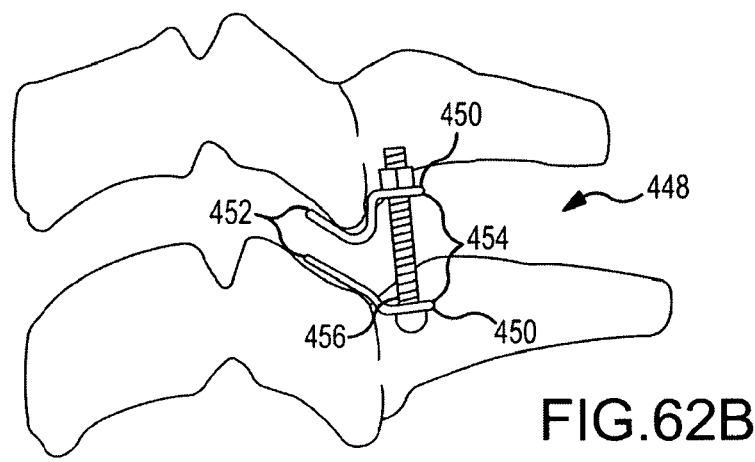
Figure 62C:
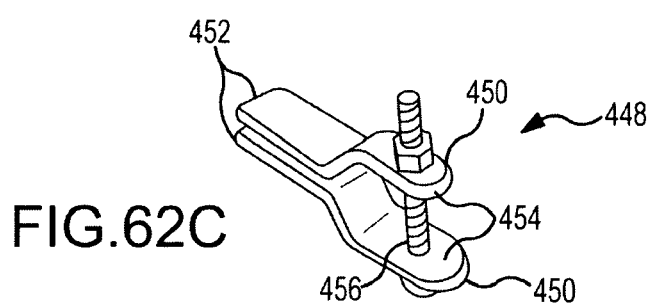

FIGS. 62A-C show yet another embodiment of an implant 448. In this embodiment, bracket type structures 450 may each have a leg 452 for positioning within a facet joint and another leg 454 for receiving a bolt 456. As with the bracket above, the bolt 456 may be configured to create distraction energy. That is, it may be connected to one of the superior or inferior bracket 450 so as to allow rotation but not relative translation. The other bracket 450 may threadably engage the bolt 456. As such, when the bolt 456 is "unscrewed" it may function to push the brackets apart resulting in and increased foraminal area.

Figure 63A:
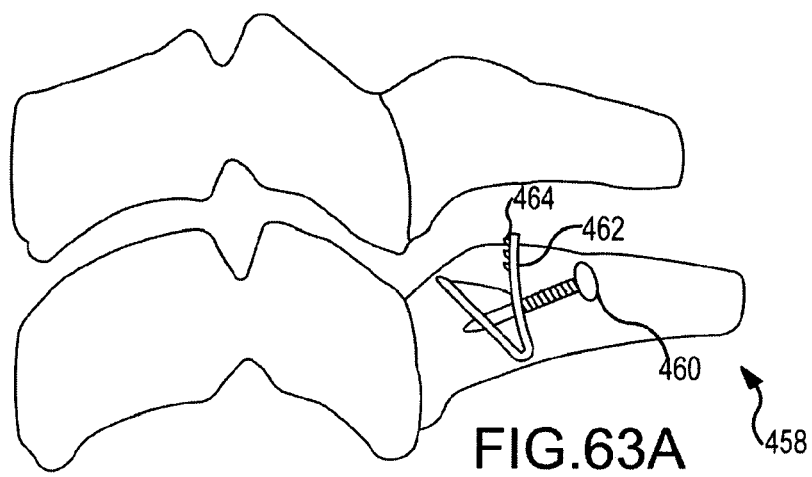
FIGS. 63A-C include side and perspective views of an implant, according to certain embodiments.
Figure 63B:
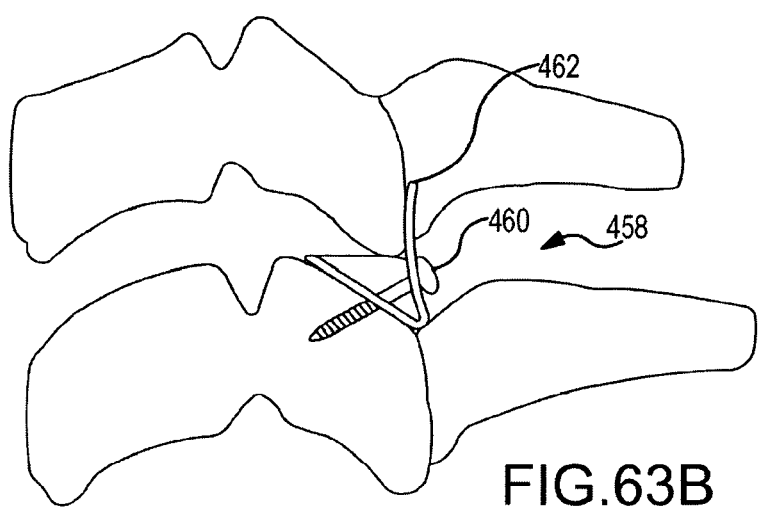
Figure 63C:
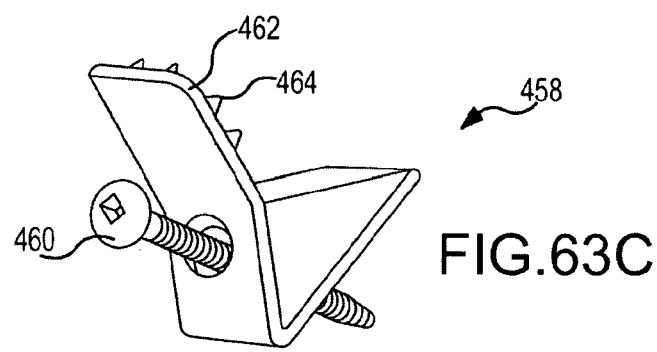

FIGS. 63A-C show yet another embodiment of an implant 458. In this embodiment, a triangular shaped implant 458 including a bent plate and a filler wedge may be inserted in the facet joint. As the triangular implant 458 is inserted progressively more anterior, the joint may be distracted to an optimal level. Once the desired distraction is achieved, an anchoring screw 460 may be inserted through the implant 458 and into the inferior lateral mass. The superior aspect of the implant 458 may include a metal flap 462 with teeth, spikes, or cleats 464. This maleable flap 462 may be contoured to the superior lateral mass and anchored using its teeth, spikes, or cleats 464. The metal flap 462 and inferior screw 460 may provide permanent fixation of the triangular implant 458 to enable permanent distraction of the facet and immobilization of the joint facilitating permanent fusion of the joint.

Figure 64A:
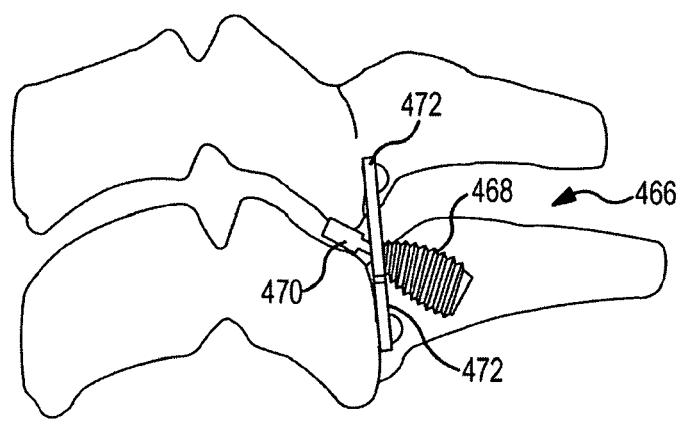
FIGS. 64A-C include side and perspective views of an implant, according to certain embodiments.
Figure 64B:
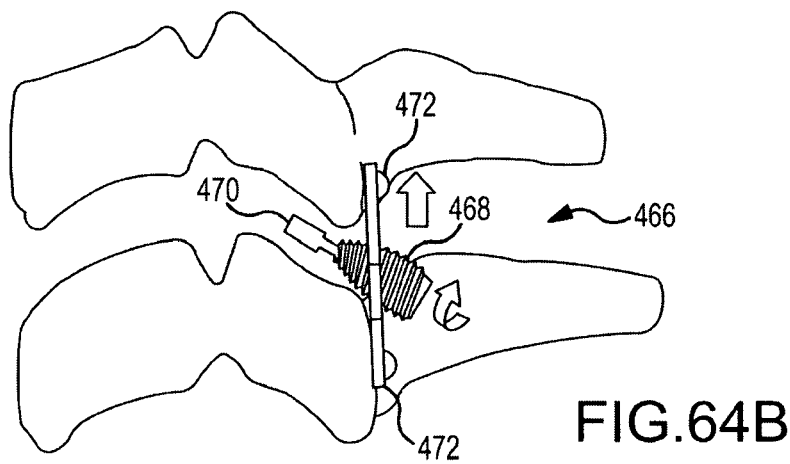
Figure 64C:
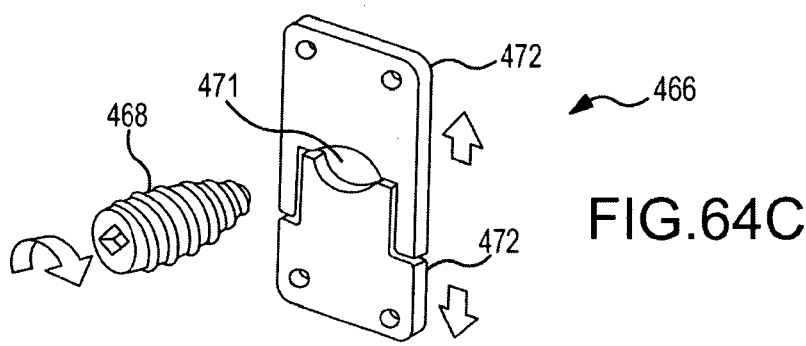

FIGS. 64A-C show yet another embodiment of an implant 466. In this embodiment, a distraction system consists of a central anchoring plug 468, an initiating plate 470, and two external plates 472. The two external (superior and inferior) plates 472 may be attached to the lateral masses of a motion segment and may be anchored using screws. The initiating plate 470 may then be inserted in the gap 471 between the external plates 472 to initiate opening of the plates 472 and the joint and allow for further insertion of the anchoring plug 468. Following the insertion of this initiating plate 470 and turning or manipulating the plate 470 to open the external plates 472, the central anchoring plug 468 may then be advanced into the gap 471 between the external plates 472 causing expansion of the plates and distraction and separation of the joint.

Figure 65A:
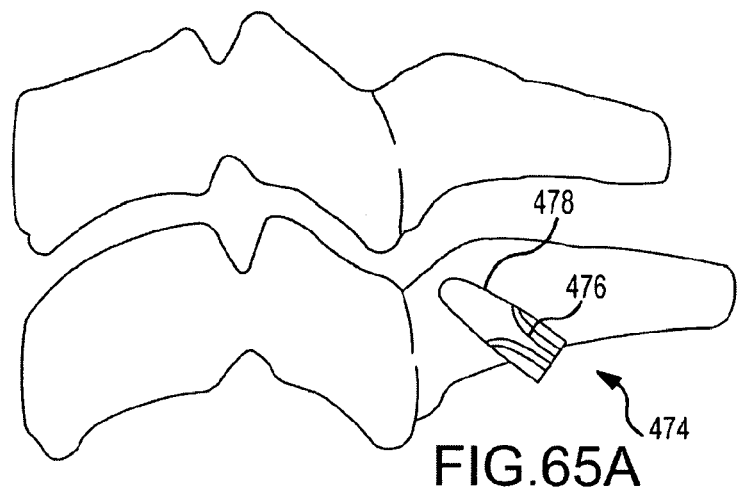
FIGS. 65A-C include side and perspective views of an implant, according to certain embodiments.
Figure 65B:
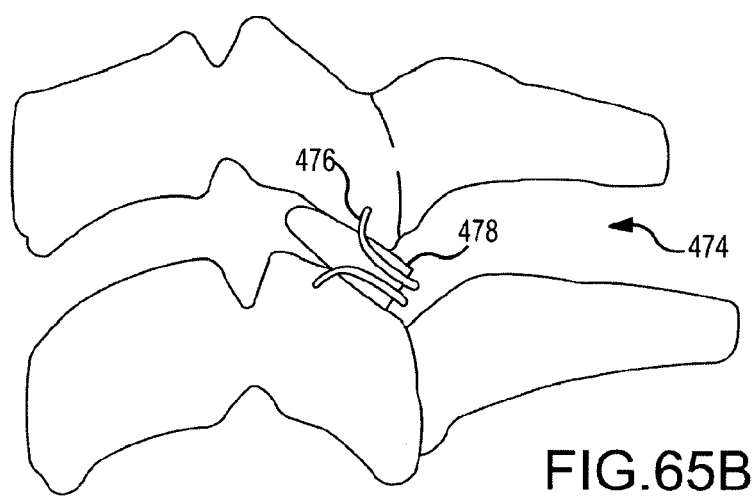
Figure 65C:
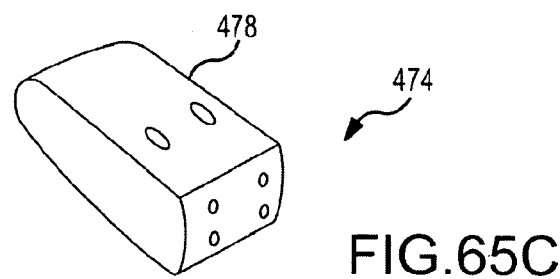

FIGS. 65A-C show yet another embodiment of an implant 474. In this embodiment, nitinol hooks 476 may be configured to have a memory. The hooks 476 may be flattened and inserted through a delivery system 478. The delivery system 478 may be placed in a facet joint. Once inserted within the facet, the nitinol hooks 476 may be activated via temperature, force, or other activation means causing them to assume their original (pre-flattened) shape and hook into the opposing facet surfaces. As the hooks 476 engage the cortical bone of the facet surfaces, they distract the joint. This separation results in increased foraminal area and reduced nerve root compression.

Figure 66A:
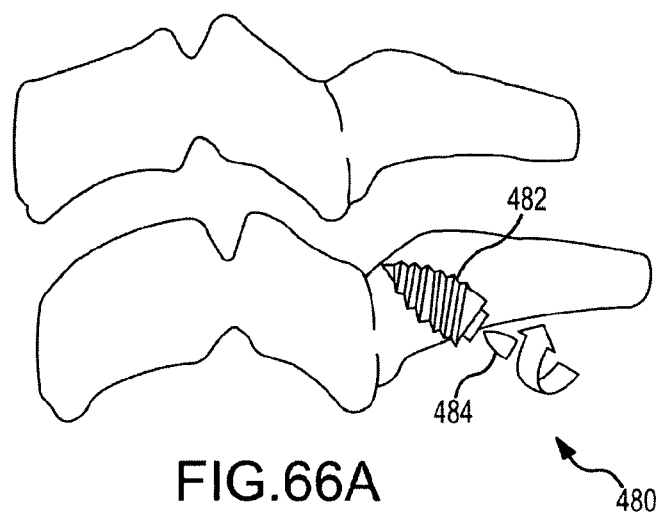
FIGS. 66A-C include side views of an implant, according to certain embodiments.
Figure 66B:
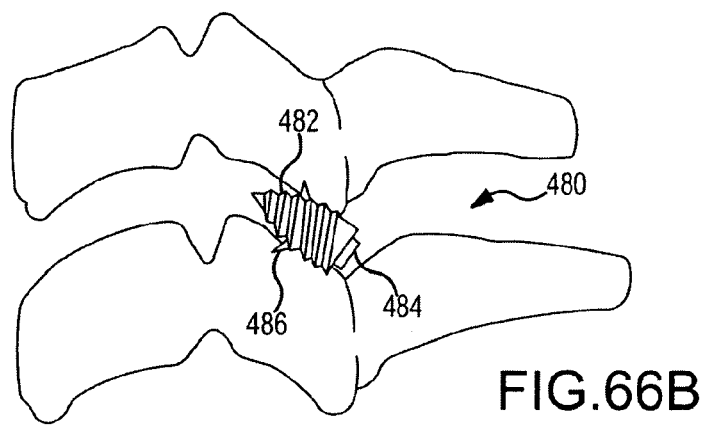
Figure 66C:
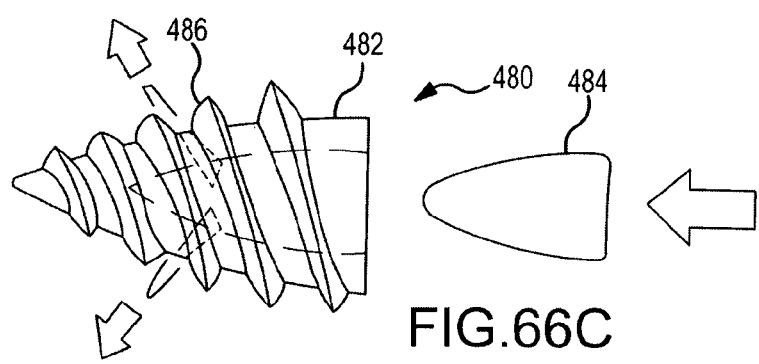

FIGS. 66A-C show yet another embodiment of an implant 480. In this embodiment, a hollow screw sleeve 482 may be placed within the facet joint. A wedge 484 may then be placed within the hollow screw sleeve 482 causing it to expand and distract the joint. Additionally, the screw sleeve 482 may include sharp barbs 486 having a retracted position and a ejected position. As the wedge 484 is inserted, the wedge 484 displaces the sharp barbs 486 causing them to be ejected through the screw sleeve 482 and engage the facet surfaces. These barbs 486 may provide acute fixation of the implant 480 to the joint and prevent migration of the implant 480. The distraction and separation of the joint result in increased foraminal area and reduced nerve root compression.

Figure 67A:
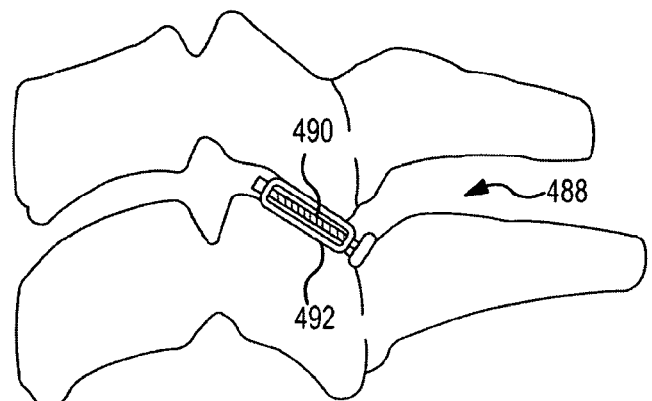
FIGS. 67A-C include side and perspective views of an implant, according to certain embodiments.
Figure 67B:
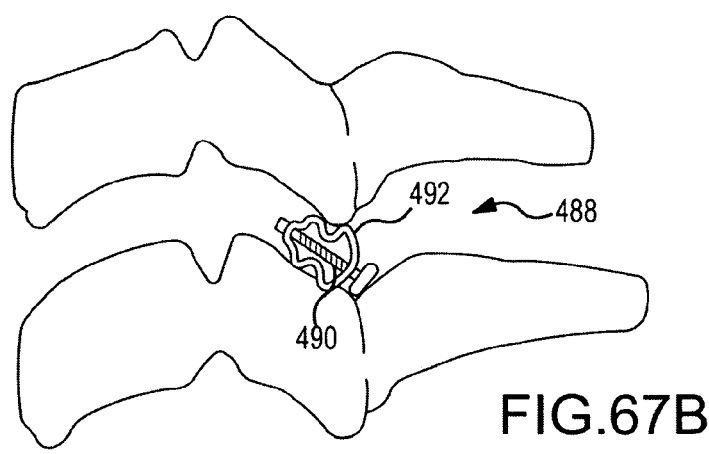
Figure 67C:
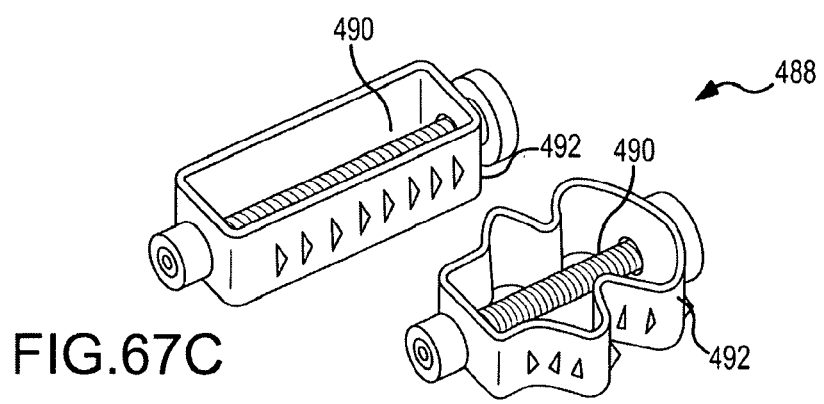

FIGS. 67A-C show yet another embodiment of an implant 488. In this embodiment, a panel anchor implant 488 may be placed within the facet joint. The implant 488 may include a bolt 490 and collapsible nut 492 that is rotationally free from the bolt 490 near the head of the bolt 490 and threadably engaged with the bolt 490 near the end opposite the head. As such, when the bolt 490 is advanced, the distal end of the nut 492 is squeezed toward the proximal end of the nut 492 and the nut 492 may collapse with an accordion effect. As shown, the compression of the nut 492 results in a taller structure that applies a distraction force to the opposing facet surfaces. This distraction leads to increased foraminal area and reduced nerve root compression.

Figure 68A:
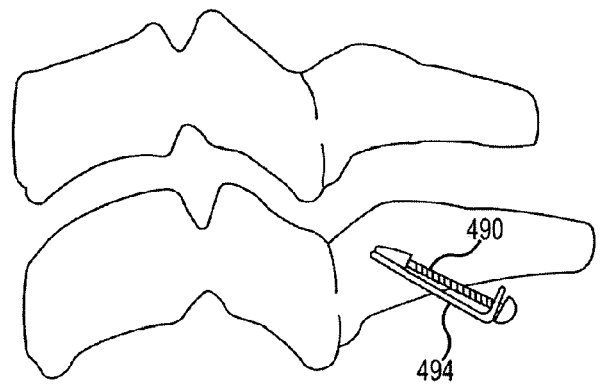
FIGS. 68A-C include side and perspective views of an implant, according to certain embodiments.
Figure 68B:
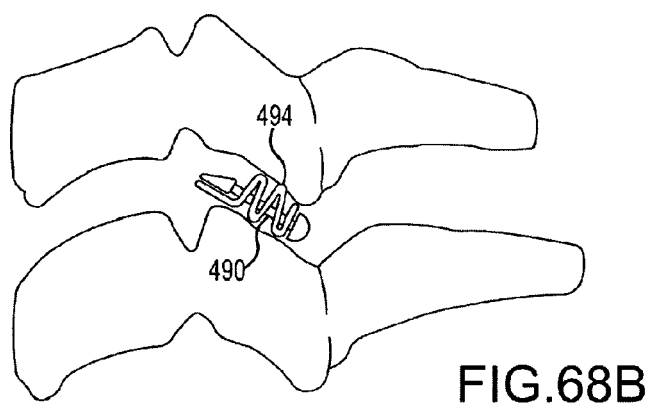
Figure 68C:
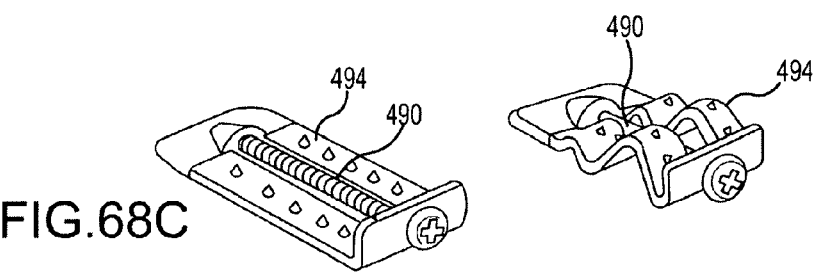

In similar fashion, the embodiment shown in FIGS. 68A-C may collapse causing distraction of the joint. In lieu of the nut 492 shown in FIGS. 67A-C, this embodiment, shows a flat plate 494 that collapses into an accordion shape.

Figure 69A:
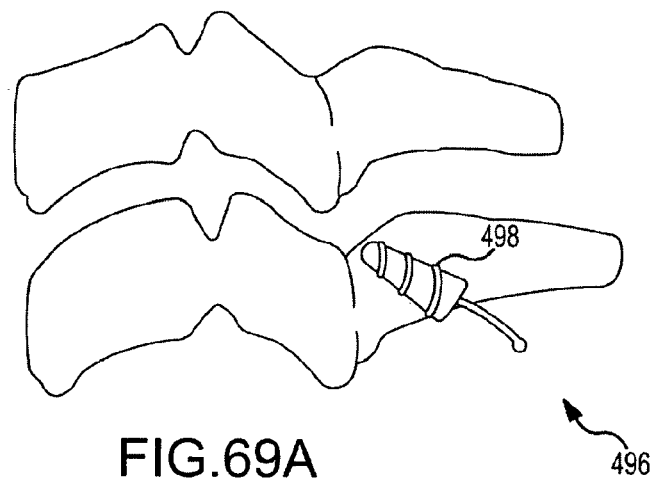
FIGS. 69A-C include side and perspective views of an implant, according to certain embodiments.
Figure 69B:
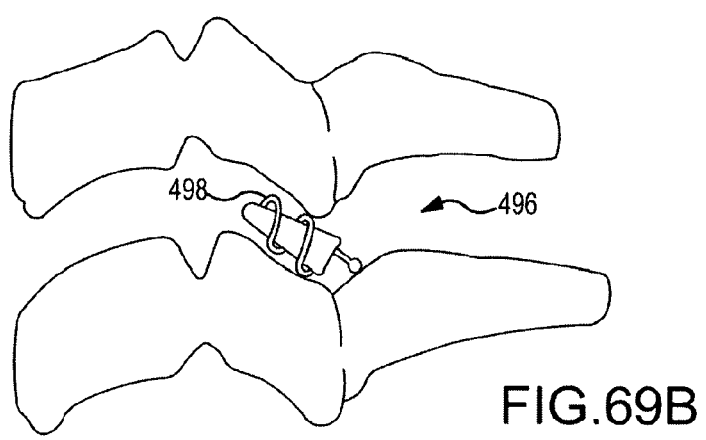
Figure 69C:
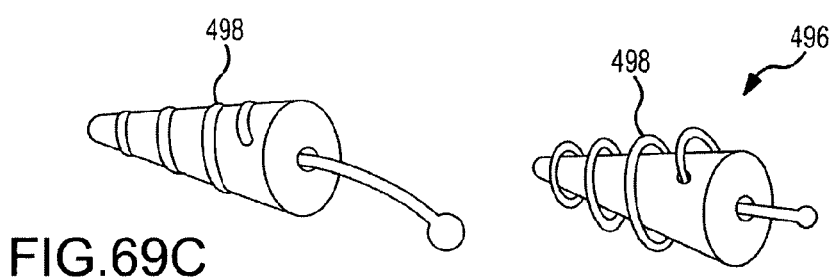

FIGS. 69A-C show yet another embodiment of an implant 496. In this embodiment, an implant 496 is placed within the facet joint. The implant could have a number of shapes and sizes but, in this embodiment, has a tension wire 498 that surrounds the implant 496 and is pulled taught during implantation. Once the implant 496 is properly positioned, the wire's tension is released. The release of this tension causes the wire 498 to return to a preset expanded shape and height that causes the implant 496 to expand. The expansion of the implant 496 as the wire returns to its preset, and larger profile, shape causes separation of the facet joint. This distraciton results in increased foraminal area and reduced nerve root compression.

Figure 70A:
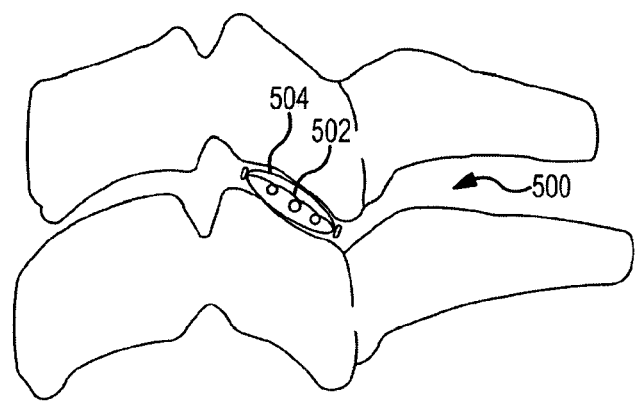
FIGS. 70A-C include side views of an implant, according to certain embodiments.
Figure 70B:
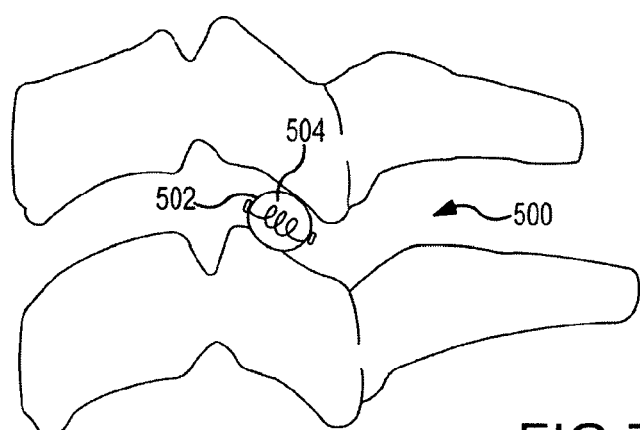
Figure 70C:
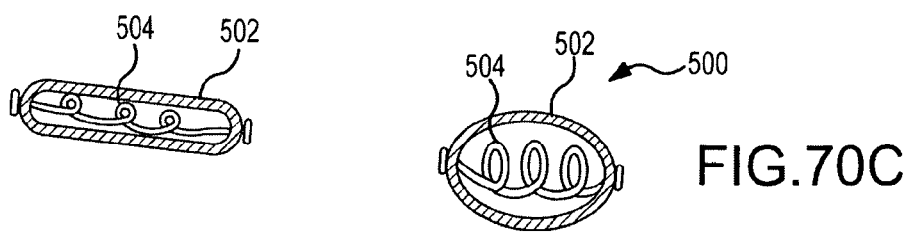

Similarly, as shown in FIGS. 70A-C, an implant 500 with an outer housing 502 and an internal spring 504 may be positioned in the facet joint with the wire spring 504 in a tensioned or elongated position. Once properly positioned, the tension on the spring 504 may be released thus collapsing the spring 504 and expanding the associated housing 502 of the implant 500.

Figure 71A:
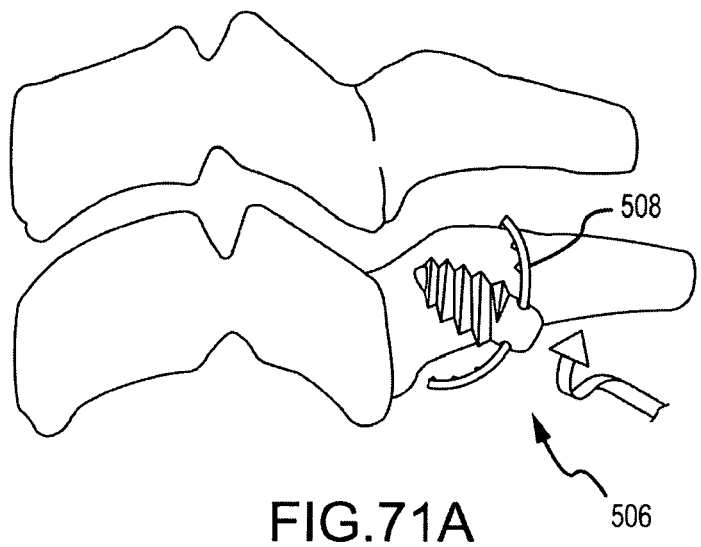
FIGS. 71A-C include side and perspective views of an implant, according to certain embodiments.
Figure 71B:
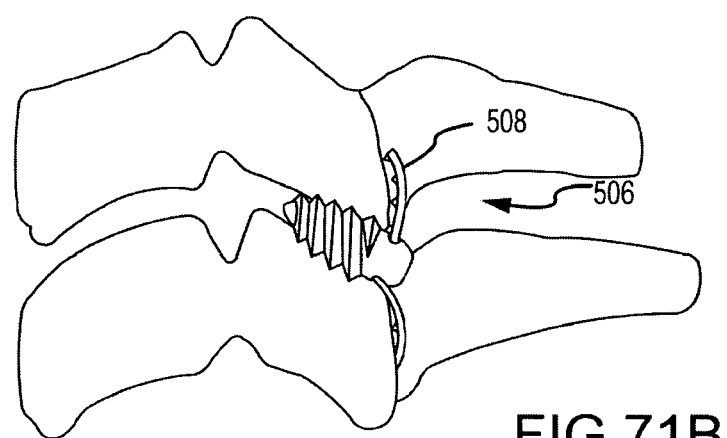
Figure 71C:
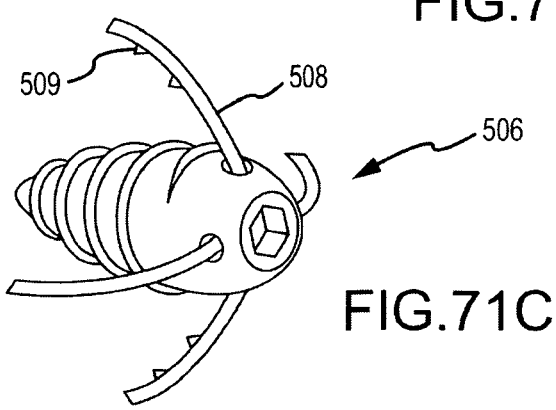

FIGS. 71A-C show yet another embodiment of an implant 506. In this embodiment screw type implant 506 may be provided and may also include an arm type locking mechanism 508. The locking mechanism 508 may extend from all sides of the head of the screw as shown and may be biased in a distal direction. As the screw advances, the locking mechanism 508 may anchor in the lateral mass of a vertebra. The biased position of the arm 508 pressing against the lateral mass may provide a force biasing the implant 506 against the advancing direction. However, this may cause constant friction between any newly cut threads in the surfaces of the facet joint thereby preventing unscrewing or back out of the implant. In addition, teeth 509 may be included on the arms 508 and may bite into the lateral mass further preventing backing out of the implant.

Figure 72A:
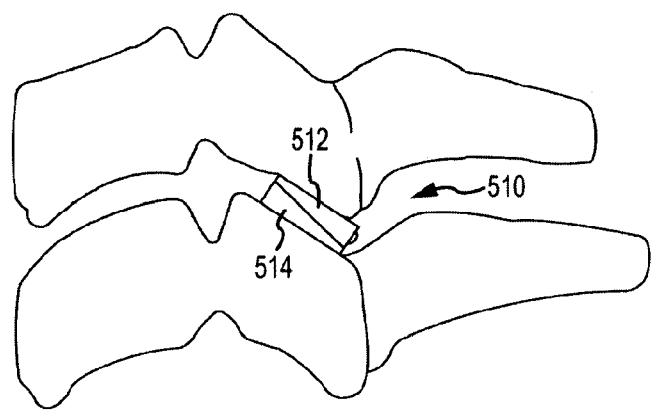
FIGS. 72A-C include side and perspective views of an implant, according to certain embodiments.
Figure 72B:
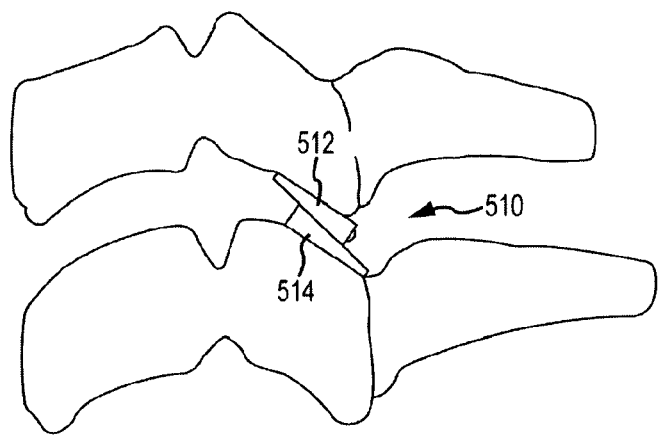
Figure 72C:
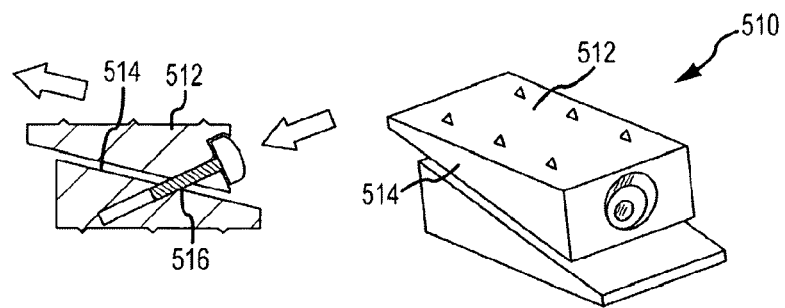

FIGS. 72A-C show yet another embodiment of an implant 510. In this embodiment, two wedge shape opposing structures 512 are shown separated by a sloping plane 514. The structures 512 may have a predetermined relative position, or a series of predetermined relative positions, where a bolt or screw 516 may be advanced at an angle as shown through one of the structures 512 and into a predrilled hole of the other 512 to maintain their relative position. Alternatively, the relative positions may not predetermined and a self-drilling screw 516 may be used. In either case, the implant 510 may be positioned in the facet joint in minimal profile position and then the two structures 512 may be slid relative to each other along the sloping plane 514 to expand the implant 510 and thus the facet joint. Once the desired position is achieved, the bolt, pin, screw, or other fastener 516 may be inserted to maintain the relative position of the structures 512.

Figure 73A:
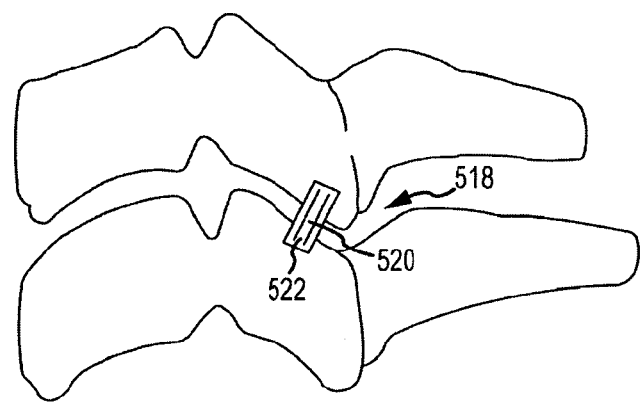
FIGS. 73A-C include side and perspective views of an implant, according to certain embodiments.
Figure 73B:
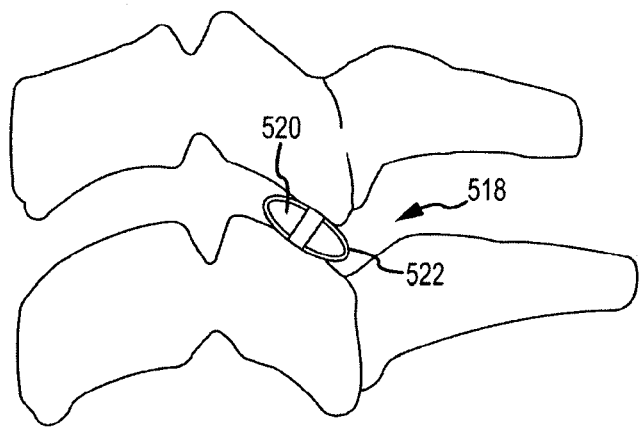
Figure 73C:
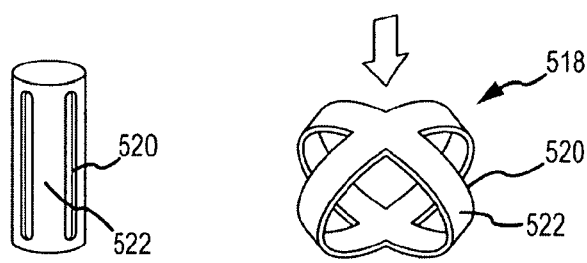

FIGS. 73A-C show yet another embodiment of an implant 518. In this embodiment, an implant 518 is configured to be inserted in a collapsed state. In its non collapsed state, it has a vertical cylindrical profile with side cutouts 520. When the implant is compressed, the side cutouts 520 allow the wall panels 522 to bend out as the height of the cylindrical implant 518 is reduced. These wall panels 522 create an anchor shape that can enage bone structures. This implant 518 may be placed within the facet join in its flattened, compressed profile. Once it is positioned correctly, a distraction energy may be applied to the implant 518 to cause it to expand or decompress. This decompression causes the implant 518 to attempt to return to its vertical cylindrical shape. The implant 518 may be made from a resilient elastic material such as nitinol, stainless steel, or other known materials. As the implant 518 becomes more cylindrical, it pushes against the opposing facet surfaces. This force causes distraction of the facet joint and results in increase foraminal area and reduced nerve root compression.

Figure 74A:
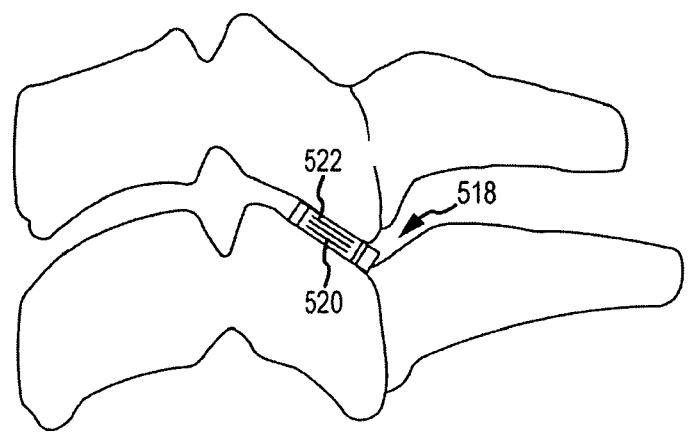
FIGS. 74A-C include side and perspective views of an implant, according to certain embodiments.
Figure 74B:
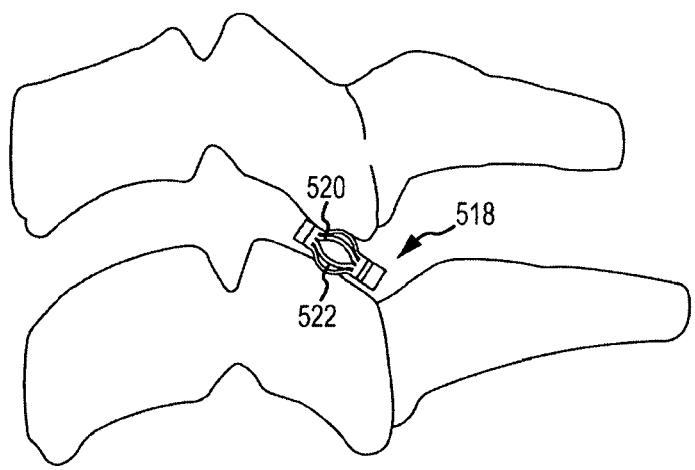
Figure 74C:
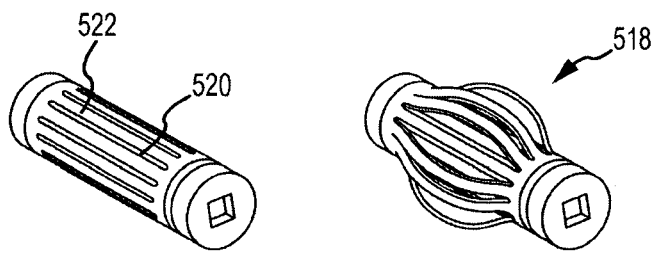

Similarly, as shown in FIGS. 74A-C, the implant 518 may be positioned on its side and the distraction energy may cause the implant 518 to collapse from its cylindrical shape and expand laterally to distract the facet joint.

Figure 75A:
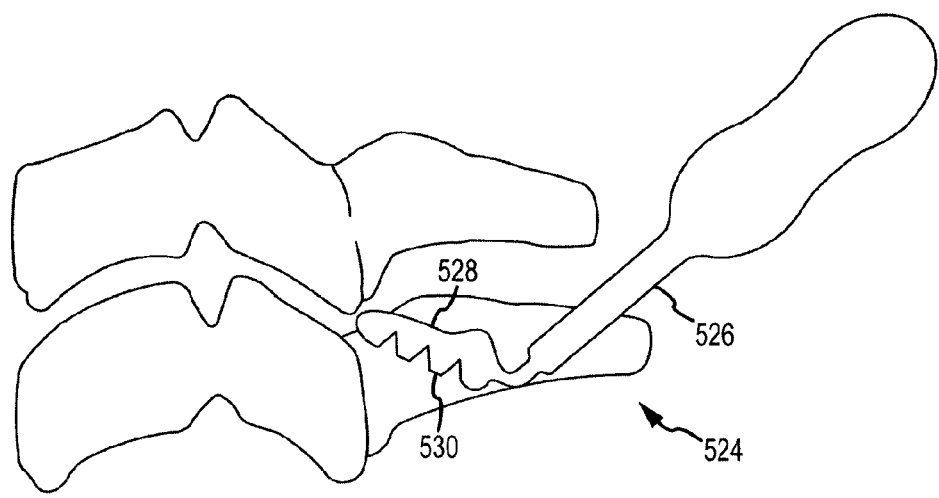
FIGS. 75A-B include side views of an implant, according to certain embodiments.
Figure 75B:
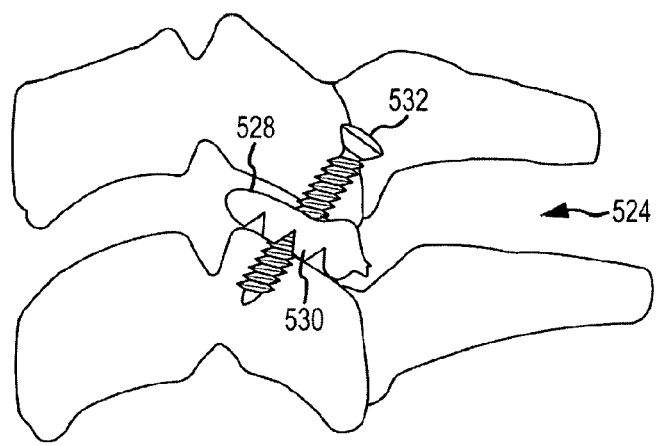

FIGS. 75A-B show yet another embodiment of an implant 524. In this embodiment, a delivery tool 526 is inserted within the facet joint. The distal tip 528 of the delivery tool 526 is shaped to distract the joint. Once the tool 526 is inserted into the facet joint and the desired amount of distraction is achieved, the distal tip 528 (part that is in the facet joint) may be detached from the delivery tool 526. In one configuration of this embodiment, the detachable tip 528 would have teeth, cleats, spikes, or keels 530 to prevent it from migrating within the joint once it is detached. In another configuration of this embodiment, the implant 524 may be anchored in the facet joint by inserting a screw 532 through the superior facet, the implant, and the inferior facet. In both configurations, the detachable tip 526 (implant) may provide permanent distraction of the joint resulting in increased foraminal area and reduced nerve root compression.

Figure 76A:
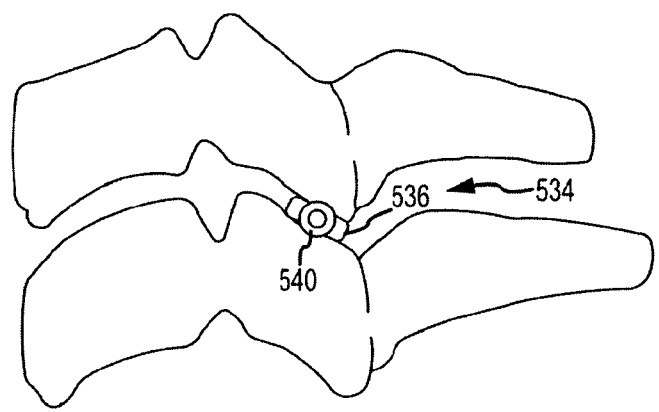
FIGS. 76A-C include side and perspective views of an implant, according to certain embodiments.
Figure 76B:
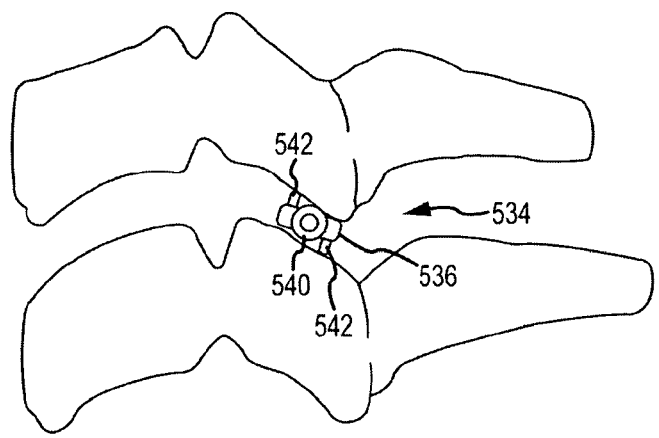
Figure 76C:
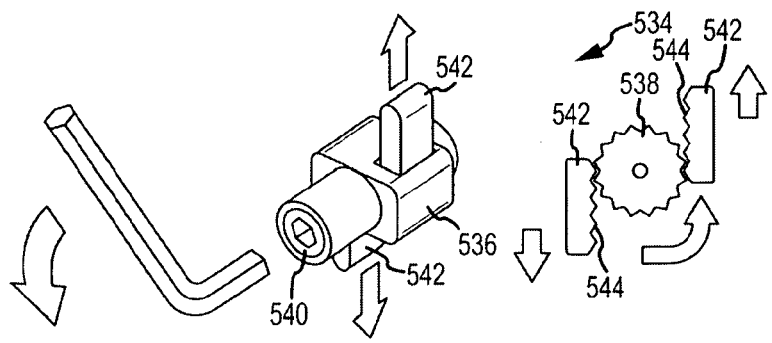

FIGS. 76A-C show yet another embodiment of an implant 534. In this embodiment, the implant 534 may include a housing 536 with a central gear 538 turnable by an allen type head 540 or other known attachment for turning, such as any known screwdriver heads. Adjacent the central gear 538 on each side, the implant 534 may include two plates 542 slidable in the housing 536 in a direction tangential to the gear surface. The plates 542 may include teeth 544 engaging the central gear 538 such that when the gear 538 turns, the plates 542 slide tangentially to the gear 538 and extend beyond an outer surface of the housing 536. As such, the implant 534 may be positioned in a facet joint as shown in FIG. 76A. Once positioned, the gear 538 may be turned thus extending the plates 542 in opposite directions and distracting the facet joint.

Figure 77A:
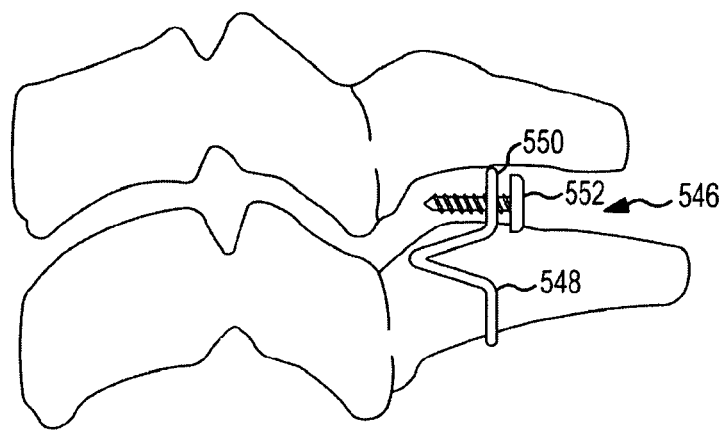
FIGS. 77A-C include side and perspective views of an implant, according to certain embodiments.
Figure 77B:
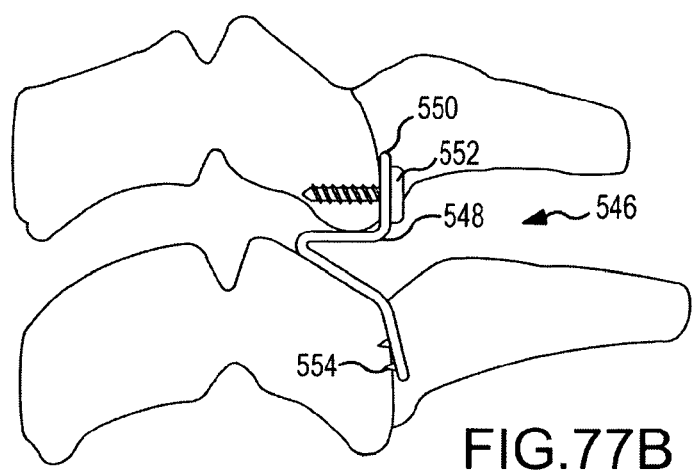
Figure 77C:
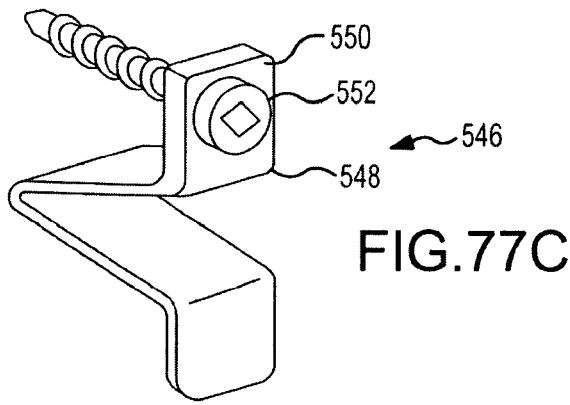

FIGS. 77A-C show another embodiment of an implant 546. In this embodiment a triangular shaped implant 546 in the form of a bent plate 548 may be wedged into the facet causing distraction and separation of the joint. On one side of the triangular distraction structure 548 is a bracket 550 with a screw 552. The screw 552 may be inserted into the lateral mass to provide anchoring of the facet distraction implant 546. The other side of the triangular distraction structure 548 may include teeth or other features 554 for biting into the assocatiated lateral mass. The implant 546 would provide permanent distraction of the joint resulting in increase foraminal area and reduced nerve root compression.

Figure 78A:
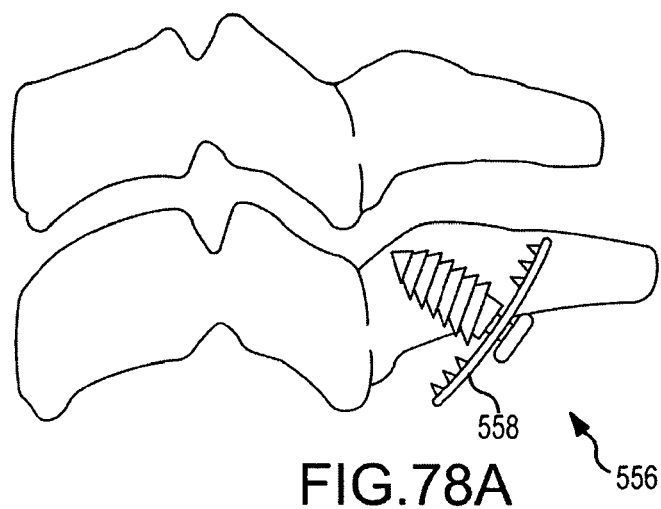
FIGS. 78A-C include side and perspective views of an implant, according to certain embodiments.
Figure 78B:
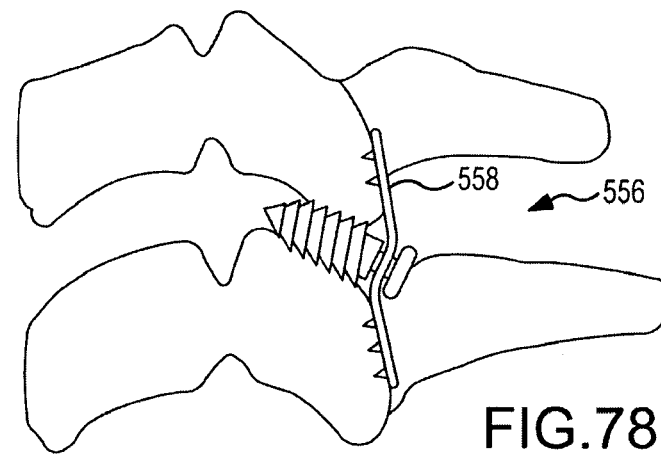
Figure 78C:
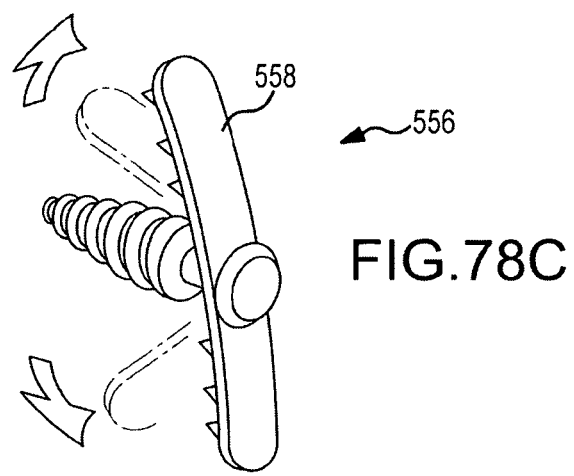

FIGS. 78A-C show another embodiment of an implant 556. In this embodiment, the implant 556 may have a tapered shape that is taller at the posterior aspect relative to the anterior aspect. The implant could be tapped in, malleted in, screwed in with threads, or pushed in with hand pressure. Once the implant 556 is positioned correctly, the head 558 of the implant 556 (posterior aspect) may be configured to have sharp teeth, spikes, or cleats that can be pushed into the cortical bone of the superior and inferior lateral masses of a motion segment. These flaps 558 could be hinged on the posterior aspect of the implant 556 to allow the flaps 558 to be pushed anterior enough to match the irregular contours of the lateral mass. The implant 556 would provide permanent distraction of the joint resulting in increase foraminal area and reduced nerve root compression.

Figure 79A:
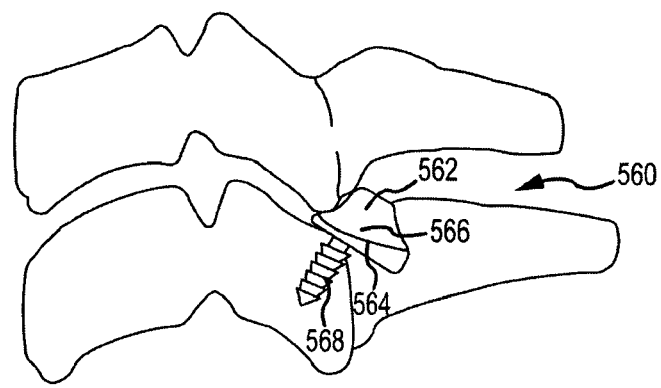
FIGS. 79A-C include side and perspective views of an implant, according to certain embodiments.
Figure 79B:
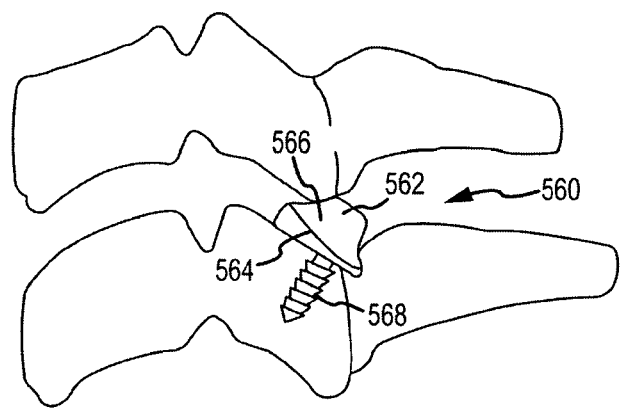
Figure 79C:
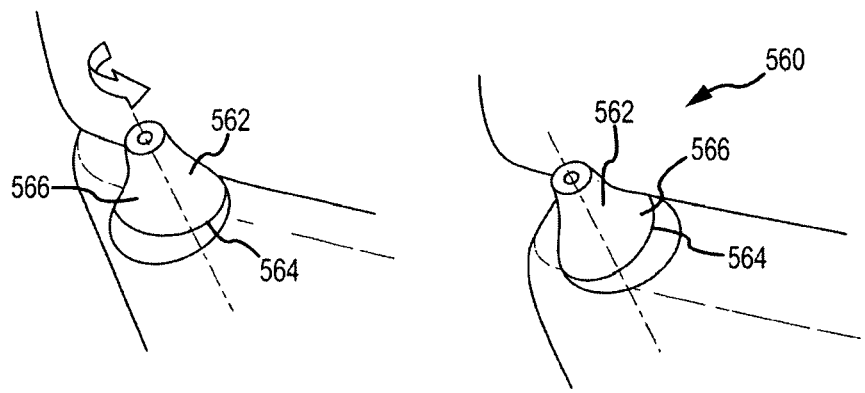

FIGS. 79A-C show another embodiment of an implant 560. In this embodiment, the implant 560 includes a single rotatable cone 562 with a shoulder shaped ledge 564 defining a cam surface 566, the distance between the ledge and the bottom of the implant defining a shoulder height. The shoulder height may vary gradually from low to high and back to low along the circumferential perimeter of the cone 562. In use, the implant 560 may be initially positioned such that the shoulder portion with the low ledge height enters the facet joint. Once in position, the implant 560 may be rotated to cause the higher ledge height to enter the joint thereby distracting the posterior portion of the joint by causing the superior articular face to ride upward along the cam surface 566. The implant 560 may then be secured with a screw 568 extending along the longitudinal axis of the implant.

FIGS. 80A-D show yet another embodiment of an implant 570. In this emobiment, an implant 570 may include a housing 572 with penetrations 574 adapted for ejection of retracted spikes 576. Within the housing 572, a wire 578 may be routed between the spikes 576 as shown in FIG. 80D. The implant 570 may be inserted into the facet joint while the wire 578 is relaxed and the spikes 576 are contained within the folds/curves in the collapsed wire 578. Once the implant 570 is positioned correctly, the wire 578 may be pulled taught causing the spikes 576 to displace outwardly, extending out of the housing 572 and engaging the opposing facet surfaces with a force. This force may create distraction and separation of the joint, while the pointed tips of the spikes 576 would penetrate the surface of the facet joint and provide acute fixation preventing migration of the implant 570. The implant 570 would provide permanent distraction of the joint resulting in increase foraminal area and reduced nerve root compression.

Figure 81A:
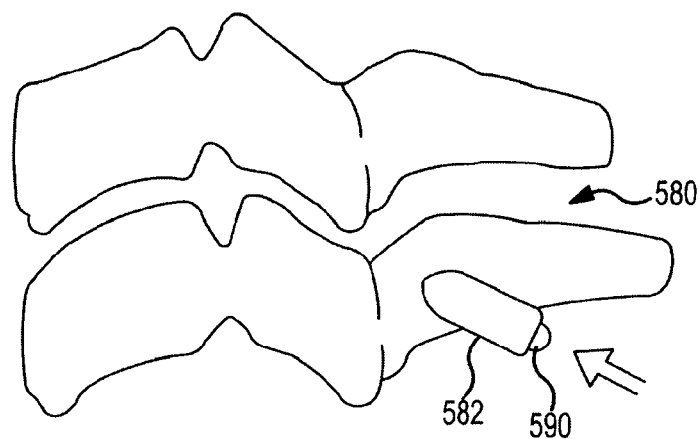
FIGS. 81A-C include side views of an implant, according to certain embodiments.
Figure 81B:
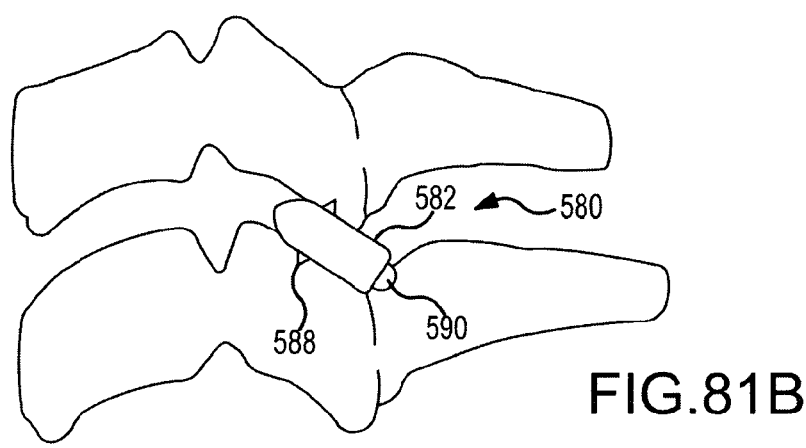
Figure 81C:
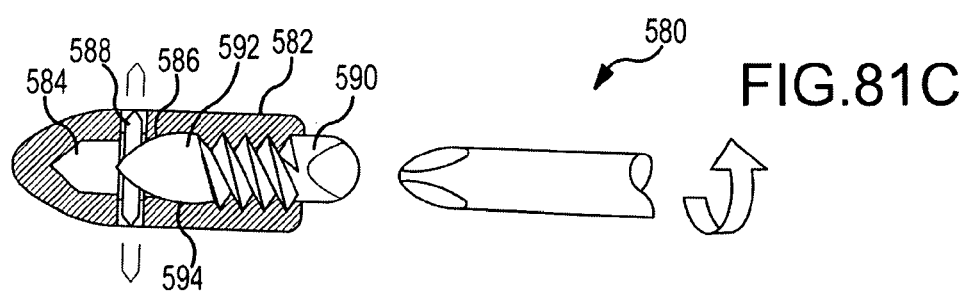

FIGS. 81A-C show yet another embodiment of an implant 580. In this embodiment, an implant 580 may include a housing 582 with a cavity 584 and penetrations 586 on lateral surfaces extending from the cavity 584 through the wall of the housing 582, the penetrations 586 adapted for ejection of retracted spikes 588. Within the housing 582, a threaded piston 590 may be positioned at a distal end and may be adapted for displacement through the cavity 584 in the proximal direction. The piston 590 may have a torpedo shaped distal end 592 and may engage the a beveled inner surface 594 of the retracted spikes 588. The implant 580 may be positioned within a facet joint and when properly postioned, the piston 590 may be advanced via a turning tool, the torpedo shaped distal end 592 of the piston 590 thus engaging the beveled end 594 of the spikes 588 and advancing them laterally relative to the implant 580 out of the housing 582 with a force and into the face of the facets. This force may create distraction and separation of the joint, while the pointed tips of the spikes 588 would penetrate the surface of the facet joint and provide acute fixation preventing migration of the implant 580.

Figure 82A:
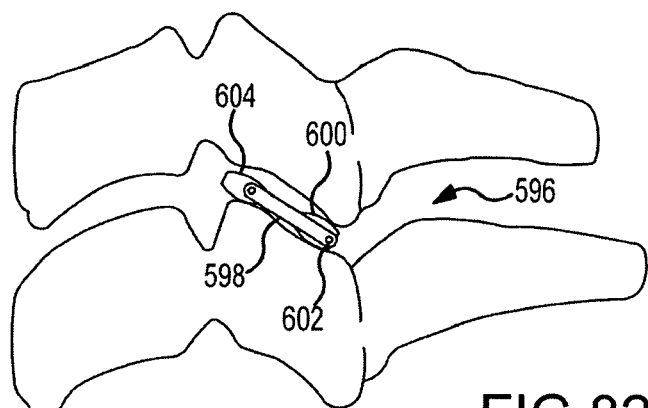
Figure 82B:
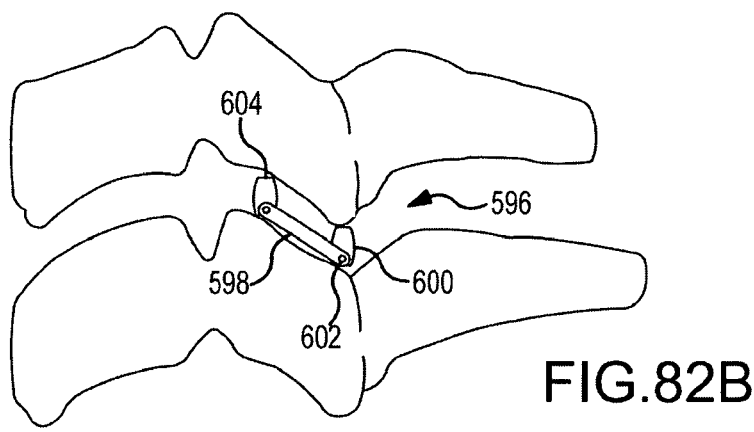
Figure 82C:
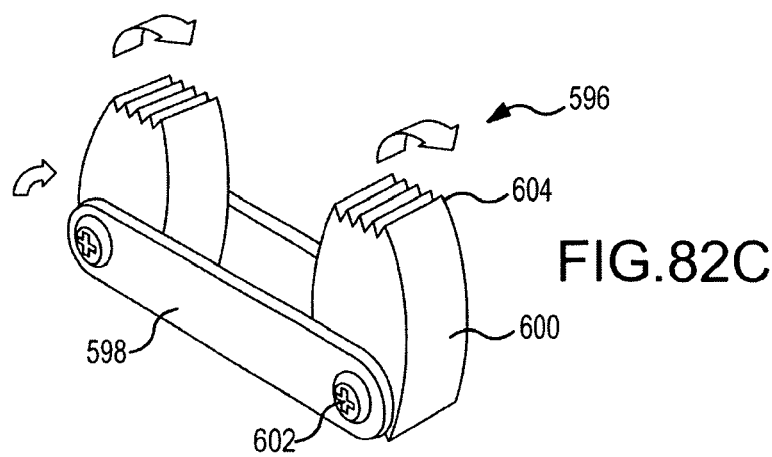

FIGS. 82A-F show yet another embodiment of an implant 596. In this embodiment, the implant 596 may include two parallel equal length side bars 598 with pivoting struts 600 positioned on a pin 602 between the bars 598 at each end. The pivoting struts 600 may include textured surfaces 604 on each end and the struts 600 may be pinned to the side bars 598 through one end. As shown in FIG. 82F, the struts 600 may have length so as to allow them to be pivoted to lie parallel to one another in the plane of the side bars 598. In this position, the implant 596 may be positioned in the facet joint as shown in FIG. 82A or anterior to the facet joint as shown in FIG. 82D. Once properly positioned, the struts 600 of the implant 596 may be rotated so as to be approximately perpendicular to parallel side bars 598 thus separating an inferior vertebra from a inferior vertebra. It is noted that the generally stout shape of the struts 600 with relatively broad textured ends 604 may facilitate stability preventing the implant 596 from racking back to the parallel condition.

Figure 83A:
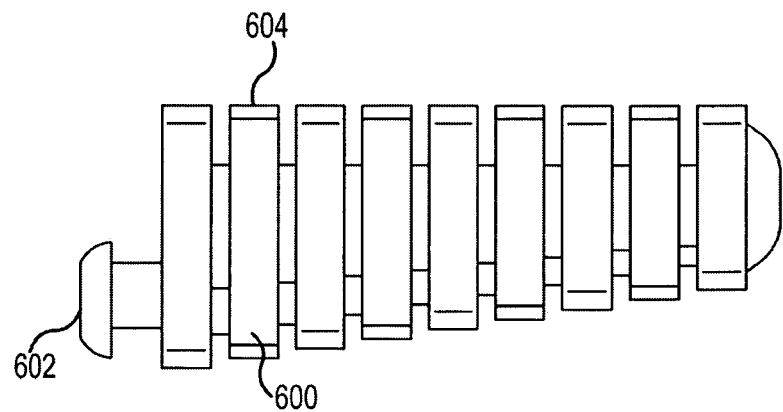
FIGS. 83A-B include side and perspective views of an implant, according to certain embodiments.
Figure 83B:
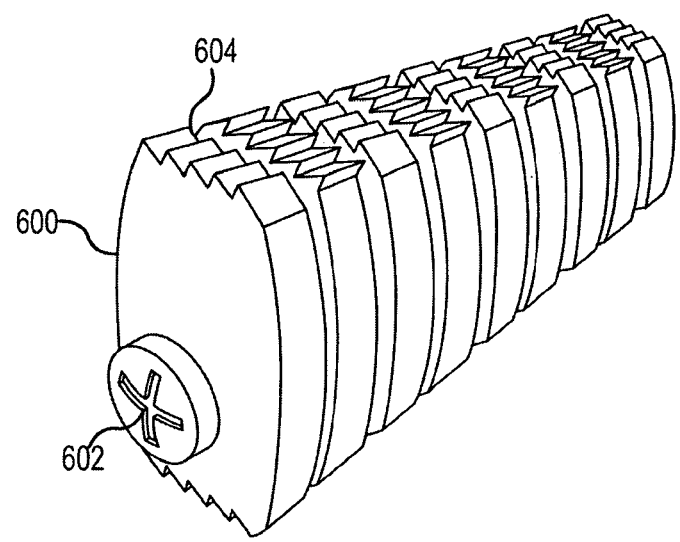

Another variation of this embodiment is shown in FIGS. 83A-B, where a series of varying height struts 600 are positioned along a shaft. The entire implant may be placed within a facet joint on its side and then a single ninety degree turn may position the implant and distract the joint.

Figure 84A:
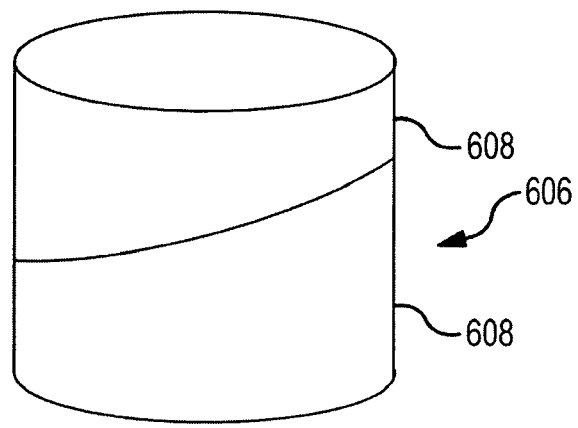
FIGS. 84A-B include perspective views of an implant, according to certain embodiments.
Figure 84B:
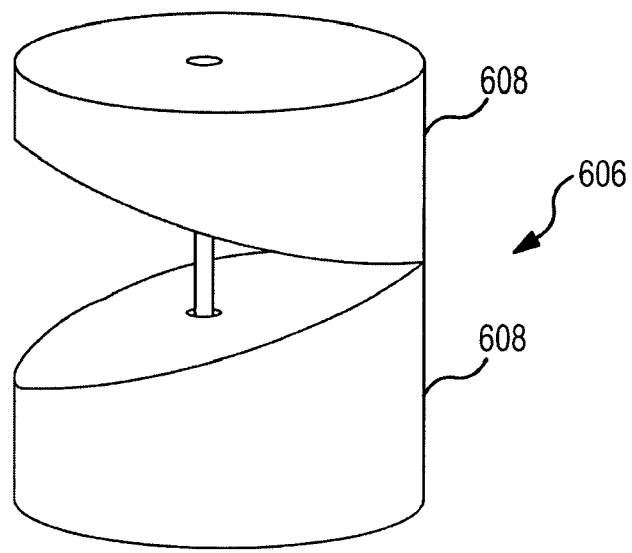

FIGS. 84A-B show yet another embodiment of an implant 606. In this embodiment, two rotatable cams 608 may be positioned in a facet joint. It is noted that the cams may have a relatively low profile and the proportions in the FIGS. may be exaggerated for purposes of showing the concept. Once placed in the joint, a distraction/rotation energy may be applied to the cams causing them to rotate open to reveal two circular halves of the cam implant. As one half of the implant rotates superiorly, it may push the superior vertebra upward creating an increase in foraminal area and nerve root decompression.

Figure 85:
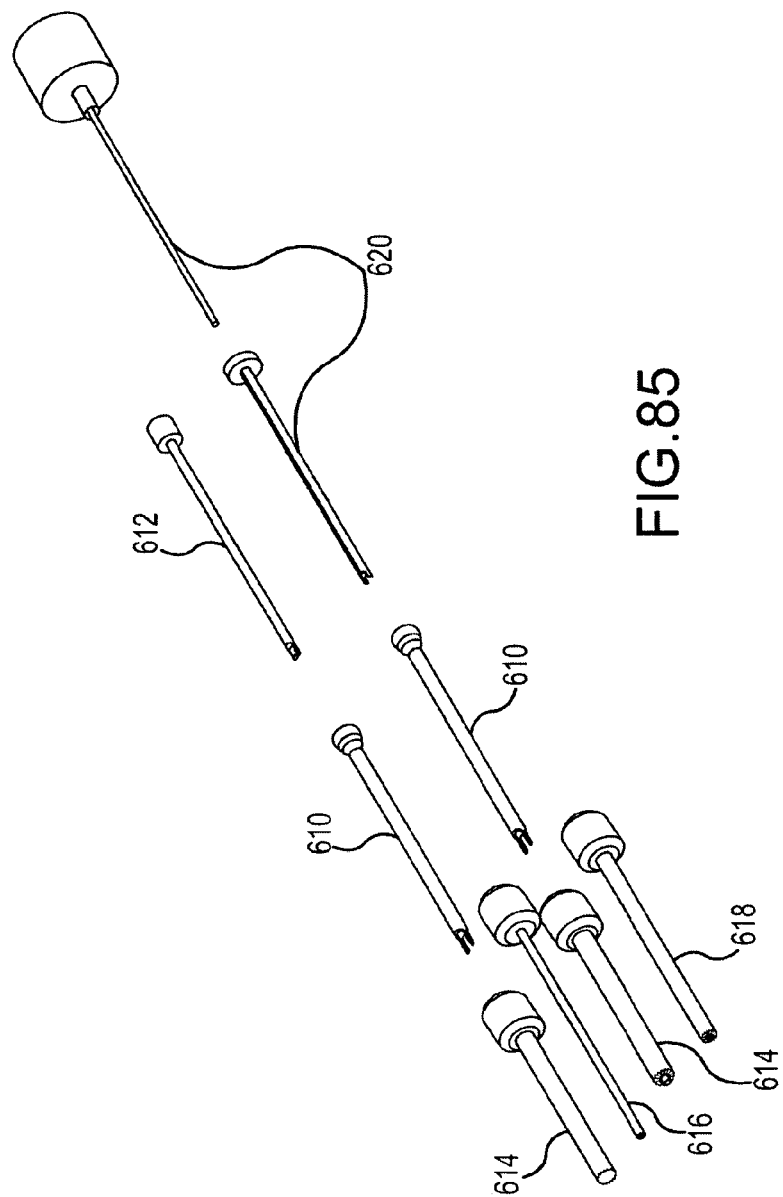
FIG. 85 is an exploded perspective view of a kit, according to certain embodiments.
Figure 86:
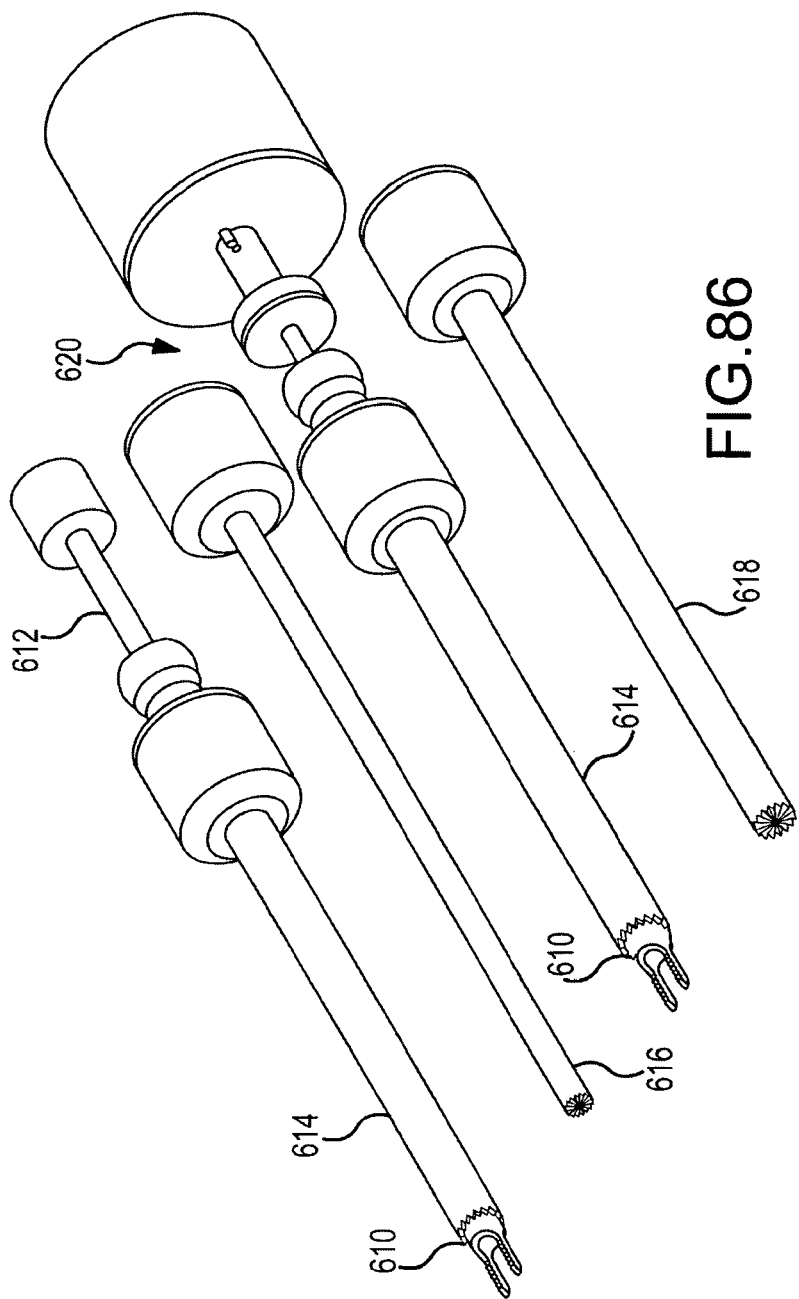
FIG. 86 is an assembled perspective view of a kit, according to certain embodiments.
Figures 87, 88:
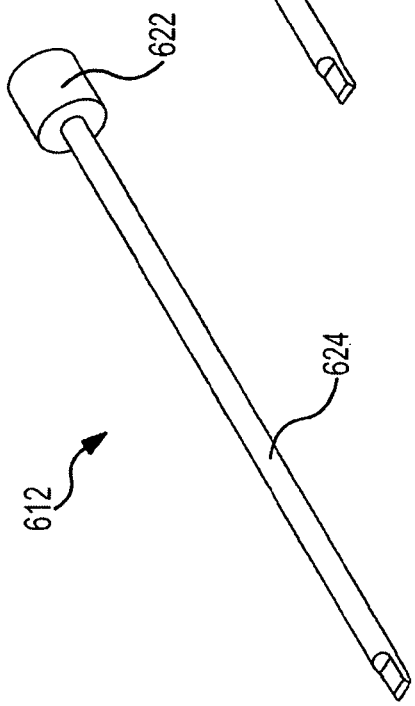
FIGS. 87 and 88 are perspective views of a chisel portion of the kit shown in FIGS. 85 and 86.
Figure 90:
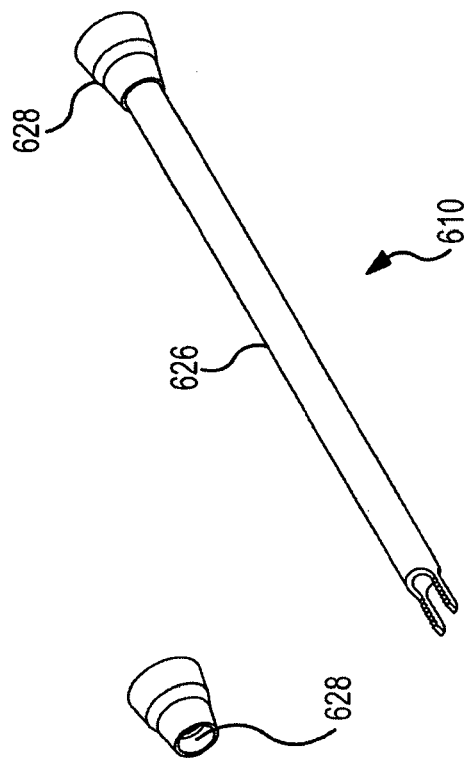
FIGS. 89 and 90 are perspective views of a delivery device portion of the kit shown in FIGS. 85 and 86.
Figure 89:
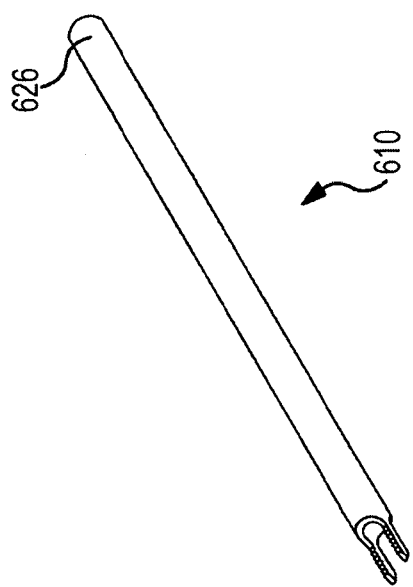
Figure 91:
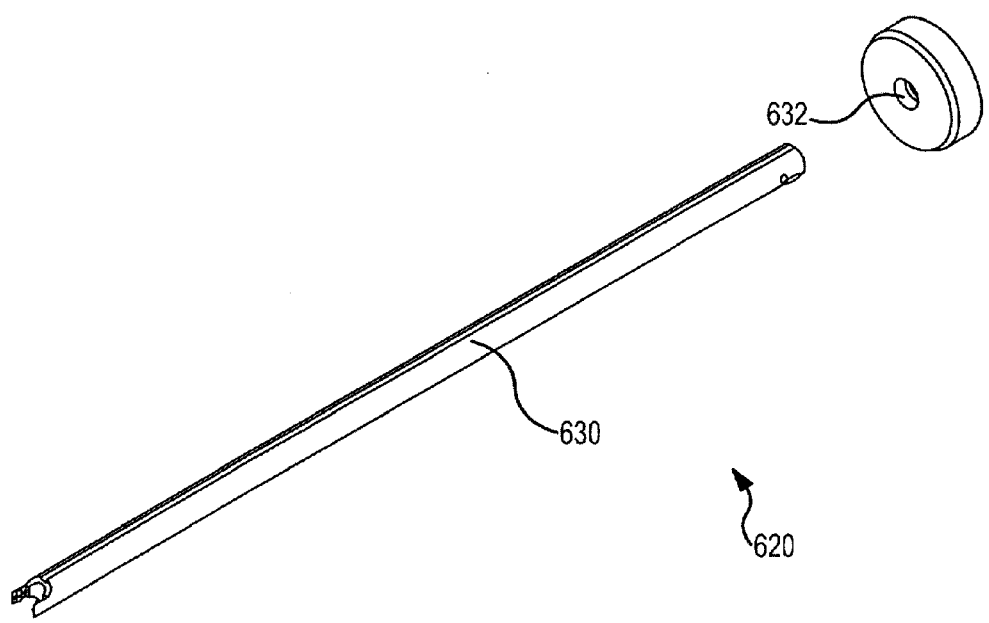
FIG. 91 is a perspective view of part of a driver assembly portion of the kit shown in FIGS. 85 and 86.

In another embodiment, a kit is provided. As shown in FIGS. 85 and 86, the kit may include a delivery device 610, a chisel 612, several internal and external decorticators 614, 616, 618, and a driver assembly 620. As shown in FIGS. 87 and 88, the chisel head 622 and shaft 624 may be provided in two pieces that may be combined with a press fit. As shown in FIG. 89, the delivery device 610 may be provided in two pieces combinable with a press fit, the first piece being a tubular shaft and fork piece 626 and the second piece being a receiving assembly piece 628. As show in FIGS. 90-93, the driver assembly 620 may be provided in several pieces including the internal actuator and the implant shaft/arms/handle portion. FIG. 90 shows the shaft/arms/handle portion comprising two pieces, the first piece being a shaft with arms 630 and the second piece being the handle 632. FIGS. 91 and 92 show the internal actuator including a tip 634, a shaft portion 636, an adapter 638, a pin 640, and a distractor knob 642. In addition to the elements shown, one or several implants may be provided as well as an injector as previously described. Several traditional instruments for use in accessing the surgical site and closing the surgical site may also be provided.

Referring now to FIGS. 94-116, another embodiment of a tool 800 is shown. FIGS. 94-98 show a chisel 808, a delivery device 804, a decorticator 806, a driver assembly 842, an internal actuator 852, and an injector 902.

Figure 95:
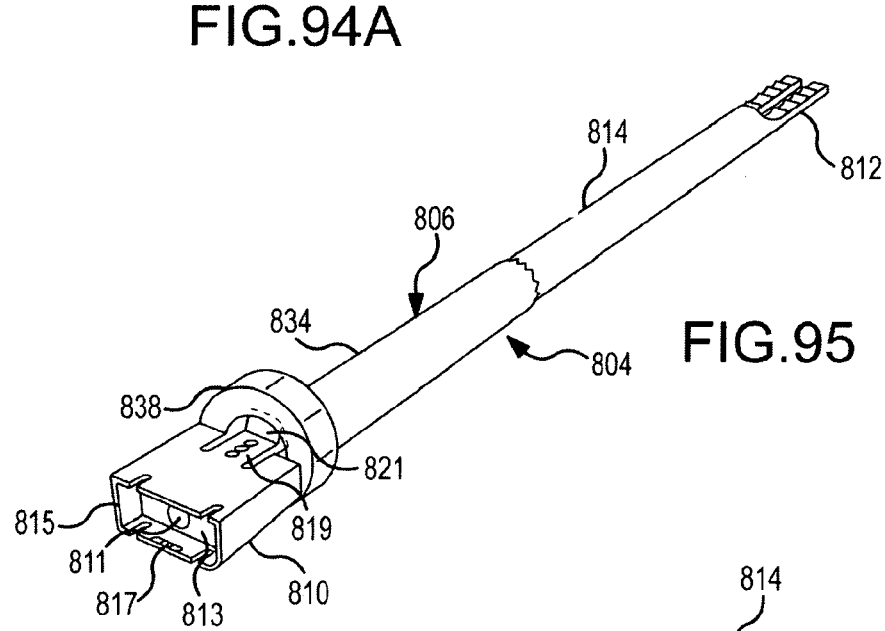
FIGS. 95, 95A and 95B are views of a delivery device according to certain embodiments.

As shown in FIG. 95, the delivery device 804 may include a receiving assembly 810 at a proximal end, anchoring forks 812 at a distal end, and a generally tubular shaft 814 defining a longitudinal axis and extending between the receiving assembly 810 and the anchoring forks 812. The tubular shaft 814 may have an annular shaped cross-section with an inner radius and an outer radius, where the difference between the two radii defines a thickness of the tubular shaft 814. Some of the features of the delivery device 804 will now be described and additional features of the delivery device 804 may include those features shown and described with respect to delivery device 104. For example, the delivery device 804 may include two anchoring forks 812.

The receiving assembly 810 of the delivery device 804 may have a generally rectangular outer surface defining a generally solid volume with a bore 811 therethrough. The bore 811 may be positioned proximal to and in alignment with the tubular shaft 814 and may have an inner radius matching that of the tubular shaft 814 allowing for a smooth transition of devices from the receiving assembly into the tubular shaft. The receiving assembly 810 may include a seating cavity 813 at its proximal end for receiving and seating of other devices such as the driver assembly 842 or the injector 902. The seating cavity 813 may be defined by an outer shell 815 that is substantially flush with the outer surface of the receiving assembly 810. The shell 815 may include protrusions or recesses 817 on its inner surface, the protrusions or recesses 817 corresponding to protrusions or recesses on other devices. As such, these protrusions or recesses 817 may provide for a detent relationship between the delivery device 804 and other devices. The rectangular outer surface of the receiving assembly 810 may have a long side and a short side. The long side may be oriented parallel to a line connecting the forks 812 in turn aligning the seating cavity 813 with the forks 812. As such, devices used with the delivery device 804 may be properly aligned relative to the forks 812 by positioning and seating them in the seating cavity 813. Additionally shown on the outer surface of the receiving assembly 810 is a decorticator release button 819. As shown, the button 819 may include slots on either side creating a cantilevered tab condition for the button 819. As such, the button 819 may deflect about its proximal end when depressed. The button 819 may also include recesses or bumps on its surface for gripping. The button 819 may extend beyond the distal end of the receiving assembly 810 and may include an upwardly extending ridge 821. The ridge 821 may be shaped and adapted to engage the decorticator 806 as described in greater detail below. There may be one button 819, or two buttons 819, one on each face of the receiving assembly 810. Any number of buttons 819 may be included, for example in the case of a varying shaped receiving assembly, 810.

Figure 94:
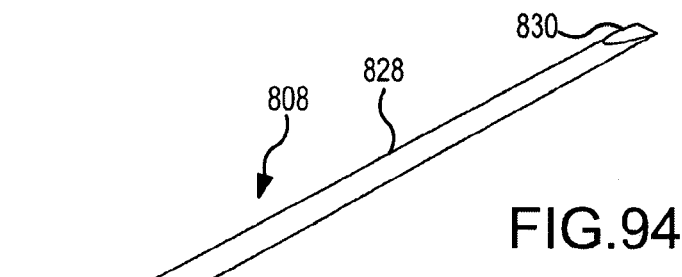
FIGS. 94 and 94A are views of a chisel according to certain embodiments.
Figure 94A:
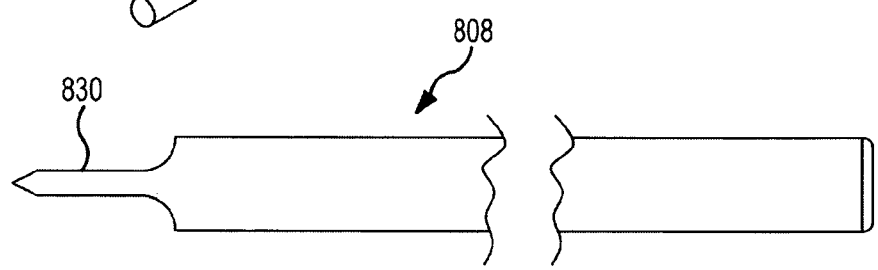

Referring to FIG. 94, the chisel 808 may have a generally cylindrical cross-section forming a shaft 828. The shaft 828 may have a radius substantially equal to the inner radius of the tubular shaft 814 portion of the delivery device 804 allowing for slidable insertion of the chisel 808 within the delivery device 804. Alternatively, the radius of the shaft 828 may be smaller than the inner radius of the tubular shaft 814 providing for more play and adjustability of the chisel 808 and delivery device 804 relative to one another. The chisel 808 may include a single or doubly chamfered tip 830 at a distal end or may have a coped distal end. The chisel 808 may include a head or, in contrast to the chisel 108 described with respect to FIG. 1, the chisel 808 may not include a head as shown in FIG. 94. The chisel 808 may have an overall length slightly larger than the delivery device 804 so as to allow the chisel to be manipulated by its proximal end when sleeved within the delivery device 804. Additional features of the chisel 808 may include those features shown and described with respect to chisel 108. For example, similar to the chisel shown and described with respect to FIG. 1A, the chisel 808 may also include a longitudinally extending lumen 131. A more detailed view of the chisel 808 and its chamfered tip 830 may be seen in FIG. 94A. As shown, the chisel 808 may include a circumferential bevel at its proximal end opposite the chamfered tip 830.

In comparison to the use described with respect to FIG. 5 above, it is noted that the chisel 808 may allow the option of inserting the chisel 808 prior to the delivery device 804 and sleeving the delivery device 804 over the chisel 808. This is in contrast to the chisel 108, with the head 132, where the head 132 prevents the delivery device 104 from being sleeved over the chisel 108. As such, the facet joint may be distracted by the chisel 808 initially allowing for smoother insertion of the delivery device 804. Upon placement and proper positioning of the delivery device 804, the chisel 808 may then be removed. Those of skill in the art will understand and appreciate that a chisel with a removable head may also be provided and may allow for either order of insertion of the delivery device 804 and chisel 808 and the removable head, once replaced, may then be used to more readily manipulate and properly position the chisel 808.

Figure 95A:
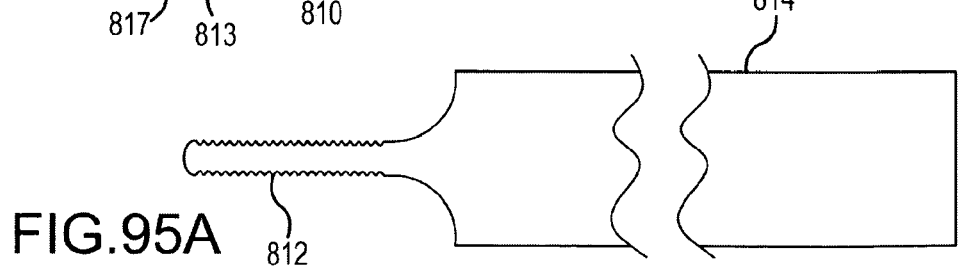
Figure 95B:
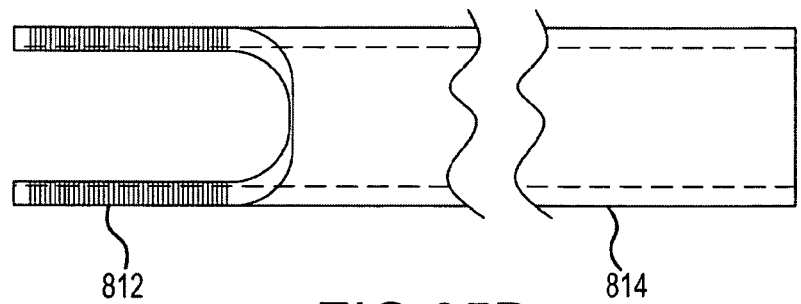
Figures 96, 97:
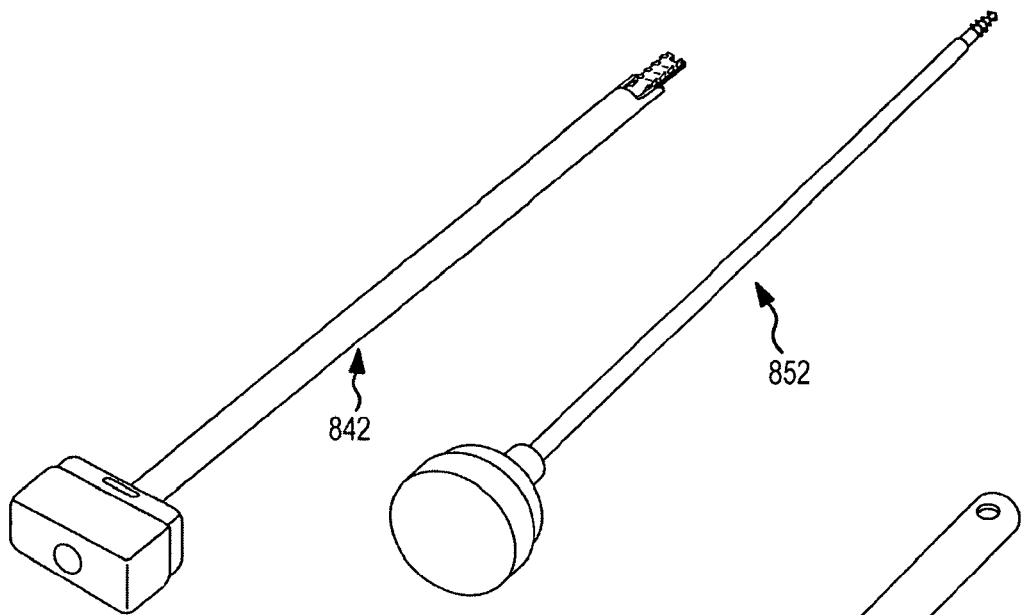
FIG. 96 is a perspective view of a driver assembly according to certain embodiments.
FIG. 97 is a perspective view of an internal actuator according to certain embodiments.
Figure 98:
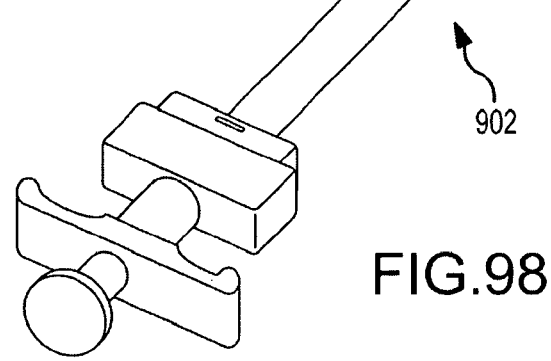
FIG. 98 is a perspective view of an injector according to certain embodiments.

In some embodiments, the forks 812 at the distal end of the delivery device 804 may have a bull nose tip as shown in FIG. 95A. This is in contrast to the relatively sharp tip shown in FIGS. 2-4 with respect to forks 112. The use of a chisel 808 without a handle, which may allow for insertion of the chisel 808 prior to the delivery device 804, may, in turn, allow for this bull nose tip because the facet joint may be distracted prior to insertion of the delivery device 804.

Referring again to FIG. 95, the decorticator 806 may have a tubular shaft portion 834, an abrasive distal end 836, and a handle 838 at a proximal end. The tubular shaft 834 may have an inner radius substantially equal to the outer radius of the tubular shaft 814 of the delivery device 804 and may allow for sliding movement of the decorticator 806 along the length of the delivery device 804 and rotationally around the delivery device 804. In some embodiments, the inner radius of the tubular shaft 834 may be slightly or substantially larger than the outer radius of the tubular shaft 814 of the delivery device allowing for more freedom of movement of the decorticator 806. The abrasive distal end 836 may include serrated teeth as shown, or may include a more flat annular surface with a gritty surface. The handle 838 may include a generally cylindrically shaped knob with a gripping surface along its peripheral edge. The handle 838 may also include a cavity on its proximal face for receiving a distal end of the decorticator release button 819. The cavity may thus create an inner cylindrical surface opposite the gripping surface of the handle 838. The inner cylindrical surface may be beveled or may include a groove for receiving the tip of the ridge 821 extending upwardly from the release button 819. As such, where the release button 819 is in its natural state, the ridge 821 may project into the groove or opposed to the beveled surface of the handle 838 preventing the decorticator from being advanced distally. Where the release button 819 is depressed, the ridge may be removed from the groove or beveled surface allowing the decorticator to advance freely. Additional features of the decorticator 806 may include those features shown and described with respect to decorticator 106. For example, the decorticator 806 may alternatively be separate from the delivery device 804 and may be slidably inserted within the delivery device 804 similar to that shown and described with respect to FIG. 4 or FIGS. 6A-6C.

Referring now to FIGS. 99-101, the delivery device 804 and a driver assembly 842 are shown. As shown in FIG. 99, the driver assembly 842 includes a handle 844, an implant shaft 846, and implant holding arms 848. The driver assembly 842 shown is holding an implant 154. The handle 844 of the driver assembly 842 may have an outer surface defining a generally rectangular volume with a bore 843 there through. The bore 843 may have an inner diameter substantially equal to the inner diameter of the implant shaft 846 allowing for a smooth transition of devices passing through the driver assembly 842. The handle 844 may have a necked down portion 845 at its distal end. The necked down portion 845 may have protrusions or recesses 847 on its outer surface corresponding to respective protrusions or recesses 817 on the inner surface of the shell 815 of the receiving assembly 810 on the delivery device 804. As such, and as shown in FIGS. 100 and 101, the driver assembly 842 may be sleevably positioned within the delivery device 804 to deliver an implant 154/854 to the facet joint. When fully advanced as shown in FIG. 101, the handle 844 may be seated securely in the seating cavity 813 of the receiving assembly 810 and anchored with a detent relationship. Additional features of the driver assembly 842 may include those features shown and described with respect to driver assembly 142.

A more detailed view of the implant holding arms 848 is shown in FIG. 99A. As shown, the implant holding arms 848 may include a chamfered tip. Additional features of the arms 848 may include features similar to those shown and described with respect to arms 148 in relation to FIG. 11. For example, the inside surface of the arms 848 may include a longitudinal ridge 862 extending the length of the arms 848. The arms 848 may also include a bull nose engagement feature 858 extending transverse to the longitudinal axis of the implant shaft 846 along the inside face of the arm 848. Where the arms 848 are engaged with and holding the implant 154/854, the longitudinal ridges 862 of each arm 848 may be positioned between upper and lower planar members of the implant 154/854 and the bull nose engagement features 858 may be positioned in the U-shaped receiving feature slots on the lateral edges of the implant 154/854.

In contrast to the driver assembly 142 described above, in the present embodiment shown in FIGS. 102-105, the internal actuator 852 may be a separate device from the driver assembly 842. That is, while the internal actuator 852 may still function by passing longitudinally through the driver assembly 842, the internal actuator 852 may be a separate device with its own handle 853. The internal actuator 852 may include a longitudinal shaft 855 and an internal rod 857. The longitudinal shaft 855 may be cylindrically shaped with an annular cross-section. The shaft 855 may have an outer diameter substantially the same as or smaller than the inner diameter of the implant shaft 846 of the driver assembly 842. The shaft 855 may extend from the handle 853 proximally to a distal end. The internal rod 857 may be positioned within the shaft 855 and also may extend from the handle 853 to a distal end. The internal rod 857 may include an engagement feature 859 at its distal end for engaging and holding the implant distractor 850. This engagement feature 859 may be any shape and provide for any engagement known in the art from a hex, allen, phillips, star, square, sleeve, or other connection capable of transmitting longitudinal and/or rotational forces from the internal rod 857 to the implant distractor 850. As shown, in one embodiment, the engagement feature 859 includes a collet type device that is described in more detail with respect to FIG. 109 below. As shown, the internal rod 857 may sleevably receive the implant distractor 850. The internal rod 857 may be sleevably positioned within the longitudinal shaft 855, such that when the longitudinal shaft 855 is in an advanced position over the end of the internal rod 857, the longitudinal shaft 855 causes a clamping force of the collet to restrain the implant distractor 850 against being dislodged from the collet. Each of the shaft 855 and the internal rod 857 may engage the handle 853 at their respective proximal ends. The handle 853 may be used to retract the longitudinal shaft 855 along the length of the internal rod 857 thereby exposing the collet and reducing the clamping force. As such, when the longitudinal shaft 855 is in a retracted position, an implant distractor may be inserted into and/or removed from the collet.

As shown in FIGS. 104 and 105, the handle 853 may be a cylindrical/spherical handle or a T-type handle. Referring to FIG. 104, the cylindrical/spherical handle may include an outer cylindrical portion 861 capped at a proximal end by a first spherical portion 863, the first outer cylindrical portion 861 being open at a distal end. The handle 853 may also include an inner cylindrical portion 865 capped at a distal end by a second spherical portion 867, the inner cylindrical portion 865 being open at a proximal end. As shown, the proximal open end of the outer cylindrical portion 861 may be positioned opposing the distal open end of the inner cylindrical portion 865 and the inner cylindrical portion 865 may sleevably slide within the outer cylindrical portion 861. The handle 853 may further include a collar 869 integral with the second spherical portion 867, positioned concentrically to each of the outer and inner cylindrical portions 861, 865 and extending distally away from the second spherical portion 865. Those of skill in the art will understand and appreciate that the collar 869 could also extend in a proximal direction. In either case, the shaft 855 of the internal actuator 852 may be connected to the distal end of the collar 869 and extend distally there from. The internal rod 857 of the internal actuator 852 passing proximally through the shaft may sleevably penetrate the collar 869 and the second spherical portion 867, extend through the handle 853 to the inner/distal surface of the first spherical portion 863, and be coupled thereto. In addition, the first and second spherical portions 863, 867 may have a biasing mechanism 871 positioned between them in the form of a spring, balloon, or other force inducing device. Those of skill in the art will understand and appreciate that the spherical portions 863, 867 could be flat, concave, or otherwise shaped and are not limited to spherical shaped caps.

In use, as understood by a review of FIGS. 103 and 104, a user may insert the internal actuator 852 through the driver assembly 842, which is positioned and seated in the delivery device 804. The internal actuator 852 may be used to advance and position the implant distractor 850 for advancement into the implant. Once properly positioned, the internal actuator 852 may be rotated via the handle 853 to advance the implant distractor 850. In the cases of other implant distractors, the handle 853 may be otherwise manipulated to advance the implant distractor. Once the implant distractor is advanced and the implant is distracted, a user may compress the first and second spherical portions 863, 867 toward one another against the force of the biasing mechanism 871 (e.g. by squeezing the handle with their hand). The inner cylindrical portion 865 of the handle 853 may retract relative to the outer cylindrical portion 861 causing the longitudinal shaft 855 also to retract relative to the to the outer cylindrical portion 861. This retracting motion relative to the internal rod 857 may cause the distal end of the longitudinal shaft 855 to be retracted and expose the collet on the distal end of the internal rod 857. As such, the clamping force of the collet on the implant distractor 850 may be reduced allowing for removal of the internal actuator 852, while leaving the implant distractor 850 behine and in place in the implant. It is noted that the shaft portion 855 of the implant distractor 852 may include a keyway for engagement with the inner surface of the implant shaft 846 of the driver assembly 842. As such, the shaft 855 of the internal actuator 852 may be prevented from rotating relative to the internal rod 857.

Referring now to FIG. 105, the T-type handle may have a cylindrical, rectangular, square, or other transverse cross-section, with a longitudinal axis extending generally perpendicular to the longitudinal axis of the internal rod 857 and shaft 855 and forming a T-shape. The longitudinal cross-section of the handle 853, as depicted in FIG. 105, may include a proximal portion 873 and a distal portion 875 connected at one end and separated by a gap 877. The proximal portion 873 may be a relatively thick portion and the distal portion 875 may be relative thin. As such, the handle 853 may be squeezable and may provide a biasing force which works to maintain the gap 877 between the distal and proximal portions 873, 875. The handle 853 may also include a generally cylindrical or conical collar 879 positioned near the middle of the handle 853 along its longitudinal length. The collar 879 may be positioned parallel to and concentrically with the internal rod 857. The shaft portion 855 of the internal actuator 852 may extend distally from the distal end of the collar 879. The internal rod 857 may sleevably penetrate the collar 879 and the distal portion 875 of the handle 853 and may further be coupled to the proximal portion 873 of the handle 853 in a cylindrical bore 881. A stop may be provided to prevent the internal rod 857 from passing proximally through the proximal portion 873 of the handle 853. This may be in the form of a cap on the proximal portion 873 of the handle 853 covering the bore 881, or the bore 881 may not pass all the way through the proximal portion 873 of the handle 853. Alternatively, the internal rod 857 may be secured within the bore.

In this embodiment, as understood by a review of FIGS. 103 and 105, the internal actuator 852 may be inserted through the driver assembly 842 and the implant distractor 850 may be advanced in the same or similar fashion as that described with respect to the internal actuator 852 of FIG. 104. When the internal actuator is ready for removal, a user may compress the proximal 873 and distal 875 portions of the handle 853 toward one another against the biasing force by squeezing the handle 853. The distal portion 875 of the handle 853 may retract relative to the proximal portion 873 causing the longitudinal shaft 855 also to retract relative to the proximal portion 873. This retracting motion of the longitudinal shaft 855 relative to the internal rod 857 may cause the distal end of the longitudinal shaft 855 to be retracted and expose the collet on the distal end of the internal rod 857. As such, the clamping force of the collet on the implant distractor 850 may be reduced allowing for removal of the internal actuator 852, while leaving the implant distractor 850 behind and in place in the implant.

Still another embodiment of a handle 853 is shown in FIGS. 106-108. In this embodiment, a gripping mass 883 with a knob 885 is shown. A knob 885 is positioned on the proximal end of the internal rod 857 via a bore 887. The knob 885 may be affixed against relative rotation with the internal rod 857. The gripping mass 883 may include a generally rectangular mass spaced from the knob 885 along the internal rod 857 and including a bore 889 for the internal rod 857 to pass there through. The bore 889 may sleevably receive the internal rod 857. The gripping mass 883 and the internal rod 857 may form the shape of a T and the gripping mass 883 may be affixed to the proximal end of the longitudinal shaft 855. The gripping mass 883 may be held apart from the knob 885 along the internal rod 857 by a biasing mechanism 891 in the form of a spring, balloon, or other known device.

The implant distractor 852 shown in FIGS. 106 and 107 may be inserted through the driver assembly similar to that shown and described with respect to FIG. 103 above. The implant distractor may be rotated or otherwise manipulated to advance the implant distractor 850. Once the implant distractor is positioned, a user may grip the gripping mass 883 with their fingers and allow the knob 885 to settle into the palm of their hand. The user may then squeeze the knob 885 toward the gripping mass 883 depressing the biasing mechanism 891 between the two and retracting the longitudinal shaft 855 along the internal rod 857 and causing the distal end of the longitudinal shaft 855 to be retracted and expose the collet on the distal end of the internal rod 857. As such, the clamping force of the collet on the implant distractor 850 may be reduced allowing for removal of the internal actuator 852, while leaving the implant distractor 850 behind and in place in the implant.

As shown in more detail in FIG. 108, the engagement feature 859 at the distal end of the internal rod 857 may take the form of a collet 893 for holding the implant distractor 850. The collet 893 may be affixed to the distal end of the internal rod 857 and may be adapted to hold the implant distractor 850. Those of skill in the art will understand and appreciate that the collet 893 may be permanently affixed to the distal end of the internal rod 857 or may be interchangeably coupled thereto. Those of skill will further understand that several collet and chuck arrangements are known in the tool industry for receiving bits or other devices, which are within the scope of the invention. As shown, the collet 893 is extending slightly out of the distal end of the longitudinal shaft 855 and is thus in position to receive an implant distractor or is in position to allow removal of the internal actuator 852 after placement of the implant distractor 850.

Figure 109:
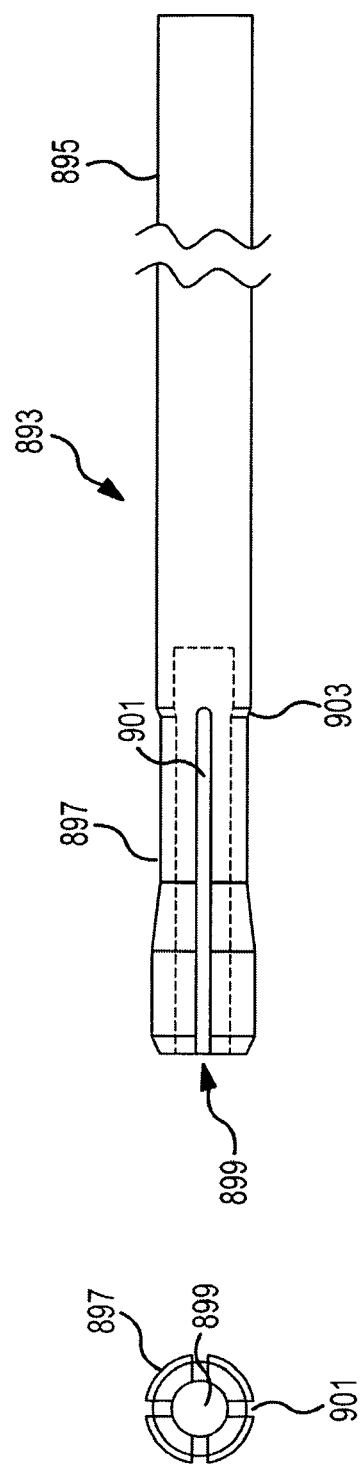
FIG. 109 is a side view of a collet according to certain embodiments.

The collet 893, positioned on the distal end of the internal rod 857 and shown in FIG. 108, may be seen more clearly in FIG. 109. In some embodiments as shown, the collet 893 may include a generally cylindrical body member 895 with four receiving fingers 897 equally spaced around a bore 899. The body member 895 may be the internal rod 857 or may be a separate piece which is affixed to the end of the internal rod 857. Each of the fingers 897 may extend distally from the body member 895 and be separated by slots 901. The fingers 897 may extend laterally across approximately one quarter of a cylinder wall and may have constant thickness as they extend from the body 895. Near the distal end of the fingers 897, the outer surface of each finger 897 may be tapered up to define a thicker finger thickness and then tapered back down at the very distal end. As such, when the longitudinal shaft 855 is advanced over the collet 893, the tapered outer surface causes the fingers 897 to deflect inward creating a clamping force on the implant distractor positioned within the collet. Those of skill in the art will understand and appreciate that the collet may include as few as two fingers 897 and may include any number of fingers. The bore 899 defined by the fingers 897 may extend into the cylindrical body 895 a specified distance. At the transition 903 between the body 895 and fingers 897, which location is defined by the depth of the slots 901, the transition 903 defines a neck where a wider body portion 895 necks down to the finger portion 897.

Figure 110:
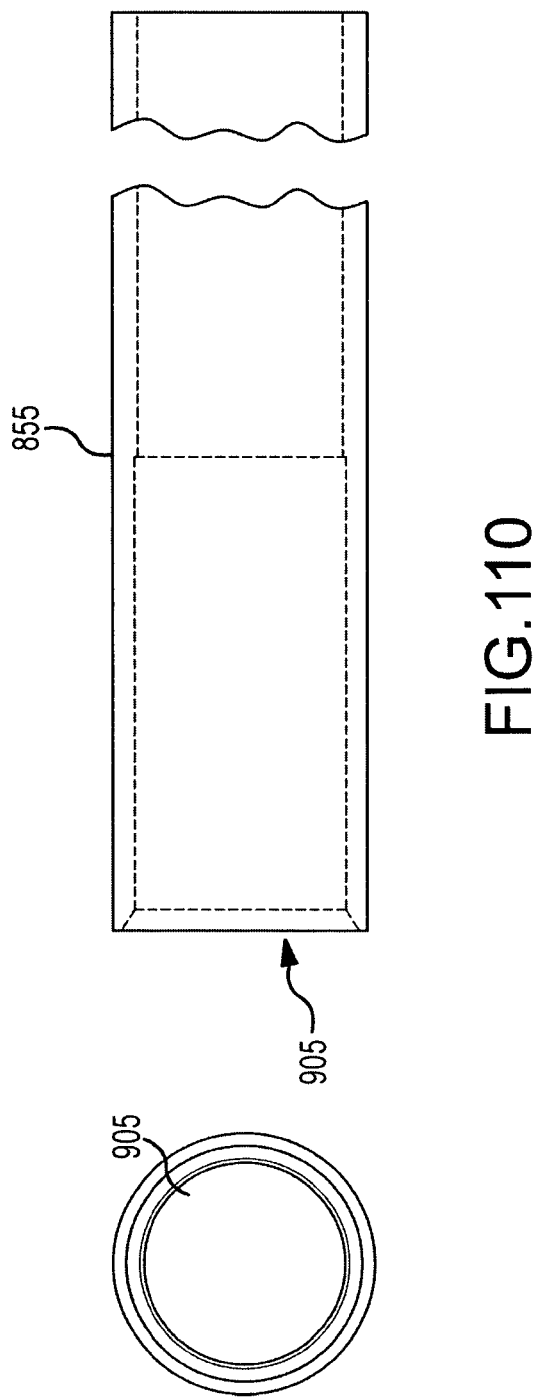
FIG. 110 is a side view of a longitudinal shaft of an internal actuator according to certain embodiments.
Figure 117:
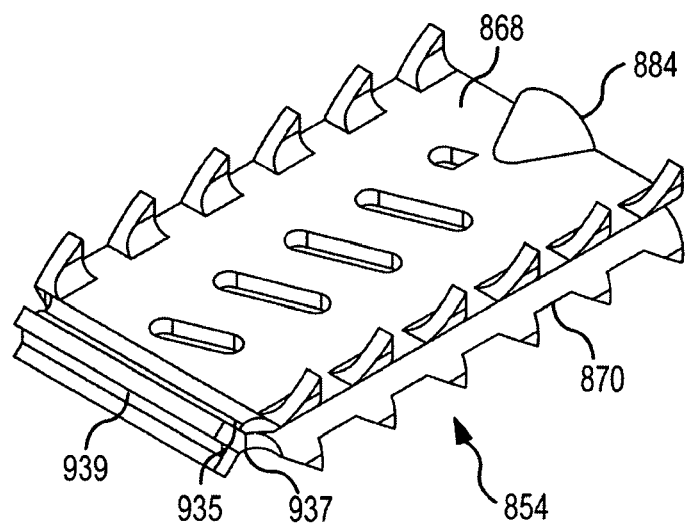
FIGS. 117-120 include several perspective views of an implant according to certain embodiments.

Referring now to FIG. 110, a cross-section of the longitudinal shaft 855 is shown. As shown, the longitudinal shaft 855 may include an internal bore 905 at its distal end for receiving the internal rod 857 and the collet 893. The internal bore 905 may be the same or similar to the bore extending the length of the longitudinal shaft 855. The distal end of the bore 905 may include an outwardly beveled edge for riding along the beveled outer surface of the collet 893 when the longitudinal shaft is advanced and creates a clamping force on the collet. 893

Referring now to FIGS. 111-113 an implant distractor 850 is shown. The implant distractor 850 may be a generally narrow element having a cylindrical body 907 which tapers to a point at a distal end. At a proximal end 864, the implant distractor 850 may have a square cross-section and may include a circumferential groove 909 positioned just proximal to the distal end of the implant distractor 850. This groove 909 may correspond to a protrusion or spring ball on the inner surface of the engagement feature 859 of the internal actuator 852 forming a detent connection between the engagement feature 859 and the implant distractor 850. Alternatively or additionally, where a collet 893 is used the groove 909 may engage a feature inside the collet 893 so as to prevent the implant distractor 850 from inadvertently dislodging from the collet 893. The square proximal end 864 may be isolated from the cylindrical body 907 by an annular stop ring 911. The annular stop ring 911 may have an outer radius similar to the inner radius of the driver assembly 842. This stop ring 911 may allow for sliding movement of the implant distractor 850 through the implant shaft 846 of the driver assembly 842. The stop ring 911 may prevent over advancement of the implant distractor 850 by creating an abutting relationship between the distal face of the stop ring and the proximal edge of the implant.

As best shown in FIGS. 112 and 113, the implant distractor 850 may include a generally continuous coil-shaped thread feature 866. The thread feature 866 may have an abrupt proximal end 913 just distal to the annular stop ring 911 and may continue to the distal end of the implant distractor 850. The thread feature 866 may gradually terminate at the distal end of the implant distractor 850 by gradually minimizing its cross-sectional profile. This may occur over several turns or in some embodiments, this transition may occur within a 180 degree turn. In other embodiments, this transition occurs between a 90 degree and a 180 degree turn. While the thread feature 866 is generally continuous, as shown in FIG. 112, the thread feature 866 may be interrupted by at least one cross-cut 915 at one or more locations along the threaded feature 866. In one embodiment, as shown in FIG. 112, a single cross-cut 915 may be positioned just proximal to the distal end. This cross-cut 915 may be positioned approximately 180 degrees out of phase from the abrupt proximal end 913 of the thread feature 866. Both the cross-cut 915 and the abrupt proximal end 913 may provide for interlocking engagement of the implant distractor 850 with the implant 154/854 and thus prevent backing out of the implant distractor 850.

Turning now to FIGS. 114-116, an injector 902 and delivery device 804 are shown. As shown in FIG. 114, the injector 902 may include a longitudinal delivery shaft 917, a seating feature 919, a gripping feature 921, and a plunger 923 with a handle 925. The longitudinal delivery shaft 917 may have any cross-section and may have a cross-sectional size adapted to fit within the delivery device 804. The longitudinal shaft 917 may have an opening 927 on its distal end for directing bone paste toward the lateral mass portion of a facet joint. In another embodiment, the shaft 917 may include two opposing openings 927 or a series of openings 927 on its distal end. The openings 927 may be positioned to penetrate the wall of shaft 917. The seating feature 919 may include a rectangular or other shaped block positioned around the shaft 917 and sized and shaped to engage the seating recess 813 in the receiving assembly 810 of the delivery device 804. As shown, the seating feature 919 may include a necked down portion on its distal end which may be received by the shell portion 815 of the receiving assembly 810. As with the driver assembly 842, the seating feature 919 of the injector 902 may include protrusions or recesses 929 corresponding to protrusions or recesses 817 on the inner surface of the shell 815 allowing for a detent relationship for securing the injector 902 to the delivery device 804. The seating feature 919 may have an orientation perpendicular to the orientation of the openings 927 at the distal end of the shaft 917 such that once in position, the openings 927 may direct bone paste or other material perpendicular to the facet joint surface along the spine and adjacent to the facet joint. The gripping feature 921 may be any shape and may be affixed to the proximal end of the shaft 917. This feature 921 may include a gripping profile on its distal face for receiving 1, 2, or any number of fingers on one or either side of the shaft 917. The gripping feature 921 may allow the user to grasp the injector 902 and squeeze the plunger handle 925 toward the gripping feature 921 thus advancing the internal piston and ejecting the bone paste or other material.

As shown in FIG. 116, the injector 902 may be sleevably inserted into the delivery device 804 and advanced such that the distal end of the shaft 917 is positioned between the forks 812. The seating feature 919 may be secured with the detents thus orienting the openings 927 in the shaft 917 perpendicular to the forks 812. The plunger handle 925 may be squeezed relative to the gripping feature 921 and bone paste or other material may be injected toward the facet joint site. Additional features not mentioned may be included as shown and described with respect to the injector 202. For example, the plunger 923 may include a seal.

Figure 118:
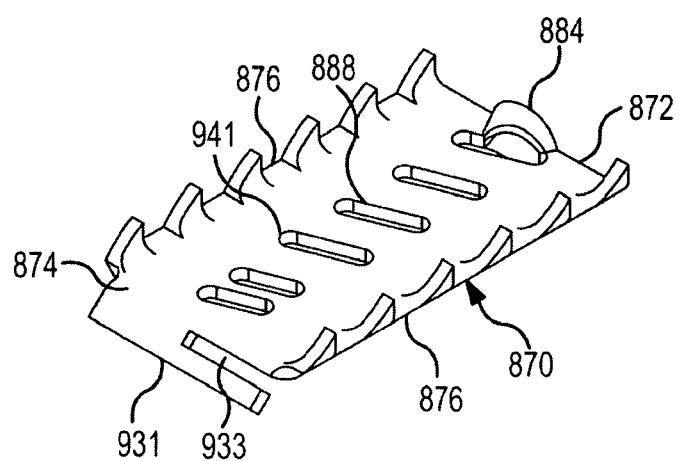
Figure 119:
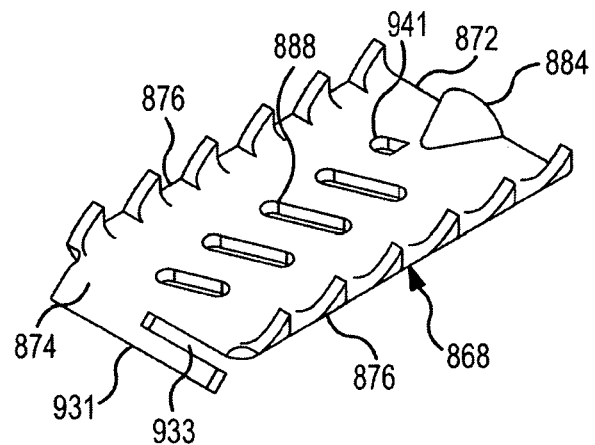
Figure 120:
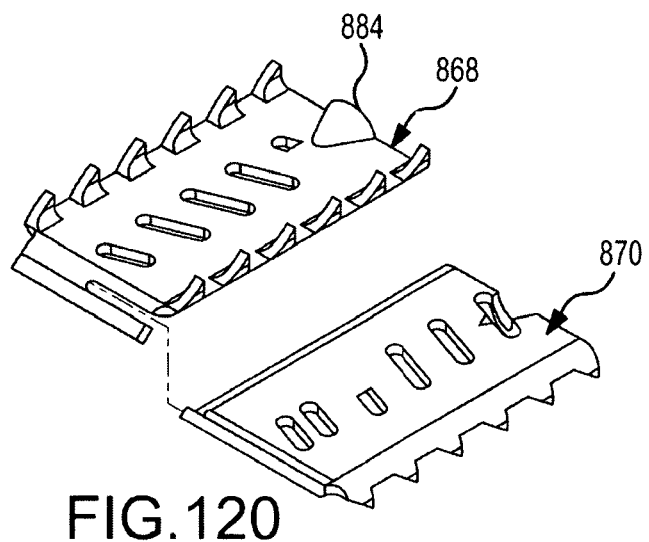

Turning now to FIGS. 117-120, another embodiment of an implant 854 is shown. The implant 854 may include upper 868 and lower 870 members. The members 868, 870 may be generally planar and may also be generally rectangular. Each of the upper 868 and lower 870 members may include a proximal edge 872, a distal edge 874, and a pair of parallel lateral edges 876 extending longitudinally between the distal edges 874 and the proximal edges 872. In the present embodiment, as shown in FIGS. 117-120, the distal edges 874 of the members 868, 870 may each include interlocking scissor features 931. As shown, a portion of the member near the distal edge 874 of each member may be radiused and bend in the direction of the opposing member. As shown in FIGS. 118 and 119, an interlocking slot 933 may be provided extending laterally halfway across the member just proximal to the distal edge 874 and within the radiused bend portion of the member. In one embodiment, the width of the slot 933 may be generally similar in width to the distance from the distal edge 874 to the slot 933. The slot 933 in the upper member 868 and lower member 870 may be positioned on the same side such that when one of the members is inverted, the slots may engage one another as best shown in FIGS. 120. The upper and lower members 868, 870 may be welded together along an upper seam 935, lower seam 937, and/or a front seam 939. Once interlocked, the planar members 868, 870 may be biased by the connection at their distal edges 874 to be generally parallel to each other, the inner faces 878 of the planar members 868, 870 facing each other in an opposed fashion and abutting or nearly abutting each other. It is noted that, while the interlocking slot 933 is shown extending anatomically laterally from the anatomical medial side of the upper member 868 and extending anatomically medially from the anatomical lateral side of the lower member 870, the orientation of this slot may be reversed. This reversed orientation may provide resistance to shearing of the upper 868 and lower 870 members relative to one another upon receiving the implant distractor. That is, as the implant distractor is advanced into the implant 854, it may be rotating in a clockwise fashion. When engaging the implant 854, this rotation may have a tendency to cause the upper member 868 to shift laterally and to cause the lower member to shift medially. The reversed orientation may resist this shifting.

Additional features of the implant 854 may include those features shown and described with respect to implant 154. For example, a guide feature 884 may be included as shown. As an additional example, threaded slots 888 may also be included in each planar member 868, 870 for receiving the coil-shaped thread feature 866 on the implant distractor 850. In the present embodiment, one of the threaded slots 888 on one of the members 868, 870 may be a truncated threaded slot 941 for engaging the cross-cut thread 915 or the abrupt proximal end 913 of the coil-shaped thread feature 866 and preventing unscrewing or backing out of the implant distractor 850 once advanced and positioned. As shown in FIGS. 118 and 119, each member 868, 870 may have one truncated threaded slot 941 for engaging either a cross-cut thread 915 or the abrupt proximal end 913 of the thread feature 866. As such, the implant distractor 850 may be held in place and prevented from backing out by both the upper and lower member 868, 870.

Those of skill in the art will understand and appreciate that the implant embodiments depicted herein may be made of several types of biocompatible materials including stainless steel, titanium, ceramics, nitinol, polymers, and other materials known in the art.

Figure 121:
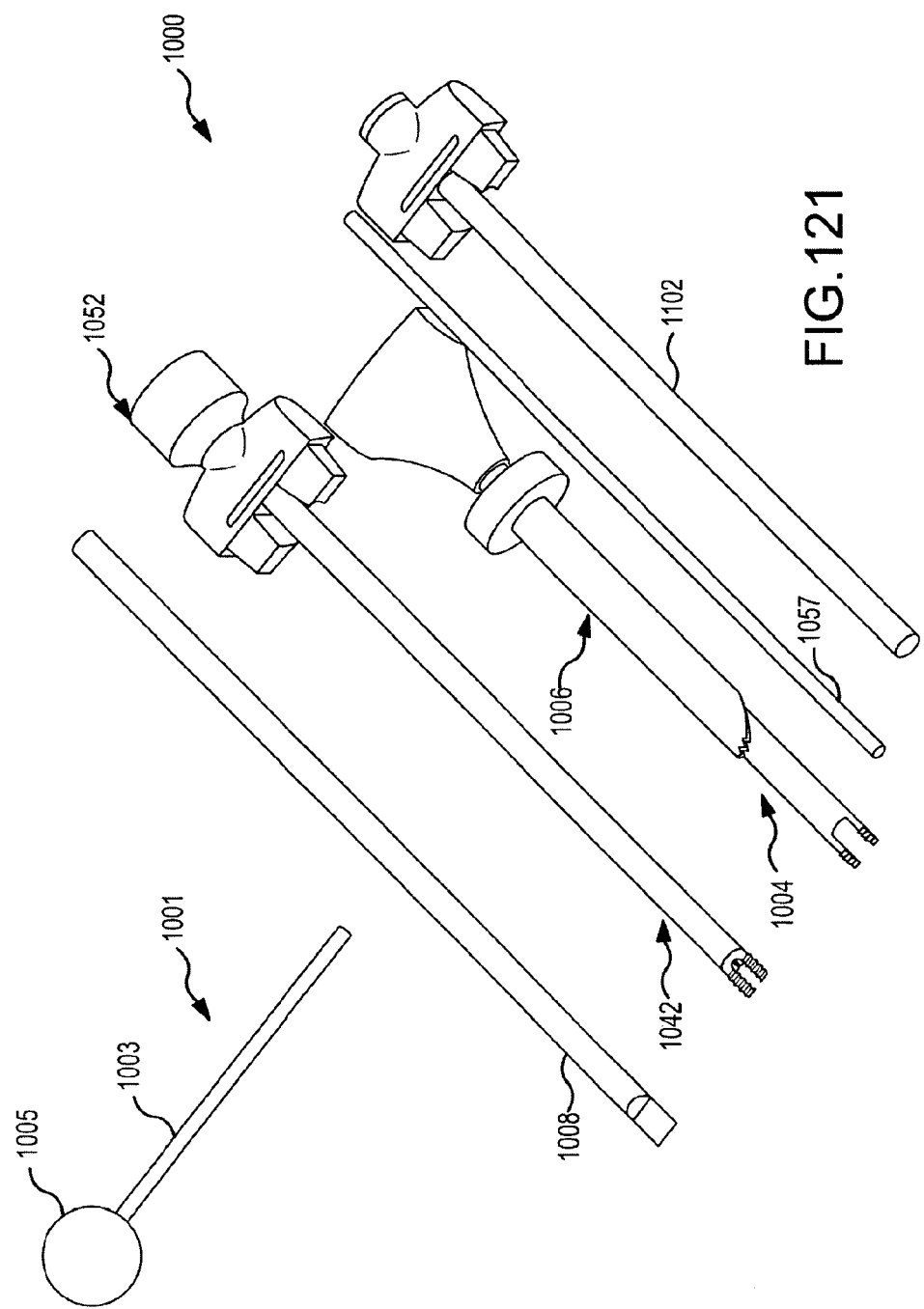
FIG. 121 includes several parts of a tool according to certain embodiments.

Referring now to FIGS. 121-128, another embodiment of a tool 1000 is shown. FIG. 121 shows a chisel 1008, a delivery device 1004, a decorticator 1006, a driver assembly 1042, an internal actuator 1052, an internal rod 1057 for the internal actuator 1052, an injector 1102, and a gripping tool 1001.

Figure 122:
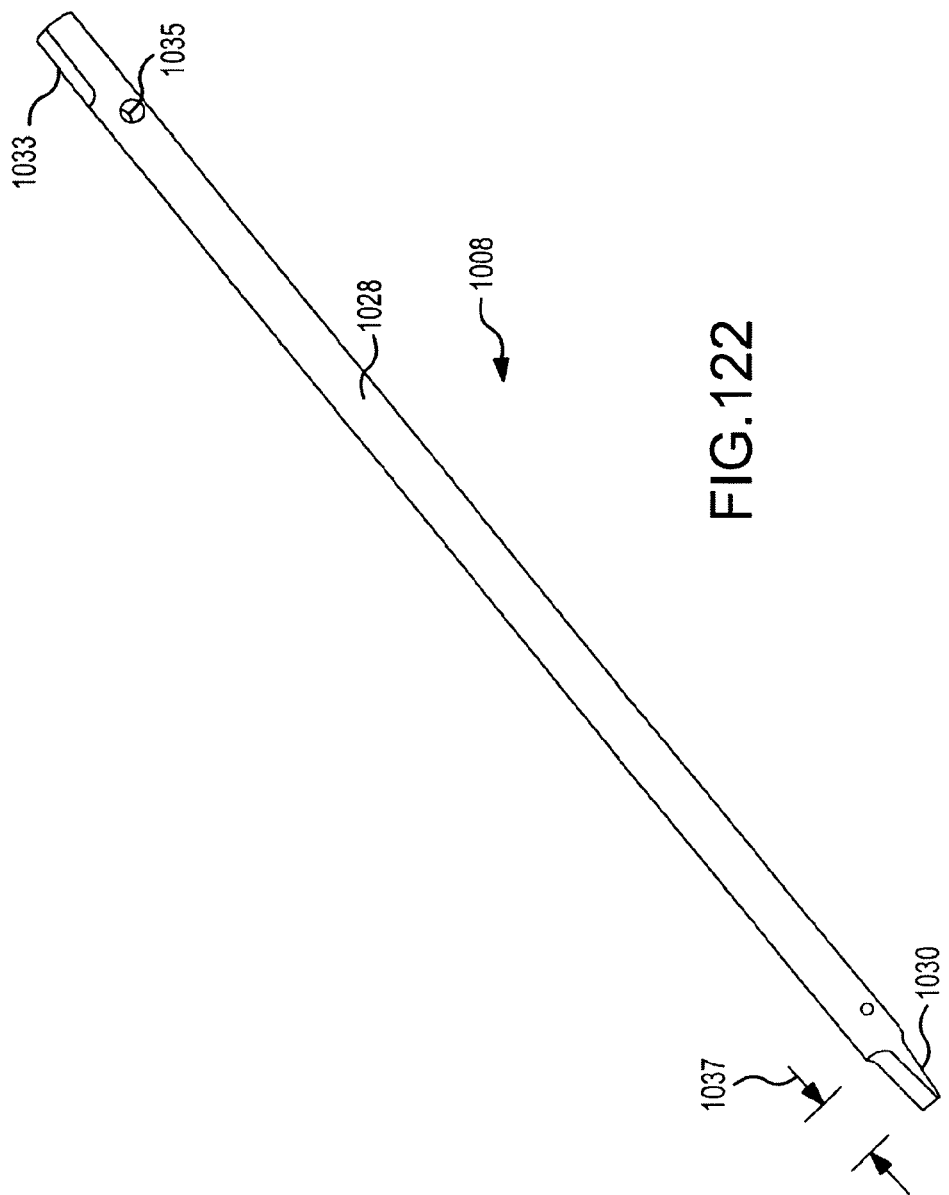
FIG. 122 is a perspective view of a chisel according to certain embodiments.

Referring to FIG. 122, the chisel 1008 may have a generally cylindrical cross-section forming a shaft 1028. The shaft 1028 may have a radius substantially equal to the inner radius of the tubular shaft portion 1014 of the delivery device 1004 (shown in FIG. 123) allowing for slidable insertion of the chisel 1008 within the delivery device 1004. Alternatively, the radius of the shaft 1028 may be smaller than the inner radius of the tubular shaft 1014 providing for more play and adjustability of the chisel 1008 and delivery device 1004 relative to one another. In some embodiments the shaft 1028 may have a radius ranging from approximately 1 mm to approximately 8 mm. In other embodiments, the shaft 1028 may have a radius of approximately 4 mm. The chisel 1008 may include a single or doubly chamfered tip 1030 at a distal end or may have a coped distal end or a combination of coping and chamfering. The tip 1030 may include a roughened surface on one or more sides to aid in anchoring or docking the chisel in the facet joint. Additionally, this roughened surface may allow for roughening or decorticating the inner surfaces of the facet joint. The tip 1030 may have a length 1037 adapted to extend substantially across the facet joint. As such, the length 1037 may be any length corresponding to the distance across a given facet joint. In one embodiment, the length 1037 may fall within a range from approximately 5 mm to approximately 35 mm long. In another embodiment, the length may fall within a range from approximately 10 mm to approximately 30 mm. In yet another embodiment, the length may fall within a range from approximately 14 mm to approximately 29 mm.

The chisel 1008 may include a head or, in contrast to the chisel 108 described with respect to FIG. 1, the chisel 1008 may not include a head as shown in FIG. 122. The chisel 1008 may have an overall length slightly larger than the delivery device 1004 so as to allow the chisel 1008 to be manipulated by its proximal end when sleeved within the delivery device 1004. The chisel 1008 may have a coped proximal end 1033 as shown. The cope 1033 may occur on one or more sides of the chisel 1008 and may allow for easier grasping of the chisel 1008 with other tools. For example, a slap hammer may be used to grasp the chisel 1008 and hammer back on the chisel 1008 during removal. Additionally, a hemostat may be used to grasp, manipulate, or otherwise distance the surgeon's hand and/or body from the proximal end of the chisel 1008 to facilitate taking of x-rays. Further shown in FIG. 122 is a horizontal bore 1035 for receiving a shaft portion of the gripping tool 1001. As such, the gripping tool 1001, may be inserted into the horizontal bore 1035 in the proximal end of the chisel 1008 forming a T-shaped grip that may be used to manipulate the chisel 1008 and/or remove the chisel 1008.

Additional features of the chisel 1008 may include features of the other chisels shown and described herein. For example, similar to the chisel shown and described with respect to FIG. 1A, the chisel 1008 may also include a longitudinally extending lumen. In this embodiment, the chisel 1008 may allow for insertion of a scope or flushing fluids as discussed above. Also, the chisel 1008 may allow for diagnostic processes. That is, the chisel 1008 may be positioned in a facet joint and a diagnostic balloon catheter may be inserted through the lumen of the chisel 1008 to distract the joint. Feedback from a consciously sedated patient may allow a provider to obtain information relating to symptom relief. As such, one or more joints may be reviewed diagnostically and thus may allow for treatment of one or several problematic joints with confidence that the proper joints are being treated. An exemplary diagnostic balloon catheter and method suitable for this application is described in U.S. patent application Ser. No. 12/110,548, entitled Cervical Distraction Method, filed on Apr. 28, 2008, the contents of which are hereby incorporated by reference herein.

In comparison to the use described with respect to FIG. 5 above, it is noted that the chisel 1008 may allow the option of inserting the chisel 1008 prior to the delivery device 1004 and sleeving the delivery device 1004 over the chisel 1008. This is in contrast to the chisel 108, with the head 132, where the head 132 may prevent the delivery device 104 from being sleeved over the chisel 108. As such, the facet joint may be distracted by the chisel 1008 by inserting the chisel 1008 and tapping, hammering, or otherwise advancing the chisel 1008 into the facet joint. Once in place, the delivery device 1004 may be inserted. Upon placement and proper positioning of the delivery device 1004, the chisel 1008 may then be removed. In another embodiment, a chisel with a removable head may also be provided and may allow for either order of insertion of the delivery device 1004 and chisel 1008. In the case of inserting the chisel 1008 first, the removable head may initially be removed from the chisel 1008. Once replaced, the removable head may then be used to more readily manipulate and properly position the chisel 1008.

Figure 123:
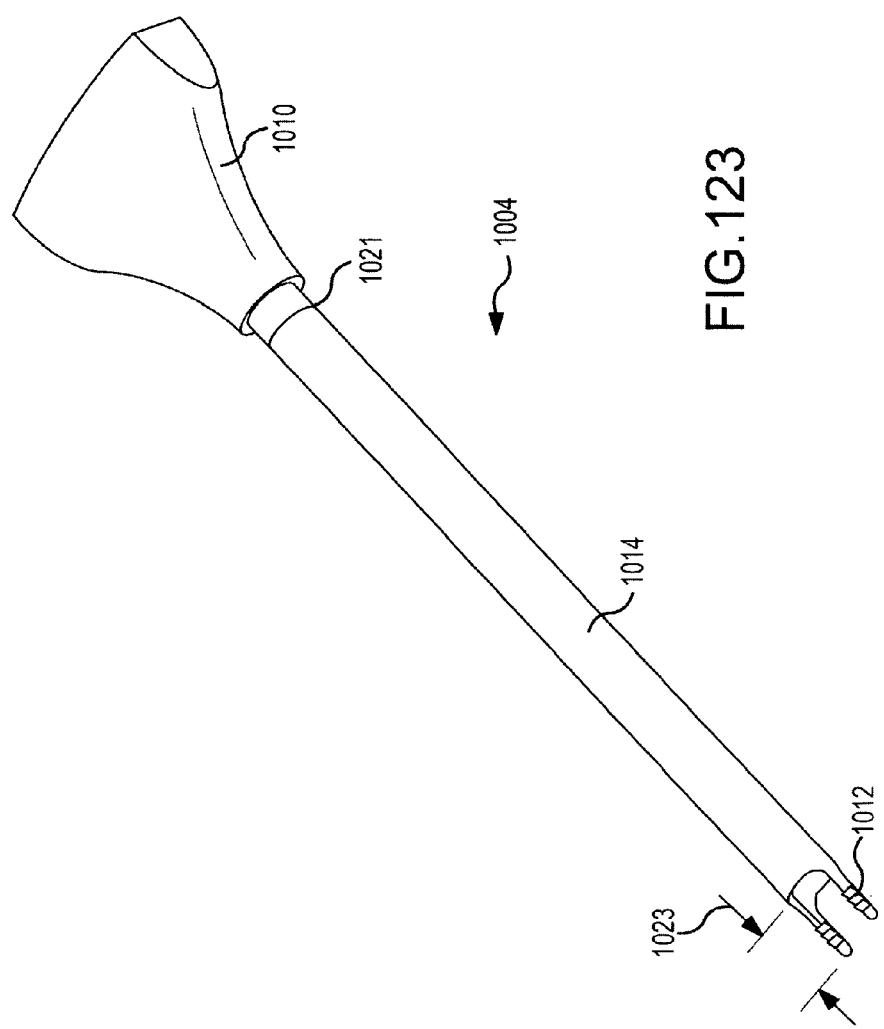
FIG. 123 is a perspective view of a delivery device according to certain embodiments.

In some embodiments, the forks 1012 at the distal end of the delivery device 1004 may have a bull nose tip as shown in FIG. 123. This is in contrast to the relatively sharp tip shown in FIGS. 2-4. The use of a chisel 1008 without a handle, which may allow for insertion of the chisel 1008 prior to the delivery device 1004, may, in turn, allow for this bull nose tip because the facet joint may be distracted prior to insertion of the delivery device 1004.

In still further embodiments, the chisel 1008 may be radiolucent. That is, the chisel may be made of plastic or other material not reflected by an x-ray. This may allow for lateral fluoroscopy to more readily show the position of a chisel, delivery device, or other device in a contra lateral facet joint without obstructing the view.

As shown in FIG. 123, the delivery device 1004 may include a receiving assembly 1010 at a proximal end, anchoring forks 1012 at a distal end, and a generally tubular shaft 1014 defining a longitudinal axis and extending between the receiving assembly 1010 and the anchoring forks 1012. The tubular shaft 1014 may have an annularly shaped cross-section with an inner radius and an outer radius, where the difference between the two radii defines a thickness of the tubular shaft 1014. The delivery device may and all of the associated elements may be any size and may be adapted for the particular anatomy being addressed. In some embodiments, the outer radius of the tubular shaft 1014 may range from approximately 2 mm to approximately 8 mm. In some embodiments, the tubular shaft 1014 may have an outer radius of approximately 5 mm.

Some of the features of the delivery device 1004 will now be described and additional features of the delivery device 1004 may include features of other delivery devices shown and described herein, such as, for example, the anchoring forks 1012.

Figure 123A:
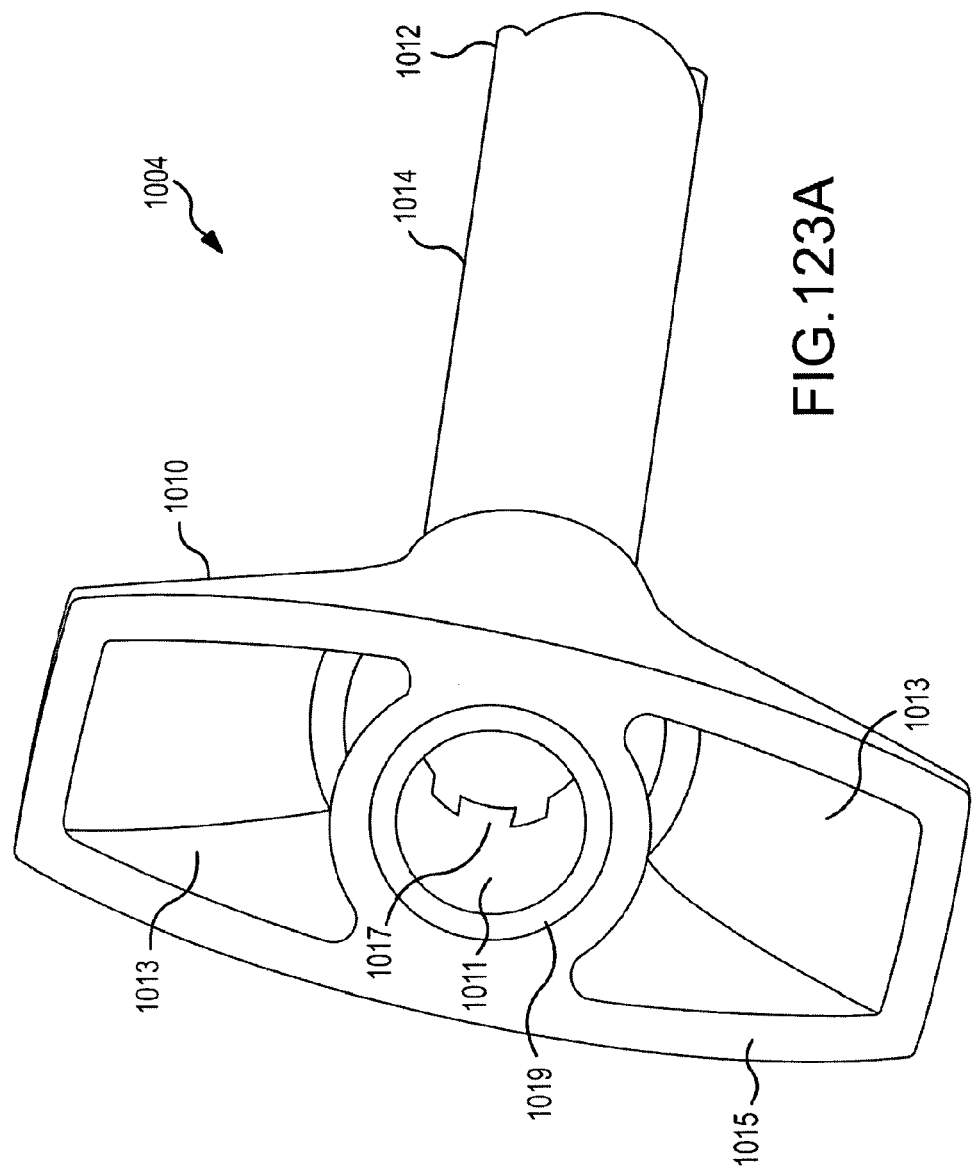
FIG. 123A is a perspective view of the proximal end of a delivery device according to certain embodiments.

The receiving assembly 1010 of the delivery device 1004, shown in FIGS. 123 and 123A, may have a generally smooth contoured outer surface that transitions from a generally rectangular cross-section at a proximal end to a narrower and generally circular cross-section at a distal end, the receiving assembly defining a volume with a bore 1011 extending there through. The bore 1011 may be positioned proximal to and in alignment with the tubular shaft 1014 and may have an inner radius matching that of the tubular shaft 1014 allowing for a smooth transition of devices from the receiving assembly 1010 into the tubular shaft 1014. As best shown in FIG. 123A, the tubular shaft 1014 may engage the receiving assembly 1010 with a dove tail connection 1017 around the periphery of the proximal end of the tubular shaft 1014. Also shown in FIG. 123A is a tapered entrance 1019 to the bore 1011 at its proximal end to facilitate ease of entry of other devices. The receiving assembly 1010 may include one or more seating cavities 1013 opening in a proximal direction for receiving and seating of other devices such as the driver assembly 1042 or the injector 1102. These seating cavities 1013 may be defined by an outer shell 1015 that is substantially flush with the outer surface of the receiving assembly 1010. The seating cavities 1013 may be positioned radially adjacent to the bore 1011. In the present embodiment, two seating cavities are shown adjacent to the bore 1011 and on opposite sides of the bore 1011. While not shown, the shell 1015 may include protrusions or recesses on its inner surface, the protrusions or recesses corresponding to protrusions or recesses on other devices. As such, these protrusions or recesses may provide for a detent relationship between the delivery device 1004 and other devices. Alternatively or in addition to the protrusions or recesses, the seating cavities 1013 may have an inner surface that tapers such that the cross-section of the cavity 1013 also tapers from a relatively broad cross-section at its proximal end to a relatively narrow cross-section at its distal end. As such, these seating cavities 1013 may provide for a friction fit between the receiving assembly 1010 and another device, where the other device may have a male portion with a shape corresponding to the shape of the seating cavity 1013. The cross-sectional shape of the cavities 1013 may include a relatively trapezoidal shape with a concave base as shown, the base bordering along the perimeter of the bore 1011. Any cross-sectional shape including square, rectangular, triangular, circular, or a more undefined random shape may be used.

The generally rectangular cross-section of the proximal portion of the receiving assembly 1010 may have a long side and a short side. The long side may be oriented parallel to a line connecting the forks 1012 in turn aligning the seating cavities 1013 with the forks 1012. As such, devices used with the delivery device 1004 may be properly aligned relative to the forks 1012 by positioning and seating them in the seating cavities 1013.

Just distal to the receiving assembly 1010, a circumferential groove 1021 is shown on the tubular shaft 1014. The groove 1021 may be adapted to aid in securing the decorticator (not shown), further described below. Alternatively, the groove 1021 may be adapted for gripping by a hemostat or other tool. For example, a hemostat may be used to hold the delivery device 1004 where the delivery device 1004 is being held in position for an x-ray and the practitioner or other user may be attempting to distance their hand from the x-ray field.

Also shown in FIG. 123 are the forks 1012. These forks 1012 may be adapted to anchor the delivery device 1004 in the facet joint. As such, similar to the chisel 1008, the forks 1012 may include a roughened or toothed surface. Additionally, the distal ends of the forks 1012 may be beveled to aid in advancing the tool through tissues and avoid snags. Moreover, the length 1023 of the forks 1012 may be adapted to extend substantially across the facet joint. As such, in one embodiment, the length 1023 of the forks 1012 may range from approximately 5 mm to approximately 35 mm. In another embodiment, the length 1023 may range from approximately 10 mm to approximately 30 mm. In still another embodiment, the length 1023 may range from approximately 14 mm to approximately 29 mm.

Referring now to FIG. 124, the decorticator 1006 may have a tubular shaft portion 1034, an abrasive distal end 1036, and a handle 1038 at a proximal end. The tubular shaft 1034 may have an inner radius substantially equal to the outer radius of the tubular shaft 1014 of the delivery device 1004 and may allow for sliding movement of the decorticator 1006 along the length of the delivery device 1004 and rotationally around the delivery device 1004. In some embodiments, the inner radius of the tubular shaft 1034 may be slightly or substantially larger than the outer radius of the tubular shaft 1014 of the delivery device 1004 allowing for more freedom of movement of the decorticator 1006. In some embodiments, the outer radius of the decorticator may range from approximately 2 mm to approximately 10 mm. In another embodiment, the decorticator may have an outer radius of approximately 6 mm.

The abrasive distal end 1036 of the decorticator 1006 may include serrated teeth 1037 as shown, or may include a more flat annular surface with a gritty surface. In the embodiment shown in FIG. 124, the distal end of the tubular shaft portion 1034 is chamfered and the serrated teeth 1037 are located on the distal most end of the chamfered end allowing for a more directed and controllable decorticating process. As such, the decorticator 1006 shown is well suited for the intra facet process reflected by many of the embodiments described herein. That is, the human anatomy of the cervical spine may be such that the lateral mass of the facet joints are not perpendicular to the surface of the facet joint. Additionally, to properly place the forks 1012 of the delivery device 1004 within the joint, the delivery device 1004 may be positioned substantially parallel to articular surfaces of the facet joint. As such, the delivery device 1004 may not be positioned perpendicular to the lateral masses of the facet joints and may actually be directed with a downward slope as it extends in the distal direction. Where the decorticator 1006 has an non-chamfered annular end, depending on anatomy, the decorticator 1006 may be able to be placed in contact with the superior lateral mass, but may be unable to reach or contact the inferior lateral mass. In the present embodiment, the chamfered end of the tubular shaft portion 1034 will allow the distal tip of the chamfered end to reach and decorticate the inferior lateral mass. This chamfered distal end may define an angle to the longitudinal axis. In some embodiments this angle may range from approximately 10 degrees to approximately 80 degrees. In other embodiments, this angle may range from approximately 30 degrees to approximately 60 degrees. In other embodiments, this angle may be approximately 45 degrees. Additionally, the teeth 1037 may be relatively large as shown in FIG. 124, or they may relatively small. Moreover, the teeth 1037 may extend along the full perimeter surface of the chamfered end rather being positioned solely at the tip of the chamfered end.

Additionally shown in FIG. 124 is a beveled edge 1039 along the periphery of the chamfered end. That is, along the ovular shape created by the chamfered tubular shaft portion 1034, the edge is beveled. As such, when the delivery device 1004 is inserted into the patient and/or when the decorticator 1006 is advanced along the delivery device 1004, the beveled edge 1039 may assist in avoiding tissue snags and the decorticator 1006 may be placed in contact with the lateral mass of the facet joints in a much smoother process and may avoid damage to neighboring tissues.

The handle 1038 of the decorticator 1006 may include a generally cylindrically shaped knob with a gripping surface along its peripheral edge and may sleevably receive the tubular shaft portion 1034. The handle 1038 may also include radially extending bores 1041 adapted to receive the gripping tool 1001. The bores 1041 may extend from the outer surface of the handle radially inward and end at the outer surface of the tubular shaft portion 1034. As such, one or several gripping tools 1001 may be inserted into any one or several of the bores 1041 in the handle 1038 and may provide for better control and a higher amount of torsional leverage when decorticating the lateral masses of the facet joint. Additionally, the gripping tool 1001 extending laterally from the handle 1038 may allow for malleting in the longitudinal direction of the decorticator 1006. That is, the gripping tool 1001 may be inserted into the bore 1041 and the decorticator 1006 may be advanced to contact the lateral mass of the facet joint. A mallet may be used to strike the side of the gripping tool 1001 to cause forceful decortication of the lateral mass. The decorticator may then be retracted, rotated to a new radial position, advanced, and struck again for additional decortication. In some embodiments, the handle 1038 may be shaped relatively oblong so as to provide a mass of material that extends laterally away from the longitudinal axis of the decorticator 1006. In this embodiment, the bore 1041 may not be a radial bore 1041, but may be offset from the passing through the center point of the decorticator 1006 a distance equal to or greater than a radius of the tubular shaft portion 1034. As such, the bore may pass all the way through the handle without encountering the tubular shaft 1034. Accordingly, the gripping tool may be inserted into the bore 1041 and extended all the way through the handle 1038, allowing for additional ability to grip and/or mallet the gripping tool 1001 and manipulate the decorticator 1006.

In still another embodiment, the bores 1041 may be positioned on the distal face of the handle 1038. In this embodiment, the bores may receive the gripping tool 1001, the tool being oriented parallel to the longitudinal axis of the decorticator 1006 and allowing for malleting the proximal end of the gripping tool 1001 to decorticate the lateral mass. In still another embodiment a series of gripping tools 1001 may be inserted into a series of bores 1041 positioned on the distal face of the handle 1038, each available to be used for malleting or manipulating the decorticator 1006. In still another embodiment, a single malleting tool (not shown) may be included, which has a series of longitudinally extending rods each receivable by a series of bores 1041 on the distal face of the handle 1038. At a positioned proximal to the receiving assembly 1010 of the delivery device 1004, the series of rods may converge to a centrally positioned malleting surface. As such, this malleting surface may be used to mallet the decorticator 1006 allowing for the force of the mallet to be positioned along the longitudinal axis of the decorticator.

Additionally shown in FIG. 124 is a radially extending threaded bore 1047 adapted to receive a corresponding threaded set screw. This threaded bore 1047 may extend from the outer surface of the handle 1038 radially inward through the wall of the tubular shaft portion 1034 allowing access to the tubular shaft 1014 of the delivery device 1004. The set screw may be advanced through the handle 1038 to engage the delivery device 1004 and prevent the decorticator 1006 from advancing or twisting inadvertently. As mentioned and shown in FIG. 123, the delivery device 1004 may include a groove 1021 on the outside surface of the tubular shaft 1014 for receiving the tip of the set screw or otherwise creating a catch point for the decorticator. As such, when the decorticator 1006 is in its fully retracted and most proximal position, the threaded bore 1047 and set screw may align with the groove 1021 in the tubular shaft 1014 and thus hold the decorticator 1006 in its most proximal position. The set screw may be a thumbscrew-type with a head that includes longitudinally extending ribs around its periphery for purposes of gripping the screw. Alternatively the head may be a wing nut type head for ease of setting and unsetting of the screw. In still another embodiment, the decorticator may have a relatively snug friction fit at the proximal end that engages the groove 1021 when retracted. In still another embodiment, the tubular shaft portion 1034 of the decorticator may include a protruding rib on its inside surface adapted to engage the groove 1021 on the tubular shaft 1014. A key slot 1049 extending transversely across the threaded bore 1047 may also be provided. Additional features of the decorticator 1006 may include features of other decorticators shown and described herein. For example, the decorticator 1006 may alternatively be separate from the delivery device 1004 and may be slidably inserted within the delivery device 1004 similar to that shown and described with respect to FIG. 4 or FIGS. 6A-6C.

Figure 125:
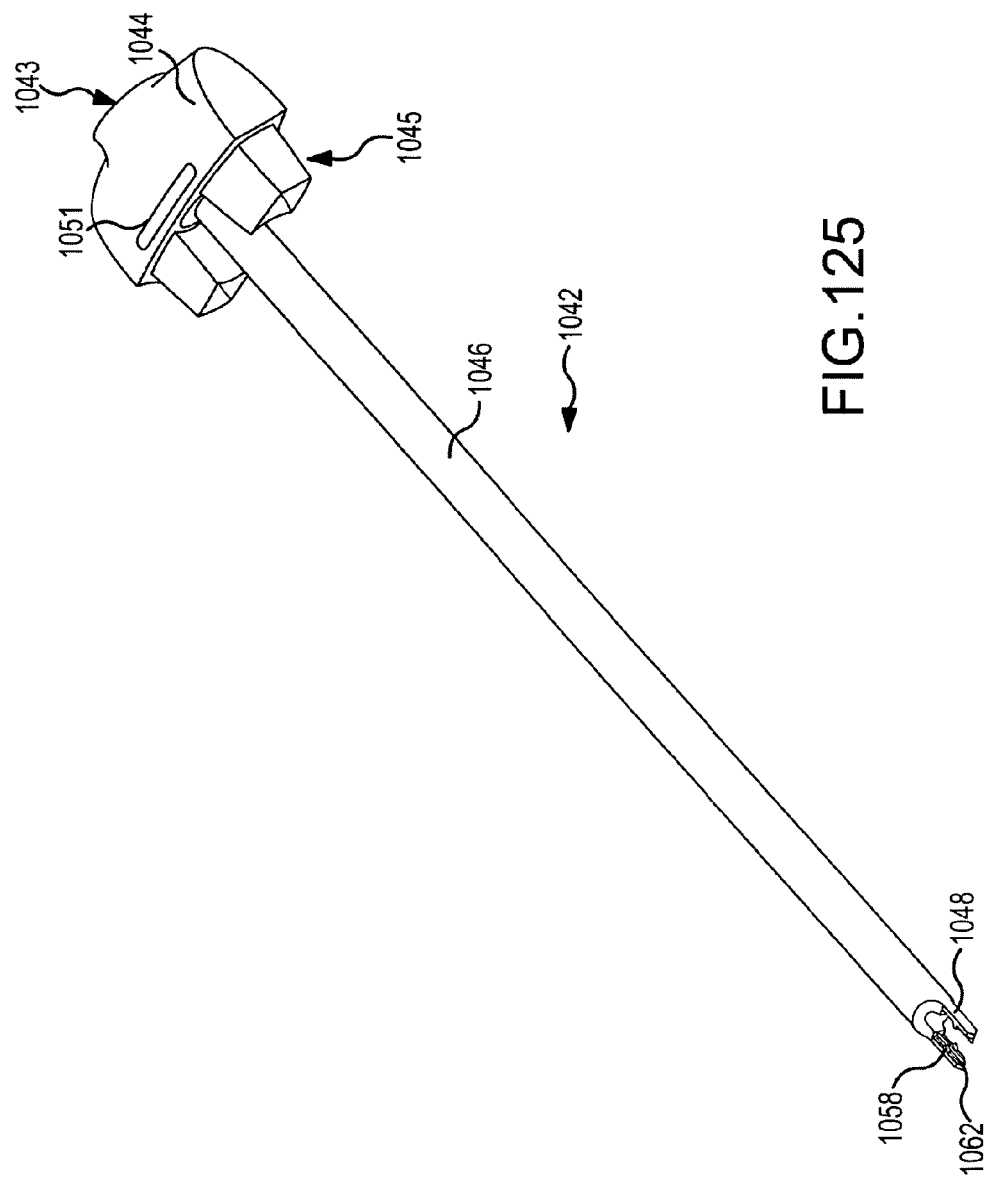

Referring now to FIG. 125, the driver assembly 1042 is shown. As shown, the driver assembly 1042 includes a handle 1044, an implant shaft 1046, and implant holding arms 1048.

The implant shaft 1046 may have an outer radius substantially equal to the inner radius of the tubular shaft portion 1014 of the delivery device 1004 (shown in FIG. 123) allowing for slidable insertion of the driver assembly 1042 within the delivery device 1004. Alternatively, the outer radius of the implant shaft 1046 may be smaller than the inner radius of the tubular shaft 1014 providing for more play and adjustability of the driver assembly 1042 and delivery device 1004 relative to one another. In some embodiments the implant shaft 1046 may have a radius ranging from approximately 1 mm to approximately 8 mm. In other embodiments, the implant shaft 1046 may have a radius of approximately 4 mm.

The handle 1044 of the driver assembly 1042 may have an outer surface defining a volume with a bore 1043 extending there through. The bore 1043 may have an inner diameter substantially equal to the inner diameter of the implant shaft 1046 allowing for a smooth transition of devices passing through the driver assembly 1042. The handle 1044 may have a generally rectangular shape at its distal end corresponding to the proximal end of the receiving assembly 1010. The handle 1044 may include gripping slots 1051 near its distal end to aid users with gloves in securely holding the driver assembly 1042. Additionally, these slots 1051 may aid a user in hold the assembly 1042 with a hemostat or other gripping device. Additionally, the handle 1044 may have a necked down portion 1045 at its distal end in the form of one or more projections. In one embodiment, the necked down portion 1045 may have protrusions or recesses (not shown) on its outer surface corresponding to respective protrusions or recesses on the inner surface of the shell 1015 of the receiving assembly 1010 on the delivery device 1004. As such, the driver assembly 1042 may be sleevably positioned within the delivery device 1004 to deliver an implant to the facet joint. When fully advanced, similar to that shown in FIG. 101, the handle 1044 may be seated securely in the seating cavity 1013 of the receiving assembly 1010. Where protrusions are included on the necked down portion 1045 and recesses are included on the inner surface of the shell 1015, the handle may be anchored with a detent relationship. The projections of the necked down portion 1045 of the handle 1044 may correspond to the seating cavities 1013 of the receiving assembly. Additionally, these projections may taper as they extend distally to provide a friction type fit into the seating cavities 1013 of the receiving assembly 1010.

The seating relationship provided by necked down portion 1045 of the driver assembly 1042 and the receiving assembly 1010 of the delivery device 1004 may allow the user to control the placement of the implant in both a longitudinal and a rotational direction. That is, once the anchoring forks 1012 of the delivery device 1004 are properly placed in the facet joint, proper placement of the driver assembly 1042 may then be ensured by aligning and seating the handle 1044 of the driver assembly 1042 in the receiving assembly 1010 of the delivery device 1004. Thus, the seating relationship may prevent the driver assembly 1042 from being inserted too far and may also allow the driver assembly 1042 to be aligned with the delivery device 1004 rotationally to ensure proper rotational orientation of the implant. Additional features of the driver assembly 1042 may include those features shown and described with respect to driver assembly 142.

The implant holding arms 1048 may include features similar to other arms shown and described herein. For example, the inside surface of the arms 1048 may include a longitudinal ridge 1062 extending the length of the arms 1048. The arms 1048 may also include a bull nose engagement feature 1058 extending transverse to the longitudinal axis of the implant shaft along the inside face of the arm 1048. Where the arms 1048 are engaged with and holding the implant, the longitudinal ridges 1062 of each arm 1048 may be positioned between upper and lower planar members of the implant and the bull nose engagement features 1058 may be positioned in the U-shaped receiving feature slots on the lateral edges of the implant.

Figure 126:
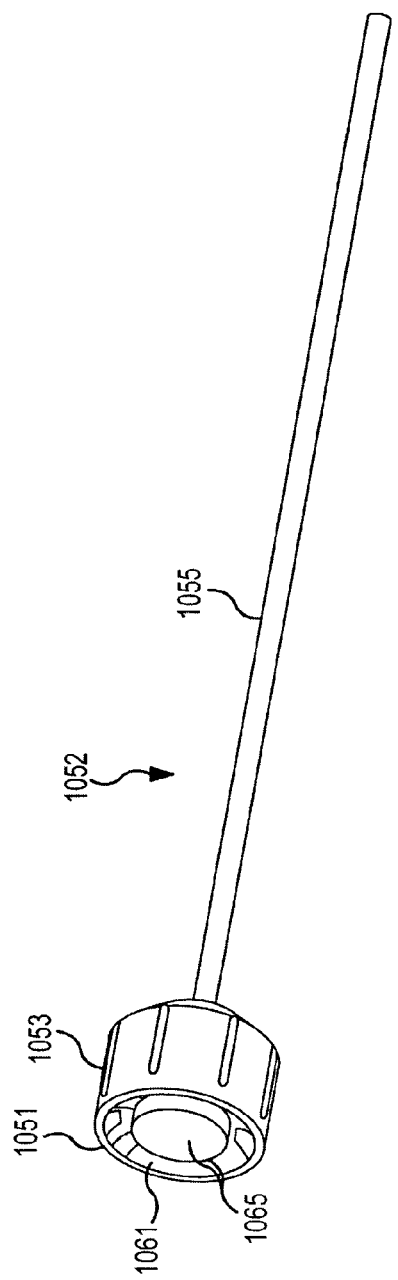

In contrast to the driver assembly 142 and consistent with the driver assembly 842, each described above, in the present embodiment, the internal actuator 1052 may be a separate device from the driver assembly 1042. As shown in FIGS. 126, the internal actuator 1052 may include a longitudinal shaft 1055 a handle 1053, and an internal rod 1057 (not shown in FIGS. 126-126B). The longitudinal shaft 1055 may be cylindrically shaped with an annular cross-section. The shaft 1055 may have an outer diameter substantially the same as or smaller than the inner diameter of the implant shaft 1046 of the driver assembly 1042. The shaft 1055 may extend from the handle 1053 proximally to a distal end. The internal actuator 1052 may be used in conjunction with the internal rod 1057 positioned within the shaft 1055.

The internal rod 1057, shown separately in FIG. 127, may be positioned within the shaft 1055 and may extend from the handle 1053 to the distal end of the longitudinal shaft 1055. The internal rod 1057 may include an engagement feature 1059 at its distal end for engaging and holding the implant distractor. This engagement feature 1059 may be any shape and provide for any engagement known in the art from a hex, allen, phillips, star, square, sleeve, or other connection capable of transmitting longitudinal and/or rotational forces from the internal rod 1057 to the implant distractor. In one embodiment, the engagement feature 1059 includes a collet type device that is described in more detail with respect to FIG. 127A below.

The internal rod 1057 may sleevably receive the implant distractor. The internal rod 1057 may be sleevably positioned within the longitudinal shaft 1055, such that when the longitudinal shaft 1055 is in an advanced position over the end of the internal rod 1057, the longitudinal shaft 1055 causes a clamping force of the collet to restrain the implant distractor against being dislodged from the collet. Each of the shaft 1055 and the internal rod 1057 may engage the handle 1053 at their respective proximal ends and be affixed there to. The shaft 1055 may be securely affixed to the handle 1053 such that rotational and longitudinal motion of the handle 1053 imparts the same motion on the shaft 1055. In contrast, the internal rod 1057 may be slidably affixed to the handle 1053 such that rotational motion of the handle 1053 imparts the same motion on the internal rod 1057, but longitudinal motion of the handle 1053 is isolated from the internal rod 1057 via a biasing mechanism. As such, the handle 1053 may be used to retract the longitudinal shaft 1055 along the length of the internal rod 1057 thereby exposing the collet and reducing the clamping force on the implant distractor, but when the handle 1053 is rotated, both the longitudinal shaft 1055 and internal rod 1057 rotate with the handle 1053. When the longitudinal shaft 1055 is in a retracted position, an implant distractor may be inserted into and/or removed from the collet due to the reduced clamping force.

Figure 126A:
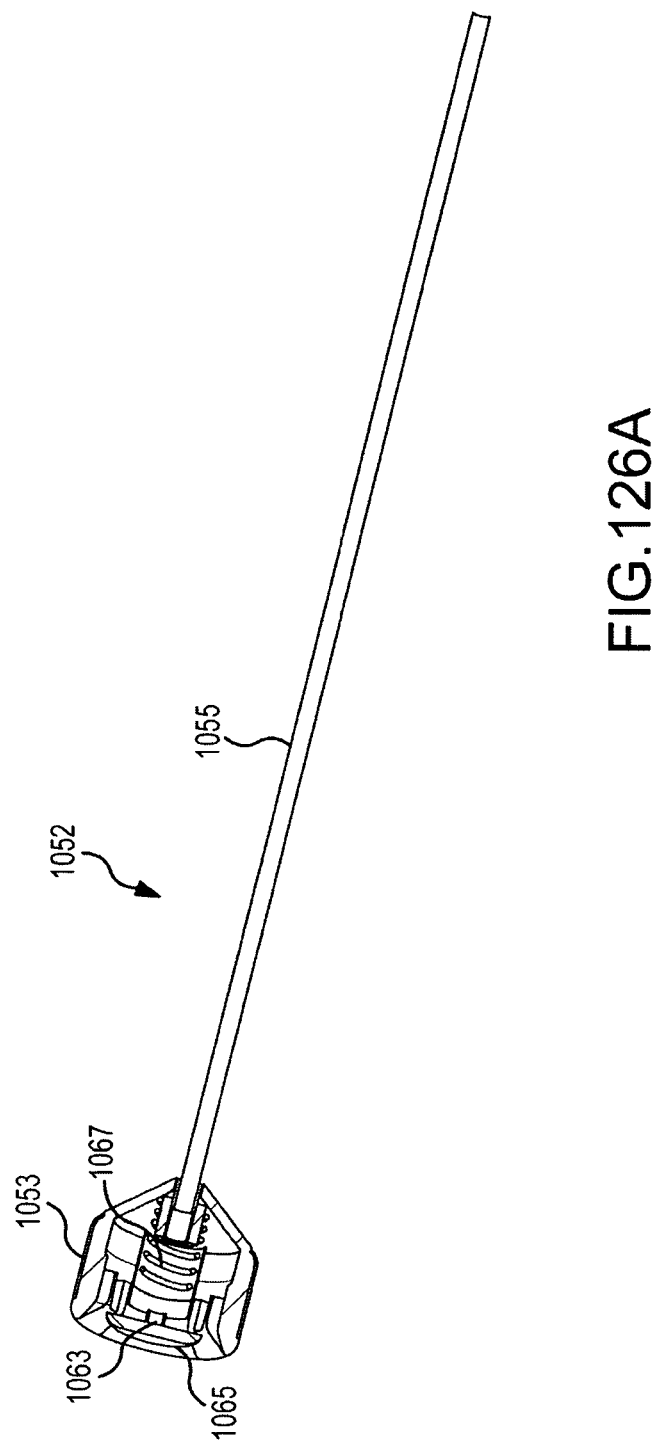
Figure 126B:
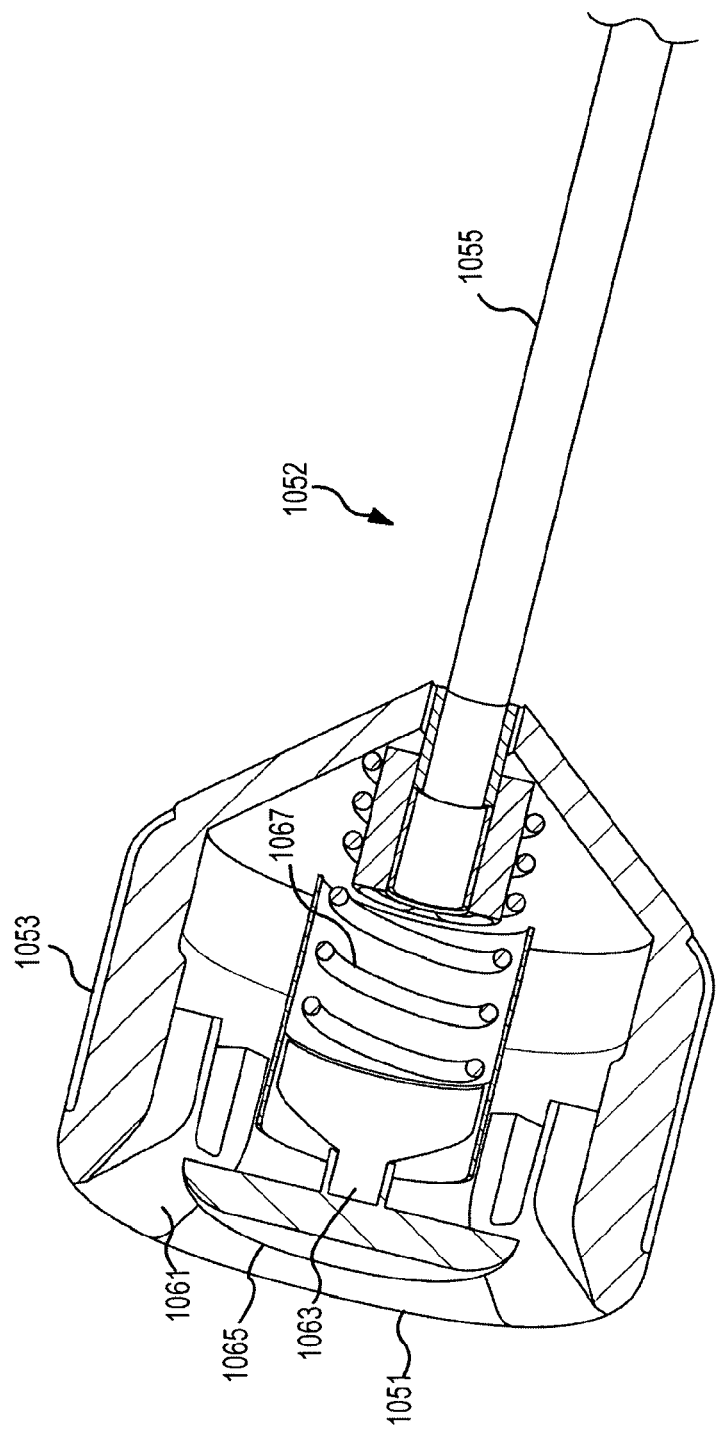

As shown in FIGS. 126A and 126B, the handle 1053 may be a generally cylindrical shape with a cone shaped distal end and a relatively flat proximal end. As shown, the proximal end of the handle 1053 may include a circumferential ridge 1051 projecting proximally and extending along the periphery of the cylindrical shape. The inner face of the ridge may be braced by a plurality of radially spaced ribs 1061. The center of the proximal end may include a button 1063 covered by a flexible membrane 1065, the proximal end of the button 1063 being recessed slightly from the circumferential ridge 1051, which protects the button 1063 against inadvertent triggering when the handle 1053 is being used to twist or turn the implant distractor. As such, the handle 1053 shown may reduce the chance that the implant distractor will become dislodged or released from the engagement feature 1059 of the internal actuator 1052 prior to being fully advanced and fully distracting the implant.

As shown in the cross-section of the handle 1053 in FIG. 126B, the button may be held in position by an internal spring 1067 or other biasing mechanism or device and may also include longitudinal keyways allowing for relative longitudinal motion of the button relative to the handle 1053, but preventing relative rotational motion. In use, the implant distractor may be placed in the engagement feature 1059 at the distal end of the internal rod 1057 and the internal rod 1057 may be in position inside the longitudinal shaft 1055. As mentioned above, in the embodiment, shown, when the internal rod 1057 has a collet type engagement feature 1059, the retraction of the internal rod 1057 within the longitudinal shaft 1055 may cause a circumferential clamping force from the longitudinal shaft 1055 onto the engagement feature 1059 of the internal rod 1057, thereby securing the implant distractor in the engagement feature 1059 of the internal rod 1057. Once assembled, the internal actuator 1052 may be inserted and advanced through the driver assembly 1042 positioning the implant distractor just proximal to the implant being held by the implant holder arms of the driver assembly. The handle 1053 may then be rotated to cause the implant distractor to advance into the implant thereby distracting the implant.

Once the implant distractor is fully advanced, the handle 1053 may be grasped and the button may be pressed, while pulling on the cone shaped portion of the handle 1053, which may counteract the biasing force of the spring 1067 or other biasing mechanism and cause relative longitudinal motion between the internal rod 1057 and the longitudinal shaft 1055. Accordingly, the distal end of the internal rod 1057 may extend beyond the distal end of the longitudinal shaft 1055 and the clamping force on the engagement feature 1059 may be removed allowing the internal actuator 1052 to be removed leaving the implant distractor behind.

As shown in more detail in FIGS. 127 and 127A, the engagement feature 1059 at the distal end of the internal rod 1057 may take the form of a collet 1093 for holding the implant distractor. The collet 1093 may be affixed to the distal end of the internal rod 1057 and may be adapted to hold the implant distractor. The collet 1093 may be permanently affixed to the distal end of the internal rod 1057 or may be interchangeably coupled thereto. Several collet and chuck arrangements are known in the tool industry for receiving bits or other devices and are within the scope of the invention.

The collet 1093 may include any or all of the features of other collets shown and described herein. For example, the collet 1093 may include a generally cylindrical body member 1095 with four receiving fingers 1097 equally spaced around a bore 1099. The collet 1093 may include as few as two fingers 1097 and may include any number of fingers 1097.

In still another embodiment, a second internal actuator may be provided. This second internal actuator may include a handle securely affixed to a shaft and an engagement feature securely affixed to a distal end of the shaft. The engagement feature may correspond to the shape of the proximal end of the implant distractor. In one embodiment, this shape is a female square shape corresponding to a square shaped proximal end of the implant distractor. This engagement feature may include any shape known in the art as mentioned with respect to the engagement feature 1059 discussed above. This second internal actuator may be used to advance the implant distractor. For example, the second internal actuator may be used if the internal actuator 1052 were to lose its grip on the implant distractor. That is, if the collet loses its grip for any reason including deformation of the fingers of the collet or due to malfunction of the internal actuator 1052 for any reason, the second internal actuator may be used. The second internal actuator may be passed down the tubular shaft 1046 of the driver assembly 1042 to engage the proximal end of the implant distractor. The engagement feature on the distal end of the second internal actuator may be brought into engagement with the proximal end of the implant distractor and the second implant distractor may be used to rotate or otherwise advance the implant distractor thereby distracting the implant.

Figure 128:
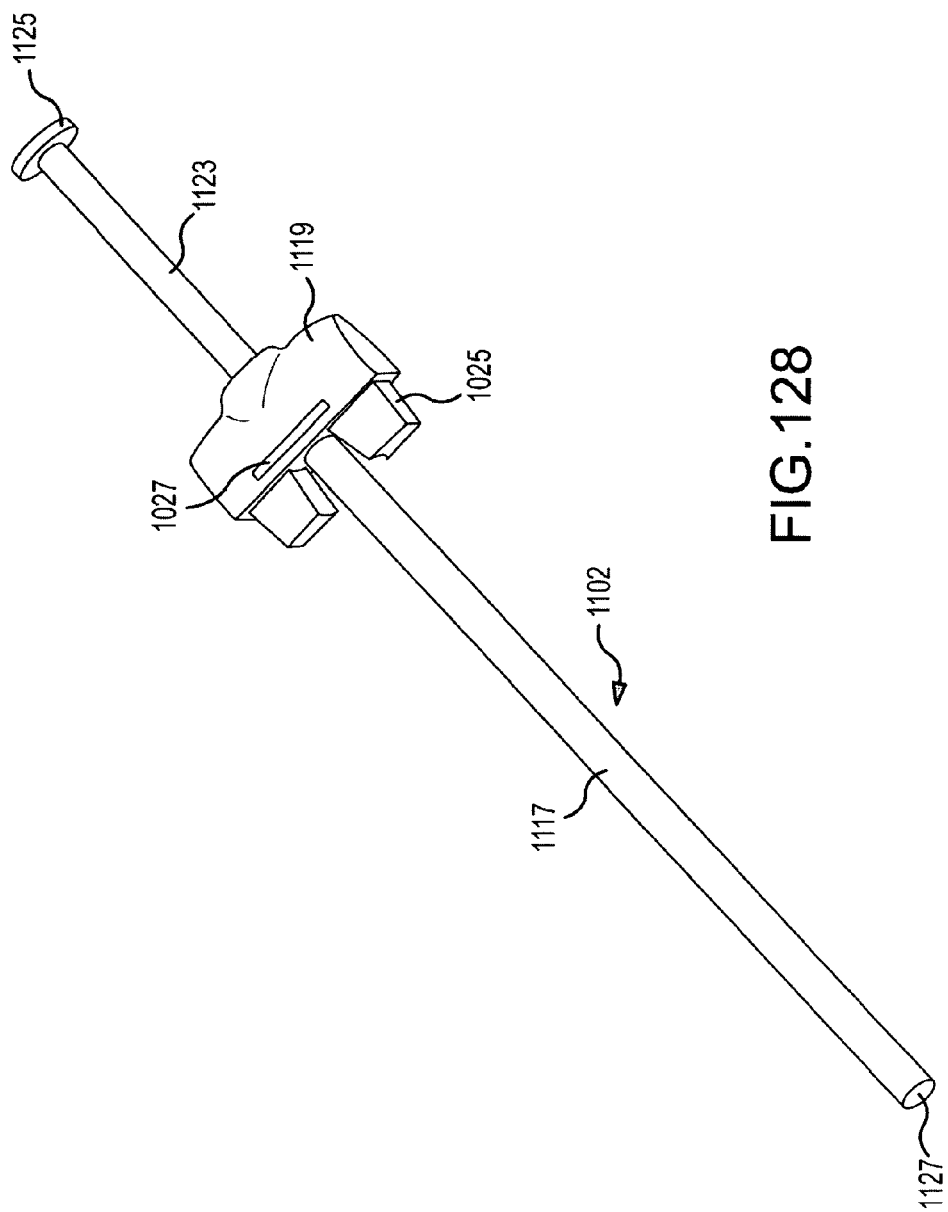

Turning now to FIG. 128, an injector 1102 is shown. The injector 1102 may include a longitudinal delivery shaft 1117, a seating feature 1119, and a plunger 1123 with a handle 1125. The longitudinal delivery shaft 1117 may have any cross-section and may have a cross-sectional size adapted to fit within the delivery device 1004. The longitudinal shaft 1117 may have an opening 1127 on its distal end for directing bone paste out the distal end of the shaft 1117 allowing the paste to flow into and/or over the facet joint and/or outward toward the lateral mass of a facet joint. The seating feature 1119 may include a rectangular or other shaped block positioned around the shaft 1117, which may be sized and shaped to abut the receiving assembly 1010 of the delivery device 1004. As with the driver assembly 1042, the distal end of the seating feature 1119 may have a shape corresponding to the shape of the proximal end of the receiving assembly 1010. As shown, this is a generally rectangular shape, but may be any shape. Additionally, the seating feature 1119 may include gripping slots 1027 nears its distal end. Additionally, the seating feature 1119 may include a necked down portion 1025 on its distal end which may be received by the seating cavities 1013 of the receiving assembly 1010. As with the driver assembly 1042, the seating feature 1119 of the injector 1102 may include protrusions or recesses (not shown) corresponding to protrusions or recesses on the inner surface of the shell 1015 allowing for a detent relationship for securing the injector 1102 to the delivery device 1004.

The injector 1102 may be sleevably inserted into the delivery device 1004 and advanced such that the distal end of the shaft 1117 is positioned between the forks 1012. The plunger handle 1125 may be pressed distally and bone paste or other material may be injected toward the facet joint site. Additional features not mentioned may be included as shown and described with respect to the injector 202 and/or 902. For example, the plunger 1123 may include a seal.

A gripping tool 1001 has been referenced for use with several of the above devices, including, but not limited to the chisel 1008 and the decorticator 1006. As shown in FIG. 121, the gripping tool 1001 may include a shaft 1003 and a handle 1005. The shaft 1003 may be made of a relatively rigid material and may have a diameter adapted to fit into the bores provided in the chisel 1008 and the decorticator 1006. The handle 1005 of the gripping tool 1001 may be any shape. In one embodiment, the handle 1005 is a T-type handle 1005. In anther embodiment, as shown, the handle 1005 is a spherically shaped handle 1005. The handle 1005 may be adapted in size and shape to nest in the palm of a human hand and such that it can be used to push, pull, or rotate the devices it is connected to or be struck with a mallet.

Referring now to FIGS. 129-135B, a dilator set 1200 is shown. FIGS. 129-131 show an assembled set of dilators including a dilator rod 1202 and a plurality of dilator sleeves 1204, including a small 1204A, medium 1204B, and large 1204C dilator. Any number of dilator sleeves 1204 may be included. Each of the dilator sleeves 1204 may have an inner diameter corresponding to the outer diameter of the next smallest sleeve, the smallest sleeve 1204A having an inner diameter corresponding to the outer diameter of the dilator rod 1202. Each of the dilator sleeves 1204 and dilator rod 1202 may have varying lengths, the largest of the sleeves 1204C having the shortest length, the dilator rod 1202 having the longest length, and the other sleeves 1204A, 1204B having lengths there between, such that each rod 1202 or sleeve 1204 is longer than the next largest sleeve. Each of the dilator rods 1202 and sleeves 1204 may include a tapered tip.

As shown in FIGS. 132 and 132A, the dilator rod 1202 is shown. The dilator rod 1202 may be a generally solid shaft or may include an interior lumen for receiving a guide wire. The rod 1202 may have any outer diameter. In one embodiment, the rod 1202 has an outer diameter of between approximately 1 mm and 5 mm. In another embodiment, the rod 1202 has an outer diameter of approximately 3 mm. The rod 1202 may have any length. In one embodiment, the rod 1202 has a length of between approximately 200 mm and 400 mm. In another embodiment, the rod 1202 has a length of approximately 290 mm. The tip of the rod 1202 may be tapered and may further include a radiused distal tip. As such, the tip may be adapted to penetrate and dilate tissue.

FIGS. 133, 133A, and 133B show the small dilator sleeve 1204A. The small sleeve 1204A may have an inner diameter adapted to slide over the dilator rod 1202. The inner diameter of the small sleeve 1204A may be only slightly larger than the rod diameter or may be much larger. In one embodiment, the inner diameter of the small sleeve 1204A is 0.6 mm larger than the dilator rod diameter. The small sleeve 1204A may have any outer diameter and any length. In one embodiment, the small sleeve 1204A has an outer diameter of between approximately 3 mm and 9 mm. In another embodiment, the small sleeve 1204A has an outer diameter of approximately 6 mm. In one embodiment, the small sleeve 1204A has a length of between approximately 200 mm and 300 mm. In another embodiment, the small sleeve 1204A has a length of approximately 260 mm. The small sleeve 1204A may include a tapered tip with a radiused distal edge and, as such, the small sleeve may be adapted to slide over the dilator rod and further dilate tissue.

FIGS. 134 and 134A and FIGS. 135, 135A, and 135B, show a medium dilator sleeve 1204B and a large dilator sleeve 1204C respectively. The medium sleeve 1204B may have an inner diameter adapted to slide over the small sleeve 1204A and the large sleeve 1204C may have an inner diameter adapted to slide over the medium sleeve 1204B. Each of the medium sleeve 1204B and large sleeve 1204C may have an inner diameter only slightly larger than the outer diameters of the small 1204A and medium 1204B sleeve respectively or they may have an inner diameter that is much larger. In one embodiment, the medium sleeve 1204B and the large sleeve 1204C may have an inner diameter that is approximately 0.6 mm larger than the outer diameter of the small sleeve 1204A and the medium sleeve 1204B respectively. The medium sleeve 1204B may have any outer diameter and any length. In one embodiment, the medium sleeve 1204B has an outer diameter of between approximately 4 mm and 12 mm. In another embodiment, the medium sleeve 1204B has an outer diameter of approximately 8 mm. In one embodiment, the medium sleeve 1204B has a length of between approximately 180 mm and 280 mm. In another embodiment, the medium sleeve 1204B has a length of approximately 230 mm. The large sleeve 1204C may also have any outer diameter and any outer length. In one embodiment, the large sleeve 1204C has an outer diameter of between approximately 6 mm and 18 mm. In another embodiment, the large sleeve 1204C has an outer diameter of approximately 11 mm. In one embodiment, the large sleeve 1204C may have a length of between approximately 150 mm and 250 mm. In another embodiment, the large sleeve 1204C may have a length of 200 mm. Each of the medium 1204B and large 1204C sleeves may include a tapered tip with a radiused distal edge. As such, each of the medium 1204B and large 1204C sleeves may be adapted to dilate tissue slightly more than the corresponding smaller sleeve.

In use, the dilator set of FIGS. 129-135B may be used to dilate tissues to access a facet joint. That is, once an incision is made, the dilator rod 1202 may be advanced alone or over a guidewire through the tissues of the back up to and/or into the facet joint. Once the rod 1202 is in position, the small sleeve 1204A may be advanced over the rod 1202 from the proximal end of the rod 1202 and may be advanced along the full length of the rod 1202. The longer length of the rod 1202 may allow the rod 1202 to extend out of the proximal end of the small sleeve 1204A such that control of both elements of the dilator set are maintained. The small sleeve 1204A may be advanced fully such that the tip of the small sleeve 1204A is flush with the tip of the rod 1202, thus dilating the tissues in an amount equal to the outer diameter of the small sleeve 1204A. This process may continue with larger and larger sleeves 1204 to appropriately dilate the tissues and allow access to the facet joint. Depending on the dilation necessary, the order and type of dilation may vary. That is, in some instances, the rod may not be necessary. In other instances, some of the sleeves may be omitted or skipped.

Referring now to FIGS. 136-170, another embodiment of a tool 2000 is shown. FIG. 136 shows a chisel 2008, a place holding chisel 2009, a delivery device 2004, a decorticator 2006, a driver assembly 2042, an injector 2102, and a malleting tool 2001.

Referring more particularly to FIGS. 138-143, a chisel 2008 may be the same or similar to other chisel embodiments described herein. For example it may have a tubular shaft portion 2028 and tip portion 2030 the same or similar to the chisel 1008 described above. Additionally, the chisel 2008 may include a handle 2032 the same or similar to the handle 1044 on the driver assembly 1042. However, in contrast to the driver assembly handle 1044, the chisel handle 2032 may include a recessed slot cavity on its distal face for receiving a malleting anvil 2041 of the receiving assembly 2010. The handle 2032 can also include a malleting head 2031 for advancing the chisel 2008 via malleting.

With reference to FIGS. 140-141, one embodiment of the malleting head 2031 is shown. The malleting head 2031 can include a cylindrical shaft portion 2051 and a flattened circular head portion 2053. The cylindrical shaft portion 2051 can be sized for sleevable insertion into the proximal face of the handle 2032. Additionally, the cylindrical shaft portion 2051 can include a key slot 2055 extending longitudinally along its length. The key slot 2055 can be adapted to receive a longitudinal rib on an inner surface of a bore extending through the handle 2032. Accordingly, the malleting head 2031 can be prevented from twisting relative to the handle 2032 once assembled. Additionally, as shown in FIG. 141 the malleting head 2031 can include a flattened surface on the inner surface of the cylindrical shaft portion 2051. As shown in FIG. 142 the proximal end of the shaft portion 2028 of the chisel 2008 can include a corresponding flattened portion. Accordingly, once assembled, the shaft portion 2028 of the chisel 2008 can be prevented from twisting relative to the malleting head 2031. The malleting head 2031 can also include a counter bored hold extending into the circular head portion 2053 and the proximal end of the shaft portion 2028 of the chisel 2008 can include a corresponding pilot hole. Accordingly, once assembled, a screw can be inserted in the proximal end of malleting head 2031 and can extend into the proximal end of the shaft portion 2028 of the chisel 2008 thereby securing the two portions to one another.

As shown in FIGS. 139A-139C, the proximal end of the shaft portion 2028 of the chisel 2008 can extend through the distal face of the chisel handle 2032. The distal end of the malleting head 2031 can extend through the proximal face of the chisel handle 2032 until the bottom face of the circular head abuts the proximal surface of the handle 2032. The proximal end of the shaft portion 2028 can be sleevably positioned within the cylindrical shaft portion 2051 of the malleting head 2031 and a screw can secure the malleting head 2031 to the shaft portion 2028 of the chisel 2008. In alternative embodiments, the shaft portion 2028 can be integral with the malleting head such that the two portions of the chisel are monolithic. It is noted, in the embodiment described, that once assembled, the malleting head 2031 can extend beyond the base of the slot cavity of the handle 2032. The malleting head 2031, being positioned on the proximal face of the handle 2032 and being directly attached to the shaft portion, can provide for forces from malleting the head 2031 of the chisel 2008 to transfer directly down the shaft portion 2028 of the chisel. Moreover, the distal end of the malleting head 2031, extending slightly beyond the base of the slot cavity, can allow the malleting head 2031 to directly abut the malleting anvil 2041 of the receiving assembly 2010 when the chisel 2008 is inserted into the deliver device 2004 as shown in FIG. 144. As such, when the malleting head 2031 of the chisel 2008 is struck, any advancing force of the chisel 2008 relative to the delivery device 2004 can be resisted by the interaction between the malleting head 2031 and the malleting anvil 2041 thereby preventing relative advancing motion between the chisel 2008 and the delivery device 2004.

Referring to FIGS. 145 and 149, the distal end of the chisel 2008 is shown extending slightly beyond the distal tip of the delivery device 2004. In some embodiments, the distal end of the chisel 2008 can be flush with the distal tip of the delivery device 2004 or it can extend up to approximately 6 mm beyond the end of the delivery device 2004. In the embodiment shown, the distal end of the chisel 2008 extends approximately 2 mm beyond the end of the delivery device 2004.

As also shown in FIG. 149, the surfaces of the tip 2030 of the chisel can include a series of ridges 2033. The ridges 2033 can be relatively sharp and can aid the user in roughening or decorticating the facet surfaces as the chisel 2008 is inserted and removed from a facet joint. The ridges 2033 can include a pattern adapted to maintain the chisel's position in a facet joint. In some embodiments, the ridges 2033 can include a sloping distal face and a relatively vertical (e.g., perpendicular to axis of chisel 2008) proximal face. As the chisel 2008 is advanced, the surfaces in contact with the chisel 2008 may ride up along the sloping distal face until the chisel 2008 is positioned. The relatively sharp apex of the ridges 2033 formed by the sloping distal face and relatively vertical proximal face can function to hold the chisel in place. Moreover, the ridges 2033 can be arranged in a surface pattern suitable for holding the chisel 2008 in place. In one embodiment, the ridges 2033 can include a chevron pattern as shown. Patterns such as straight rows, diagonal rows, wavy rows, or other alternative patterns can be included.

Referring particularly to FIG. 143, the distal end of the chisel can include a positioning opening 2059. The positioning opening 2059 can extend transversely through the chisel 2008 and can be positioned near the proximal portion of the tip 2030 of the chisel 2008. This opening 2059 can function to allow for longitudinal positioning of the chisel 2008 through lateral fluoroscopy. That is, the opening 2059 can be visible during lateral fluoroscopy due to the absence of material and the chisel 2008 can be advanced into a facet joint until the opening 2059 is at, near, or slightly beyond the posterior edge of the facet joint. It is noted that the position of the opening 2059 can be such that it aligns with a corresponding opening 2015 in the forks 2012 of the delivery device 2004.

Referring to FIG. 138, the handle 2032 can include connection features 2043 on the necked down portion of the handle 2032. The connection features 2043 can create a detent relationship between the handle 2032 and the receiving assembly 2010 of the delivery device 2004 such that the two elements can resist separation without some force being applied. The detent relationship can be created by protrusions as shown, which engage a lip around the proximal end of the receiving assembly 2010 or a recess on the inner surface of the receiving assembly 2010. Alternatively, the detent relationship can be created by recesses for receiving protrusions positioned on the inner surface of the receiving assembly 2010.

Referring to FIGS. 139A-C, 159, and 155A-B, the connection feature 2043 can also take the form of a latch type feature. For example, the feature 2043 can be wedge shaped and adapted to engage a corresponding ledge on the inside of the receiving assembly 2010, as best shown in FIG. 155B. The connection feature 2043 can be positioned on a deflectable lateral side of the handle 2032 and the deflectable lateral side can include a push button for disengaging the connection feature 2043. When the chisel 2008 is advanced into the delivery device 2004, the deflectable lateral side of the handle 2032 can deflect to allow the connection feature 2043 to clear the opposing and corresponding ledge on the inside of the receiving assembly 2010 allowing the handle 2032 to snap into place in the receiving assembly 2010. To remove the chisel 2008, the push button can be depressed to clear the connection feature 2043 from the corresponding ledge and the chisel 2008 can then be removed. It is noted that a similar connection can be used on any of the handles or seating features described herein; particularly handles or seating features adapted to engage the receiving assembly 2010.

In this embodiment, the chisel 2008 may be engaged with the delivery device 2004 via a connection between the handle 2032 and the receiving assembly 2010. In this embodiment, both the chisel 2008 and the delivery device 2004 may be introduced into the facet joint at the same time allowing for a one-step process of initially entering the facet joint rather than initially entering the joint with the chisel 1008 and then passing the delivery device 1004 over the chisel 1008 as with the tool 1000. Once the chisel 2008 and the deliver device 2004 are properly positioned, the chisel 2008 may be removed.

As shown in FIG. 136, the tool 2000 can also include a place holding chisel 2009. The place holding chisel 2009 can have a square cross-section adapted to be inserted into the delivery device 2004. The diagonal dimension of the cross-section can be at least slightly smaller than the inner diameter of the delivery device 2004. Alternatively, other cross-sections can be provided and can be adapted for insertion in the delivery device 2004.

The place holding chisel 2009 can be a radiolucent chisel and as such can be made from a radiolucent material such as plastic, PEEK, or a polyetherimide material such as, for example, Ultem®. Other radiolucent materials can be used. The place holding chisel 2009 may include a positioning marker 2011 adapted to assist the user in properly positioning the place holding chisel 2009. The positioning marker 2011 can include a guide line, a mark, or another surface indication on the surface of the chisel 2009 for alignment with a portion of the delivery device 2004. In one embodiment, as shown, the positioning marker 2011 can be in the form of a double triangle separated by an alignment line. The double triangles can be positioned to form an alignment line on the place holding chisel 2009 such that when the alignment line is aligned with the proximal end of the delivery device 2004 (e.g., the proximal face of the receiving assembly 2010), the distal end of the chisel 2009 is properly positioned to extend slightly out the end of the delivery device 2004. Additionally, where the alignment line is not aligned with the distal end of the delivery device 2004, the triangles can function as arrows indicating which direction to move the chisel 2009. That is, the triangle closest to the distal face of the receiving assembly, may indicate which direction to move the chisel 2009. As also shown, the proximal end of the chisel 2009 can include a hole extending transversely there through. The hole can adapted to receive a transverse rod or shaft extending into the hole and/or through the hole. The rod or shaft and the chisel 2009 can form a T-grip or L-shaped grip for use in pulling on the chisel 2009 for removal.

Referring again to FIG. 149, the distal tip of the place holding chisel 2009 can include a tip the same or similar to the chisel 2008. For example, the chisel 2009 can include a coped and/or chamferred tip 2035 similar to chamferred tip 2030. Additionally, the chisel 2009 can include ridges 2037 arranged in a pattern similar to that shown and described with respect to chisel 2008. Additionally, the chisel 2009 can include a radiopaque portion 2039 adapted to allow recognition of the chisel's location while avoiding occlusion of the lateral view. The radiopaque portion 2039 can include a straight, round, square, or other shaped piece of material positioned near the distal end of the chisel 2009 for locating the distal end. As shown, the radiopaque portion 2039 can be embedded in the surface of the distal tip of the chisel 2009 to cause the location of the distal tip to be ascertainable from lateral fluoroscopy.

In use, the place holding chisel 2009 can be used as a place holder without occluding the lateral view of a chisel and delivery assembly positioned in a contralateral facet joint. That is, upon placement of the chisel 2008 and the delivery device 2004 in a first facet joint, the chisel 2008 may be removed and replaced with the place holding chisel 2009 where the forks 2012 of the delivery device 2004 maintain the position of the tool 2000. The delivery device 2004 may also be removed and reassembled with the chisel 2008 once the place holding chisel 2009 is properly positioned. The delivery device 2004 and chisel 2008 may then be inserted into the contralateral facet joint or second joint. By replacing the chisel 2008 in the first joint with the place holding chisel 2009, the location of the chisel 2008 and delivery device 2004 in the second joint may be more readily ascertainable using lateral fluoroscopy. That is, if a radiopaque chisel or delivery device was left in place in the first joint, the fluoroscopic view of the contralateral facet joint would be relatively occluded. Upon placing the delivery device 2004 properly in the second facet joint, the procedure above may continue. Upon completing treatment of the second facet joint, the delivery device 2004 may be sleeved over the place holding chisel 2009 still positioned in and holding the place in the first facet joint and the first facet joint may then be treated with the above procedure. It is noted that initial placement of the deliver device 2004 can be conducted with the place holding chisel 2009 rather than the chisel 2008 to avoid having to replace the chisel 2008. Additional features of the chisel 2008 may include features of the other chisels shown and described herein. For example, an internal lumen may be provided.

Referring now to FIGS. 137 and 144, a delivery device 2004 is shown. The delivery device 2004 may include features the same as or similar to previously disclosed delivery devices. For example, the delivery device 2004 can include a receiving assembly 2010 at a proximal end and a pair of anchoring forks 2012 at a distal end with a generally tubular shaft 2014 extending there between. The delivery device 2004 can also include a malleting anvil 2041. The malleting anvil 2041 can include a raised surface positioned on the proximal face of the receiving assembly 2010 adapted for contact with the distal end of the malleting head 2031 on the chisel 2008, as described above, or on the driver assembly 2042. As such, malleting on the proximal end of the chisel 2008 or the driver assembly 2042 can cause longitudinal forces along the length of the respective tool piece. These longitudinal forces can be transferred, at least partially, through the contact between the malleting head 2031 and the malleting anvil 2041. Accordingly, relative motion between the respective tool piece and the delivery device 2004 can be prevented. As such, for example, the necked down portion 2045 of the driver assembly, can be prevented from wedging inside the receiving assembly and getting lodged or stuck therein. Moreover, at the distal end of the delivery device 2004, the relative position of the distal end of the chisel 2008 or the driver assembly 2042 relative to the distal end of the delivery device 2004 can be maintained.

Referring now to FIGS. 145 and 149, a distal tip of the delivery device 2004 is shown. As shown, the distal tip of the delivery device 2004 can include anchoring forks 2012. As shown, and previously described, the forks 2012 can include teeth or ridges along their surface for decorticating the interior surface of the facet and for temporarily anchoring the delivery device 2004 therein. In this embodiment, the teeth or ridges can extend along and across the coped portion of the tubular shaft 2014 of the delivery device 2004. This coped portion can be tapered to avoid hanging up on the lateral mass of the facet joint. That is, as the forks 1012 are inserted into the joint the outward sloping portion of the distal end of the delivery device 2004 can approach the lateral mass of the joint. Where the coped portion slopes too abruptly, the contact between the sloped surface and the lateral mass can limit how far the forks 2012 can be advanced into the joint. In some embodiments, the coped portion of the distal end of the delivery device 2004 can include a taper angle 2013 ranging from approximately 5° to approximately 45°. Preferably, the taper angle 2013 is approximately 7° to approximately 15°. The taper angle can be adjusted to accommodate several different types and/or areas of the anatomy and can thus also include angles outside the mentioned ranges. For example, use of the device in the lumbar region of the spine may involve the use of different angles.

With continued reference to FIGS. 145 and 149, along the lateral side of the tubular shaft portion 2014 near the proximal end of the forks 2012, the tubular shaft portion 2014 can include an alignment hole 2015. This alignment hole 2015 can align with the positioning opening 2059 in the chisel 2008 and can be used with lateral fluoroscopy for properly advancing the delivery device 2004 and/or the chisel 2008. As discussed with respect to the chisel 2008, the delivery device 2004 can be advanced until the alignment hole 2015 is just outside, at, or just inside the posterior edge of the facet joint.

In addition to the alignment hole 2015, near the intersection of the forks 2012 and the tubular shaft portion 2014, a bump or bull nose 2049 can be provided to further assist with properly placing the delivery device 2004. The bump 2049 can be in alignment with the alignment hole 2015 and can serve a similar purpose as the alignment hole. Thus, the bump or bull nose 2049 can function to assist the user in properly advancing the delivery device 2004 where the alignment hole 2015 is blocked, or not provided, or in addition to the alignment hole 2015. The bump 2049 can accentuate the location of the proximal end of the forks 2012 and the bumps position relative to the posterior edge of the facet joint can indicate to the user whether the forks 2012 are properly positioned. In some embodiments, the bump can also function to secure the forks 2012 in the facet joint. That is, as the delivery device 2004 is advanced into the joint, the bump or bull nose 2049 can be advanced just beyond the posterior edge of the articular surface of the facet joint. This articular surface can be relatively concave and the shape of the bump or bull nose 2049 can function to hook itself just inside the perimeter of the concave surface and resist withdrawal of the delivery device 2004.

The generally rectangular cross-section of the proximal portion of the receiving assembly 2010 may have a long side and a short side. The long side may be oriented perpendicular to a line connecting the forks 2012. This may be in contrast to the previously described embodiments, where the long side was shown parallel to a line connecting the forks 2012. In some embodiments, particularly where two contralateral facet joints are being treated, the shown orientation can assist in avoiding interference of adjacent handles. That is, the shown orientation can allow the forks of the delivery device 2004 to be inserted into the facet joint and the receiving assembly 2010 can maintain a vertical orientation relative to the patient allowing the nearby joint to be treated without interference with the receiving assembly 2010. In the present tool assembly 2000, the tool pieces adapted for insertion into the deliver device 2004 can also have a handle portion such as, for example, handle 2032 and/or 2044 that is oriented perpendicular to the chisel distal tip or the holding arms 2048 respectively. As such, devices used with the delivery device 2004 may be properly aligned relative to the forks 2012 by positioning and seating them in the seating cavities 2013 of the receiving assembly.

Referring now to FIG. 146, a decorticator 2006 is shown. The decorticator 2006 shown can include a malleting element 2038 at its proximal end and a series of decorticating teeth 2037 on a distal end. The malleting element 2038 and the teeth 2037 can be connected by a generally U-shaped and relatively thin longitudinally extending member 2034. The malleting element 2038 can include a relatively thick generally U-shaped member. As shown, the malleting element 2038 and the longitudinal member 2034 can be aligned and adapted to receive a tube from the lateral side. That is, for example, the decorticator 2006 can be applied to the delivery device 2004 from the side rather than being sleeved over the delivery device as shown in previous embodiments. The malleting element 2038 can be used for forcibly advancing the decorticator 2006. Accordingly, the malleting element can be a relatively thick element adapted to absorb and distribute a malleting force to the longitudinal member 2034. The teeth 2037 can be the same or similar to the decorticating teeth previously described, such as, for example, the serrated teeth 1037. The teeth 2038 can be positioned along all or a portion of the half annular shape formed by the distal end of the U-shaped longitudinal member 2034. As with the decorticator 1006, the present decorticator 2006 can include a chamferred distal end allowing for acute decortication by the teeth 2037 without interfering with adjacent or surrounding structures. For example, decorticator 2006 can allow for access to the inferior lateral mass without interference from the superior lateral mass of a facet joint due to the chamferred distal end and also due to the u-shape. The decorticator can include features that are the same or similar to the decorticators previously described.

The malleting element 2038 can be used with a malleting tool 2001 as shown in FIGS. 136 and 150. As shown best in FIG. 136, the malleting tool 2001 can include a longitudinally shaped shaft with a U-shaped decorticator interface 2005 at one end and a chamferred tip 2003 at the other end. The decorticator interface 2005 can be adapted for positioning around the delivery device 2004 in a position just proximal to the malleting element 2038 of the decorticator. The u-shape of the decorticator interface 2005 may allow the malleting tool 2001 to be placed in position from the side of the delivery device and selectively used as required to forcibly advance the decorticator 2006. The chamferred end of the tool 2001 can be held in position while the user mallets near the decorticator interface end causing the interface 2005 to contact the malleting element 2038 on the decorticator. The decorticator 2006 may then be retracted, rotated to a new radial position, advanced, and struck again for additional decortication. The tool 2001 may rotate with the decorticator 2006 or it may remain in a position convenient for malleting. In addition to malleting, the malleting tool 2001 can be used to assist in separating several tools. That is, in some cases, the handles of a given tool piece, for example, the handle 2032 of the chisel 2006 can be difficult to separate from the receiving assembly 2010. As mentioned, the malleting tool can include a chamferred tip 2003. The chamferred tip can be used to wedge between a given handle and the receiving assembly 2010 to assist in separating the devices.

Referring now to FIGS. 147 and 148, a driver assembly 2042 is shown. As shown, the driver assembly 2042 includes a handle 2044, an implant shaft 2046, implant holding arms 2048, and an integrated internal actuator 2052.

The handle 2044 of the driver assembly 2042 may include features the same or similar to previously described handles. In particular, the handle 2042 can include features the same or similar to the driver assembly handle 1042. In the present embodiment, the handle can also include a slot cavity, similar to the chisel 2008, for receiving and interfacing with the malleting anvil 2041 on the proximal end of the receiving assembly. Where the driver assembly 2042 is sleevably positioned within the delivery device 2004, the necked down portions 2045 of the handle 2044 can be received into the receiving assembly 2010 and the slot cavity can be positioned around the malleting anvil 2041 on the proximal face of the receiving assembly. Similar to the chisel 2008, the slot cavity on the handle 2044 can include a bearing surface 2047 for interfacing with the malleting anvil 2041. In addition, the handle 2044 can include a malleting bar 2043 extending distally from a first side of the body of the handle, laterally across the width of the body of the handle, and then proximally to a second side of the handle. The malleting bar 2043 may allow for malleting of the driver assembly 2042 and the interaction of the bearing surface with the malleting anvil can function to prevent relative longitudinal motion between the driver assembly 2042 and the delivery device 2004 when malleting the driver assembly. Additionally, as described with respect to the chisel 2008, the handle 2044 can include connection features 2043 providing for a detent relationship with the receiving assembly 2010 or the latch type connections can be provided.

The integrated internal actuator 2052 can include features the same or similar to the internal actuator 1052. In the present embodiment, the actuator can be integrated into the driver assembly 2042 and can be securably and pivotally positioned therein. For example, when compared to the internal actuator 852 and/or 1052, the tubular shaft 855/1055 can be omitted and an internal rod 2057, the same or similar to rods 857 and 1057, can be positioned within the implant shaft 2046 of the driver assembly. As mentioned with respect to internal actuator 152, the distal tip of the internal actuator can include flat screwdriver types, phillips head types, square drives, etc. As best shown in FIG. 148, the distal tip of the internal actuator 2052 can be a flat screwdriver type tip.

The handle 2053 can be pivotally secured to the handle 2044 of the driver assembly 2042 allowing for pivotal motion of the handle 2053 relative to the implant shaft 2046 causing rotation of the internal rod 2057. As shown, the handle 2053 can be positioned just proximal to the body of the handle 2044 and the malleting bar 2043 can extend around its perimeter. A gap may be provided between the malleting bar 2043 and the handle 2053 to avoid interference with the rotation of the handle 2053 and to avoid transferring malleting force through the internal actuator. The handle 2053 can be adapted to advance as it is turned and can further be adapted to properly advance the implant distractor 2050. That is, the clearance provided within the handle 2044 can be such that a particular advancing distance of the handle 2053 will cause the handle 2053 to interact with or abut the handle 2044 preventing over-advancing the internal rod 2057 and the implant distractor 2050. This allows the advancement of the implant distractor 2050 and the associated distraction of the joint with the implant to be reproducible and consistent. In one embodiment, the implant distractor 2050 is advanced to a point where a cross-cut of a thread feature on the implant distractor 2050 engages a truncated slot on the implant. In one embodiment, the implant distractor 2050 can be started in the implant by 1½ turns prior to insertion of the driver assembly 2042 in the delivery device 2004 where the leading portion of the thread feature on the implant distractor 2050 is engaged in the leading slot on the implant. The turning of the handle 2053 can then advance the implant distractor 2050 the remaining distance relative to the implant.

The implant holding arms 2048, shown most clearly in FIG. 149 may include features similar to other arms shown and described herein. For example, an engagement feature 2058 similar to the bull nose engagement feature 1058 may be provided. In the present embodiment, the engagement feature 2058 can include a raised portion on the surface of the holding arms 2048 that can be adapted to be positioned in the U-shaped receiving feature slots on the lateral edges of the implant. The present embodiment can be contrasted with the arms 1048 shown in FIG. 125. As shown, the arms 2048 are adapted to be positioned within the implant and do not extend along side the implant. This can allow for a narrower transverse dimension and an overall smaller system. The arms 2048 can include steps as the arms transition from the implant shaft 2046 of the driver assembly to the arms 2048. The step can be adapted to accommodate the thickness of one of the upper and/or lower members of the implant such that, when placed thereon, an outer surface of the implant can be relatively flush with the upper level of the step.

The interaction of the driver assembly 2042 with the deliver device 2004 can function to properly position the implant. That is, both the alignment hole 2015 and the bump or bull nose 2049 can function to properly position the delivery device 2004 as described above. The driver assembly 2042 can include a length and handle engagement adapted to position the implant between the forks 2012 of the delivery device 2004 by fully inserting the driver assembly 2042 in the delivery device and engaging the connection features. Accordingly, the driver assembly 2042 can allow the implant to be positioned anterior to the alignment hole 2015 and/or the bumps 2049 of the delivery device 2004 and thus can be used to properly position the implant. This engagement of the handle of the driver assembly 2042 with the receiving assembly 2010 of the delivery device 2004 can simplify the delivery process. That is, once the delivery device 2004 is properly positioned, the mechanical engagement of the several pieces of the tool 2000 can control the proper position of the implant thereby simplifying and expediting the delivery and implantation process. The user can rely on the position of the delivery device 2004 for placement of the implant thereby minimizing time and/or adjustments to ensure that the implant is properly positioned.

Turning again to FIGS. 136 and 137, several views of an injector 2102 are shown. The injector 2102 may include features the same or similar to the injectors previously described. In particular, the injector 2102 can include features the same or similar to the injector 1102. In the present embodiment, the injector seating feature 2119 can include connection features 2043 the same or similar to those described on the necked down portion of the handles of the chisel 2006 and the driver assembly 2042. In addition, the seating feature 2119 of the injector 2102 can include a slot cavity for positioning around and receiving the malleting anvil on the receiving assembly 2010 of the delivery device 2004. The plunger 2123 of the injector 2102, as shown in FIG. 151, can include a handle 2125, a shaft 2127, and a seal 2129. The plunger 2123 can be advanced through the injector 2102 to eject bone paste or other materials into and/or around the facet joint.

It is noted that when comparing tool 1000 to tool 2000 at least two differences include the handle 2032 on the chisel 2008 and the integration of the internal actuator 2052 with the driver assembly 2042. With respect to the chisel difference, the tool 2000 can be adapted for a one-step facet joint access process. That is, rather than first advancing the chisel 1006 and then sleeving the delivery device 1004 over the chisel, both the chisel 2008 and the deliver device 2004 can be advanced into the facet joint at the same time. With respect to the driver assembly difference, the tool 2000 can be adapted for a smaller diameter than the tool 1000. That is, in integrating the driver assembly 2042 with the internal actuator 1052, one of the concentric tubes, namely the tubular shaft 1055, has been omitted. Additionally, the implant holding arms 2048 can be adapted to hold the implant from behind rather than from the sides. That is, the arms 2048 can pass within the implant and remain within the width defined by the implant. This allows the driver assembly 2042 to have a smaller size than the driver assembly 1042 and also allows the delivery device 2004 to have a smaller size than the delivery device 1004. Accordingly, the driver assembly 2042 can have a radius of approximately 1 mm to approximately 5 mm. In a preferred embodiment, the driver assembly can have a radius of approximately 3 mm. Additionally, the delivery device 2004 can have a radius of approximately 1.5 mm to approximately 6 mm. Preferably the delivery device 2004 can have a radius of approximately 4 mm. In one embodiment, the delivery device 2004 can have a radius of approximately 5 mm for a majority of its length and can have a radius of 4 mm near the forks 2012. For example, as shown in FIG. 149, the outer surface of the delivery device 2004 can neck down at or near the alignment hole. This necked down portion can be by way of squaring off the outside surface of the forks such that the outside surface of the forks is not radiused like the outer surface of the shaft portion of the delivery device 2004.

Referring to FIGS. 152 and 153A-C, an implant distractor 2050 is shown. The implant distractor 2050 can include features the same as or similar to the features of the implant distractor 850. For example, the implant distractor 2050 can include a continuous coil-shaped thread feature 2066. Additionally, the thread feature 2066 may be interrupted by at least one cross-cut 2115 at one or more locations along the threaded feature 2066. In one embodiment, as shown, a single cross-cut 2115 may be positioned just proximal to the distal end. This cross-cut 2115 may be positioned approximately 180 degrees out of phase from the abrupt proximal end 2113 of the thread feature 866. Both the cross-cut 2115 and the abrupt proximal end 2113 may provide for interlocking engagement of the implant distractor 2050 with the implant 154/854 and thus prevent backing out of the implant distractor 2050. As shown, the implant distractor 2050 can include a slotted proximal end 2064 adapted to receive a flat screwdriver type distal end of the internal actuator 2052 shown in FIG. 148.

The implant distractor 2050 can include a generally elongate cylindrical body 2107 adapted to be advanced between the upper and lower members of the implant causing them to distract. The distal tip of the cylindrical body 2107 can be tapered to accommodate initial engagement with the implant and the remaining portion of the cylindrical body 2107 can be generally elongate with parallel extending edges. Accordingly, a relatively uniform outward force can be induced by the implant distractor 2050 as it advances through the implant 2054. It is noted that other distractors other than those with thread features can be included and can include alternative advancing mechanisms or can be forcibly advanced.

Referring now to FIG. 156, an implant 2054 is shown. The implant may include features that are the same as or similar to the implants 154 and/or 854 described with respect to FIGS. 16-24 and FIGS. 117-120 respectively. The implant 2054 can be made from a variety of materials including stainless steel, tungsten, titanium, PEEK, and nitinol. Other suitable materials can be used. The material can be a malleable material and the combination of the material properties and the thickness can be adapted to allow the implant to conform to the shaped of the implant distractor and/or the articular surfaces of the facet joint. For example, the thickness of the upper and lower members 2068, 2070 can range from approximately 0.05 mm to approximately 2 mm. In a preferred embodiment, the thickness can be approximately 0.38 mm.

Figure 157:
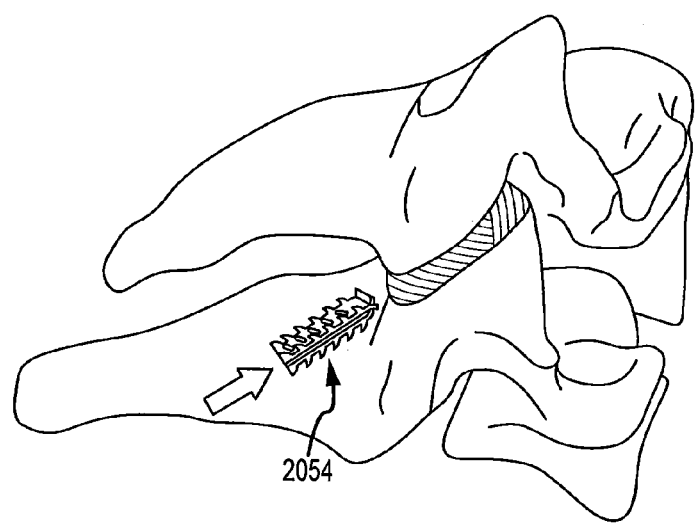
Figure 158:
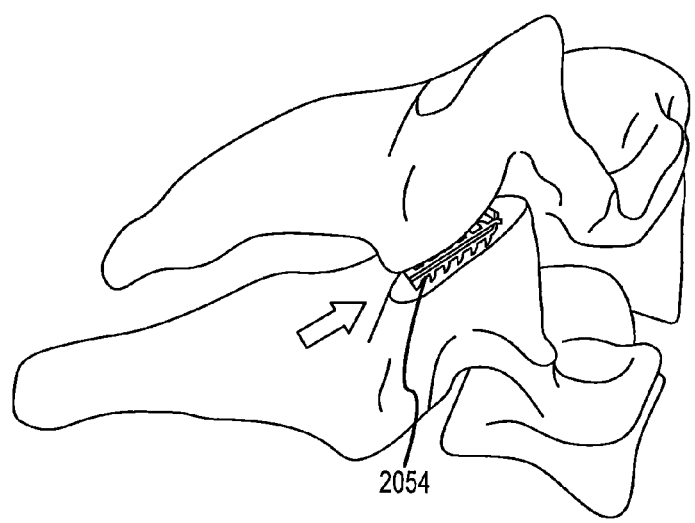
Figure 159:
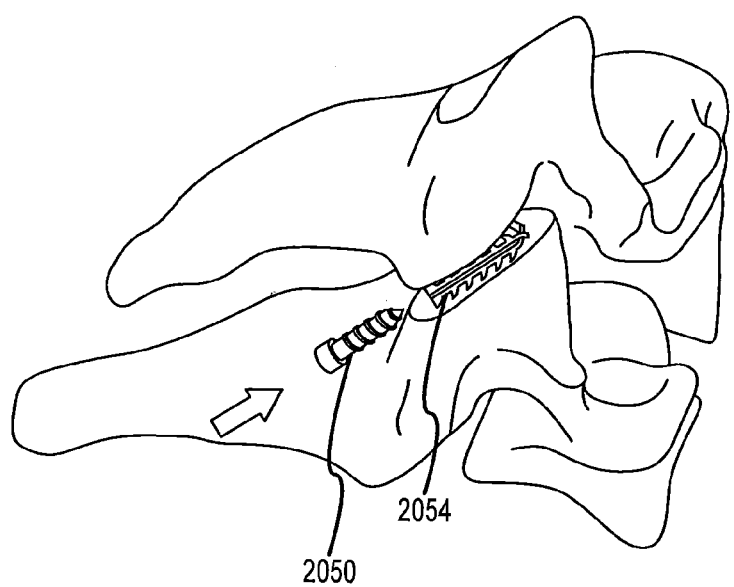

Referring to FIGS. 157-162, several perspective views of an implant 2054 are shown. It is noted that the delivery tool has been omitted for clarity and the method/order of insertion of the implant and the distractor may be different from that depicted here. In FIG. 157, the implant 2054 is shown prior to insertion into a facet joint. The implant can include upper and lower planar members similar to that described with respect to implants 154 and 854. The planar members can be generally parallel to one another. As shown in FIG. 158, the implant 2054 can be inserted into a facet joint. As further shown in FIG. 159, an implant distractor can be advanced between the relatively planar members forcing the members apart and against the opposing surfaces of the facet joint.

Figures 160A, 160B, 160C:
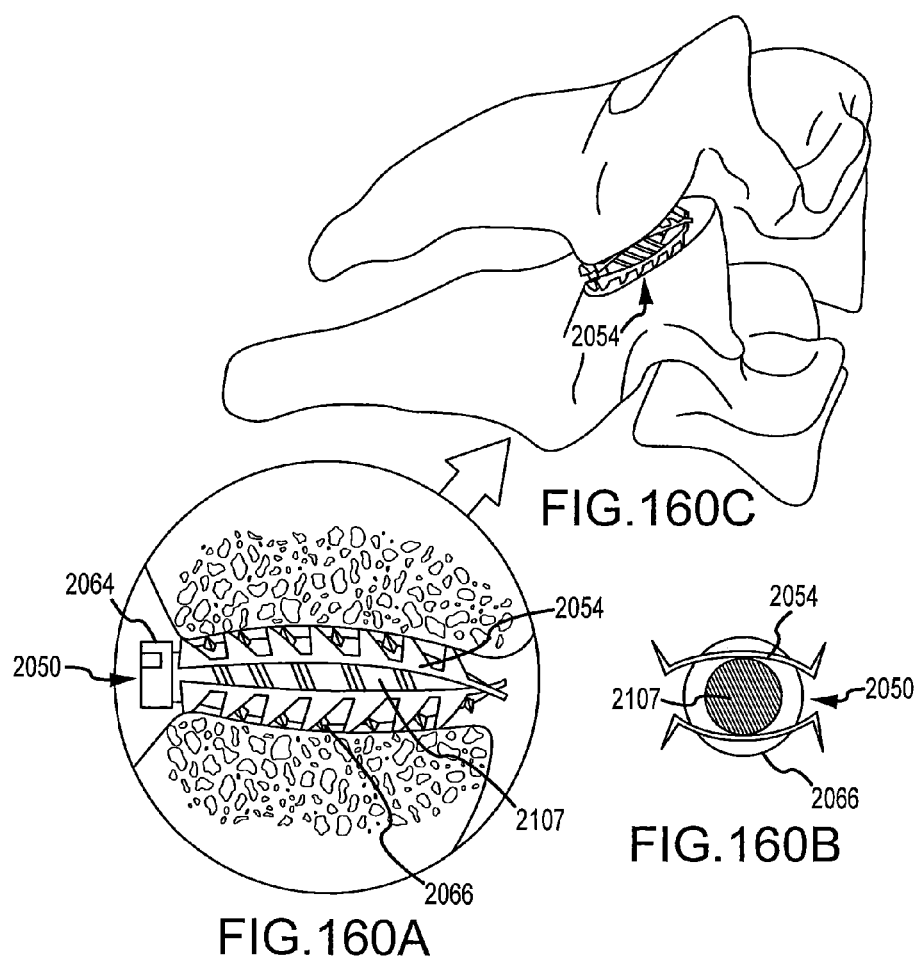

Referring to FIGS. 160A-C, the force of the distractor within the implant 2054 can cause the teeth of the implant to gain purchase in the facet joint surface and can further cause distraction of the joint. The relatively malleable nature of the implant 2054 can cause the implant 2054 to conform to the shape of either the implant distractor or the articular surfaces of the facet joint, or both, while still distracting the joint.

In the embodiment shown, the generally elongate implant distractor can be positioned generally centered across the width of the upper and lower members of the implant. Additionally as shown, the teeth of the implant can be positioned along the lateral edges of the implant. In this embodiment, as the implant distractor is advanced into the implant, the spreading force of the implant distractor can force the teeth of the implant into the opposing facet surfaces causing them to gain purchase therein as shown in FIG. 160A. The teeth can engage the bone substantially. In some embodiments, the teeth can be completely seated in the facet surfaces such that the upper and/or lower members abut the surface of the facet joint. The thread feature of the implant distractor can also engage the facet surfaces as it protrudes through the slots in the implant.

The separation force of the implant distractor can act near the center of the upper and lower members between the teeth of the implant. This spreading force can be counteracted by the naturally resistive force of the articular surfaces of the facet. In this embodiment, this naturally resistive force can act on the engaged teeth of the implant. The concurrent spreading force and opposing resistive force can thus function to form or bend the implant around the axis of the elongate implant distractor forcing it to generally conform to the shape of the implant distractor, as best shown in FIG. 160B. This forming can allow the center portion of the upper and lower member to more closely approach the articular surfaces of the facet joint rather than being held off from the articular surface by any remaining height of the teeth. Accordingly, the threaded slots in the upper and lower member can allow the thread feature of the implant distractor to project through and further engage the articular surfaces of the facet. It is also noted that to the extent the articular surface of the facet joint is concave across its lateral width, the forming of the implant can be emphasized. This is because the edges of the articular surface can continue to force the lateral edges of the implant around the implant distractor.

In some embodiments, the implant distractor can be generally straight with a tapered tip or it can include a tapered tip transitioning into a relatively barrel-shaped mid section followed by a tapered trailing end. In either case, and as shown best in FIG. 160A, the outward forces of the implant distractor in conjunction with the compressive forces of the articular surfaces of the facet can cause the implant to conform to the shape of the implant in this direction also creating an generally elliptically shaped implant. Accordingly, and as shown by review of FIGS. 160A and 160B, the planar members of the implant 2054 can take on a doubly curved shaped corresponding to the shaped of implant and resembling the concave shape of the articular surfaces.

Figure 161A:
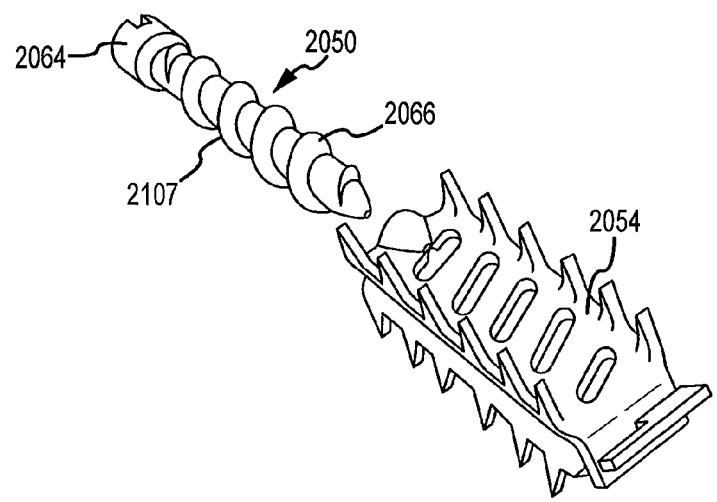
Figure 161B:
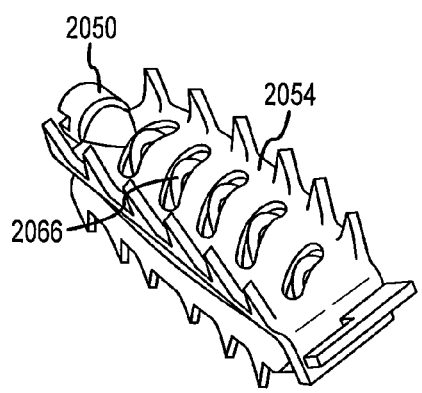

FIGS. 161A and 161B show additional views of the implant 2054 reflecting a similar conforming transition between opposed planar members of the implant 2054 in FIG. 161A, and opposed doubly curved members of the implant 2054 in FIG. 161B. In these views, the facet joint has been omitted for clarity. As can be seen from a review of FIG. 161B, the upper member of the implant 2054 can be concave and can form about the longitudinal axis of the elongate distractor. Additionally, as can be seen by viewing the longitudinal seam between the upper and lower member, the upper member and lower member can also form a relatively elliptical shape about an axis perpendicular thereto.

It is noted that alternative implant distractors can be used depending on the shape of the implant desired. For example, a broader implant distractor can be provided for broader joints to broaden the longitudinal cross-section of the implant and better distribute the compressive forces. The anterior to posterior profile of the implant distractor can be adjusted to reflect the shape of the articular surfaces of a particular joint thereby allowing the implant to do the same. Implant distractors that provide a relatively uniform expansive pressure to separate the upper and lower members can also be provided to cause the implant to more uniformly conform to the shape of the articular surfaces of a particular joint. These distractors can include fluid type distractors or other relatively uniform pressure devices.

Referring to FIG. 162, a mechanically tested implant is shown exhibiting the conforming properties described. That is, the implant has conformed under compressive pressure to reflect the shape of the implant distractor and/or the contour of the opposing surfaces of a facet joint. The implant exhibits a formed shaped around the longitudinal axis and an axis transverse thereto.

Referring to FIGS. 163-170, the dimensions of a particular embodiment of the tool are shown. FIG. 163 includes exemplary dimensions of an implant. FIG. 164 includes exemplary dimensions of a delivery device. FIG. 165 includes exemplary dimensions of an implant distractor. FIG. 166 includes exemplary dimensions of a chisel. FIG. 167 includes exemplary dimensions of a place holding chisel. FIG. 168 includes exemplary dimensions of a driver assembly. FIG. 169 includes exemplary dimensions of a decorticator. FIG. 170 includes exemplary dimensions of a malleting tool. FIGS. 163-170 reflect dimensions of just one example of an embodiment of a tool. The tool can be constructed with alternative configurations, dimensions, and relationships and is not limited to these particular examples.

Referring now to FIGS. 171-174, an additional embodiment of a chisel 2209 is shown. The chisel 2209 can be adapted to facilitate easier initial access of the facet joint. The chisel 2209 can include features the same or similar to previously disclosed chisels, for example, chisel 2008 and/or chisel 2009. As shown in FIG. 171, the chisel 2209 can include a distal portion 2211 and a proximal portion 2213. The combined length of the distal portion 2211 and the proximal portion 2213 can form the overall length of the chisel 2209. The overall length of the chisel 2209 can be the same or similar to the length of the chisel 2009. As such, when the distal tip of the chisel is in place in a facet joint within, for example, a delivery device 2004, the distal end of the chisel 2209 can extend out of the distal end of the delivery device 2004 to allow for manipulation of the chisel 2209.

Referring now to FIG. 172, a close-up view of the distal portion 2211 of the chisel 2209 is shown. The distal portion 2211 can include a chamfered tip 2230 similar to the previously disclosed chamfered tips. However, the chamfered tip shown includes ridges 2037 on one face of the tip 2230 as shown in FIG. 172 and not on the opposing face as shown in FIG. 173. In some embodiments, ridges 2037 can be included on each face or may be omitted altogether. Where the ridges 2037 are omitted on one or both faces, resistance experienced by a user attempting to access a facet joint with the tip of the chisel 2209 may be minimized. However, the ability to decorticate the facet surfaces may also be reduced.

Referring still to FIG. 172, the distal portion 2211 of the chisel 2209 can be a generally elongate and cylindrically shaped member with a longitudinal bore 2215 extending there through. The cylindrical cross-section of the distal portion 2211 can have a radius ranging from approximately 1 mm to approximately 6 mm. In other embodiments, the radius can range from approximately 3 mm to approximately 5 mm. In one embodiment, the radius can be approximately 4 mm. The bore 2215 can be sized and adapted to receive and pass through a needle. In some embodiments, the needle can be approximately a 12 GA to approximately a 28 GA needle. In other embodiments, the needle can be a gauge somewhere in between 12 to 28 or a gauge beyond 12 to 28. In one embodiment, the needle may be a 22 GA needle.

The bore 2215 can be generally centered in the circular cross-section of the distal portion 2211 and can extend from the transition between the proximal portion 2213 and the distal portion 2211 to the distal tip of the chisel 2209. The bore can extend through the chamfered tip 2230 creating a notch 2217 in the chamfered tip 2230 at its distal edge. The bore 2215 can be exposed to the environment surrounding the chisel 2209 via a plurality of holes 2219 and/or a slot 2221.

The distal portion 2211 can have a length adapted to accommodate standard length needles. That is, the distal portion 2211 can have a length adapted to accommodate a 5", an 8", or a 10" standard length surgical needle for example. In these embodiments, the distal portion 2211 of the chisel 2209 can have a length such that when the needle is inserted into the bore 2215 from the proximal end and the needle hub provided on the needle abuts the transition between the distal portion 2211 and the proximal portion 2213, the distal tip of the needle can extend between approximately, 5 mm to approximately 35 mm beyond the distal tip of the chisel 2209. In some embodiments, the length of the distal portion 2211 is such that a standard length needle can extend between approximately 15 mm to approximately 25 mm beyond the distal tip of the chisel 2209.

Referring now to FIG. 174, the proximal portion 2213 is shown. The proximal portion 2213 of the chisel 2209 can extend from the distal portion 2211 and be adapted for manipulating the distal tip of the chisel 2209. The proximal portion 2213 can have a length adapted to extend from a delivery device 2004 when a delivery device is inserted over the chisel 2209. In the present embodiment, the proximal portion 2213 includes a semi-circular cross-section and is generally solid. The cross-sectional shape can define an arcuate surface and a generally flat surface of the proximal portion 2213. The arcuate portion can be a continuation of an arcuate ½ of the distal portion 2211 and the flat portion can extend from the transition at approximately the mid-depth of the distal portion 2211 proximally to the proximal end of the chisel 2209. The proximal portion 2213 can be hollow and/or can include alternatively shaped cross-sections. As shown, the proximal portion 2213, near the transition to the distal portion 2211, can include an entry feature 2223 adapted to receive a needle and facilitate advancing the needle into and through the bore 2215 of the distal portion. The entry feature 2223 can be centered on the proximal portion 2213 in alignment with the bore 2215 and can be in the form of a groove or trough in the flat surface of the proximal portion 2213. The entry feature 2223 can extend from the transition proximally away from the transition and along the flat surface.

The above description has included some references to use to allow for a better understanding of the structure. Below is a more detailed discussion of that use including the devices and techniques for distracting and retaining a facet joint in a distracted and forwardly translated condition. The implantation procedure may be performed under conscious sedation in order to obtain intra-operative patient symptom feedback.

The joint, which can be difficult to access, may be accessed pursuant, for example, to a method and apparatus disclosed in U.S. Non-provisional application Ser. No. 61/350,609, filed Jan. 8, 2009, which is commonly owned with the present application and hereby incorporated by reference. Pursuant to the disclosure in that application, the access system may include one or more cannulas made of steel, titanium, or plastic. The initial facet joint access cannula may have a sharp spatula tip on the distal end. The spatula tip may have a flat configuration to enable access into the flat facet joint. Once the spatula tip achieves access into the flatly oriented facet joint, subsequent stylets and working instruments may be passed down this access channel to complete a distraction procedure. Alternatively, the dilation set 1200 may be used. Alternatively, one or a plurality of the chisel and delivery devices described above may be used to access the joint. The distraction procedure may then begin.

More particularly, initially, an incision may be made in the patients back. Tools known in the art may be used to create this incision and the dilator set 1200 may be used to open an access path through the tissues of the back as described above.

In the case of a tool 1000, once an access path is created, the chisel 1008 described above may be advanced through the incision and the distal tip 1030 may be positioned adjacent the target facet joint. It is noted that chisel 1008 with an interior lumen may allow for visualization to be provided by including a scope within the chisel 1008. Additionally, an incision in the facet joint capsule may be made prior to beginning the procedure, and thus prior to insertion of the chisel 1008. Once the distal tip of the chisel 1008 is properly positioned adjacent the facet joint, the chisel 1008 may be inserted into the facet joint. The chisel 1008 may be used to decorticate the articular surfaces of the facet joint by manipulating the chisel 1008 within the joint. This may include tapping the chisel with a device such as a hammer, mallet, or other instrument to advance the distal tip 1030 of the chisel 1008 and may also include moving the proximal end of the chisel laterally from side to side, up and down, or rotationally, to decorticate the joint. The chisel 1008 may then be tapped into place anteriorly such that it extends substantially through the joint. Fluoroscopy from one or more directions may be used to verify the location of the chisel.

The delivery device 1004 may be slidably advanced over the chisel 1008 and the forks 1012 of the delivery device 1004 may be advanced into the facet joint. Additional fluoroscopy from one or more directions may be used to verify proper placement of the delivery device 1004 and forks 1012. The chisel 1008 may be removed.

An implant may be placed in the driver assembly 1042 and the implant and driver assembly 1042 may be slidably advanced through the delivery device 1004. The forks 1012 of the delivery device 1004 may be holding the facet joint slightly distracted. As such, the implant, in its relatively flat and parallel position, may slide relatively easily into the facet joint. To the extent that it does not, the proximal end of the driver assembly 1042 may be tapped to properly advance and position the implant.

The button on the handle 1053 of the internal actuator 1052 may be pressed to expose the engagement feature 1059 at the distal end of the internal rod 1057 of the internal actuator 1052 and the implant distractor may be placed therein. The button may be released causing at least the proximal end of the implant distractor and the engagement feature 1059 to be retracted within the longitudinal shaft 1055 of the internal actuator 1052 thereby causing a clamping force on the engagement feature 1059 and securing the implant distractor.

The internal actuator 1052 may then be inserted into the proximal end of the driver assembly 1042 and advanced to a point just proximal to the implant. Once properly positioned, the handle 1053 may be rotated or otherwise actuated to advance the implant distractor into the implant thereby distracting implant and the facet joint.

The button on the handle 1053 may be pressed again to expose the engagement feature 1059 at the distal end of the internal rod 1057 from the longitudinal shaft 1055 thereby reducing the clamping force of the engagement feature on the implant distractor and allowing for removal of the internal acuator, while the implant distractor is threadably engaged with the implant. Additionally, the distraction of the implant may cause the upper and lower members of the implant to clear the engagement features 1058 of the holder arms 1048 thus allowing the driver assembly 1042 to be freely removed from the delivery device 1004 leaving the implant and the implant distractor behind.

The injector 1102 may be advanced through the delivery device 1004 and positioned adjacent to the facet joint. The handle 1025 of the plunger 1023 may be depressed thus advancing the plunger 1023 and ejecting the bone paste or other anchoring material. The injector 1102 may be removed. The delivery device 1004 may also be removed and the incision may be closed. The above procedure may be conducted to treat one or both contralateral facet joints.

An implant may additionally or alternatively be delivered with the tool 2000. As discussed with respect the chisel 2008, the delivery device 2004 and the chisel 2008 can be inserted in a one step process. That is, after the incision is made and the tissues of the back are properly dilated, the chisel 2008 and delivery device 2004 can be advanced into the facet joint. Once properly positioned, the chisel 2008 can be removed from the receiving assembly 2010 by prying it free with the malleting tool 2001 or using available push buttons. The removal of the chisel 2008 can prepare the tool 2000 for insertion of the driver assembly 2042. Where contralateral facet joints are being treated, the placing holding chisel 2009 can be placed down the shaft of the delivery device 2004 and the delivery device 2004 can be removed. The delivery device 2004 and the chisel 2008 can then be inserted in the contralateral joint and once properly positioned, the chisel 2008 can be removed to prepare for insertion of the driver assembly 2042.

In some embodiments, the chisel 2209 can be used to initially establish the location of the joint and the proper trajectory of the tool. In this embodiment, the chisel 2209 can be inserted toward a facet joint and be advanced to the lateral mass of the facet joint. This can be done prior to insertion of the tool as mentioned above. A needle can be inserted through the chisel 2209 and extended out the end of the chisel 2209. The surrounding lateral mass can be probed with the needle to determine the location of the facet joint and the position and trajectory of the chisel 2209 can be adjusted until the needle enters the facet joint. Additionally, using lateral fluoroscopy, the needle can be used to determine if the trajectory of the entry is aligned with the slope of the facet joint. That is, if the needle enters the joint, but bends as it continues into and across the joint, the trajectory may not be aligned with the slope of the joint. The chisel trajectory can thus be adjusted, which may include adjusting the bodily entry point.

When the proper trajectory and location are established, the chisel 2209 can be advanced over the needle and into the joint. To transition back to the tool 2000, a series of dilation tubes can be used. That is, as mentioned, in one embodiment, the chisel 2209 can have a cross-section radius of 4 mm. A 5 mm radius tube can be advanced over the chisel 2209 and a 6 mm radius tube can be advanced over the 5 mm radius tube and the 5 mm radius tube can then be removed, leaving the 6 mm radius tube sleevably positioned over the 4 mm radius chisel 2209. Dilations tubes similar to those described with respect to FIGS. 129-135 can be used.

The one-step tool 2000 can thus be used by removing the chisel 2008 from the delivery device 2004 and the delivery device 2004 can be sleevably advanced over the chisel 2209 and within the 6 mm radius dilation tube and the forks 2012 can be advanced into the facet joint. The 6 mm radius dilation tube can be removed and the chisel 2209 can also be removed. To the extent decortication is desired, the chisel 2008 or 2009 can be inserted through the delivery device 2004 and the joint can be decorticated. Where contralateral joints are being addressed, the place holding chisel 2009 can be inserted in the joint to maintain the access to the joint without occluding fluoroscopic view of the contralateral joint.

An implant, for example implant 2054, can be positioned on the distal end of the driver assembly 2042 and the U-shaped receiving feature slots on the lateral sides of the implant can be positioned over the engagement features 2058. It is noted that, when in position, the width of the driver assembly 2042 can be the same or similar to the width of the implant. This is in contrast to that, which is depicted in FIG. 12, for example, with driver assembly 142. The upper and lower surfaces of the implant can be biased toward a parallel position and, as such, when placed over the distal end of the driver assembly 2042, may provide a slight clamping force on the distal end of the driver assembly 2042. In addition, an implant distractor such as, for example distractor 2050, can be advanced slightly into the proximal end of the implant causing the continuous thread feature 2066 to engage the threaded slots of the implant and further secure the implant to the driver assembly. Moreover, this initial starting of the implant distractor 2050 in the implant 2054 can help avoid mis-threading of the distractor 2050. In one embodiment, the implant distractor can be advance, for example, 2 turns into the implant.

Having placed the implant on the distal end of the driver assembly 2042, the driver assembly 2042 and the implant can be advanced through the delivery device 2004 and the implant can be positioned in the facet joint. Rotation of the handle 2053 can cause rotation of the internal rod 2057 thereby causing rotation of the implant distractor 2050. Accordingly, the thread feature 2066 can cause the implant distractor 2050 to advance relative to the implant 2054 thereby distracting the implant 2054 and, in turn, also distracting the facet joint. It is noted that distraction of the implant 2054 can cause the implant to be free from the engagement features 2058 on the distal end of the driver assembly 2042 and as such, once distracted, the driver assembly 2042 can be removed.

In another embodiment, a tool 3000 may include some or all of the elements described with respect to tool 1000. However, rather than combining the driver assembly 1042 and the internal actuator 1052, as with tool 2000, in this embodiment, the driver assembly 1042 may be omitted. In this embodiment of a tool 3000, delivery of the implant may be conducted with the internal actuator 1052. That is, the implant distractor may be initially partially engaged with or "started" in the implant sufficiently to hold the two together. This engagement may be due to the implant being biased to keep the upper and lower members in a parallel position thus creating a threaded and frictional resistance to separation of the implant and the implant distractor. Additionally or alternatively, this engagement may be due to engagement of a cross-cut thread on the implant distractor being engaged with a truncated threaded slot of the implant. Once the implant distractor is started in the implant, the implant distractor may be engaged with the engagement feature on the internal actuator 1052 thus stringing the internal actuator 1052, the implant distractor, and the implant together. The internal actuator 1052 together with the implant distractor and the implant may then be advanced down the tubular shaft 1014 of the delivery device 1004 in lieu of the driver assembly 1042.

In this embodiment, the omission of the driver assembly 1042 may allow for smaller sized shafts of several devices similar to tool 2000. In one embodiment, the outer radius of the tubular shaft 1014 of the delivery device 1004 may be approximately 4 mm and the outer radius of the decorticator may be approximately 5 mm.

In still another embodiment, the several handles/seating features (e.g., 1044, 2044, 1119) may include a slot opening on their distal end for use in separating the handles from the receiving assembly 1010. That is, when the handles are engaged with the receiving assembly and the projections are seated in the seating cavities, the frictional/suctional fit of the handles in the receiving assembly may be difficult to separate. Accordingly, a slot opening on the distal end of the handles may be provided, which may provide for accessing the joint between the handles and the receiving assembly with a separation device which may assist in working the elements apart via prying, scissor action, or other known methods. Alternatively or additionally, the frictional engagement of the several handles in the receiving assembly may be reduced.

The delivery system disclosed herein is advantageous for at least the following reasons. First, the system facilitates delivery of an implant to a facet joint via a minimally invasive or percutaneous procedure, reducing the risk, surgical time and recovery time associated with the implantation of the implant in the facet joint. Accordingly, many of the dimensional characteristics associated with the delivery system, its components, and the implant are advantageous in that they facilitate or make possible the minimally invasive or percutaneous procedures described herein. Second, the system facilitates the implant being delivered while the patient is capable of providing verbal feedback as to the impact of the implant relative to symptoms being felt by the patient.

Referring now to FIGS. 175-177, an implant is shown positioned between vertebral bodies of the lumbar spine and adapted for an interbody fusion. While the majority of this application has addressed the use of implants placed in one or more facet joints, the implants and delivery devices herein described can also be used in other joints of the spine. As shown, for example, the implant can be used where a disc has deteriorated and/or been removed from a spinal joint between vertebral bodies. In the case of a discectomy type procedure, the implants can be used after the disc has been removed to secure two adjacent vertebral bodies and maintain their separation. The currently described delivery tools and implants are not limited to use in the cervical or lumbar spine and further are not limited to facet joints or joints between vertebral bodies.

Discectomy type procedures are often performed from one of three different access points. In one procedure, the spinal column is approached from the posterior. In another procedure, the spinal column is approached anteriorly and in another, from the lateral side of the patient. Referring particularly to FIG. 175, an implant procedure is shown where a posterior approach has been used. That is, where the discectomy is performed from the posterior, the implant can be delivered from the posterior as well. Referring particularly to FIG. 176, an implant procedure is shown where a lateral approach has been used and FIG. 177, shows the implant where an anterior approach has been used. It is noted that the implant can be delivered from any position and the delivery approach does not have to be consistent with the discectomy approach. That is, for example, if the discectomy is performed anteriorly, the implant delivery may be done anteriorly as well, but could also be performed posteriorly or laterally. However, it may be advantageous to use the same delivery approach as the discectomy for purposes of minimizing incisions.

In any of the above approaches, the procedure to place an implant between vertebral bodies can be the same or similar to the procedure to place the implants in a facet joint. For example, the chisel 2008 and delivery device 2004 of tool 2000, for example, can be advanced into the joint between vertebral bodies. As shown in FIGS. 175-177, this can be completed from one of several directions. The teeth of the chisel 2008 can be used to decorticate the joint as desired. Once properly positioned and decorticated, the chisel 2008 can be removed from the receiving assembly 2010 by prying it free with the malleting tool 2001 or using available push buttons. The removal of the chisel 2008 can prepare the tool 2000 for insertion of the driver assembly 2042. Fluorscopy can be used to verify proper placement of the delivery device 2004 to ensure proper placement of an implant.

An implant, for example implant 2054, can be positioned on the distal end of the driver assembly 2042. The U-shaped receiving feature slots on the lateral sides of the implant 2054 can be positioned over the engagement features 2058 and an implant distractor 2050 can be advanced slightly into the proximal end of the implant 2054, for example, 2 turns into the implant. The driver assembly 2042 and the implant 2054 can be advanced through the delivery device 2004 and the implant 2054 can be positioned in the joint between the vertebral bodies. Rotation of the handle 2053 can cause rotation of the internal rod 2057 thereby causing rotation of the implant distractor 2050. Accordingly, the thread feature 2066 can cause the implant distractor 2050 to advance relative to the implant 2054 thereby distracting the implant 2054 and, in turn, also distracting the joint between the vertebral bodies. It is noted that distraction of the implant 2054 can cause the implant to be free from the engagement features 2058 on the distal end of the driver assembly 2042 and as such, once distracted, the driver assembly 2042 can be removed. A similar procedure can be performed to place a second implant 2054. While this procedure has been described with regard to tool 2000 and implant 2054, any of the described tools and implants described can be used.

Some additional methods of use are described below with reference to FIGS. 178-185. In each of the shown methods, any combination of the steps shown or portion of the steps can be included. Additionally, the order of the steps can be rearranged and is not limited the orders of the boxes or label numbers shown.

Figure 178:
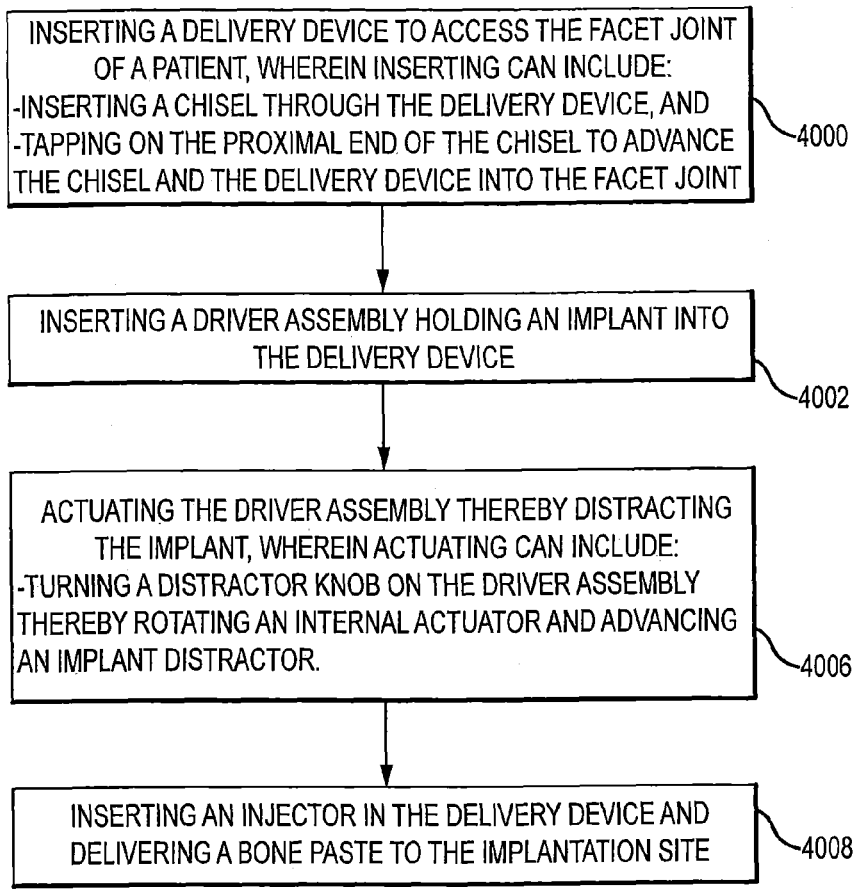

Referring to FIG. 178, in one embodiment, a method of distracting a facet joint of the spine can include inserting a delivery device to access the facet joint of a patient (4000), inserting a driver assembly holding an implant into the delivery device (4002), and actuating the driver assembly thereby distracting the implant (4006). Inserting the delivery device can include inserting a chisel through the delivery device and tapping on the proximal end of the chisel to advance the chisel and the delivery device into the facet joint. Actuating the driver assembly can include turning a distractor knob on the driver assembly thereby rotating an internal actuator and advancing an implant distractor. The method can also include inserting an injector in the delivery device and delivering a bone paste to the implantation site. (4008)

Figure 179:
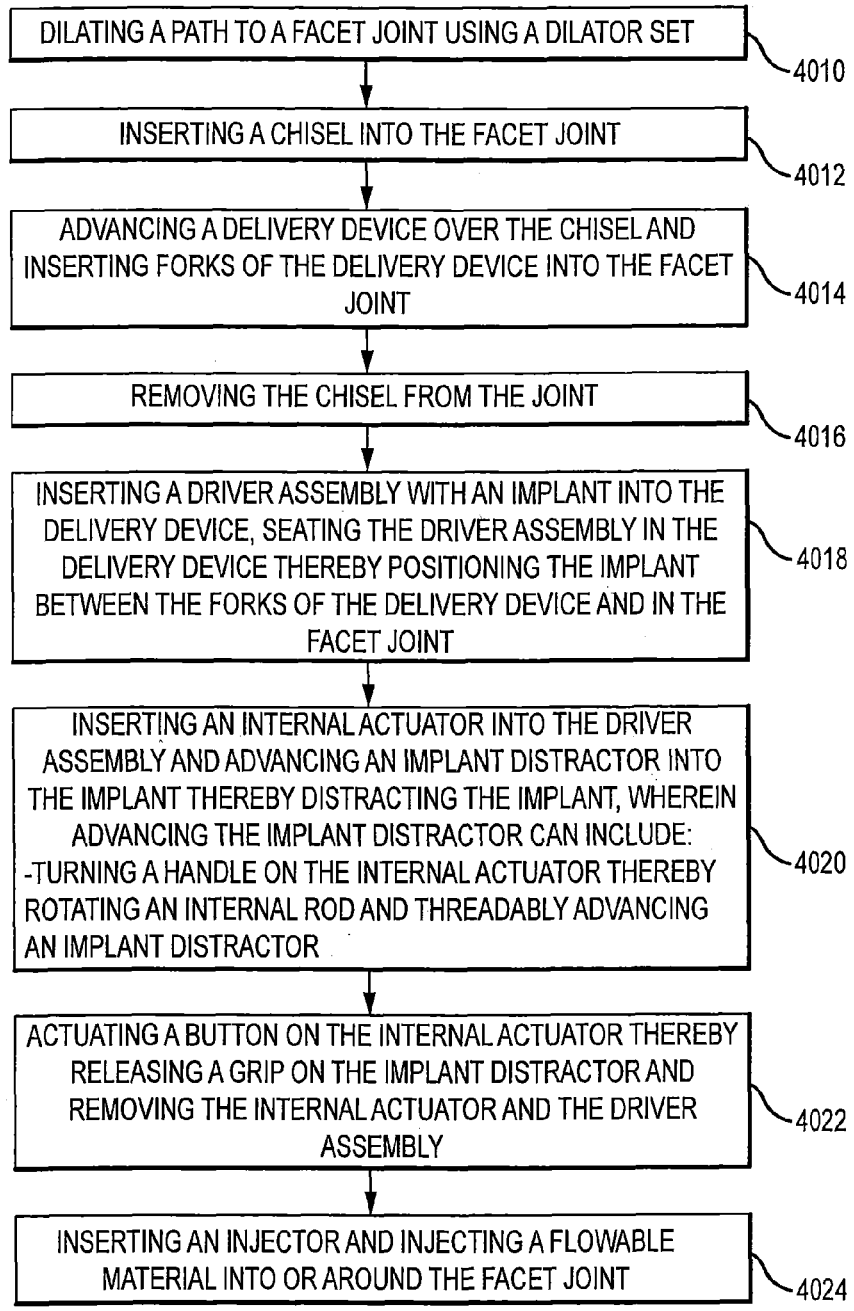

Referring to FIG. 179, in one embodiment, a method of distracting a facet joint of the spine can include dilating a path to a facet joint using a dilator set (4010), inserting a chisel into the facet joint (4012), advancing a delivery device over the chisel and inserting forks of the delivery device into the facet joint (4014), removing the chisel from the joint (4016), inserting a driver assembly with an implant into the delivery device, seating the driver assembly in the delivery device thereby positioning the implant between the forks of the delivery device and in the facet joint (4018), inserting an internal actuator into the driver assembly and advancing an implant distractor into the implant thereby distracting the implant (4020), actuating a button on the internal actuator thereby releasing a grip on the implant distractor and removing the internal actuator and the driver assembly (4022), and inserting an injector and injecting a flowable material into or around the facet joint (4024). In some embodiments, advancing the implant distractor can include turning a handle on the internal actuator thereby rotating an internal rod and threadably advancing an implant distractor.

Figure 180:
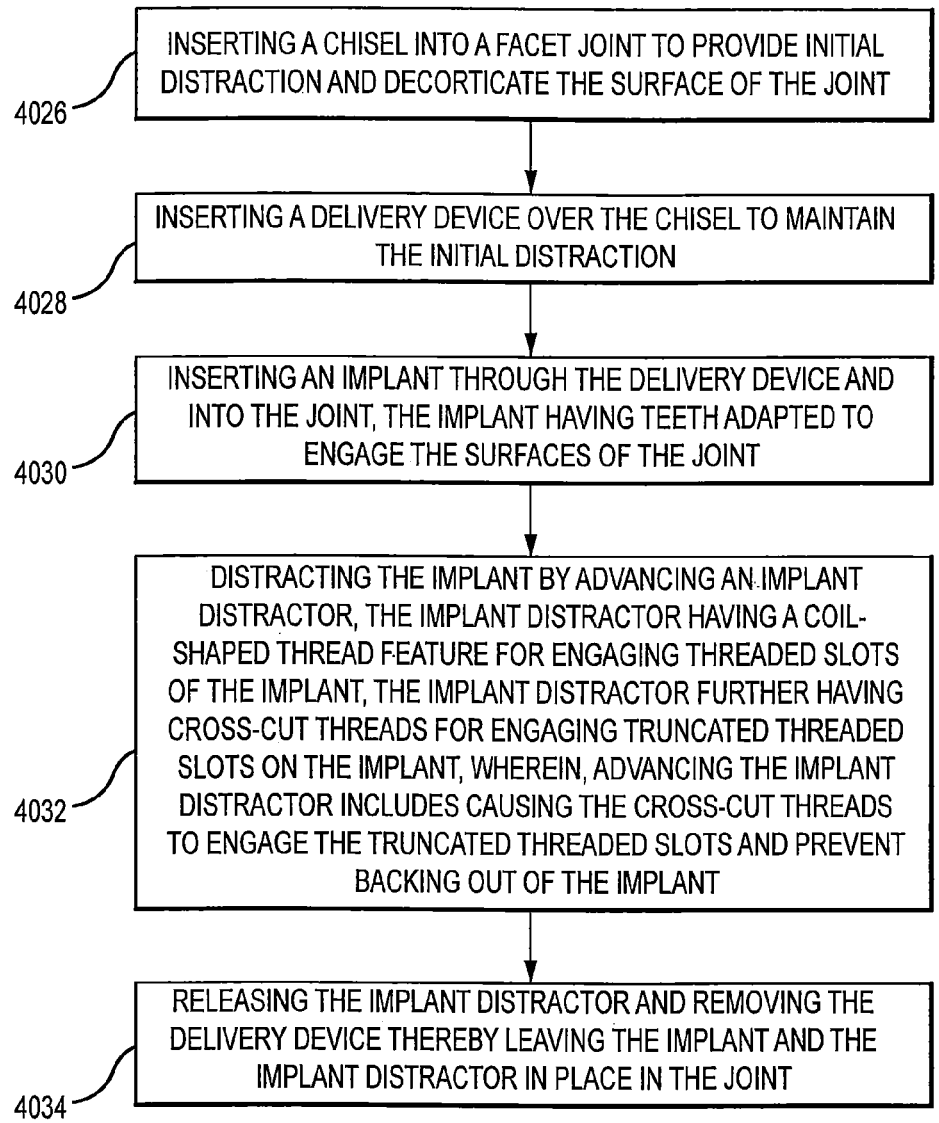

Referring to FIG. 180, a method of distracting a facet joint of the spine can include inserting a chisel into a facet joint to provide initial distraction and decorticate the surface of the joint (4026), inserting a delivery device over the chisel to maintain the initial distraction (4028), inserting an implant through the delivery device and into the joint, the implant having teeth adapted to engage the surfaces of the joint (4030), distracting the implant by advancing an implant distractor, the implant distractor having a coil-shaped thread feature for engaging threaded slots of the implant, the implant distractor further having cross-cut threads for engaging truncated threaded slots on the implant, wherein, advancing the implant distractor includes causing the cross-cut threads to engage the truncated threaded slots and prevent backing out of the implant (4032), and releasing the implant distractor and removing the delivery device thereby leaving the implant and the implant distractor in place in the joint (4034).

Figure 181:
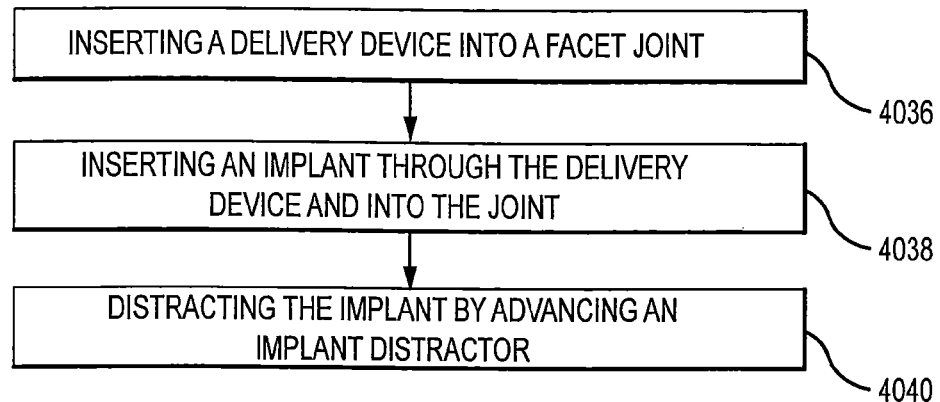

Referring to FIG. 181 a method of distracting a facet joint of the spine can include inserting a delivery device into a facet joint (4036), inserting an implant through the delivery device and into the joint (4038), and distracting the implant by advancing an implant distractor (4040).

Figure 182:
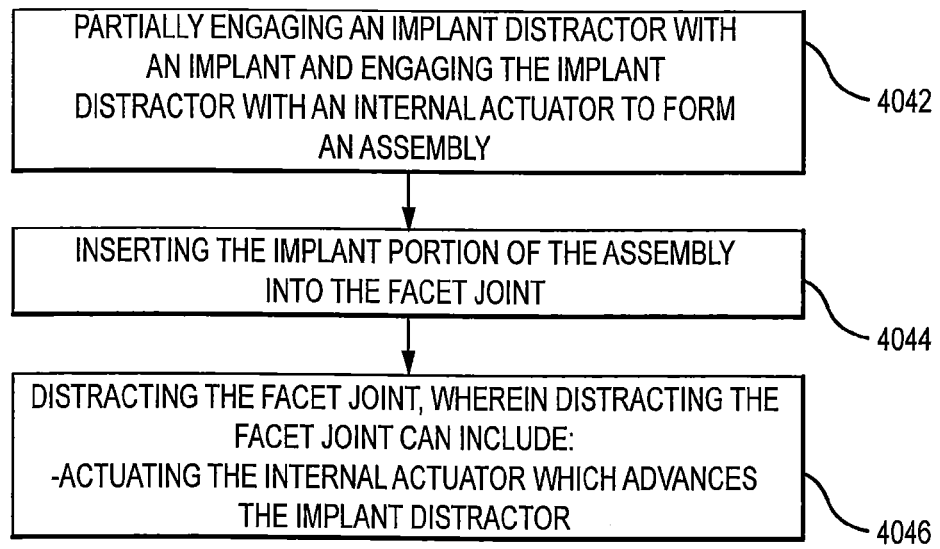

Referring to FIG. 182, a method of distracting a facet joint of the spine can include partially engaging an implant distractor with an implant and engaging the implant distractor with an internal actuator to form an assembly (4042), inserting the implant portion of the assembly into the facet joint (4044), and distracting the facet joint (4046). In some embodiments, distracting the facet joint can include actuating the internal actuator which advances the implant distractor.

Figure 183:
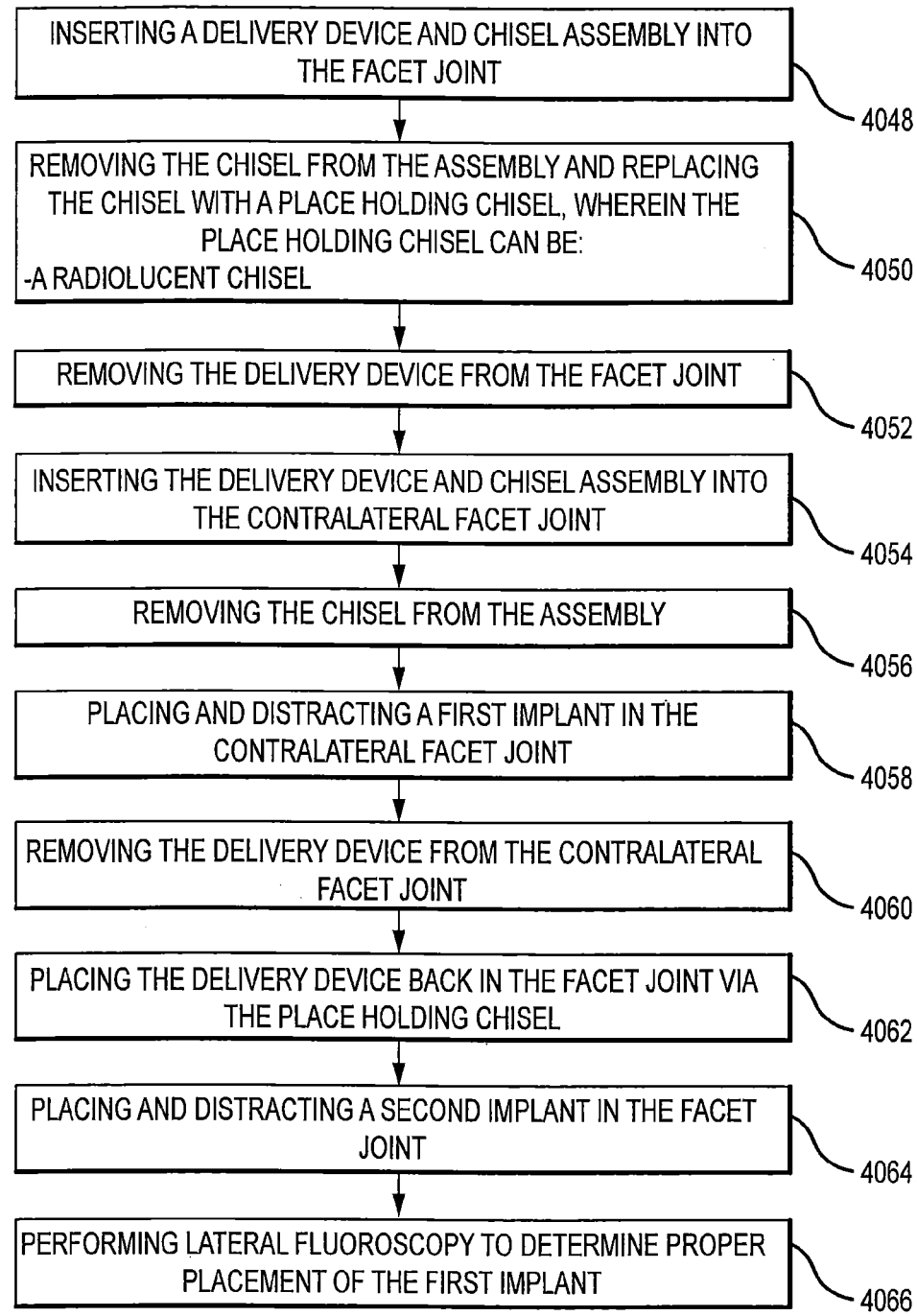

Referring to FIG. 183, a method of distracting a facet joint and a contralateral facet joint of a spine can include inserting a delivery device and chisel assembly into the facet joint (4048), removing the chisel from the assembly and replacing the chisel with a place holding chisel (4050), removing the delivery device from the facet joint (4052), inserting the delivery device and chisel assembly into the contralateral facet joint (4054), removing the chisel from the assembly (4056), placing and distracting a first implant in the contralateral facet joint (4058), removing the delivery device from the contralateral facet joint (4060), placing the delivery device back in the facet joint via the place holding chisel (4062); and placing and distracting a second implant in the facet joint (4064). In some embodiments, the place holding chisel can be a radiolucent chisel. The method can also include performing lateral fluoroscopy to determine proper placement of the first implant (4066).

Figure 184:
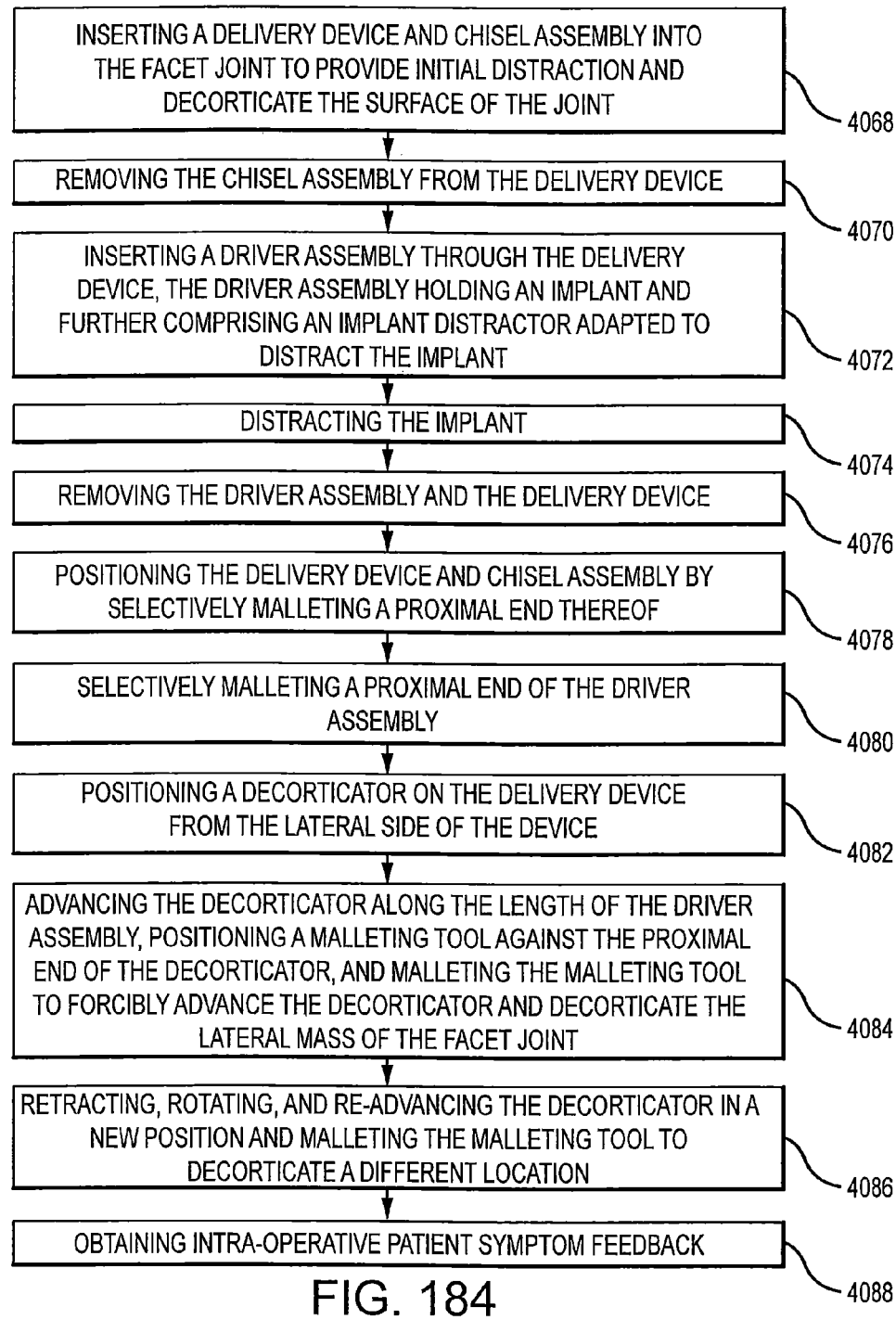

Referring to FIG. 184, a method of distracting a facet joint of the spine can include inserting a delivery device and chisel assembly into the facet joint to provide initial distraction and decorticate the surface of the joint (4068), removing the chisel assembly from the delivery device (4070), inserting a driver assembly through the delivery device, the driver assembly holding an implant and further comprising an implant distractor adapted to distract the implant (4072), distracting the implant (4074), and removing the driver assembly and the delivery device (4076). The method can also include positioning the delivery device and chisel assembly by selectively malleting a proximal end thereof (4078). The method can also include selectively malleting a proximal end of the driver assembly (4080) and can further include positioning a decorticator on the delivery device from the lateral side of the device (4082). Still further, the method can include advancing the decorticator along the length of the driver assembly, positioning a malleting tool against the proximal end of the decorticator, and malleting the malleting tool to forcibly advance the decorticator and decorticate the lateral mass of the facet joint (4084). The method can also include retracting, rotating, and re-advancing the decorticator in a new position and malleting the malleting tool to decorticate a different location (4086). In addition, the method can include obtaining intra-operative patient symptom feedback (4088).

Figure 185:
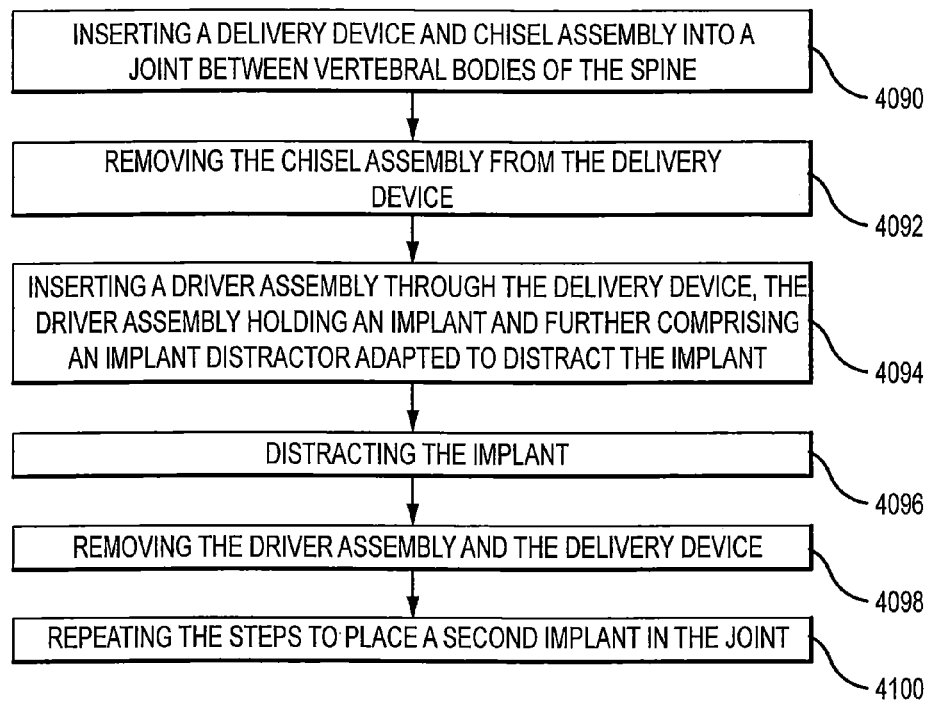

Referring to FIG. 185, a method of performing an interbody fusion can include inserting a delivery device and chisel assembly into a joint between vertebral bodies of the spine (4090), removing the chisel assembly from the delivery device (4092), inserting a driver assembly through the delivery device, the driver assembly holding an implant and further comprising an implant distractor adapted to distract the implant (4094), distracting the implant (4096), and removing the driver assembly and the delivery device (4098). The method can also include repeating the steps to place a second implant in the joint (4100).

Although the present invention has been described with a certain degree of particularity, it is understood the disclosure has been made by way of example, and changes in detail or structure may be made without departing from the spirit of the invention as defined in the appended claims.

What is claimed is:

1. A method of implanting an implant in a spinal facet joint space, the method comprising:
 a) minimally invasively routing into the spinal facet joint space via a posterior approach a first chamfered tip of a first tool, the first tool comprising a proximal portion, a distal portion opposite the proximal portion, and a shaft extending between the proximal and distal portions, the distal portion distally terminating as the first chamfered tip; b) routing a second tool over the first tool, the second tool comprising a proximal region, a distal region opposite the proximal region, and a tubular body extending between the proximal and distal regions and comprising a lumen extending through the tubular body between the proximal and distal regions, the distal region distally terminating as a second chamfered tip, wherein the second tool is routed over the first tool until the second chamfered tip is received in the spinal facet joint adjacent the first chamfered tip; c) routing a third tool through the lumen of the second tool, the third tool comprising an implant support structure releasably coupled to the implant, the third tool further comprising a proximal part, a distal part opposite the proximal part, and an elongated body extending between the proximal and distal parts, the distal part terminating as the implant support structure, wherein the third tool is routed through the lumen until the implant is received in the spinal facet joint adjacent the second chamfered tip; and d) releasing the implant from the third tool, wherein the implant support structure comprises a first arm and a second arm offset from the first arm by a distance transverse to a longitudinal axis of the elongated body, and the implant is supported between the first and second arms when the implant is releasably coupled to the implant support structure, wherein the first arm comprises a radially inward surface with a longitudinally extending ridge that projects radially inward from the radially inward surface, and the longitudinally extending ridge is received between a pair of longitudinally extending features of the implant.

2. The method of claim 1, wherein the first chamfered tip comprises a first planar surface approximately parallel to a longitudinal axis of the shaft.

3. The method of claim 2, wherein the first chamfered tip is a double chamfer tip and further comprises a second planar surface opposite the first planar surface.

4. The method of claim 2, wherein the distal portion further includes a transition region between the first planar surface and an outer surface of the shaft.

5. The method of claim 4, wherein the transition region includes an arcuate surface.

6. The method of claim 1, wherein the first chamfered tip has a proximal-distal length adapted to extend substantially across the spinal facet joint space.

7. The method of claim 6, wherein the proximal-distal length of the first chamfered tip is between approximately 5 mm to approximately 35 mm.

8. The method of claim 1, wherein routing the second tool over the first tool comprises slidably receiving the first tool in the lumen of the second tool.

9. The method of claim 1, wherein a longitudinal cross section of the first chamfered tip is generally similar to a longitudinal cross section of the second chamfered tip.

10. The method of claim 1, wherein the second chamfered tip comprises a first fork and a second fork offset from the first fork by a distance transverse to a longitudinal axis of the tubular body.

11. The method of claim 10, wherein the first fork distally tapers towards a distal point.

12. The method of claim 10, wherein the proximal region of the second tool includes a first structure and the proximal part of the third tool includes a second structure configured to matingly engage with the first structure, and when the first and second structures are matingly engaged, the first arm and second arm are respectively generally aligned with the first fork and second fork.

13. The method of claim 1, wherein the pair of longitudinally extending features of the implant comprises opposed planar members of the implant.

14. The method of claim 1, wherein releasing the implant further comprises acting on the proximal part of the third tool to release the implant from the implant support structure.

15. The method of claim 14, wherein the elongated body of the third tool comprises a lumen extending between the proximal and distal parts, the third tool further comprising a rod extending through the lumen of the elongated body, and wherein acting on the proximal part of the third tool to release the implant from the implant support structure causes the rod to distally displace within the lumen of the elongated body to act upon the implant.

16. The method of claim 15, wherein acting on the proximal part of the third tool to release the implant from the implant support structure further comprises causing the rod to rotate about a longitudinal axis of the rod within the lumen of the elongated body.

17. The method of claim 16, wherein the implant includes a pair of opposed members and a threaded member, and, when the threaded member is acted on by the rod both rotating and distally displacing, the threaded member is caused to be threadably received between the pair of opposed members.

18. The method of claim 1, further comprising:
   causing a hollow body of a decorticator to receive a longitudinally extending member that comprises a distal termination located in the spinal facet joint space, the decorticator comprising a proximal end, a distal end opposite the proximal end and the hollow body extending between the proximal and distal ends, the distal end distally terminating in a decorticating surface including an abrasive surface or a plurality of teeth; and
   routing the decorticator over the longitudinally extending member until the distal end of the decorticator is brought into contact with a lateral mass of the spinal facet joint; and
   rotating the decorticator about a longitudinal axis of the longitudinally extending member to cause the decorticating surface to decorticate the lateral mass.

19. The method of claim 18, wherein the longitudinally extending member includes the second tool.

20. The method of claim 18, wherein the distal end terminates at a sloped angle relative to a longitudinal axis of the hollow body.

21. The method of claim 20, wherein the sloped angle allows the decorticating surface to contact a superior lateral mass without contacting an inferior lateral mass.

22. The method of claim 1, further comprising:
   routing a rasp through the lumen of the second tool, the rasp comprising a proximal aspect, a distal aspect opposite the proximal aspect and an elongated member extending between the proximal and distal aspects, the distal aspect comprising a rasp configuration, wherein the rasp is routed through the lumen until the rasp configuration is received in the spinal facet joint adjacent the second chamfered tip; and
   rasping tissue from a surface of the spinal facet joint space.

23. The method of claim 22, wherein a longitudinal cross section of the rasp configuration is generally similar to a longitudinal cross section of the second chamfered tip.

24. The method of claim 23, wherein the second chamfered tip comprises a first fork and a second fork offset from the first fork by a distance transverse to a longitudinal axis of the tubular body, and the rasp configuration is received between the first and second forks when the rasp configuration is received in the spinal facet joint adjacent the second chamfered tip.

25. The method of claim 24, wherein when the rasp configuration is received between the first and second forks, an upper surface of each fork is generally aligned with an upper surface of the rasp configuration.

26. The method of claim 25, wherein when the rasp configuration is received between the first and second forks, a lower surface of each fork is generally aligned with a lower surface of the rasp configuration.

* * * * *